US012545639B2

(12) United States Patent
Naik et al.

(10) Patent No.: US 12,545,639 B2

(45) Date of Patent: Feb. 10, 2026

(54) 3-SUBSTITUTED PHENYLAMIDINE COMPOUNDS, PREPARATION AND USE THEREOF

(71) Applicant: PI INDUSTRIES LTD., Udaipur-Rajasthan (IN)

(72) Inventors: Maruti Naik, Karnataka (IN); Vishal A. Mahajan, Maharashtra (IN); S. Sivakumar, Tamilnadu (IN); Kishor Singh Rathod, Jodhpur-Rajasthan (IN); Sachin Nagnath Gumme, Maharashtra (IN); Santosh Shridhar Autkar, Maharashtra (IN); Ruchi Garg, Uttar Pradesh (IN); Hagalavadi M Venkatesha, Karnataka (IN); Alexander G. M. Klausener, Pulheim (DE)

(73) Assignee: PI INDUSTRIES LTD., Udaipur-Rajasthan (IN)

( * ) Notice: Subject to any disclaimer, the term of this patent is extended or adjusted under 35 U.S.C. 154(b) by 1175 days.

(21) Appl. No.: 17/310,038

(22) PCT Filed: Jan. 13, 2020

(86) PCT No.: PCT/IB2020/050213

§ 371 (c)(1),
(2) Date: Jul. 13, 2021

(87) PCT Pub. No.: WO2020/148617

PCT Pub. Date: Jul. 23, 2020

(65) Prior Publication Data

US 2022/0089523 A1 Mar. 24, 2022

(30) Foreign Application Priority Data

Jan. 14, 2019 (IN) ............................ 201911001543

(51) Int. Cl.

| | |
|---|---|
| ***C07C 251/06*** | (2006.01) |
| ***A01N 43/32*** | (2006.01) |
| ***A01N 43/40*** | (2006.01) |
| ***A01N 43/54*** | (2006.01) |
| ***A01N 43/60*** | (2006.01) |
| ***A01N 47/40*** | (2006.01) |
| ***A01P 3/00*** | (2006.01) |
| ***C07C 249/02*** | (2006.01) |
| ***C07C 253/30*** | (2006.01) |
| ***C07C 255/61*** | (2006.01) |
| ***C07C 319/02*** | (2006.01) |

(Continued)

(52) U.S. Cl.

CPC ............ *C07C 251/06* (2013.01); *A01N 43/32* (2013.01); *A01N 43/40* (2013.01); *A01N 43/54* (2013.01); *A01N 43/60* (2013.01); *A01N 47/40* (2013.01); *A01P 3/00* (2021.08); *C07C 249/02* (2013.01); *C07C 253/30* (2013.01); *C07C 255/61* (2013.01); *C07C 319/02* (2013.01); *C07C 323/23* (2013.01); *C07D 213/74* (2013.01); *C07D 239/42* (2013.01); *C07D 241/20* (2013.01); *C07D 277/64* (2013.01); *C07D 319/20* (2013.01)

(58) Field of Classification Search

CPC ... C07C 251/06; C07C 249/02; C07C 253/30; C07C 255/61; C07C 319/02; C07C 323/23; C07C 211/52; C07C 251/24; C07C 255/58; C07C 209/68; C07C 253/02; C07C 319/14; A01N 43/32; A01N 43/40; A01N 43/54; A01N 43/60; A01N 47/40; A01N 37/52; A01N 43/78; A01N 37/34; A01P 3/00; C07D 213/74; C07D 239/42; C07D 241/20; C07D 277/64; C07D 319/20; C07D 213/58; C07D 241/12

See application file for complete search history.

(56) References Cited

U.S. PATENT DOCUMENTS 6,893,650 B1 * 5/2005 Charles ................ C07D 251/34
546/261
2006/0194801 A1 8/2006 Kelly et al.

(Continued)

FOREIGN PATENT DOCUMENTS

| | | | |
|---|---|---|---|
| JP | S61-53260 | A | 3/1986 |
| JP | S61-165360 | A | 7/1986 |
| JP | S612-89072 | A | 12/1986 |
| NO | 03/024219 | A1 | 3/2003 |
| WO | 00/46184 | A1 | 8/2000 |
| WO | 03/093224 | A1 | 11/2003 |
| WO | 2005/089547 | A1 | 9/2005 |
| WO | 2007/031507 | A1 | 3/2007 |
| WO | 2012/029942 | A1 | 3/2012 |

(Continued)

*Primary Examiner* — James H Alstrum-Acevedo

*Assistant Examiner* — Pierre Paul Eleniste

(74) *Attorney, Agent, or Firm* — Lippes Mathias LLP

(57) ABSTRACT

The present invention disclosed 3-substituted phenylamidine compounds of general formula (I), wherein $R^1$, $R^2$, $R^3$, $R^4$, $R^{4a}$, $R^{4b}$, A and E have the same meanings as defined in description. The present invention further discloses methods for their preparation and use of the compounds of general formula (I) as a crop protection agent.

Formula (I)

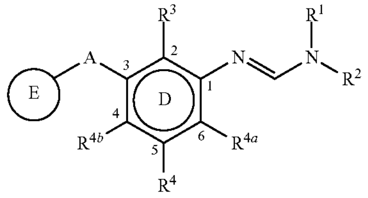

21 Claims, No Drawings

(51) Int. Cl.

| | |
|---|---|
| ***C07C 323/23*** | (2006.01) |
| ***C07D 213/74*** | (2006.01) |
| ***C07D 239/42*** | (2006.01) |
| ***C07D 241/20*** | (2006.01) |
| ***C07D 277/64*** | (2006.01) |
| ***C07D 319/20*** | (2006.01) |

(56) References Cited

U.S. PATENT DOCUMENTS

| | | | | |
|---|---|---|---|---|
| 2011/0082036 | A1* | 4/2011 | Desbordes | A01N 55/00 514/331 |
| 2011/0130282 | A1 | 6/2011 | Kunz et al. | |
| 2017/0174668 | A1 | 6/2017 | Kley et al. | |
| 2017/0355679 | A1 | 12/2017 | Edwards et al. | |

FOREIGN PATENT DOCUMENTS

| | | | | |
|---|---|---|---|---|
| WO | 2014/072244 | A1 | 5/2014 | |
| WO | 2014/206922 | A1 | 12/2014 | |
| WO | 2016/210234 | A1 | 12/2016 | |
| WO | 2017/076739 | A1 | 5/2017 | |
| WO | 2018/069841 | A1 | 4/2018 | |
| WO | 2018/069842 | A1 | 4/2018 | |
| WO | 2019/141740 | A1 | 7/2019 | |
| WO | 2019/196622 | A1 | 10/2019 | |
| WO | WO-2019202459 | A1 * | 10/2019 | A01N 37/52 |
| WO | 2019/214634 | A1 | 11/2019 | |

* cited by examiner

3-SUBSTITUTED PHENYLAMIDINE COMPOUNDS, PREPARATION AND USE THEREOF

This application is a National Stage Entry of International Application No. PCT/IB2020/050213, filed Jan. 13, 2020, and entitled "3-SUBSTITUTED PHENYLAMIDINE COMPOUNDS, PREPARATION AND USE THEREOF"; which claims priority to Indian Application No. 201911001543, filed Jan. 14, 2019, and entitled "3-SUBSTITUTED PHENYLAMIDINE COMPOUNDS, PREPARATION AND USE THEREOF", the contents of which are incorporated by reference herein.

FIELD OF THE INVENTION

The present invention relates to 3-substituted phenylamidine compounds. More particularly, the present invention relates to 3-substituted phenylamidine compounds of general formula (I), to a process for preparation and to a use thereof as a crop protection agent.

BACKGROUND OF THE INVENTION

Fungal pathogens continue to pose a serious threat to public health and agriculture. Therefore, the control of plant diseases caused by fungal plant pathogens is extremely important in achieving high crop efficiency. The plant diseases damage to ornamental, vegetable, field, cereal and fruit crops can cause significant reduction in productivity and thereby result in increased costs to the consumer. In addition to often being highly destructive, plant diseases can be difficult to control and may develop resistance to commercial fungicides. Many products are commercially available for these purposes, but the need continues for new fungicidal compounds which are more effective, less costly, less toxic, environmentally safer or have different sites of action.

For example, WO2000046184, WO2003024219, WO2005089547, WO2003093224, WO2007031507, discloses the phenylamidine derivatives and their use, either alone or as part of compositions, as fungicides.

The effectiveness of phenylamidine derivatives described in the prior art is good, but leaves something to be desired in various cases. Therefore, it is always of high interest in agriculture to use novel pesticidal compounds in order to avoid and/or control the development of microorganisms such as fungal or bacterial pathogens or pests being resistant to known active ingredients. It is therefore of high interest to use novel compounds being more active than those already known, with the aim of decreasing the amounts of active compound to be used, whilst at the same time maintaining an effectiveness at least equivalent to the already known compounds.

Currently, the environmental and economic demands for fungicides are continuously increasing for example with respect to activity spectrum, toxicity, selectivity, application rate, formation of residues and favorable manufacturing processes, and also expand the occurrence, for example of resistance problems, therefore there is a continuous need to provide new fungicide compounds which will overcome these environmental and economic requirements and/or alleviate the problems associated with pathogens resistance. Accordingly, the present invention provides a new family of compounds which possesses the above mentioned effects or advantages, thus allowing an unexpected and significantly higher activity against undesired microorganisms such as fungal or bacterial pathogens.

SUMMARY OF THE INVENTION

Accordingly, the present invention provides a 3-substituted phenylamidine compound of general formula (I) or agriculturally acceptable salts, structural isomers, stereoisomers, diastereomers, enantiomers, tautomers, metal complexes, polymorphs or N-oxides thereof.

Formula (I)

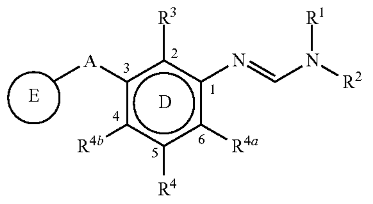

wherein, $R^1$, $R^2$, $R^3$, $R^4$, $R^{4a}$, $R^{4b}$, A and E are as defined in the detailed description.

In an embodiment, the present invention provides a process for preparing a compound of general formula (I) or agriculturally acceptable salt thereof.

In another embodiment, the present invention provides a composition comprising at least one compound of general formula (I) and optionally at least one other active compound selected from fungicides, insecticides, nematicides, acaricides, biopesticides, herbicides, plant growth regulators, antibiotics, fertilizers and or mixtures thereof.

In yet another embodiment, the present invention provides use of compounds of formula (I) and compositions thereof, for controlling and/or preventing phytopathogenic microorganisms of agricultural crops and/or horticultural crops.

In still another embodiment, the present invention provides use of at least one compound of the present invention, in combinations or compositions, and methods of using the same, particularly in the field of agriculture, mainly for protecting plants.

The compounds of the present invention have enhanced activity against microbials, particularly against phytopathogenic fungi. The compounds of the present invention can be applied in the field of agriculture or may be used as intermediates for synthesizing compounds having wider applications.

DETAILED DESCRIPTION OF THE INVENTION

Definitions

The following definitions provided for the terminologies used in the present disclosure are for illustrative purpose only and in no manner limit the scope of the present invention disclosed in the present disclosure.

The transitional phrase "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited, except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition "A" or "B" is satisfied by any one of the following: A is true (or present) and B is false (or not present), A is false (or not present) and B is true (or present), and both A and B is true (or present).

Also, the indefinite articles "a" and "an" preceding an element or component of the present invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "pesticide" in each case also always comprises the term "crop protection agent".

The term "undesired microorganisms" or "phytopathogenic microorganisms" such as fungal or bacterial pathogens includes namely Plasmodiophoromycetes, Oomycetes, Chytridiomycetes, Zygomycetes, Ascomycetes, Basidiomycetes and Deuteromycetes and Pseudomonadaceae, Rhizobiaceae, Enterobacteriaceae, Corynebacteriaceae and Streptomycetaceae respectively.

The term "agronomic" refers to the production of field crops such as for food, fuels, biofuels, any biomaterials and fiber and includes namely the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries), biofuel production crops such as corn, sugar/starch crops, sugar-beet and sweet sorghum, cellulosic crops such as switchgrass, miscanthus, corn stover, poplar, biodiesel crops rapeseed (canola), soybeans, palm oil, mustard, camelina, safflower, sunflower and jatropha and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

The terms alkyl, alkenyl, alkynyl, carbocyclyl, heterocyclyl, aryl and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction under normal conditions (temperature, pressure, air etc.). Unless otherwise indicated, a "substituted" group has a substituent at one or more substitutable positions of the group, and when more than one position in any given structure is substituted, the substituent is either the same or different at each position.

The term "alkyl", used either alone or in compound words such as "alkylthio" or "haloalkyl" includes straight-chain or branched $C_1$ to $C_{24}$ alkyl, preferably $C_1$ to $C_{15}$ alkyl, more preferably $C_1$ to $C_{10}$ alkyl, most preferably $C_1$ to $C_6$ alkyl. Non limiting examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, carbonyl, carbonyloxy and the like, are at the end.

The term "alkenyl", used either alone or in compound words includes branched or straight-chain $C_2$ to $C_{24}$ alkenes, preferably $C_2$ to $C_{15}$ alkenes, more preferably $C_2$ to $C_{10}$ alkenes, most preferably $C_2$ to $C_6$ alkenes. Non limiting examples of alkenes include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl and the different isomers. “Alkenyl” also includes polyenes such as 1,2-propadienyl and 2,4-hexadienyl. This definition also applies to alkenyl as a part of a composite substituent, for example haloalkenyl and the like, unless defined specifically elsewhere.

The term “alkenyl”, used either alone or in compound words includes branched or straight-chain $C_2$ to $C_{24}$ alkynes, preferably $C_2$ to $C_{15}$ alkynes, more preferably $C_2$ to $C_{10}$ alkynes, most preferably $C_2$ to $C_6$ alkynes. Non limiting examples of alkynes include ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl and the different isomers. This definition also applies to alkynyl as a part of a composite substituent, for example haloalkynyl etc., unless specifically defined elsewhere. “Alkynyl” can also include moieties comprised of multiple triple bonds such as 2,5-hexadiynyl.

The term “cycloalkyl” means alkyl closed to form a ring. Non limiting examples include but are not limited to cyclopropyl, cyclobutyl, cyclopentyl and cyclohexyl. This definition also applies to cycloalkyl as a part of a composite substituent, for example cycloalkylalkyl etc., unless specifically defined elsewhere.

The term “cycloalkenyl” means alkenyl closed to form a ring including monocyclic, partially unsaturated hydrocarbyl groups. Non limiting examples include but are not limited to cyclopentenyl and cyclohexenyl. This definition also applies to cycloalkenyl as a part of a composite substituent, for example cycloalkenylalkyl etc., unless specifically defined elsewhere.

The term “cycloalkynyl” means alkynyl closed to form a ring including monocyclic, partially unsaturated groups. This definition also applies to cycloalkynyl as a part of a composite substituent, for example cycloalkynylalkyl etc., unless specifically defined elsewhere.

The term “cycloalkoxy”, “cycloalkenyloxy” and the like are defined analogously. Non limiting examples of cycloalkoxy include cyclopropyloxy, cyclopentyloxy and cyclohexyloxy. This definition also applies to cycloalkoxy as a part of a composite substituent, for example cycloalkoxy alkyl etc., unless specifically defined elsewhere.

The term “alkoxy” used either alone or in compound words included $C_1$ to $C_{24}$ alkoxy, preferably $C_1$ to Cis alkoxy, more preferably $C_1$ to $C_{10}$ alkoxy, most preferably $C_1$ to $C_6$ alkoxy. Non limiting examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy and the different isomers. This definition also applies to alkoxy as a part of a composite substituent, for example haloalkoxy, alkynylalkoxy, etc., unless specifically defined elsewhere.

The term “alkylthio” includes branched or straight-chain alkylthio moieties such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio and the different isomers.

Non limiting examples of “alkylsulfinyl” include but are not limited to methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentyl sulphinyl, 3-methylpentyl sulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutyl sulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl and the different isomers. The term “arylsulfinyl” includes Ar—S(O), wherein Ar can be any carbocyle or heterocylcle. This definition also applies to alkylsulphinyl as a part of a composite substituent, for example haloalkylsulphinyl etc., unless specifically defined elsewhere.

Non limiting examples of “alkylsulfonyl” include but are not limited to methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentyl sulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl and the different isomers. The term “arylsulfonyl” includes Ar—$S(O)_2$, wherein Ar can be any carbocyle or heterocylcle. This definition also applies to alkylsulphonyl as a part of a composite substituent, for example alkylsulphonylalkyl etc., unless defined elsewhere.

The term “hydroxy” means —OH, “amino” means —NRR, wherein R can be H or any possible substituent such as alkyl; "carbonyl" means —C(O)—, "carbonyloxy" means —OC(O)—, "sulfinyl" means SO, "sulfonyl" means $S(O)_2$.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different.

Non limiting examples of "haloalkyl" include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, for example haloalkylaminoalkyl etc., unless specifically defined elsewhere.

The terms "haloalkenyl" and "haloalkynyl" are defined analogously except that, instead of alkyl groups, alkenyl and alkynyl groups are present as a part of the substituent.

The term "haloalkoxy" means straight-chain or branched alkoxy groups where some or all of the hydrogen atoms in these groups may be replaced by halogen atoms as specified above. Non limiting examples of haloalkoxy include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as a part of a composite substituent, for example haloalkoxyalkyl etc., unless specifically defined elsewhere.

The term "haloalkylthio" or "haloalkylsulfanyl" means straight-chain or branched alkylthio groups where some or all of the hydrogen atoms in these groups may be replaced by halogen atoms as specified above. Non limiting examples of haloalkylthio include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio. This definition also applies to haloalkylthio as a part of a composite substituent, for example haloalkylthioalkyl etc., unless specifically defined elsewhere.

Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

The term "bicyclic ring or ring system" denotes a ring system consisting of two or more common atom.

The term "aromatic" indicates that the Hueckel rule is satisfied and the term "non-aromatic" indicates that the Hueckel rule is not satisfied.

The terms "carbocycle" or "carbocyclic" or "carbocyclyl" include "aromatic carbocyclic ring system" and "nonaromatic carbocylic ring system" or polycyclic or bicyclic (spiro, fused, bridged, nonfused) ring compounds in which the ring may be aromatic or non-aromatic (where aromatic indicates that the Huckel rule is satisfied and non-aromatic indicates that the Huckel rule is not satisfied).

Non limiting examples of non-aromatic carbocyclic ring system are cyclopropyl, cyclobutyl, cyclopentyl, norbornyl and the like.

Non limiting examples of aromatic carbocyclic ring system are phenyl, naphthyl and the like.

The term "aryl" as used herein is a group that contains any carbon-based aromatic group including, but not limited to phenyl, naphthalene, biphenyl, anthracene, and the like. The aryl group can be substituted or unsubstituted. In addition, the aryl group can be a single ring structure or comprise multiple ring structures that are either fused ring structures or attached via one or more bridging groups such as a carbon-carbon bond.

The term "aralkyl" refers to aryl hydrocarbon radicals including an alkyl portion as defined above. Non limiting examples include benzyl, phenylethyl, and 6-napthylhexyl. As used herein, the term "aralkenyl" refers to aryl hydrocarbon radicals including an alkenyl portion, as defined above, and an aryl portion, as defined above. Non limiting examples include styryl, 3-(benzyl) prop-2-enyl, and 6-napthylhex-2-enyl.

The term "hetero" in connection with rings refers to a ring in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs.

The term "heterocycle" or "heterocyclic" includes "aromatic heterocycle" or "heteroaryl ring system" and "non-aromatic heterocycle ring system" or polycyclic or bicyclic (spiro, fused, bridged, non-fused) ring compounds in which ring may be aromatic or non-aromatic, wherein the heterocycle ring contains at least one heteroatom selected from N, O, $S(O)_{0-2}$, and or C ring member of the heterocycle may be replaced by C(═O), C(═S), C(═CR*R*) and C═NR*, * indicates integers.

The term "non-aromatic heterocycle" or "non-aromatic heterocyclic" means three- to fifteen-membered, preferably three- to twelve-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxiranyl, aziridinyl, oxetanyl, azetidinyl, thietanyl, 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-1-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, pyrrolinyl, 2-pyrrolin-2-yl, 2-pyrrolin-3-yl, 3-pyrrolin-2-yl, 3-pyrrolin-3-yl, 2-isoxazolin-3-yl, 3-isoxazolin- 3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, piperidinyl, 2-piperidinyl, 3-piperidinyl, 4-piperidinyl, pyrazynyl, morpholinyl, thiomorphlinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, cycloserines. This definition also applies to heterocyclyl as a part of a composite substituent, for example heterocyclylalkyl etc., unless specifically defined elsewhere.

The term "heteroaryl" means 5 or 6-membered, fully unsaturated monocyclic ring system containing one to four heteroatoms from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) furyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl, 1,3,4-oxadiazolyl, 1,3,4-thiadiazolyl, 1,3,4-triazolyl, tetrazolyl; nitrogen-bonded 5-membered heteroaryl containing one to four nitrogen atoms, or benzofused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example (but not limited to) 1-pyrrolyl, 1-pyrazolyl, 1,2,4-triazolyl, 1-imidazolyl, 1,2,3-triazolyl and 1,3,4-triazolyl.

6-membered heteroaryl which contains one to four nitrogen atoms: 6-membered heteroaryl groups which, in addition to carbon atoms, may contain, respectively, one to three and one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl; benzofused 5-membered heteroaryl containing one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl; benzofused 6-membered heteroaryl which contains one to three nitrogen atoms: for example (but not limited to) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

Non limiting examples of fused 6-5-membered heteroaryl include Indolizinyl; pyrazolo[1,5-a]pyridinyl; imidazo[1,2-a]pyridinyl; pyrrolo[1,2-a]pyrimidinyl; pyrazolo[1,5-a]pyrimidinyl; imidazo[1,2-a]pyrimidinyl; pyrrolo[1,2-a]pyrazinyl; pyrazolo[1,5-a]pyrazinyl; imidazo[1,2-a]pyrazinyl and the like.

This definition also applies to heteroaryl as a part of a composite substituent, for example heteroarylalkyl etc., unless specifically defined elsewhere.

The term "amide" means A-R'C═ONR"—B, wherein R' and R" indicates substituents and A and B indicate any group.

The term "thioamide" means A-R'C═SNR"—B, wherein R' and R" indicates substituents and A and B indicate any group.

The term "leaving group" means, all substituents which have sufficient nucleofilicity under the prevailing reaction conditions or nucleophilically replaceable group; by way of example, halogens, triflate, mesylate, tosylate or $SO_2$-Me may be mentioned as suitable leaving groups.

The total number of carbon atoms in a substituent group is indicated by the "$C_1$-$C_1$" prefix where i and j are numbers from 1 to 21. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript indicates that the number of said substituents can exceed 1, said substituents (when they exceed 1) are independently selected from the group of defined substituents. Further, when the subscript m in $(R)_m$ indicates an integer ranging from for example 0 to 4, then the number of substituents may be selected from the integers from 0 and 4 inclusive.

When a group contains a substituent which can be hydrogen, then, when this substituent is taken as hydrogen, it is recognized that said group is being un-substituted.

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skilled in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned in the description and the foregoing claims though might form a critical part of the present invention of the present disclosure, any deviation from such numerical values shall still fall within the scope of the present disclosure if that deviation follows the same scientific principle as that of the present invention disclosed in the present disclosure.

The term "pest" for the purpose of the present disclosure includes but is not limited to fungi, stramenopiles (oomycetes), bacteria, nematodes, mites, ticks, insects and rodents.

The term "plant" is understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights.

For the purpose of the present disclosure the term "plant" includes a living organism of the kind exemplified by trees, shrubs, herbs, grasses, ferns, and mosses, typically growing in a site, absorbing water and required substances through its roots, and synthesizing nutrients in its leaves by photosynthesis. Examples of "plant" for the purpose of the present invention include but are not limited to agricultural crops such as wheat, rye, barley, triticale, oats or rice; beet, e.g. sugar beet or fodder beet; fruits and fruit trees, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit and citrus trees, such as oranges, lemons, grapefruits or mandarins; any horticultural plants, vegetables, such as spinach, lettuce, asparagus, cabbages, carrots, onions, tomatoes, potatoes, cucurbits or paprika; lauraceous plants, such as avocados, cinnamon or camphor; cucurbitaceae; oleaginous plants; energy and raw material plants, such as cereals, corn, soybean, other leguminous plants, rape, sugar cane or oil palm; tobacco; nuts; coffee; tea; cacao; bananas; peppers; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferably, the plant for the purpose of the present invention include but is not limited to cereals, corn, rice, soybean and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and vegetables, ornamentals, any floricultural plants and other plants for use of human and animals.

The term "plant parts" is understood to mean all parts and organs of plants above and below the ground.

For the purpose of the present disclosure the term plant parts includes but is not limited to cuttings, leaves, twigs, tubers, flowers, seeds, branches, roots including taproots, lateral roots, root hairs, root apex, root cap, rhizomes, slips, shoots, fruits, fruit bodies, bark, stem, buds, auxiliary buds, meristems, nodes and internodes.

The term "locus thereof" includes soil, surroundings of plant or plant parts and equipment or tools used before, during or after sowing/planting a plant or a plant part.

Application of the compounds of the present disclosure or the compound of the present disclosure in a composition optionally comprising other compatible compounds to a plant or a plant material or locus thereof include application by a technique known to a person skilled in the art which include but is not limited to spraying, coating, dipping, fumigating, impregnating, injecting and dusting.

The term "applied" means adhered to a plant or plant part either physically or chemically including impregnation.

In view of the above, the present invention provides a compound of general formula (I), Formula (I)

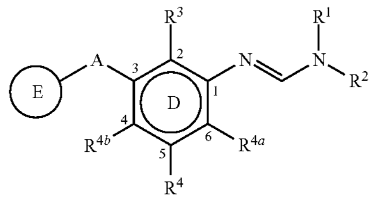

wherein, $R^1$ is selected from the group consisting of hydrogen, cyano, $C_1$-$C_{12}$-alkyl, $C_2$-$C_{12}$-alkenyl, $C_2$-$C_{12}$-alkynyl, $C_1$-$C_{12}$-haloalkyl, $C_1$-$C_{12}$-alkoxy, $C_3$-$C_8$-cycloalkyl and $C_4$-$C_8$-cycloalkylalkyl; wherein one or more carbon atoms in cycloalkyl ring may be replaced by heteroatoms selected from the group consisting of N, O, $S(O)_m$ and optionally including 1 to 3 ring members selected from the group consisting of C(═O) or C(═S);

$R^2$ is selected from the group consisting of $C_1$-$C_{12}$-alkyl, $C_2$-$C_{12}$-alkenyl, $C_2$-$C_{12}$-alkynyl, $C_1$-$C_{12}$-haloalkyl, (C═O)—R" and $C_3$-$C_8$-cycloalkyl; wherein one or more carbon atoms in cycloalkyl ring may be replaced by heteroatoms selected from the group consisting of N, O, $S(O)_m$ and optionally including 1 to 3 ring members selected from the group consisting of C(=O) or C(=S); or $R^1$ and $R^2$ together with the atoms to which they are attached or together with further atoms selected from the group consisting of C, N, O, $S(O)_m$ and optionally including 1 to 3 ring members selected from the group consisting of C(=O) or C(=S) may form a three to seven membered non aromatic ring, which for its part may be substituted by one or more groups selected from the group consisting of X, CN, R', OR', SR', $N(R')_2$, COOR' and $CON(R')_2$;

each group of $R^1$ and $R^2$ may optionally be substituted with one or more groups selected from the group consisting of X, CN, R', OR', SR', $N(R')_2$, COOR' and $CON(R')_2$;

$R^3$ is selected from the group consisting of X, cyano, $C_1$-$C_{12}$-alkyl, $C_2$-$C_{12}$-alkenyl, $C_2$-$C_{12}$-alkynyl, $C_1$-$C_{12}$-haloalkyl, N(R'R'''), OR'', $S(O)_nR'''$, (C=O)—R'' and $C_3$-$C_8$-cycloalkyl; wherein one or more carbon atoms in cycloalkyl ring may be replaced by heteroatoms selected from the group consisting of N, O, $S(O)_m$ and optionally including 1 to 3 ring members selected from the group consisting of C(=O) or C(=S);

$R^4$ is selected from the group consisting of X, cyano, $C_1$-$C_{12}$-alkyl, $C_2$-$C_{12}$-alkenyl, $C_2$-$C_{12}$-alkynyl, $C_1$-$C_{12}$-haloalkyl, N(R'R'''), OR'', $S(O)_nR'''$, (C=O)—R'', $C_3$-$C_8$-cycloalkyl and $C_7$-$C_{12}$-aralkyl; wherein one or more carbon atoms in cyclic ring may be replaced by heteroatoms selected from the group consisting of N, O, $S(O)_m$ and optionally including 1 to 3 ring members selected from the group consisting of C(=O) or C(=S);

$R^{4a}$ and $R^{4b}$ are independently selected from the group consisting of hydrogen, X, cyano, $C_1$-$C_4$-alkyl, $C_2$-$C_4$-alkenyl, $C_2$-$C_4$-alkynyl, $C_1$-$C_4$-haloalkyl, OR'', S(O)R', and $C_3$-$C_5$-cycloalkyl;

each group of $R^3$ and $R^4$ may optionally be substituted by one or more groups selected from the group consisting of X, CN, R', OR', SR', $N(R')_2$, COOR' and $CON(R')_2$;

A represent $—\{[C(R^6R^7)]_{0-2}—(B)_{0-1}\}—$, $—\{[B—C(R^6R^7)]_{0-1}—C(=Y)\}—$; wherein B represent O, S, $NR^5$ or $CR^6R^7$; and Y represents O or S;

$R^5$ is selected from the group consisting of hydrogen, $C_1$-$C_8$-alkyl, $C_2$-$C_8$-alkenyl, $C_2$-$C_8$-alkynyl, $C_1$-$C_8$-haloalkyl, $S(O)_nR'''$, OR'', NR'R'', (C=O)—R'' and $C_3$-$C_8$-cycloalkyl; wherein one or more carbon atoms in cycloalkyl ring may be replaced by heteroatoms selected from the group consisting of N, O, $S(O)_m$ and optionally including 1 to 3 ring members selected from the group consisting of C(=O), C(=S);

$R^6$ and $R^7$ are independently selected from the group consisting of hydrogen, X, cyano, $C_1$-$C_8$-alkyl, $C_2$-$C_8$-alkenyl, $C_2$-$C_8$-alkynyl, $C_1$-$C_8$-haloalkyl, $N(R'')_2$, OR'', (C=O)—R'' and $C_3$-$C_8$-cycloalkyl; wherein one or more carbon atoms in cycloalkyl ring may be replaced by heteroatoms selected from the group consisting of N, O, $S(O)_m$ and optionally including 1 to 3 ring members selected from the group consisting of C(=O) or C(=S); or $R^6$ and $R^7$ together with the atom to which they are attached or together with further atoms selected from the group consisting of C, N, O, $S(O)_m$ and optionally including 1 to 3 ring members selected from the group consisting of C(=O) or C(=S) may form a three to six membered ring, which for its part may be substituted by one or more groups selected from the group consisting of X, CN, R', OR', SR', $N(R')_2$, COOR' and $CON(R')_2$;

each group of $R^5$, $R^6$ and $R^7$ may optionally be substituted by one or more groups selected from the group consisting of X, CN, R', OR', SR', $N(R')_2$, COOR' and $CON(R')_2$;

ring E is selected from the group consisting of fused or non-fused $C_3$-$C_{18}$-carbocyclyl and $C_3$-$C_{18}$-heterocyclyl, which may optionally be substituted by one or more groups of $R^8$;

$R^8$ is selected from the group consisting of hydrogen, X, cyano, nitro, $C_1$-$C_{12}$-alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, $C_3$-$C_8$-cycloalkyl, $C_4$-$C_8$-cycloalkenyl, $C_4$-$C_8$-cycloalkynyl, $C_7$-$C_{19}$-aralkyl, $C_5$-$C_{12}$-bicycloalkyl, $C_6$-$C_{10}$-aryl, $C_3$-$C_6$-heterocyclyl, SCN, $SF_5$, N(R'R''), OR'', $S(O)_nR'''$, (C=O)—R''', $C_1$-$C_8$-alkyl-S(O)R'', $C_1$-$C_8$-alkyl-(C=O)—R'', CR'=NR'', $—S(R^9)=N(R^{10})$, $—S(R^9)(O)=N(R^{10})$, $S(R^9)_2=N—$, $S(R^9)_2(O)=N—$ and $S(R^9)_2(O)=N—C(R^{6a}R^{7a})—$; wherein one or more carbon atoms in cyclic ring may be replaced by heteroatoms selected from the group consisting of N, O, $S(O)_m$ and optionally including 1 to 3 ring members selected from the group consisting of C(=O) or C(=S);

$R^{6a}$ and $R^{7a}$ are independently selected from the group consisting of hydrogen, X, cyano, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $(NR'')_2$, OR'', S(O)R''', (C=O)—R'' and $C_3$-$C_8$-cycloalkyl; or $R^{6a}$ and $R^{7a}$ together with the atom to which they are attached or together with further atoms selected from the group consisting of C, N, O, $S(O)_m$ and optionally including 1 to 3 ring members selected from the group consisting of C(=O) or C(=S), may form a three to six membered ring, which for its part may be substituted by one or more group selected from the group consisting of X, CN, R', OR', SR', $N(R')_2$, COOR' and $CON(R')_2$; or $R^{6a}$ and $R^{7a}$ together with the atom to which they are attached may form a group of =O or =S;

$R^9$ is independently selected from the group consisting of $C_1$-$C_8$-alkyl and $C_3$-$C_8$-cycloalkyl;

$R^{10}$ is selected from the group consisting of hydrogen, cyano, $C_1$-$C_8$-alkyl, $C_2$-$C_8$-alkenyl, $C_2$-$C_8$-alkynyl, (C=O)—R'', S(O)R''' and $C_3$-$C_8$-cycloalkyl; or $R^9$ and $R^{10}$ together with the atom to which they are attached or together with further atoms selected from the group consisting of C, N, O, $S(O)_m$ and optionally including 1 to 3 ring members selected from the group consisting of C(=O) or C(=S) may form a three to seven membered ring, which for its part may be substituted by one or more groups selected from the group consisting of X, CN, R', OR', SR', $N(R')_2$, COOR' and $CON(R')_2$; or $R^8$ and $R^9$ or $R^{10}$ together with the atom to which they are attached or together with further atoms selected from the group consisting of C, N, O, $S(O)_m$ and optionally including 1 to 3 ring members selected from the group consisting of C(=O) or C(=S) may form a three to seven membered ring, which for its part may be substituted by one or more groups selected from the group consisting of X, CN, R', OR', SR', $N(R')_2$, COOR' and $CON(R')_2$;

$R^5$ or $R^6$ or $R^7$ and $R^8$ or two $R^8$ together with the atom to which they are attached or together with further atoms selected from the group consisting of C, N, O, $S(O)_m$ and optionally including 1 to 3 ring members selected from the group consisting of C(═O) or C(═S), may form a three to ten membered ring, which for its part may be substituted by one or more groups selected from the group consisting of X, CN, R', OR', SR', $N(R')_2$, COOR' and $CON(R')_2$;

each group of $R^8$, $R^9$ or $R^{10}$ may optionally be substituted with one or more groups selected from the group consisting of X, CN, R', OR', SR', N(R'R"), COOR' and CON(R'R");

X represents halogen;

R' is selected from the group consisting of hydrogen, $C_1$-$C_8$-alkyl and $C_3$-$C_8$-cycloalkyl; wherein alkyl and cycloalkyl group may be optionally substituted by one or more X;

R" is selected from the group consisting of hydrogen, $C_1$-$C_8$-alkyl, $C_1$-$C_8$-haloalkyl, $C_3$-$C_8$-cycloalkyl, $N(R')_2$, OR' and $C_6$-$C_{18}$-aryl; wherein one or more carbon atoms in cyclic ring may be replaced by heteroatoms selected from the group consisting of N, O, $S(O)_m$ and optionally including 1 to 3 ring members selected from the group consisting of C(═O) or C(═S);

R'" is selected from the groups consisting of cyano, R", $C_2$-$C_8$-alkenyl, $C_2$-$C_8$-alkynyl, $C_3$-$C_8$-cycloalkyl, $C_4$-$C_8$-cycloalkenyl, $C_4$-$C_8$-cycloalkynyl, OR', (C═O)—R', COOR', $CON(R')_2$, $C_6$-$C_{18}$-aryl and $C_7$-$C_{19}$-aralkyl; wherein one or more carbon atoms in cyclic ring may be replaced by heteroatoms selected from the group consisting of N, O, $S(O)_m$ and optionally including 1 to 3 ring members selected from the group consisting of C(═O) or C(═S);

each group of R" and R'" may be substituted by one or more groups selected from the group consisting of X, CN, R', OR', SR', $N(R')_2$, COOR' and $CON(R')_2$;

n represents integer 0, 1 or 2;

m represents an integer 0, 1 or 2;

or agrochemically acceptable salts, isomers/structural isomers, stereo-isomers, diastereoisomers, enantiomers, tautomers, polymorphs, metal complexes or N-oxides thereof;

with the proviso that the following compounds are excluded from the definition of compound of formula (I); N'-(2-cyano-3-((3,3-difluoro-1-methylpiperidin-4-yl)oxy)-5-methoxyphenyl)-N,N-dimethylformimidamide and N'-(5-bromo-2-cyano-3-((2,4-dimethoxybenzyl)oxy)phenyl)-N,N-dimethylformimidamide.

In another embodiment, the present invention provides compound of formula (Ia),

Formula (Ia)

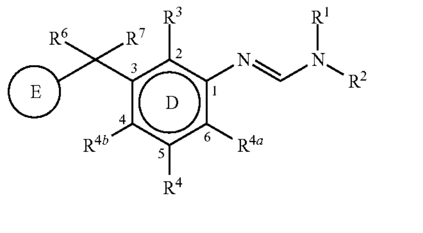

wherein, $R^1$, $R^2$, $R^3$, $R^4$, $R^{4a}$, $R^{4b}$, $R^6$, $R^7$ and E are as defined above.

In yet another embodiment, the present invention provides compound of formula (Ib and Ic), Formula (Ib/Ic)

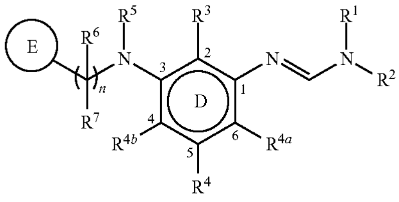

n = 0 (Ib); n = 1 (Ic)

wherein, $R^1$, $R^2$, $R^3$, $R^4$, $R^{4a}$, $R^{4b}$, $R^5$, $R^6$, $R^7$ and E are as defined above.

In yet another embodiment, the present invention provides compound of formula (Id and Ie), Formula (Id/Ie)

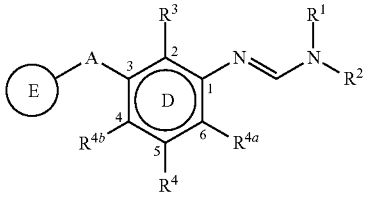

A = O (Id); A = S (Ie)

wherein, $R^1$, $R^2$, $R^3$, $R^4$, $R^{4a}$, $R^{4b}$, A and E are as defined above.

In yet another embodiment, the present invention provides compound of formula (If and Ig), Formula (If/Ig)

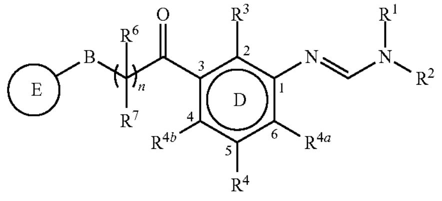

n = 0 (If); n = 1 (Ig)

wherein, $R^1$, $R^2$, $R^3$, $R^4$, $R^{4a}$, $R^{4b}$, $R^6$, $R^7$, B and E are as defined above.

In a preferred embodiment of the present invention, the present invention provides a compound of formula (I) wherein, $R^1$ is selected from the group consisting of $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_3$-$C_5$-cycloalkyl and $C_4$-$C_8$-cycloalkylalkyl;

$R^2$ is selected from the group consisting of $C_1$-$C_6$-alkyl, $C_2$-$C_6$-alkenyl, $C_2$-$C_6$-alkynyl, $C_3$-$C_8$-cycloalkyl and $C_1$-$C_6$-haloalkyl;

$R^3$ and $R^4$ are independently selected from the group consisting of X, cyano, $C_1$-$C_6$-alkyl, $C_2$-$C_6$-alkenyl, $C_2$-$C_6$-alkynyl, $C_1$-$C_6$-haloalkyl, N(R'R'"), OR", $S(O)_n$R'", (C═O)—R" and $C_3$-$C_8$-cycloalkyl;

$R^5$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl and OR';

$R^6$ and $R^7$ are independently selected from the group consisting of hydrogen, X, cyano, $C_1$-$C_4$-alkyl, $C_2$-$C_4$-alkenyl, $C_2$-$C_4$-alkynyl, $C_1$-$C_4$-haloalkyl and $C_3$-$C_4$-cycloalkyl; wherein one or more carbon atoms in cycloalkyl ring may be replaced by heteroatoms selected from the group consisting of N, O, $S(O)_m$ and optionally including 1 to 3 ring members selected from the group consisting of C(=O) or C(=S);

ring E is selected from the group consisting of fused or non-fused $C_3$-$C_{10}$-carbocyclyl and $C_5$-$C_{10}$)-heterocyclyl, which may optionally be substituted by one or more groups of $R^8$;

or agriculturally acceptable salts, isomers/structural isomers, stereo-isomers, diastereomers, enantiomers, tautomers, metal complexes, polymorphs, or N-oxides thereof.

In more preferred embodiment of the present invention, the present invention provides a compound of formula (I) wherein, $R^1$ and $R^2$ are independently selected from the group consisting of $C_1$-$C_6$-alkyl, $C_2$-$C_6$-alkenyl, $C_3$-$C_5$-cycloalkyl and $C_4$-$C_8$-cycloalkylalkyl;

$R^3$ and $R^4$ are independently selected from the group consisting of X, cyano, $C_1$-$C_6$-alkyl, $C_2$-$C_6$-alkenyl, $C_2$-$C_6$-alkynyl, $C_1$-$C_6$-haloalkyl, $C_3$-$C_5$-cycloalkyl and OR";

$R^5$ is selected from the group consisting of hydrogen, $C_1$-$C_6$-alkyl, $C_2$-$C_6$-alkenyl, $C_2$-$C_6$-alkynyl, $C_1$-$C_6$-haloalkyl, $C_3$-$C_5$-cycloalkyl and OR'.

$R^6$ and $R^7$ are independently selected from the group consisting of hydrogen, X, cyano, $C_1$-$C_4$-alkyl, $C_2$-$C_4$-alkenyl, $C_2$-$C_4$-alkynyl, $C_1$-$C_4$-haloalkyl, OR" and $C_3$-$C_5$-cycloalkyl;

ring E is selected from cyclopropyl, cyclobutyl, phenyl, napthalenyl, furyl, thienyl, pyrrolyl, isoxazolyl, thiazolyl, isothiazolyl, thiadiazolyl, pyrazolyl, oxazolyl, imidazolyl, oxadiazolyl, triazolyl, pyridinyl, pyridazinyl, pyrimidinyl, pyrazinyl, triazinyl, indolyl, benzimidazolyl, indazolyl, benzofuranyl, benzothiophenyl, benzothiazolyl, benzoxazolyl, quinolinyl, isoquinolinyl, iquinazolinyl, cinnonyl, indolizinyl, pyrazolo[1,5-a]pyridinyl, imidazo[1,2-a]pyridinyl, pyrrolo[1,2-a]pyrimidinyl, pyrazolo[1,5a]pyrimidinyl, imidazo[1,2-a]pyrimidinyl, pyrrolo[1,2-a]pyrazinyl, pyrazolo[1,5-a]pyrazinyl, imidazo[1,2-a]pyrazinyl; wherein each substituent of E is optionally substituted with one or more $R^8$;

or agriculturally acceptable salts, isomers/structural isomers, stereo-isomers, diastereomers, enantiomers, tautomers, metal complexes, polymorphs, or N-oxides thereof.

In preferred embodiment, the compound of formula (I) is selected from the group consisting of N'-(2-chloro-5-methyl-3-(p-tolylamino)phenyl)-N-ethyl-N-methylformimidamide, N'-(2,5-dimethyl-3-(4-methylbenzyl)phenyl)-N-ethyl-N-methylformimidamide, N'-(3-(3-chlorobenzyl)-2,5-dimethylphenyl)-N-ethyl-N-methylformimidamide, N'-(2,5-dimethyl-3-(2-methylbenzyl)phenyl)-N-ethyl-N-methylformimidamide, N-ethyl-N'-(3-(3-fluorobenzyl)-2,5-dimethylphenyl)-N-methylformimidamide, N-ethyl-N'-(3-((2-fluorophenyl)amino)-2,5-dimethylphenyl)-N-methylformimidamide, N-ethyl-N'-(3-((2-fluorophenyl)(methyl)amino)-2,5-dimethylphenyl)-N-methylformimidamide, N-ethyl-N'-(5-fluoro-2-methyl-3-(phenylamino)phenyl)-N-methylformimidamide, N'-(2-chloro-5-methyl-3-(phenylamino)phenyl)-N-ethyl-N-methylformimidamide, N'-(2-chloro-5-methyl-3-(methyl(phenyl)amino)phenyl)-N-ethyl-N-methylformimidamide, N-ethyl-N'-(5-fluoro-2-methyl-3-(methyl(phenyl)amino)phenyl)-N-methylformimidamide, N'-(2-chloro-5-methyl-3-(2-methylbenzyl)phenyl)-N-ethyl-N-methylformimidamide, N'-(2-chloro-3-(2-chlorobenzyl)-5-methylphenyl)-N-ethyl-N-methylformimidamide, N'-(2-chloro-3-(2-fluorobenzyl)-5-methylphenyl)-N-ethyl-N-methylformimidamide, N-ethyl-N'-(5-fluoro-2-methyl-3-(o-tolylamino)phenyl)-N-methylformimidamide, N-ethyl-N'-(5-fluoro-2-methyl-3-((4-((trifluoromethyl)thio)phenyl)amino)phenyl)-N-methylformimidamide, N'-(2-chloro-5-methyl-3-(3-methylbenzyl)phenyl)-N-ethyl-N-methylformimidamide, N'-(2-chloro-5-methyl-3-(4-methylbenzyl)phenyl)-N-ethyl-N-methylformimidamide, N-ethyl-N'-(5-fluoro-3-((2-fluorophenyl)amino)-2-methylphenyl)-N-methylformimidamide, N'-(3-((4-(tert-butyl)phenyl)amino)-5-fluoro-2-methylphenyl)-N-ethyl-N-methylformimidamide, N'-(2-chloro-5-methyl-3-(2-(trifluoromethyl)benzyl)phenyl)-N-ethyl-N-methylformimidamide, N'-(2-chloro-3-(3-fluorobenzyl)-5-methylphenyl)-N-ethyl-N-methylformimidamide, N'-(2-chloro-3-((2-fluorophenyl)amino)-5-methylphenyl)-N-ethyl-N-methylformimidamide, N'-(2-chloro-5-methyl-3-(o-tolylamino)phenyl)-N-ethyl-N-methylformimidamide, N'-(3-((4-(tert-butyl)phenyl)amino)-2-chloro-5-methylphenyl)-N-ethyl-N-methylformimidamide, N'-(2-chloro-5-methyl-3-((4-((trifluoromethyl)thio)phenyl)amino)phenyl)-N-ethyl-N-methylformimidamide, N'-(2-chloro-3-(3-chlorobenzyl)-5-methylphenyl)-N-ethyl-N-methylformimidamide, N'-(2-chloro-3-(3-methoxybenzyl)-5-methylphenyl)-N-ethyl-N-methylformimidamide, N-ethyl-N'-(5-fluoro-3-((3-fluorophenyl)amino)-2-methylphenyl)-N-methylformimidamide, N-ethyl-N'-(5-fluoro-3-((3-methoxyphenyl)amino)-2-methylphenyl)-N-methylformimidamide, N-ethyl-N'-(5-fluoro-2-methyl-3-(m-tolylamino)phenyl)-N-methylformimidamide, N-ethyl-N'-(5-fluoro-3-((3-fluorophenyl)(methyl)amino)-2-methylphenyl)-N-methylformimidamide, N'-(3-((3-chlorophenyl)(methyl)amino)-5-fluoro-2-methylphenyl)-N-ethyl-N-methylformimidamide, N'-(2-chloro-3-((3-chlorophenyl)amino)-5-methylphenyl)-N-ethyl-N-methylformimidamide, N'-(2-chloro-3-((3-fluorophenyl)amino)-5-methylphenyl)-N-ethyl-N-methylformimidamide, N'-(2-chloro-5-methyl-3-(m-tolylamino)phenyl)-N-ethyl-N-methylformimidamide, N'-(3-((3-chlorophenyl)amino)-5-fluoro-2-methylphenyl)-N-ethyl-N-methylformimidamide, N-ethyl-N'-(5-fluoro-2-methyl-3-(methyl(m-tolyl)amino)phenyl)-N-methylformimidamide, N-ethyl-N'-(5-fluoro-3-((3-methoxyphenyl)(methyl)amino)-2-methylphenyl)-N-methylformimidamide, N'-(2-chloro-3-((3-fluorophenyl)(methyl)amino)-5-methylphenyl)-N-ethyl-N-methylformimidamide, N'-(2-chloro-3-((3-chlorophenyl)(methyl)amino)-5-methylphenyl)-N-ethyl-N-methylformimidamide, N'-(2-chloro-3-((3-methoxyphenyl)amino)-5-methylphenyl)-N-ethyl-N-methylformimidamide, N'-(2-chloro-5-methyl-3-(methyl(m-tolyl)amino)phenyl)-N-ethyl-N-methylformimidamide, N'-(2-chloro-3-(4-fluorobenzyl)-5-methylphenyl)-N-ethyl-N-methylformimidamide, N'-(3-(2-bromobenzyl)-2-chloro-5-methylphenyl)-N-ethyl-N-methylformimidamide, N'-(2-chloro-3-(4-cyanobenzyl)-5-methylphenyl)-N-ethyl-N-methylformimidamide, N'-(2-chloro-3-(2-cyanobenzyl)-5-methylphenyl)-N-ethyl-N-methylformimidamide, N'-(2-chloro-3-(3-cyanobenzyl)-5-methylphenyl)-N-ethyl-N-methylformimidamide, N'-(2-chloro-3-((3-methoxyphenyl)(methyl)amino)-5-methylphenyl)-N-ethyl-N-methylformimidamide, N'-(2-chloro-5-methyl-3-(2-

(trifluoromethoxy)benzyl)phenyl)-N-ethyl-N-methylformimidamide, N'-(2-chloro-5-methyl-3-(4-(trifluoromethyl)benzyl)phenyl)-N-ethyl-N-methylformimidamide, N'-(2-chloro-5-methyl-3-(4-(trifluoromethoxy)benzyl)phenyl)-N-ethyl-N-methylformimidamide, N'-(2-chloro-5-methyl-3-(3-(trifluoromethyl)benzyl)phenyl)-N-ethyl-N-methylformimidamide, N'-(2-chloro-3-(3-chloro-4-fluorobenzyl)-5-methylphenyl)-N-ethyl-N-methylformimidamide, N'-(2-chloro-3-(3,5-dimethylbenzyl)-5-methylphenyl)-N-ethyl-N-methylformimidamide, N'-(2-chloro-3-(3-chloro-2-fluorobenzyl)-5-methylphenyl)-N-ethyl-N-methylformimidamide, N'-(2-chloro-3-(5-fluoro-2-methylbenzyl)-5-methylphenyl)-N-ethyl-N-methylformimidamide, N'-(2-chloro-3-((3-isopropylphenyl)amino)-5-methylphenyl)-N-ethyl-N-methylformimidamide, N'-(2-chloro-3-((4-chlorophenyl)amino)-5-methylphenyl)-N-ethyl-N-methylformimidamide, N'-(2-chloro-3-((4-fluorophenyl)amino)-5-methylphenyl)-N-ethyl-N-methylformimidamide, N'-(2-chloro-3-((4-methoxyphenyl)amino)-5-methylphenyl)-N-ethyl-N-methylformimidamide, N'-(2-chloro-3-((4-chlorophenyl)(methyl)amino)-5-methylphenyl)-N-ethyl-N-methylformimidamide, N'-(2-chloro-3-((3-isopropylphenyl)(methyl)amino)-5-methylphenyl)-N-ethyl-N-methylformimidamide, N'-(2-chloro-3-((4-methoxyphenyl)(methyl)amino)-5-methylphenyl)-N-ethyl-N-methylformimidamide, N'-(2-chloro-3-(4-fluoro-2-methylbenzyl)-5-methylphenyl)-N-ethyl-N-methylformimidamide, N'-(2-chloro-5-methyl-3-(pyridin-3-ylmethyl)phenyl)-N-ethyl-N-methylformimidamide, N'-(2-chloro-3-(3,4-difluorobenzyl)-5-methylphenyl)-N-ethyl-N-methylformimidamide, N'-(2-chloro-3-(4-fluoro-3-methylbenzyl)-5-methylphenyl)-N-ethyl-N-methylformimidamide, N'-(2-chloro-3-((4-fluorophenyl)(methyl)amino)-5-methylphenyl)-N-ethyl-N-methylformimidamide, N'-(3-benzyl-2-chloro-5-methylphenyl)-N-ethyl-N-methylformimidamide, N'-(2-chloro-3-(3,5-difluoro-4-methoxybenzyl)-5-methylphenyl)-N-ethyl-N-methylformimidamide, N'-(2-chloro-3-((3,4-difluorophenyl)amino)-5-methylphenyl)-N-ethyl-N-methylformimidamide, N'-(3-((3,4-difluorophenyl)amino)-5-fluoro-2-methylphenyl)-N-ethyl-N-methylformimidamide, N'-(2-chloro-3-((3,5-difluorophenyl)(methyl)amino)-5-methylphenyl)-N-ethyl-N-methylformimidamide, N'-(2-chloro-3-((2,4-difluorophenyl)amino)-5-methylphenyl)-N-ethyl-N-methylformimidamide, N'-(3-((2,4-difluorophenyl)amino)-5-fluoro-2-methylphenyl)-N-ethyl-N-methylformimidamide, N'-(3-((3,5-difluorophenyl)amino)-5-fluoro-2-methylphenyl)-N-ethyl-N-methylformimidamide, N'-(2-chloro-3-((3,5-difluorophenyl)amino)-5-methylphenyl)-N-ethyl-N-methylformimidamide, N'-(3-benzyl-5-chloro-2-methylphenyl)-N-ethyl-N-methylformimidamide, N'-(3-((2,4-difluorophenyl)(methyl)amino)-5-fluoro-2-methylphenyl)-N-ethyl-N-methylformimidamide, N'-(2-chloro-3-((3,4-difluorophenyl)(methyl)amino)-5-methylphenyl)-N-ethyl-N-methylformimidamide, N'-(2-chloro-3-((2,4-difluorophenyl)(methyl)amino)-5-methylphenyl)-N-ethyl-N-methylformimidamide, N'-(3-((3,4-difluorophenyl)(methyl)amino)-5-fluoro-2-methylphenyl)-N-ethyl-N-methylformimidamide, N'-(3-((3,5-difluorophenyl)(methyl)amino)-5-fluoro-2-methylphenyl)-N-ethyl-N-methylformimidamide, N'-(2-chloro-5-methyl-3-(pyridin-2-ylamino)phenyl)-N-ethyl-N-methylformimidamide, N'-(2-chloro-5-methyl-3-((3-methylpyridin-2-yl)amino)phenyl)-N-ethyl-N-methylformimidamide, N'-(5-chloro-3-(4-fluoro-3,5-dimethylbenzyl)-2-methylphenyl)-N-ethyl-N-methylformimidamide, N'-(5-chloro-2-methyl-3-(2-methylbenzyl)phenyl)-N-ethyl-N-methylformimidamide, N'-(5-chloro-3-(2-chlorobenzyl)-2-methylphenyl)-N-ethyl-N-methylformimidamide, N'-(3-(2-bromobenzyl)-5-chloro-2-methylphenyl)-N-ethyl-N-methylformimidamide, N'-(2-chloro-3-(2,6-difluorobenzyl)-5-methylphenyl)-N-ethyl-N-methylformimidamide, N'-(2-chloro-3-(2-chloro-6-fluorobenzyl)-5-methylphenyl)-N-ethyl-N-methylformimidamide, N'-(3-(4-bromobenzyl)-2-chloro-5-methylphenyl)-N-ethyl-N-methylformimidamide, N'-(5-chloro-2-methyl-3-(3-methylbenzyl)phenyl)-N-ethyl-N-methylformimidamide, N-ethyl-N'-(5-fluoro-2-methyl-3-(pyridin-2-ylamino)phenyl)-N-methylformimidamide, N'-(3-((3-chloro-5-fluorophenyl)amino)-5-fluoro-2-methylphenyl)-N-ethyl-N-methylformimidamide, N'-(2-chloro-3-((3-chloro-5-fluorophenyl)amino)-5-methylphenyl)-N-ethyl-N-methylformimidamide, N'-(3-((5-chloro-2-methylphenyl)(methyl)amino)-5-fluoro-2-methylphenyl)-N-ethyl-N-methylformimidamide, N'-(2-chloro-3-((3-chloro-5-fluorophenyl)(methyl)amino)-5-methylphenyl)-N-ethyl-N-methylformimidamide, N'-(2-chloro-3-((5-chloro-2-methylphenyl)amino)-5-methylphenyl)-N-ethyl-N-methylformimidamide, N'-(5-chloro-3-(3-chlorobenzyl)-2-methylphenyl)-N-ethyl-N-methylformimidamide, N'-(5-chloro-3-(3-fluorobenzyl)-2-methylphenyl)-N-ethyl-N-methylformimidamide, N'-(5-chloro-3-(2-fluorobenzyl)-2-methylphenyl)-N-ethyl-N-methylformimidamide, N'-(5-chloro-3-(2-cyanobenzyl)-2-methylphenyl)-N-ethyl-N-methylformimidamide, N'-(5-chloro-2-methyl-3-(4-methylbenzyl)phenyl)-N-ethyl-N-methylformimidamide, N'-(3-((3-chloro-5-fluorophenyl)(methyl)amino)-5-fluoro-2-methylphenyl)-N-ethyl-N-methylformimidamide, N'-(2-chloro-5-methyl-3-(methyl(pyridin-2-yl)amino)phenyl)-N-ethyl-N-methylformimidamide, N'-(2-chloro-5-methyl-3-(methyl(3-methylpyridin-2-yl)amino)phenyl)-N-ethyl-N-methylformimidamide, N-ethyl-N'-(5-fluoro-2-methyl-3-(methyl(pyridin-2-yl)amino)phenyl)-N-methylformimidamide, N'-(2-chloro-3-((5-chloro-2-methylphenyl)(methyl)amino)-5-methylphenyl)-N-ethyl-N-methylformimidamide, N'-(2-chloro-3-((3-fluoro-5-methylphenyl)amino)-5-methylphenyl)-N-ethyl-N-methylformimidamide, N'-(2-chloro-3-((5-chloro-3-methylpyridin-2-yl)amino)-5-methylphenyl)-N-ethyl-N-methylformimidamide, N'-(3-((2-chloro-5-methylphenyl)amino)-5-fluoro-2-methylphenyl)-N-ethyl-N-methylformimidamide, N-ethyl-N'-(5-fluoro-3-((3-fluoro-5-methylphenyl)amino)-2-methylphenyl)-N-methylformimidamide, N'-(2-chloro-3-((2-chloro-5-methylphenyl)amino)-5-methylphenyl)-N-ethyl-N-methylformimidamide, N'-(3-((5-chloro-2-methylphenyl)amino)-5-fluoro-2-methylphenyl)-N-ethyl-N-methylformimidamide, N'-(3-((2-chloro-5-methylphenyl)(methyl)amino)-5-fluoro-2-methylphenyl)-N-ethyl-N-methylformimidamide, N'-(2-chloro-3-((5-chloro-3-methylpyridin-2-yl)(methyl)amino)-5-methylphenyl)-N-ethyl-N-methylformimidamide, N-ethyl-N'-(5-fluoro-3-((3-fluoro-5-methylphenyl)(methyl)amino)-2-methylphenyl)-N-methylformimidamide, N'-(2-chloro-3-((2-chloro-5-methylphenyl)(methyl)amino)-5-methylphenyl)-N-ethyl-N-methylformimidamide, N-ethyl-N'-(5-fluoro-3-((2-fluoro-6-methylphenyl)amino)-2-methylphenyl)-N-methylformimidamide, N-ethyl-N'-(5-fluoro-3-((2-fluoro-3-methylphenyl)amino)-2-methylphenyl)-N-methylformimidamide, N'-(2-chloro-3-((2-fluoro-3-methylphenyl)amino)-5-methylphenyl)-N-ethyl-N-methylformimidamide, N'-(5-chloro-3-(4-fluorobenzyl)-2-methylphenyl)-N-ethyl-N-methylformimidamide, N'-(3-(4-bromobenzyl)-5-chloro-2-methylphenyl)-N-ethyl-N-methylformimidamide, N'-(5-chloro-3-(4-chlorobenzyl)-2-methylphenyl)-N-ethyl-N-methylformimidamide, N'-(5-chloro-2-methyl-3-(3-(trifluoromethyl)benzyl)phenyl)-N-ethyl-N-methylformimidamide, N'-(5-chloro-3-(4-fluoro-3-methylbenzyl)-2-methylphenyl)-N-ethyl-N-methylformimidamide, N'-(5-chloro-3-(3,4-difluorobenzyl)-2-methylphenyl)-N-ethyl-N-methylformimidamide, N'-(5-chloro-3-(3-chloro-4-fluorobenzyl)-2-methylphenyl)-N-ethyl-N-methylformimidamide, N'-(5-chloro-3-(4-chloro-3-fluorobenzyl)-2-methylphenyl)-N-ethyl-N-methylformimidamide, N-ethyl-N'-(5-fluoro-2-methyl-3-((3-(trifluoromethyl)pyridin-2-yl)amino)phenyl)-N-methylformimidamide, N'-(2-chloro-3-((2-fluoro-6-methylphenyl)amino)-5-methylphenyl)-N-ethyl-N-methylformimidamide, N'-(2-chloro-3-((4-chloro-2-fluorophenyl)amino)-5-methylphenyl)-N-ethyl-N-methylformimidamide, N'-(2-chloro-5-methyl-3-((3-(trifluoromethyl)pyridin-2-yl)amino)phenyl)-N-ethyl-N-methylformimidamide, N'-(3-((4-chloro-2-fluorophenyl)amino)-5-fluoro-2-methylphenyl)-N-ethyl-N-methylformimidamide, N'-(2-chloro-3-((3-chloro-5-(trifluoromethyl)phenyl)amino)-5-methylphenyl)-N-ethyl-N-methylformimidamide, N'-(2-chloro-3-((2-fluoro-6-methylphenyl)(methyl)amino)-5-methylphenyl)-N-ethyl-N-methylformimidamide, N'-(2-chloro-3-((2-fluoro-3-methylphenyl)(methyl)amino)-5-methylphenyl)-N-ethyl-N-methylformimidamide, N'-(3-((4-chloro-2-fluorophenyl)(methyl)amino)-5-fluoro-2-methylphenyl)-N-ethyl-N-methylformimidamide, N-ethyl-N'-(5-fluoro-3-(2-fluorobenzyl)-2-methylphenyl)-N-methylformimidamide, N'-(3-(2-chlorobenzyl)-5-fluoro-2-methylphenyl)-N-ethyl-N-methylformimidamide, N-ethyl-N'-(5-fluoro-2-methyl-3-(2-(trifluoromethyl)benzyl)phenyl)-N-methylformimidamide, N'-(3-(3-chlorobenzyl)-5-fluoro-2-methylphenyl)-N-ethyl-N-methylformimidamide, N-ethyl-N'-(5-fluoro-3-((2-fluoro-6-methylphenyl)(methyl)amino)-2-methylphenyl)-N-methylformimidamide, N-ethyl-N'-(5-fluoro-2-methyl-3-(3-methylbenzyl)phenyl)-N-methylformimidamide, N-ethyl-N'-(5-fluoro-3-(3-fluorobenzyl)-2-methylphenyl)-N-methylformimidamide, N-ethyl-N'-(5-fluoro-2-methyl-3-(2-methylbenzyl)phenyl)-N-methylformimidamide, N'-(3-benzyl-5-fluoro-2-methylphenyl)-N-ethyl-N-methylformimidamide, N'-(2-chloro-3-(4-methoxybenzyl)-5-methylphenyl)-N-ethyl-N-methylformimidamide, N'-(3-(2-bromobenzyl)-5-fluoro-2-methylphenyl)-N-ethyl-N-methylformimidamide, N-ethyl-N'-(5-fluoro-3-((2-fluoro-3-methylphenyl)(methyl)amino)-2-methylphenyl)-N-methylformimidamide, N-ethyl-N'-(5-fluoro-2-methyl-3-(methyl(3-(trifluoromethyl)pyridin-2-yl)amino)phenyl)-N-methylformimidamide, N'-(5-chloro-2-methyl-3-(m-tolylamino)phenyl)-N-ethyl-N-methylformimidamide, N'-(5-chloro-2-methyl-3-(phenylamino)phenyl)-N-ethyl-N-methylformimidamide, N'-(2-chloro-3-((4-chloro-2-fluorophenyl)(methyl)amino)-5-methylphenyl)-N-ethyl-N-methylformimidamide, N'-(2-chloro-5-methyl-3-(methyl(3-(trifluoromethyl)pyridin-2-yl)amino)phenyl)-N-ethyl-N-methylformimidamide, N'-(2-chloro-3-((3-chloro-5-(trifluoromethyl)phenyl)(methyl)amino)-5-methylphenyl)-N-ethyl-N-methylformimidamide, N'-(5-chloro-2-methyl-3-(methyl(phenyl)amino)phenyl)-N-ethyl-N-methylformimidamide, N'-(5-chloro-2-methyl-3-(methyl(m-tolyl)amino)phenyl)-N-ethyl-N-methylformimidamide, N'-(3-((3-chloro-5-(trifluoromethyl)phenyl)amino)-5-fluoro-2-methylphenyl)-N-ethyl-N-methylformimidamide, N'-(5-chloro-3-((4-methoxyphenyl)amino)-2-methylphenyl)-N-ethyl-N-methylformimidamide, N'-(5-chloro-3-((3-chlorophenyl)amino)-2-methylphenyl)-N-ethyl-N-methylformimidamide, N'-(3-((3-bromophenyl)amino)-5-chloro-2-methylphenyl)-N-ethyl-N-methylformimidamide, N'-(5-chloro-3-((2-fluorophenyl)amino)-2-methylphenyl)-N-ethyl-N-methylformimidamide, N'-(5-chloro-3-((3-fluorophenyl)amino)-2-methylphenyl)-N-ethyl-N-methylformimidamide, N'-(5-chloro-3-((4-methoxyphenyl)(methyl)amino)-2-methylphenyl)-N-ethyl-N-methylformimidamide, N'-(3-(2-cyanobenzyl)-5-fluoro-2-methylphenyl)-N-ethyl-N-methylformimidamide, N'-(2-chloro-3-((2,3-dihydrobenzo[b][1,4]dioxin-6-yl)amino)-5-methylphenyl)-N-ethyl-N-methylformimidamide, N-ethyl-N'-(5-fluoro-2-methyl-3-(2-(trifluoromethoxy)benzyl)phenyl)-N-methylformimidamide, N-ethyl-N'-(5-fluoro-2-methyl-3-(4-methylbenzyl)phenyl)-N-methylformimidamide, N'-(3-(4-chlorobenzyl)-5-fluoro-2-methylphenyl)-N-ethyl-N-methylformimidamide, N-ethyl-N'-(5-fluoro-2-methyl-3-(3-(trifluoromethoxy)benzyl)phenyl)-N-methylformimidamide, N'-(3-(3-cyanobenzyl)-5-fluoro-2-methylphenyl)-N-ethyl-N-methylformimidamide, N'-(3-(4-bromobenzyl)-5-fluoro-2-methylphenyl)-N-ethyl-N-methylformimidamide, N-ethyl-N'-(5-fluoro-2-methyl-3-(4-(trifluoromethoxy)benzyl)phenyl)-N-methylformimidamide, N'-(2-chloro-3-((2-(difluoromethoxy)phenyl)amino)-5-methylphenyl)-N-ethyl-N-methylformimidamide, N'-(5-chloro-3-((2-fluorophenyl)(methyl)amino)-2-methylphenyl)-N-ethyl-N-methylformimidamide, N'-(5-chloro-3-((3-fluorophenyl)(methyl)amino)-2-methylphenyl)-N-ethyl-N-methylformimidamide, N'-(5-chloro-3-((3-chlorophenyl)(methyl)amino)-2-methylphenyl)-N-ethyl-N-methylformimidamide, N'-(2-chloro-5-methyl-3-((2-(trifluoromethyl)benzyl)amino)phenyl)-N-ethyl-N-methylformimidamide, N-ethyl-N'-(5-fluoro-3-((4-fluoro-3-methylbenzyl)amino)-2-methylphenyl)-N-methylformimidamide, N'-(5-chloro-3-((3-chlorobenzyl)amino)-2-methylphenyl)-N-ethyl-N-methylformimidamide, N'-(2-chloro-3-((2,3-dihydrobenzo[b][1,4]dioxin-6-yl)(methyl)amino)-5-methylphenyl)-N-ethyl-N-methylformimidamide, N'-(5-chloro-2-methyl-3-(o-tolylamino)phenyl)-N-ethyl-N-methylformimidamide, N'-(2-chloro-5-methyl-3-(pyrimidin-2-ylamino)phenyl)-N-ethyl-N-methylformimidamide, N-ethyl-N'-(5-fluoro-2-methyl-3-(pyrimidin-2-ylamino)phenyl)-N-methylformimidamide, N-ethyl-N'-(5-fluoro-2-methyl-3-(4-(trifluoromethyl)benzyl)phenyl)-N-methylformimidamide, N'-(2-bromo-3-(3-fluorobenzyl)-5-methylphenyl)-N-ethyl-N-methylformimidamide, N-ethyl-N'-(3-(3-fluorobenzyl)-5-methyl-2-(methylthio)phenyl)-N-methylformimidamide, N'-(5-chloro-2-methyl-3-(methyl(o-tolyl)amino)phenyl)-N-ethyl-N-methylformimidamide, N'-(2-chloro-5-methyl-3-(methyl(pyrimidin-2-yl)amino)phenyl)-N-ethyl-N-methylformimidamide, N-ethyl-N'-(5-fluoro-2-methyl-3-(pyrazin-2-ylamino)phenyl)-N-methylformimidamide, N'-(2-chloro-5-methyl-3-(pyrazin-2-ylamino)phenyl)-N-ethyl-N-methylformimidamide, N'-(2-chloro-5-methyl-3-((1-(pyrazin-2-yl)propan-2-yl)amino)phenyl)-N-ethyl-N-methylformimidamide, N'-(2-chloro-5-methyl-3-(((5-methylpyrazin-2-yl)methyl)amino)phenyl)-N-ethyl-N-methylformimidamide, N-ethyl-N'-(5-fluoro-2-methyl-3-((1-(pyrazin-2-yl)propan-2-yl)amino)phenyl)-N-methylformimidamide, N-ethyl-N'-(5-fluoro-2-methyl-3-

(((5-methylpyrazin-2-yl)methyl)amino)phenyl)-N-methyl-formimidamide, N-ethyl-N'-(5-fluoro-2-methyl-3-(methyl (pyrazin-2-yl)amino)phenyl)-N-methylformimidamide, N-ethyl-N'-(5-fluoro-2-methyl-3-(methyl(pyrimidin-2-yl) amino)phenyl)-N-methylformimidamide, N-ethyl-N'-(5-fluoro-2-methyl-3-(3-(trifluoromethyl)benzyl)phenyl)-N-methylformimidamide, N'-(3-(4-cyanobenzyl)-5-fluoro-2-methylphenyl)-N-ethyl-N-methylformimidamide, N-ethyl-N'-(5-fluoro-3-(4-fluoro-3-methylbenzyl)-2-methylphenyl)-N-methylformimidamide, N-ethyl-N'-(5-fluoro-3-(4-fluorobenzyl)-2-methylphenyl)-N-methylformimidamide, N'-(3-(3-bromobenzyl)-5-fluoro-2-methylphenyl)-N-ethyl-N-methylformimidamide, N'-(3-(4-chloro-3-fluorobenzyl)-5-fluoro-2-methylphenyl)-N-ethyl-N-methylformimidamide, N'-(3-benzyl-2,5-dimethylphenyl)-N-ethyl-N-methylformimidamide, N'-(2,5-dimethyl-3-(3-methylbenzyl)phenyl)-N-ethyl-N-methylformimidamide, N'-(2-bromo-5-methyl-3-(2-methylbenzyl)phenyl)-N-ethyl-N-methylformimidamide, N'-(2-chloro-5-methyl-3-(methyl (pyrazin-2-yl)amino)phenyl)-N-ethyl-N-methylformimidamide, N'-(5-chloro-2-methyl-3-(pyrazin-2-ylamino) phenyl)-N-ethyl-N-methylformimidamide, N'-(5-chloro-2-methyl-3-(pyrimidin-2-ylamino)phenyl)-N-ethyl-N-methylformimidamide, N'-(5-chloro-2-methyl-3-(methyl (pyrazin-2-yl)amino)phenyl)-N-ethyl-N-methylformimidamide, N'-(5-chloro-2-methyl-3-(methyl (pyrimidin-2-yl)amino)phenyl)-N-ethyl-N-methylformimidamide, N'-(3-(2-bromo-4-fluorobenzyl)-2-chloro-5-methylphenyl)-N-ethyl-N-methylformimidamide, N'-(3-(4-bromo-3-methylbenzyl)-2-chloro-5-methylphenyl)-N-ethyl-N-methylformimidamide, N'-(3-(4-bromo-2-fluorobenzyl)-2-chloro-5-methylphenyl)-N-ethyl-N-methylformimidamide, N'-(2-chloro-3-(4-fluoro-3-(trifluoromethyl)benzyl)-5-methylphenyl)-N-ethyl-N-methylformimidamide, N-ethyl-N'-(3-(2-fluorobenzyl)-2,5-dimethylphenyl)-N-methylformimidamide, N'-(3-(2-chlorobenzyl)-2,5-dimethylphenyl)-N-ethyl-N-methylformimidamide, N'-(3-(2-bromobenzyl)-2,5-dimethylphenyl)-N-ethyl-N-methylformimidamide, N-ethyl-N'-(3-(4-fluorobenzyl)-2,5-dimethylphenyl)-N-methylformimidamide, N'-(3-(4-bromobenzyl)-2,5-dimethylphenyl)-N-ethyl-N-methylformimidamide, N'-(3-(4-chlorobenzyl)-2,5-dimethylphenyl)-N-ethyl-N-methylformimidamide, N'-(3-(benzo[d]thiazol-6-ylamino)-5-fluoro-2-methylphenyl)-N-ethyl-N-methylformimidamide, N'-(2-chloro-3-((6-ethylpyridin-2-yl)amino)-5-methylphenyl)-N-ethyl-N-methylformimidamide, N-ethyl-N'-(3-((6-ethylpyridin-2-yl) amino)-5-fluoro-2-methylphenyl)-N-methylformimidamide, N'-(3-(benzo[d]thiazol-6-ylamino)-2-chloro-5-methylphenyl)-N-ethyl-N-methylformimidamide, N'-(3-(2-chloro-5-fluorobenzyl)-5-fluoro-2-methylphenyl)-N-ethyl-N-methylformimidamide, N'-(3-(2-bromo-4-fluorobenzyl)-5-fluoro-2-methylphenyl)-N-ethyl-N-methylformimidamide, N-ethyl-N'-(5-fluoro-3-(5-fluoro-2-methylbenzyl)-2-methylphenyl)-N-methyl-formimidamide, N'-(3-(4-bromo-3-methylbenzyl)-5-fluoro-2-methylphenyl)-N-ethyl-N-methylformimidamide, N'-(3-(2-bromo-5-fluorobenzyl)-5-fluoro-2-methylphenyl)-N-ethyl-N-methylformimidamide, N-ethyl-N'-(5-fluoro-3-(4-fluoro-3-(trifluoromethyl)benzyl)-2-methylphenyl)-N-methylformimidamide, N-ethyl-N'-(5-fluoro-3-(3-fluoro-5-methylbenzyl)-2-methylphenyl)-N-methylformimidamide, N'-(3-(4-bromo-2-fluorobenzyl)-5-fluoro-2-methylphenyl)-N-ethyl-N-methylformimidamide, N-ethyl-N'-(5-fluoro-3-(3-fluoro-5-methoxybenzyl)-2-methylphenyl)-N-methyl-formimidamide, N'-(3-(benzo[d]thiazol-6-yl(methyl) amino)-5-fluoro-2-methylphenyl)-N-ethyl-N-methylformimidamide, N-ethyl-N'-(3-((6-ethylpyridin-2-yl) (methyl)amino)-5-fluoro-2-methylphenyl)-N-methylformimidamide, N'-(3-(benzo[d]thiazol-6-yl(methyl) amino)-2-chloro-5-methylphenyl)-N-ethyl-N-methylformimidamide, N-ethyl-N'-(5-fluoro-2-methyl-3-(4-(methylthio)benzyl)phenyl)-N-methylformimidamide, N'-(3-(benzo[d]thiazol-6-ylamino)-5-chloro-2-methylphenyl)-N-ethyl-N-methylformimidamide, N'-(5-chloro-3-((6-ethylpyridin-2-yl)amino)-2-methylphenyl)-N-ethyl-N-methylformimidamide, N'-(5-chloro-2-methyl-3-(2-(trifluoromethyl)benzyl)phenyl)-N-ethyl-N-methylformimidamide, N'-(3-(3-bromobenzyl)-5-chloro-2-methylphenyl)-N-ethyl-N-methylformimidamide, N'-(5-chloro-3-(4-cyanobenzyl)-2-methylphenyl)-N-ethyl-N-methylformimidamide, N'-(5-chloro-2-methyl-3-(2-(trifluoromethoxy)benzyl)phenyl)-N-ethyl-N-methylformimidamide, N'-(5-chloro-2-methyl-3-(pyridin-3-ylmethyl)phenyl)-N-ethyl-N-methylformimidamide, N'-(5-chloro-2-methyl-3-(4-(trifluoromethyl)benzyl)phenyl)-N-ethyl-N-methylformimidamide, N'-(5-chloro-3-(3-cyanobenzyl)-2-methylphenyl)-N-ethyl-N-methylformimidamide, N'-(5-chloro-2-methyl-3-(3-(trifluoromethoxy)benzyl)phenyl)-N-ethyl-N-methylformimidamide, N'-(5-chloro-2-methyl-3-(4-(methylthio)benzyl)phenyl)-N-ethyl-N-methylformimidamide, N'-(5-chloro-3-((6-ethylpyridin-2-yl)(methyl)amino)-2-methylphenyl)-N-ethyl-N-methylformimidamide, N-ethyl-N'-(5-fluoro-3-((3-fluoro-4-methoxyphenyl)amino)-2-methylphenyl)-N-methylformimidamide, N'-(2-chloro-3-((3-fluoro-4-methoxyphenyl)amino)-5-methylphenyl)-N-ethyl-N-methylformimidamide, N'-(5-chloro-3-((3-fluoro-4-methoxyphenyl)amino)-2-methylphenyl)-N-ethyl-N-methylformimidamide, N-ethyl-N'-(5-fluoro-3-((3-fluoro-4-methoxyphenyl)(methyl)amino)-2-methylphenyl)-N-methylformimidamide, N'-(2-chloro-3-((3-fluoro-4-methoxyphenyl)(methyl)amino)-5-methylphenyl)-N-ethyl-N-methylformimidamide, N-ethyl-N'-(5-fluoro-2-methyl-3-(3-nitrobenzyl)phenyl)-N-methylformimidamide, N-ethyl-N'-(5-fluoro-2-methyl-3-(pyridin-3-ylmethyl)phenyl)-N-methylformimidamide, N-ethyl-N'-(3-(4-fluorobenzyl)-5-methoxy-2-methylphenyl)-N-methylformimidamide, N-ethyl-N'-(5-methoxy-2-methyl-3-(2-methylbenzyl)phenyl)-N-methylformimidamide, N-ethyl-N'-(5-methoxy-2-methyl-3-(4-methylbenzyl)phenyl)-N-methylformimidamide, N'-(3-(3-chlorobenzyl)-5-methoxy-2-methylphenyl)-N-ethyl-N-methylformimidamide, N'-(3-(2-chlorobenzyl)-5-methoxy-2-methylphenyl)-N-ethyl-N-methylformimidamide, N-ethyl-N'-(3-(2-fluorobenzyl)-5-methoxy-2-methylphenyl)-N-methylformimidamide, N'-(5-chloro-3-((3-fluoro-4-methoxyphenyl)(methyl)amino)-2-methylphenyl)-N-ethyl-N-methylformimidamide, N-ethyl-N'-(5-methoxy-3-((2-methoxyphenyl)amino)-2-methylphenyl)-N-methylformimidamide, N-ethyl-N'-(3-((3-fluoro-4-methoxyphenyl)amino)-5-methoxy-2-methylphenyl)-N-methylformimidamide, N-ethyl-N'-(5-methoxy-3-((2-methoxyphenyl)(methyl)amino)-2-methylphenyl)-N-methylformimidamide, N-ethyl-N'-(3-((3-fluoro-4-methoxyphenyl)(methyl)amino)-5-methoxy-2-methylphenyl)-N-methylformimidamide, N-ethyl-N'-(5-methoxy-2-methyl-3-((6-(trifluoromethyl)pyridin-2-yl) amino)phenyl)-N-methylformimidamide, N-ethyl-N'-(5-fluoro-2-methyl-3-((6-(trifluoromethyl)pyridin-2-yl)amino) phenyl)-N-methylformimidamide, N'-(5-chloro-2-methyl-3-((6-(trifluoromethyl)pyridin-2-yl)amino)phenyl)-N-ethyl-N-methylformimidamide, N'-(2-chloro-3-((4-fluoro-3-methoxyphenyl)amino)-5-methylphenyl)-N-ethyl-N-methylformimidamide, N-ethyl-N'-(3-((4-fluoro-3-methoxyphenyl)amino)-5-methoxy-2-methylphenyl)-N-methylformimidamide, N-ethyl-N'-(3-(3-fluorobenzyl)-5-methoxy-2-methylphenyl)-N-methylformimidamide, N-ethyl-N'-(5-methoxy-2-methyl-3-(3-methylbenzyl)phenyl)-N-methylformimidamide, N'-(3-(4-chlorobenzyl)-5-methoxy-2-methylphenyl)-N-ethyl-N-methylformimidamide, N-ethyl-N'-(5-methoxy-2-methyl-3-(3-nitrobenzyl)phenyl)-N-methylformimidamide, N-ethyl-N'-(3-(5-fluoro-2-methylbenzyl)-5-methoxy-2-methylphenyl)-N-methylformimidamide, N'-(3-(3-chloro-4-fluorobenzyl)-5-methoxy-2-methylphenyl)-N-ethyl-N-methylformimidamide, N'-(2-chloro-5-methyl-3-((6-(trifluoromethyl)pyridin-2-yl)amino)phenyl)-N-ethyl-N-methylformimidamide, N-ethyl-N'-(3-((4-fluoro-3-methoxyphenyl)(methyl)amino)-5-methoxy-2-methylphenyl)-N-methylformimidamide, N-ethyl-N'-(5-methoxy-2-methyl-3-(methyl(6-(trifluoromethyl)pyridin-2-yl)amino)phenyl)-N-methylformimidamide, N'-(3-(3,4-difluorobenzyl)-5-methoxy-2-methylphenyl)-N-ethyl-N-methylformimidamide, N'-(3-(4-bromobenzyl)-5-methoxy-2-methylphenyl)-N-ethyl-N-methylformimidamide, N'-(2-chloro-3-((4-fluoro-3-methoxyphenyl)(methyl)amino)-5-methylphenyl)-N-ethyl-N-methylformimidamide, N'-(5-chloro-2-methyl-3-(methyl(6-(trifluoromethyl)pyridin-2-yl)amino)phenyl)-N-ethyl-N-methylformimidamide, N'-(2-chloro-5-methyl-3-(methyl(6-(trifluoromethyl)pyridin-2-yl)amino)phenyl)-N-ethyl-N-methylformimidamide, N-ethyl-N'-(5-fluoro-2-methyl-3-(methyl(6-(trifluoromethyl)pyridin-2-yl)amino)phenyl)-N-methylformimidamide, N-ethyl-N'-(3-(3-fluoro-5-methylbenzyl)-5-methoxy-2-methylphenyl)-N-methylformimidamide, N'-(3-(2-chloro-5-fluorobenzyl)-5-methoxy-2-methylphenyl)-N-ethyl-N-methylformimidamide, N'-(3-(2-bromobenzyl)-5-methoxy-2-methylphenyl)-N-ethyl-N-methylformimidamide, N-ethyl-N'-(5-methoxy-2-methyl-3-(4-(trifluoromethyl)benzyl)phenyl)-N-methylformimidamide, N-ethyl-N'-(5-methoxy-2-methyl-3-(3-(trifluoromethyl)benzyl)phenyl)-N-methylformimidamide, N'-(5-cyano-3-(3-fluorobenzyl)-2-methylphenyl)-N-ethyl-N-methylformimidamide, N'-(3-benzyl-5-methoxy-2-methylphenyl)-N-ethyl-N-methylformimidamide, N-ethyl-N'-(5-methoxy-2-methyl-3-(2-(trifluoromethoxy)benzyl)phenyl)-N-methylformimidamide, N-ethyl-N'-(5-methoxy-2-methyl-3-((2-(trifluoromethoxy)phenyl)amino)phenyl)-N-methylformimidamide, N'-(5-chloro-2-methyl-3-((2-(trifluoromethoxy)phenyl)amino)phenyl)-N-ethyl-N-methylformimidamide, N'-(2-chloro-5-methyl-3-((2-(trifluoromethoxy)phenyl)amino)phenyl)-N-ethyl-N-methylformimidamide, N-ethyl-N'-(5-fluoro-2-methyl-3-((2-(trifluoromethoxy)phenyl)amino)phenyl)-N-methylformimidamide, N'-(3-(2-(2-chloro-4-methoxyphenoxy)acetyl)-5-fluoro-2-methylphenyl)-N-ethyl-N-methylformimidamide, N-ethyl-N'-(5-methoxy-2-methyl-3-(3-(trifluoromethoxy)benzyl)phenyl)-N-methylformimidamide, N'-(3-(3-cyanobenzyl)-5-methoxy-2-methylphenyl)-N-ethyl-N-methylformimidamide, N-ethyl-N'-(5-methoxy-2-methyl-3-(2-(trifluoromethyl)benzyl)phenyl)-N-methylformimidamide, N'-(3-benzyl-5-cyano-2-methylphenyl)-N-ethyl-N-methylformimidamide, N'-(5-cyano-3-(3-cyanobenzyl)-2-methylphenyl)-N-ethyl-N-methylformimidamide, N'-(5-cyano-3-(4-fluorobenzyl)-2-methylphenyl)-N-ethyl-N-methylformimidamide, N'-(3-(4-chlorobenzyl)-5-cyano-2-methylphenyl)-N-ethyl-N-methylformimidamide, N'-(5-cyano-2-methyl-3-(3-nitrobenzyl)phenyl)-N-ethyl-N-methylformimidamide, N'-(3-(3-bromobenzyl)-5-cyano-2-methylphenyl)-N-ethyl-N-methylformimidamide and N'-(5-cyano-2-methyl-3-(2-(trifluoromethoxy)benzyl)phenyl)-N-ethyl-N-methylformimidamide.

Any of the compounds according to the invention can exist in one or more optical, geometric or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereomers and/or the optical isomers can be separated according to the methods which are known per se by a person ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by a person ordinary skilled in the art.

Any of the compounds according to the invention, can also exist in one or more amorphic or isomorphic or polymorphic forms, depending on their preparation, purification storage and various other influencing factors. The invention thus relates all the possible amorphic, isomorphic and polymorphic forms, in all proportions. The amorphic, isomorphic and polymorphic forms can be prepared and/or separated and/or purified according to general methods, which are known per se by a person ordinary skilled in the art.

In one embodiment, the present invention provides a compound of formula (A);

Formula (A)

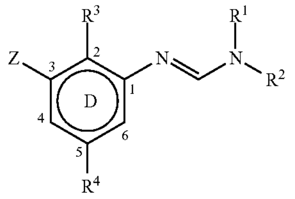

wherein,

Z represent OH, $NH_2$, SH, X, or leaving group;

$R^1$ is selected from the group consisting of $C_1$-$C_{12}$-alkyl, $C_2$-$C_{12}$-alkenyl, $C_2$-$C_{12}$-alkynyl, $C_1$-$C_{12}$-haloalkyl, and $C_3$-$C_8$-cycloalkyl;

$R^2$ is selected from the group consisting of cyano, $C_2$-$C_{12}$-alkyl, $C_2$-$C_{12}$-alkenyl, $C_2$-$C_{12}$-alkynyl, $C_1$-$C_{12}$-haloalkyl, (C═O)—R", $C_3$-$C_8$-cycloalkyl and $C_3$-$C_8$-cycloalkyl-$C_1$-$C_3$-alkyl;

$R^3$ is selected from the group consisting of X, cyano, $C_1$-$C_{12}$-alkyl, $C_2$-$C_{12}$-alkenyl, $C_2$-$C_{12}$-alkynyl, $C_1$-$C_{12}$-haloalkyl, N(R'R'"), OR", $S(O)_nR'''$, (C═O)—R" and $C_3$-$C_8$-cycloalkyl; wherein one or more carbon atoms in cycloalkyl ring may be replaced by heteroatoms selected from the group consisting of N, O, $S(O)_m$ and optionally including 1 to 3 ring members selected from the group consisting of C(═O) and C(═S);

$R^4$ is selected from the group consisting of X, cyano, $C_1$-$C_{12}$-alkyl, $C_2$-$C_{12}$-alkenyl, $C_2$-$C_{12}$-alkynyl, $C_1$-$C_{12}$-haloalkyl, N(R'R"), OR", $S(O)R''^1$, (C═O)—R", $C_3$-$C_8$-cycloalkyl and $C_7$-$C_{12}$-aralkyl; wherein one or more carbon atoms in cyclic ring may be replaced by heteroatoms selected from the group consisting of N, O, $S(O)_m$ and optionally including 1 to 3 ring members selected from the group consisting of C(=O) and C(=S).

In one embodiment, the present invention provides a compound of formula (B);

Formula (B)

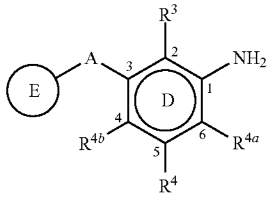

wherein, $R^3$, $R^4$, $R^{4a}$, $R^{4b}$, A and E are as defined above.

In preferred embodiment, the compound of formula (B) is selected from 2-chloro-5-methyl-$N^1$-(p-tolyl)benzene-1,3-diamine, 2,5-dimethyl-3-(4-methylbenzyl)aniline, 3-(3-chlorobenzyl)-2,5-dimethylaniline, 2,5-dimethyl-3-(2-methylbenzyl)aniline, 3-(3-fluorobenzyl)-2,5-dimethylaniline, $N^1$-(2-fluorophenyl)-2,5-dimethylbenzene-1,3-diamine, $N^1$-(2-fluorophenyl)-$N^1$,2,5-trimethylbenzene-1,3-diamine, 5-fluoro-2-methyl-$N^1$-phenylbenzene-1,3-diamine, 2-chloro-5-methyl-$N^1$-phenylbenzene-1,3-diamine, 2-chloro-$N^1$,5-dimethyl-$N^1$-phenylbenzene-1,3-diamine, 5-fluoro-$N^1$,2-dimethyl-$N^1$-phenylbenzene-1,3-diamine, 2-chloro-5-methyl-3-(2-methylbenzyl)aniline, 2-chloro-3-(2-chlorobenzyl)-5-methyl aniline, 2-chloro-3-(2-fluorobenzyl)-5-methyl aniline, 5-fluoro-2-methyl-$N^1$-(o-tolyl)benzene-1,3-diamine, 5-fluoro-2-methyl-$N^1$-(4-((trifluoromethyl)thio)phenyl)benzene-1,3-diamine, 2-chloro-5-methyl-3-(3-methylbenzyl)aniline, 2-chloro-5-methyl-3-(4-methylbenzyl)aniline, 5-fluoro-N'-(2-fluorophenyl)-2-methylbenzene-1,3-diamine, $N^1$-(4-(tert-butyl)phenyl)-5-fluoro-2-methylbenzene-1,3-diamine, 2-chloro-5-methyl-3-(2-(trifluoromethyl)benzyl)aniline, 2-chloro-3-(3-fluorobenzyl)-5-methylaniline, 2-chloro-$N^1$-(2-fluorophenyl)-5-methylbenzene-1,3-diamine, 2-chloro-5-methyl-$N^1$-(o-tolyl)benzene-1,3-diamine, $N^1$-(4-(tert-butyl)phenyl)-2-chloro-5-methylbenzene-1,3-diamine, 2-chloro-5-methyl-$N^1$-(4-((trifluoromethyl)thio)phenyl)benzene-1,3-diamine, 2-chloro-3-(3-chlorobenzyl)-5-methylaniline, 2-chloro-3-(3-methoxybenzyl)-5-methyl aniline, 5-fluoro-$N^1$-(3-fluorophenyl)-2-methylbenzene-1,3-diamine, 5-fluoro-$N^1$-(3-methoxyphenyl)-2-methylbenzene-1,3-diamine, 5-fluoro-2-methyl-$N^1$-(m-tolyl)benzene-1,3-diamine, 5-fluoro-$N^1$-(3-fluorophenyl)-$N^1$,2-dimethylbenzene-1,3-diamine, $N^1$-(3-chlorophenyl)-5-fluoro-$N^1$,2-dimethylbenzene-1,3-diamine, 2-chloro-$N^1$-(3-chlorophenyl)-5-methylbenzene-1,3-diamine, 2-chloro-$N^1$-(3-fluorophenyl)-5-methylbenzene-1,3-diamine, 2-chloro-5-methyl-$N^1$-(m-tolyl)benzene-1,3-diamine, $N^1$-(3-chlorophenyl)-5-fluoro-2-methylbenzene-1,3-diamine, 5-fluoro-$N^1$,2-dimethyl-$N^1$-(m-tolyl)benzene-1,3-diamine, 5-fluoro-$N^1$-(3-methoxyphenyl)-$N^1$,2-dimethylbenzene-1,3-diamine, 2-chloro-$N^1$-(3-fluorophenyl)-$N^1$,5-dimethylbenzene-1,3-diamine, 2-chloro-$N^1$-(3-chlorophenyl)-$N^1$,5-dimethylbenzene-1,3-diamine, 2-chloro-$N^1$-(3-methoxyphenyl)-5-methylbenzene-1,3-diamine, 2-chloro-$N^1$,5-dimethyl-$N^1$-(m-tolyl)benzene-1,3-diamine, 2-chloro-3-(4-fluorobenzyl)-5-methyl aniline, 3-(2-bromobenzyl)-2-chloro-5-methylaniline, 4-(3-amino-2-chloro-5-methylbenzyl)benzonitrile, 2-(3-amino-2-chloro-5-methylbenzyl)benzonitrile, 3-(3-amino-2-chloro-5-methylbenzyl)benzonitrile, 2-chloro-$N^1$-(3-methoxyphenyl)-$N^1$,5-dimethylbenzene-1,3-diamine, 2-chloro-5-methyl-3-(2-(trifluoromethoxy)benzyl)aniline, 2-chloro-5-methyl-3-(4-(trifluoromethyl)benzyl)aniline, 2-chloro-5-methyl-3-(4-(trifluoromethoxy)benzyl)aniline, 2-chloro-5-methyl-3-(3-(trifluoromethyl)benzyl)aniline, 2-chloro-3-(3-chloro-4-fluorobenzyl)-5-methyl aniline, 2-chloro-3-(3,5-dimethylbenzyl)-5-methyl aniline, 2-chloro-3-(3-chloro-2-fluorobenzyl)-5-methyl aniline, 2-chloro-3-(5-fluoro-2-methylbenzyl)-5-methylaniline, 2-chloro-$N^1$-(3-isopropylphenyl)-5-methylbenzene-1,3-diamine, 2-chloro-$N^1$-(4-chlorophenyl)-5-methylbenzene-1,3-diamine, 2-chloro-$N^1$-(4-fluorophenyl)-5-methylbenzene-1,3-diamine, 2-chloro-$N^1$-(4-methoxyphenyl)-5-methylbenzene-1,3-diamine, 2-chloro-$N^1$-(4-chlorophenyl)-$N^1$,5-dimethylbenzene-1,3-diamine, 2-chloro-$N^1$-(3-isopropylphenyl)-$N^1$,5-dimethylbenzene-1,3-diamine, 2-chloro-$N^1$-(4-methoxyphenyl)-$N^1$,5-dimethylbenzene-1,3-diamine, 2-chloro-3-(4-fluoro-2-methylbenzyl)-5-methylaniline, 2-chloro-5-methyl-3-(pyridin-3-ylmethyl)aniline, 2-chloro-3-(3,4-difluorobenzyl)-5-methyl aniline, 2-chloro-3-(4-fluoro-3-methylbenzyl)-5-methyl aniline, 2-chloro-$N^1$-(4-fluorophenyl)-$N^1$,5-dimethylbenzene-1,3-diamine, 3-benzyl-2-chloro-5-methyl aniline, 2-chloro-3-(3,5-difluoro-4-methoxybenzyl)-5-methyl aniline, 2-chloro-$N^1$-(3,4-difluorophenyl)-5-methylbenzene-1,3-diamine, $N^1$-(3,4-difluorophenyl)-5-fluoro-2-methylbenzene-1,3-diamine, 2-chloro-$N^1$-(3,5-difluorophenyl)-$N^1$,5-dimethylbenzene-1,3-diamine, 2-chloro-$N^1$-(2,4-difluorophenyl)-5-methylbenzene-1,3-diamine, $N^1$-(2,4-difluorophenyl)-5-fluoro-2-methylbenzene-1,3-diamine, $N^1$-(3,5-difluorophenyl)-5-fluoro-2-methylbenzene-1,3-diamine, 2-chloro-$N^1$-(3,5-difluorophenyl)-5-methylbenzene-1,3-diamine, 3-benzyl-5-chloro-2-methylaniline, $N^1$-(2,4-difluorophenyl)-5-fluoro-$N^1$,2-dimethylbenzene-1,3-diamine, 2-chloro-N'-(3,4-difluorophenyl)-$N^1$,5-dimethylbenzene-1,3-diamine, 2-chloro-$N^1$-(2,4-difluorophenyl)-$N^1$,5-dimethylbenzene-1,3-diamine, $N^1$-(3,4-difluorophenyl)-5-fluoro-$N^1$,2-dimethylbenzene-1,3-diamine, $N^1$-(3,5-difluorophenyl)-5-fluoro-$N^1$,2-dimethylbenzene-1,3-diamine, 2-chloro-5-methyl-$N^1$-(pyridin-2-yl)benzene-1,3-diamine, 2-chloro-5-methyl-$N^1$-(3-methylpyridin-2-yl)benzene-1,3-diamine, 5-chloro-3-(4-fluoro-3,5-dimethylbenzyl)-2-methylaniline, 5-chloro-2-methyl-3-(2-methylbenzyl)aniline, 5-chloro-3-(2-chlorobenzyl)-2-methylaniline, 3-(2-bromobenzyl)-5-chloro-2-methylaniline, 2-chloro-3-(2,6-difluorobenzyl)-5-methyl aniline, 2-chloro-3-(2-chloro-6-fluorobenzyl)-5-methylaniline, 3-(4-bromobenzyl)-2-chloro-5-methylaniline, 5-chloro-2-methyl-3-(3-methylbenzyl)aniline, 5-fluoro-2-methyl-$N^1$-(pyridin-2-yl)benzene-1,3-diamine, N'-(3-chloro-5-fluorophenyl)-5-fluoro-2-methylbenzene-1,3-diamine, 2-chloro-$N^1$-(3-chloro-5-fluorophenyl)-5-methylbenzene-1,3-diamine, $N^1$-(5-chloro-2-methylphenyl)-5-fluoro-$N^1$,2-dimethylbenzene-1,3-diamine, 2-chloro-$N^1$-(3-chloro-5-fluorophenyl)-$N^1$,5-dimethylbenzene-1,3-diamine, 2-chloro-$N^1$-(5-chloro-2-methylphenyl)-5-methylbenzene-1,3-diamine, 5-chloro-3-(3-chlorobenzyl)-2-methylaniline, 5-chloro-3-(3-fluorobenzyl)-2-methylaniline, 5-chloro-3-(2-fluorobenzyl)-2-methylaniline, 2-(3-amino-5-chloro-2-methylbenzyl)benzonitrile, 5-chloro-2-methyl-3-(4-methylbenzyl)aniline, $N^1$-(3-chloro-5-fluorophenyl)-5-fluoro-$N^1$,2-dimethylbenzene-1,3-diamine, 2-chloro-$N^1$,5-dimethyl-$N^1$-(pyridin-2-yl)benzene-1,3-diamine, 2-chloro-$N^1$,5-dimethyl-$N^1$-(3-methylpyridin-2-yl)benzene-1,3-diamine, 5-fluoro-$N^1$,2-dimethyl-$N^1$-(pyridin-2-yl)benzene-1,3-diamine, 2-chloro- $N^1$-(5-chloro-2-methylphenyl)-$N^1$,5-dimethylbenzene-1,3-diamine, 2-chloro-$N^1$-(3-fluoro-5-methylphenyl)-5-methylbenzene-1,3-diamine, 2-chloro-$N^1$-(5-chloro-3-methylpyridin-2-yl)-5-methylbenzene-1,3-diamine, $N^1$-(2-chloro-5-methylphenyl)-5-fluoro-2-methylbenzene-1,3-diamine, 5-fluoro-$N^1$-(3-fluoro-5-methylphenyl)-2-methylbenzene-1,3-diamine, 2-chloro-$N^1$-(2-chloro-5-methylphenyl)-5-methylbenzene-1,3-diamine, $N^1$-(5-chloro-2-methylphenyl)-5-fluoro-2-methylbenzene-1,3-diamine, $N^1$-(2-chloro-5-methylphenyl)-5-fluoro-$N^1$,2-dimethylbenzene-1,3-diamine, 2-chloro-$N^1$-(5-chloro-3-methylpyridin-2-yl)-$N^1$,5-dimethylbenzene-1,3-diamine, 5-fluoro-$N^1$-(3-fluoro-5-methylphenyl)-$N^1$,2-dimethylbenzene-1,3-diamine, 2-chloro-$N^1$-(2-chloro-5-methylphenyl)-$N^1$,5-dimethylbenzene-1,3-diamine, 5-fluoro-$N^1$-(2-fluoro-6-methylphenyl)-2-methylbenzene-1,3-diamine, 5-fluoro-$N^1$-(2-fluoro-3-methylphenyl)-2-methylbenzene-1,3-diamine, 2-chloro-$N^1$-(2-fluoro-3-methylphenyl)-5-methylbenzene-1,3-diamine, 5-chloro-3-(4-fluorobenzyl)-2-methylaniline, 3-(4-bromobenzyl)-5-chloro-2-methylaniline, 5-chloro-3-(4-chlorobenzyl)-2-methylaniline, 5-chloro-2-methyl-3-(3-(trifluoromethyl)benzyl)aniline, 5-chloro-3-(4-fluoro-3-methylbenzyl)-2-methylaniline, 5-chloro-3-(3,4-difluorobenzyl)-2-methylaniline, 5-chloro-3-(3-chloro-4-fluorobenzyl)-2-methylaniline, 5-chloro-3-(4-chloro-3-fluorobenzyl)-2-methylaniline, 5-fluoro-2-methyl-$N^1$-(3-(trifluoromethyl)pyridin-2-yl)benzene-1,3-diamine, 2-chloro-$N^1$-(2-fluoro-6-methylphenyl)-5-methylbenzene-1,3-diamine, 2-chloro-$N^1$-(4-chloro-2-fluorophenyl)-5-methylbenzene-1,3-diamine, 2-chloro-5-methyl-$N^1$-(3-(trifluoromethyl)pyridin-2-yl)benzene-1,3-diamine, $N^1$-(4-chloro-2-fluorophenyl)-5-fluoro-2-methylbenzene-1,3-diamine, 2-chloro-$N^1$-(3-chloro-5-(trifluoromethyl)phenyl)-5-methylbenzene-1,3-diamine, 2-chloro-$N^1$-(2-fluoro-6-methylphenyl)-$N^1$,5-dimethylbenzene-1,3-diamine, 2-chloro-$N^1$-(2-fluoro-3-methylphenyl)-$N^1$,5-dimethylbenzene-1,3-diamine, $N^1$-(4-chloro-2-fluorophenyl)-5-fluoro-$N^1$,2-dimethylbenzene-1,3-diamine, 5-fluoro-3-(2-fluorobenzyl)-2-methyl aniline, 3-(2-chlorobenzyl)-5-fluoro-2-methyl aniline, 5-fluoro-2-methyl-3-(2-(trifluoromethyl)benzyl)aniline, 3-(3-chlorobenzyl)-5-fluoro-2-methyl aniline, 5-fluoro-$N^1$-(2-fluoro-6-methylphenyl)-$N^1$,2-dimethylbenzene-1,3-diamine, 5-fluoro-2-methyl-3-(3-methylbenzyl)aniline, 5-fluoro-3-(3-fluorobenzyl)-2-methyl aniline, 5-fluoro-2-methyl-3-(2-methylbenzyl)aniline, 3-benzyl-5-fluoro-2-methylaniline, 2-chloro-3-(4-methoxybenzyl)-5-methylaniline, 3-(2-bromobenzyl)-5-fluoro-2-methyl aniline, 5-fluoro-$N^1$-(2-fluoro-3-methylphenyl)-$N^1$,2-dimethylbenzene-1,3-diamine, 5-fluoro-$N^1$,2-dimethyl-$N^1$-(3-(trifluoromethyl)pyridin-2-yl)benzene-1,3-diamine, 5-chloro-2-methyl-$N^1$-(m-tolyl)benzene-1,3-diamine, 5-chloro-2-methyl-$N^1$-phenylbenzene-1,3-diamine, 2-chloro-$N^1$-(4-chloro-2-fluorophenyl)-$N^1$,5-dimethylbenzene-1,3-diamine, 2-chloro-$N^1$,5-dimethyl-$N^1$-(3-(trifluoromethyl)pyridin-2-yl)benzene-1,3-diamine, 2-chloro-$N^1$-(3-chloro-5-(trifluoromethyl)phenyl)-$N^1$,5-dimethylbenzene-1,3-diamine, 5-chloro-$N^1$,2-dimethyl-$N^1$-phenylbenzene-1,3-diamine, 5-chloro-$N^1$,2-dimethyl-$N^1$-(m-tolyl)benzene-1,3-diamine, $N^1$-(3-chloro-5-(trifluoromethyl)phenyl)-5-fluoro-2-methylbenzene-1,3-diamine, 5-chloro-$N^1$-(4-methoxyphenyl)-2-methylbenzene-1,3-diamine, 5-chloro-$N^1$-(3-chlorophenyl)-2-methylbenzene-1,3-diamine, $N^1$-(3-bromophenyl)-5-chloro-2-methylbenzene-1,3-diamine, 5-chloro-$N^1$-(2-fluorophenyl)-2-methylbenzene-1,3-diamine, 5-chloro-$N^1$-(3-fluorophenyl)-2-methylbenzene-1,3-diamine, 5-chloro-$N^1$-(4-methoxyphenyl)-$N^1$,2-dimethylbenzene-1,3-diamine, 2-(3-amino-5-fluoro-2-methylbenzyl)benzonitrile, 2-chloro-$N^1$-(2,3-dihydrobenzo[b][1,4]dioxin-6-yl)-5-methylbenzene-1,3-diamine, 5-fluoro-2-methyl-3-(2-(trifluoromethoxy)benzyl)aniline, 5-fluoro-2-methyl-3-(4-methylbenzyl)aniline, 3-(4-chlorobenzyl)-5-fluoro-2-methyl aniline, 5-fluoro-2-methyl-3-(3-(trifluoromethoxy)benzyl)aniline, 3-(3-amino-5-fluoro-2-methylbenzyl)benzonitrile, 3-(4-bromobenzyl)-5-fluoro-2-methylaniline, 5-fluoro-2-methyl-3-(4-(trifluoromethoxy)benzyl)aniline, 2-chloro-$N^1$-(2-(difluoromethoxy)phenyl)-5-methylbenzene-1,3-diamine, 5-chloro-N'-(2-fluorophenyl)-N',2-dimethylbenzene-1,3-diamine, 5-chloro-$N^1$-(3-fluorophenyl)-$N^1$,2-dimethylbenzene-1,3-diamine, 5-chloro-$N^1$-(3-chlorophenyl)-$N^1$,2-dimethylbenzene-1,3-diamine, 2-chloro-5-methyl-N'-(2-(trifluoromethyl)benzyl)benzene-1,3-diamine, 5-fluoro-$N^1$-(4-fluoro-3-methylbenzyl)-2-methylbenzene-1,3-diamine, 5-chloro-$N^1$-(3-chlorobenzyl)-2-methylbenzene-1,3-diamine, 2-chloro-$N^1$-(2,3-dihydrobenzo[b][1,4]dioxin-6-yl)-$N^1$,5-dimethylbenzene-1,3-diamine, 5-chloro-2-methyl-$N^1$-(o-tolyl)benzene-1,3-diamine, 2-chloro-5-methyl-$N^1$-(pyrimidin-2-yl)benzene-1,3-diamine, 5-fluoro-2-methyl-$N^1$-(pyrimidin-2-yl)benzene-1,3-diamine, 5-fluoro-2-methyl-3-(4-(trifluoromethyl)benzyl)aniline, 2-bromo-3-(3-fluorobenzyl)-5-methylaniline, 3-(3-fluorobenzyl)-5-methyl-2-(methylthio)aniline, 5-chloro-$N^1$,2-dimethyl-$N^1$-(o-tolyl)benzene-1,3-diamine, 2-chloro-$N^1$,5-dimethyl-$N^1$-(pyrimidin-2-yl)benzene-1,3-diamine, 5-fluoro-2-methyl-$N^1$-(pyrazin-2-yl)benzene-1,3-diamine, 2-chloro-5-methyl-$N^1$-(pyrazin-2-yl)benzene-1,3-diamine, 2-chloro-5-methyl-$N^1$-(1-(pyrazin-2-yl)propan-2-yl)benzene-1,3-diamine, 2-chloro-5-methyl-$N^1$-((5-methylpyrazin-2-yl)methyl)benzene-1,3-diamine, 5-fluoro-2-methyl-$N^1$-(1-(pyrazin-2-yl)propan-2-yl)benzene-1,3-diamine, 5-fluoro-2-methyl-$N^1$-((5-methylpyrazin-2-yl)methyl)benzene-1,3-diamine, 5-fluoro-$N^1$,2-dimethyl-$N^1$-(pyrazin-2-yl)benzene-1,3-diamine, 5-fluoro-$N^1$,2-dimethyl-$N^1$-(pyrimidin-2-yl)benzene-1,3-diamine, 5-fluoro-2-methyl-3-(3-(trifluoromethyl)benzyl)aniline, 4-(3-amino-5-fluoro-2-methylbenzyl)benzonitrile, 5-fluoro-3-(4-fluoro-3-methylbenzyl)-2-methylaniline, 5-fluoro-3-(4-fluorobenzyl)-2-methylaniline, 3-(3-bromobenzyl)-5-fluoro-2-methylaniline, 3-(4-chloro-3-fluorobenzyl)-5-fluoro-2-methyl aniline, 3-benzyl-2,5-dimethyl aniline, 2,5-dimethyl-3-(3-methylbenzyl)aniline, 2-bromo-5-methyl-3-(2-methylbenzyl)aniline, 2-chloro-$N^1$,5-dimethyl-$N^1$-(pyrazin-2-yl)benzene-1,3-diamine, 5-chloro-2-methyl-$N^1$-(pyrazin-2-yl)benzene-1,3-diamine, 5-chloro-2-methyl-$N^1$-(pyrimidin-2-yl)benzene-1,3-diamine, 5-chloro-$N^1$,2-dimethyl-$N^1$-(pyrazin-2-yl)benzene-1,3-diamine, 5-chloro-$N^1$,2-dimethyl-$N^1$-(pyrimidin-2-yl)benzene-1,3-diamine, 3-(2-bromo-4-fluorobenzyl)-2-chloro-5-methylaniline, 3-(4-bromo-3-methylbenzyl)-2-chloro-5-methylaniline, 3-(4-bromo-2-fluorobenzyl)-2-chloro-5-methylaniline, 2-chloro-3-(4-fluoro-3-(trifluoromethyl)benzyl)-5-methylaniline, 3-(2-fluorobenzyl)-2,5-dimethylaniline, 3-(2-chlorobenzyl)-2,5-dimethyl aniline, 3-(2-bromobenzyl)-2,5-dimethyl aniline, 3-(4-fluorobenzyl)-2,5-dimethyl aniline, 3-(4-bromobenzyl)-2,5-dimethylaniline, 3-(4-chlorobenzyl)-2,5-dimethylaniline, N'-(benzo[d]thiazol-6-yl)-5-fluoro-2-methylbenzene-1,3-diamine, 2-chloro-$N^1$-(6-ethylpyridin-2-yl)-5-methylbenzene-1,3-diamine, $N^1$-(6-ethylpyridin-2-yl)-5-fluoro-2-methylbenzene-1,3-diamine, $N^1$-(benzo[d]thiazol-6-yl)-2-chloro-5-methylbenzene-1,3-diamine, 3-(2-chloro-5-fluorobenzyl)-5-fluoro-2-methylaniline, 3-(2-bromo-4-fluorobenzyl)-5-fluoro-2-methylaniline, 5-fluoro-3-(5-fluoro-2-methylbenzyl)-2-methylaniline, 3-(4-bromo-3-methylbenzyl)-5-fluoro-2-methylaniline, 3-(2-bromo-5-fluorobenzyl)-5-fluoro-2-methylaniline, 5-fluoro-3-(4-fluoro-3-(trifluoromethyl)benzyl)-2-methylaniline, 5-fluoro-3-(3-fluoro-5-methylbenzyl)-2-methylaniline, 3-(4-bromo-2-fluorobenzyl)-5-fluoro-2-methyl aniline, 5-fluoro-3-(3-fluoro-5-methoxybenzyl)-2-methylaniline, $N^1$-(benzo[d]thiazol-6-yl)-5-fluoro-$N^1$,2-dimethylbenzene-1,3-diamine, $N^1$-(6-ethylpyridin-2-yl)-5-fluoro-$N^1$,2-dimethylbenzene-1,3-diamine, $N^1$-(benzo[d]thiazol-6-yl)-2-chloro-$N^1$,5-dimethylbenzene-1,3-diamine, 5-fluoro-2-methyl-3-(4-(methylthio)benzyl)aniline, $N^1$-(benzo[d]thiazol-6-yl)-5-chloro-2-methylbenzene-1,3-diamine, 5-chloro-$N^1$-(6-ethylpyridin-2-yl)-2-methylbenzene-1,3-diamine, 5-chloro-2-methyl-3-(2-(trifluoromethyl)benzyl)aniline, 3-(3-bromobenzyl)-5-chloro-2-methylaniline, 4-(3-amino-5-chloro-2-methylbenzyl)benzonitrile, 5-chloro-2-methyl-3-(2-(trifluoromethoxy)benzyl)aniline, 5-chloro-2-methyl-3-(pyridin-3-ylmethyl)aniline, 5-chloro-2-methyl-3-(4-(trifluoromethyl)benzyl)aniline, 3-(3-amino-5-chloro-2-methylbenzyl)benzonitrile, 5-chloro-2-methyl-3-(3-(trifluoromethoxy)benzyl)aniline, 5-chloro-2-methyl-3-(4-(methylthio)benzyl)aniline, 5-chloro-$N^1$-(6-ethylpyridin-2-yl)-$N^1$,2-dimethylbenzene-1,3-diamine, 5-fluoro-$N^1$-(3-fluoro-4-methoxyphenyl)-2-methylbenzene-1,3-diamine, 2-chloro-$N^1$-(3-fluoro-4-methoxyphenyl)-5-methylbenzene-1,3-diamine, 5-chloro-$N^1$-(3-fluoro-4-methoxyphenyl)-2-methylbenzene-1,3-diamine, 5-fluoro-$N^1$-(3-fluoro-4-methoxyphenyl)-$N^1$,2-dimethylbenzene-1,3-diamine, 2-chloro-$N^1$-(3-fluoro-4-methoxyphenyl)-$N^1$,5-dimethylbenzene-1,3-diamine, 5-fluoro-2-methyl-3-(3-nitrobenzyl)aniline, 5-fluoro-2-methyl-3-(pyridin-3-ylmethyl)aniline, 3-(4-fluorobenzyl)-5-methoxy-2-methyl aniline, 5-methoxy-2-methyl-3-(2-methylbenzyl)aniline, 5-methoxy-2-methyl-3-(4-methylbenzyl)aniline, 3-(3-chlorobenzyl)-5-methoxy-2-methyl aniline, 3-(2-chlorobenzyl)-5-methoxy-2-methyl aniline, 3-(2-fluorobenzyl)-5-methoxy-2-methyl aniline, 5-chloro-$N^1$-(3-fluoro-4-methoxyphenyl)-$N^1$,2-dimethylbenzene-1,3-diamine, 5-methoxy-$N^1$-(2-methoxyphenyl)-2-methylbenzene-1,3-diamine, $N^1$-(3-fluoro-4-methoxyphenyl)-5-methoxy-2-methylbenzene-1,3-diamine, 5-methoxy-$N^1$-(2-methoxyphenyl)-$N^1$,2-dimethylbenzene-1,3-diamine, $N^1$-(3-fluoro-4-methoxyphenyl)-5-methoxy-$N^1$,2-dimethylbenzene-1,3-diamine, 5-methoxy-2-methyl-N'-(6-(trifluoromethyl)pyridin-2-yl)benzene-1,3-diamine, 5-fluoro-2-methyl-$N^1$-(6-(trifluoromethyl)pyridin-2-yl)benzene-1,3-diamine, 5-chloro-2-methyl-$N^1$-(6-(trifluoromethyl)pyridin-2-yl)benzene-1,3-diamine, 2-chloro-$N^1$-(4-fluoro-3-methoxyphenyl)-5-methylbenzene-1,3-diamine, $N^1$-(4-fluoro-3-methoxyphenyl)-5-methoxy-2-methylbenzene-1,3-diamine, 3-(3-fluorobenzyl)-5-methoxy-2-methylaniline, 5-methoxy-2-methyl-3-(3-methylbenzyl)aniline, 3-(4-chlorobenzyl)-5-methoxy-2-methyl aniline, 5-methoxy-2-methyl-3-(3-nitrobenzyl)aniline, 3-(5-fluoro-2-methylbenzyl)-5-methoxy-2-methyl aniline, 3-(3-chloro-4-fluorobenzyl)-5-methoxy-2-methyl aniline, 2-chloro-5-methyl-N'-(6-(trifluoromethyl)pyridin-2-yl)benzene-1,3-diamine, $N^1$-(4-fluoro-3-methoxyphenyl)-5-methoxy-$N^1$,2-dimethylbenzene-1,3-diamine, 5-methoxy-$N^1$,2-dimethyl-$N^1$-(6-(trifluoromethyl)pyridin-2-yl)benzene-1,3-diamine, 3-(3,4-difluorobenzyl)-5-methoxy-2-methylaniline, 3-(4-bromobenzyl)-5-methoxy-2-methylaniline, 2-chloro-$N^1$-(4-fluoro-3-methoxyphenyl)-$N^1$,5-dimethylbenzene-1,3-diamine, 5-chloro-$N^1$,2-dimethyl-$N^1$-(6-(trifluoromethyl)pyridin-2-yl)benzene-1,3-diamine, 2-chloro-$N^1$,5-dimethyl-$N^1$-(6-(trifluoromethyl)pyridin-2-yl)benzene-1,3-diamine, 5-fluoro-$N^1$,2-dimethyl-$N^1$-(6-(trifluoromethyl)pyridin-2-yl)benzene-1,3-diamine, 3-(3-fluoro-5-methylbenzyl)-5-methoxy-2-methylaniline, 3-(2-chloro-5-fluorobenzyl)-5-methoxy-2-methylaniline, 3-(2-bromobenzyl)-5-methoxy-2-methylaniline, 5-methoxy-2-methyl-3-(4-(trifluoromethyl)benzyl)aniline, 5-methoxy-2-methyl-3-(3-(trifluoromethyl)benzyl)aniline, 3-amino-5-(3-fluorobenzyl)-4-methylbenzonitrile, 3-benzyl-5-methoxy-2-methylaniline, 5-methoxy-2-methyl-3-(2-(trifluoromethoxy)benzyl)aniline, 5-methoxy-2-methyl-$N^1$-(2-(trifluoromethoxy)phenyl)benzene-1,3-diamine, 5-chloro-2-methyl-$N^1$-(2-(trifluoromethoxy)phenyl)benzene-1,3-diamine, 2-chloro-5-methyl-$N^1$-(2-(trifluoromethoxy)phenyl)benzene-1,3-diamine, 5-fluoro-2-methyl-N'-(2-(trifluoromethoxy)phenyl)benzene-1,3-diamine, 1-(3-amino-5-fluoro-2-methylphenyl)-2-(2-chloro-4-methoxyphenoxy)ethan-1-one, 5-methoxy-2-methyl-3-(3-(trifluoromethoxy)benzyl)aniline, 3-(3-amino-5-methoxy-2-methylbenzyl)benzonitrile, 5-methoxy-2-methyl-3-(2-(trifluoromethyl)benzyl)aniline, 3-amino-5-benzyl-4-methylbenzonitrile, 3-amino-5-(3-cyanobenzyl)-4-methylbenzonitrile, 3-amino-5-(4-fluorobenzyl)-4-methylbenzonitrile, 3-amino-5-(4-chlorobenzyl)-4-methylbenzonitrile, 3-amino-4-methyl-5-(3-nitrobenzyl)benzonitrile, 3-amino-5-(3-bromobenzyl)-4-methylbenzonitrile and 3-amino-4-methyl-5-(2-(trifluoromethoxy)benzyl)benzonitrile.

There are a large number of suitable known standard methods, such as alkylation, halogenation, acylation, amidation, oximation, oxidation and reduction. The choice of the preparation methods which are suitable are depending on the properties (reactivity) of the substituents in the intermediates. These reactions can be conveniently performed in a solvent. These reactions can be conveniently performed at various temperatures. These reactions can be conveniently performed in an inert atmosphere. The reactants can be reacted in the presence of a base.

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents. The reaction is advantageously carried out in a temperature range from approximately −80° C. to approximately +140° C., preferably from approximately −30° C. to approximately +100° C., in many cases in the range between ambient temperature and approximately +80° C.

A compound of formula (I) can be converted in a manner known per se into another compound of formula (I) by replacing one or more substituents of the starting compound of formula (I) in the customary manner by (an)other substituent(s) according to the invention. Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step. Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent. A salt is chosen depending on its tolerances for compound's use, such as agricultural or physiological tolerance. Salts of compounds of formula (I) can be converted in the customary manner into the free compounds (I), acid addition salts, for example, by treatment with a suitable basic compound or with a suitable ion exchanger reagent and salts with bases, for example, by treatment with a suitable acid or with a suitable ion exchanger reagent. Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

In one embodiment, the present invention provides a process for the preparation compounds of formula (I).

In another embodiment, the present invention provides a process for preparing the 3-substituted phenylamidine compound of formula (I), wherein the process comprises at least one of the following steps (a) to (h):

a) converting a compound of formula (XXVI) or (XXIV) to a compound of formula (XXIII) according to the reaction scheme as depicted below:

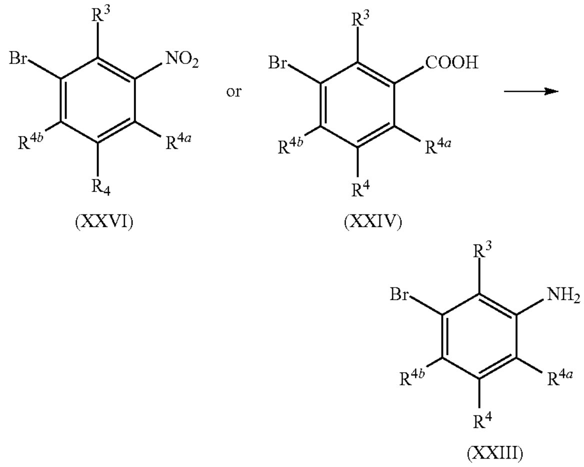

(XXVI) or (XXIV) (XXIII)

b) reacting a compound of formula (XXIII) with a suitable secondary amine ($HNR^1R^2$) to obtain a compound of formula (III) according to the reaction scheme as depicted below:

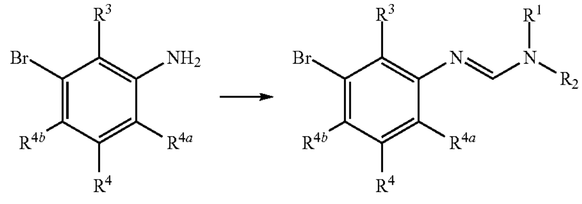

(XXIII) (III)

c) reacting a compound of formula (III) with compound of formula (XII), (XVI), (XVII) or (XXXI) to obtain the compound of formula (I) according to the reaction scheme as depicted below:

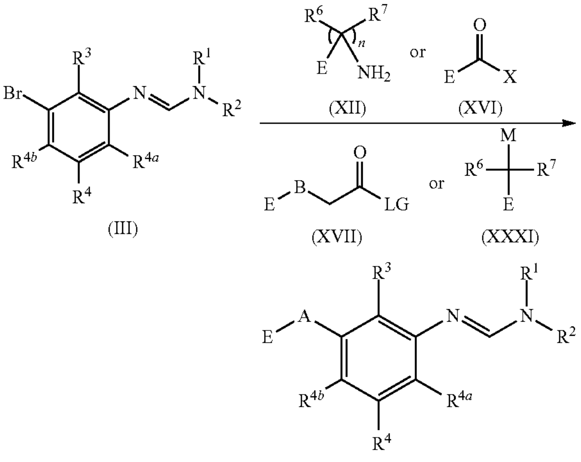

(III) (XII) or (XVI) (XVII) or (XXXI) (I)

d) converting a compound of formula (III) to a compound of formula (II) according to the reaction scheme as depicted below:

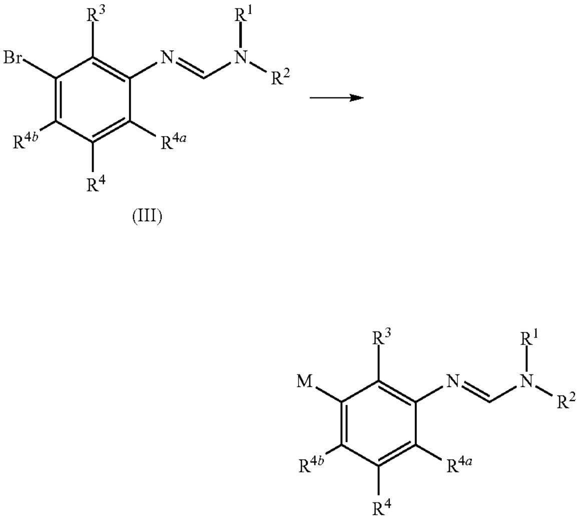

(III) (II)

e) reacting a compound of formula (II) with a compound of formula (XXX) to obtain a compound of formula (I) according to the reaction scheme as depicted below:

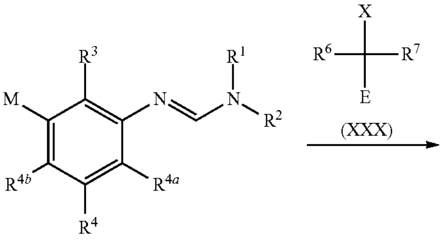

(II) (XXX)

-continued

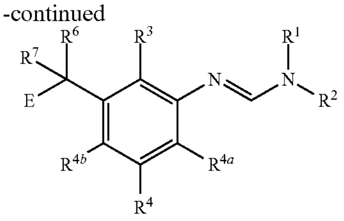

(I)

f) reacting a compound of formula (XV) with compound of formula (XII), (XVI), (XVII) or (XXXI) to obtain a compound of formula (XIV) according to the reaction scheme as depicted below:

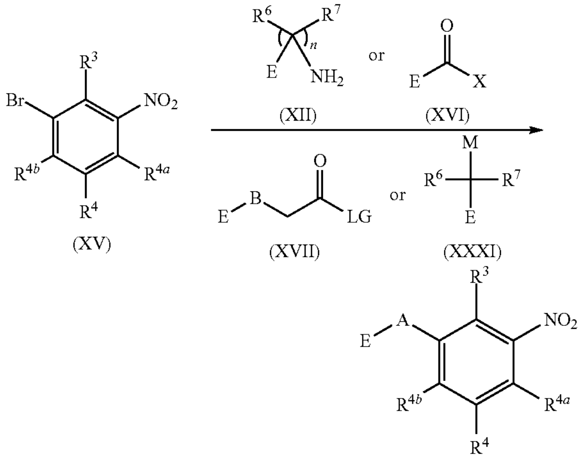

(XV) (XII) (XVI) (XVII) (XXXI) (XIV)

g) converting a compound of formula (XIV) to a compound of formula (XIII) according to the reaction scheme as depicted below:

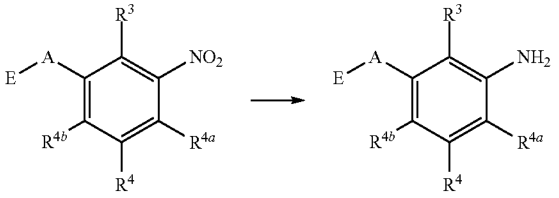

(XIV) (XIII)

h) reacting a compound of formula (XIII) with a suitable secondary amine ($HNR^1R^2$) to obtain a compound of formula (I) according to the reaction scheme as depicted below:

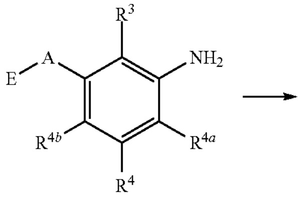

(XIII)

-continued

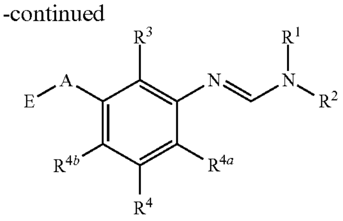

(I)

where in the above schemes, $R^1$, $R^2$, $R^3$, $R^4$, $R^{4a}$, $R^{4b}$, A, X and E have the same meanings as defined above and M is selected from the group consisting of lithium derivative, boronic ester, boronic acid, MgX and ZnX.

The compounds of the present invention as defined by general formula (I) and/or in Tables I may be prepared, in known manner, in a variety of ways as described in the schemes 1-21:

A. Synthesis of C-Bridge Amidine Derivative:

Ia

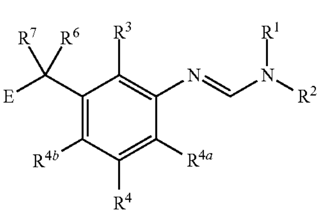

In one of the embodiment according to invention, the arylamidine of the formula (Ia) wherein $R^1$ to $R^7$ are as defined in the invention can be obtained by using the process described in following schemes 1-8.

Scheme-1

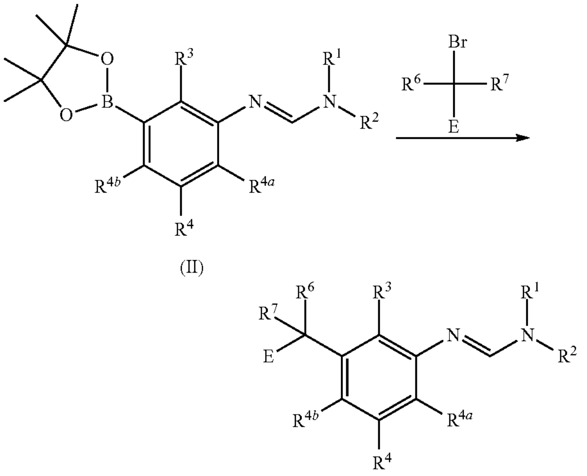

(II) (Ia)

The C-bridged amidine of formula (Ia), can be obtained by palladium catalyzed cross coupling of the corresponding boronate ester derivatives of formula (II) with suitable aryl halides in the presence of a base such as potassium carbonate or sodium bicarbonate by following the analogous procedure disclosed in prior art WO2018069841 as shown in scheme 1.

Scheme-2

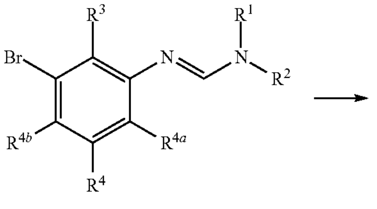

(III)

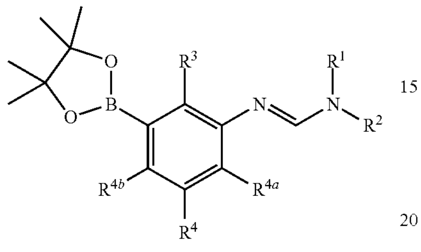

(II)

The boronate ester of amidine derivative of formula (II) is an important intermediate and can be obtained (Scheme-2) from corresponding halogen derivatives of amidine of formula (III) using bispinacolato diborane in the presence of palladium catalyst, following the miyaura borylation method as disclosed in *J. Org. Chem.,* 1995, 60, 7508-7510.

The arylamidine of the formula (Ia) wherein $R^1$-$R^7$ are defined herein above can also be obtained stepwise by using the process described in following scheme 3-8.

Scheme: 3

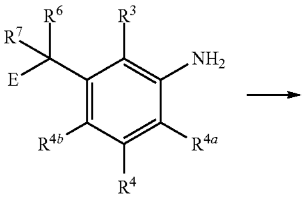

(IV)

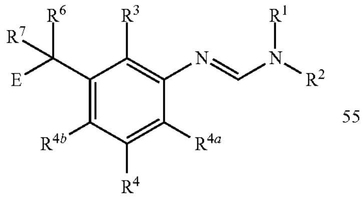

(Ia)

The C-bridged amidine of formula (Ia), can be obtained by treating the corresponding aniline derivatives of formula (IV) with N-(dimethoxymethyl)-N-methylethanamine in 1,4-dioxane using catalytic amount of anhydrous p-toluene-sulphonic acid following analogous procedure disclosed in US20110130282.

Scheme: 4

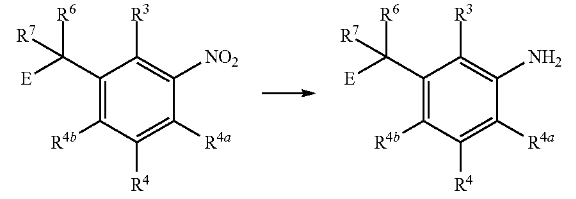

(V) (IV)

The aniline derivative of formula (IV) can be obtained by reduction of corresponding nitro intermediate of formula (V) by using various reduction methods disclosed in the literature, for example iron powder in the presence of aqueous ammonium chloride or hydrogenation in the presence of Pd/C, following analogous procedure disclosed in US2006194801A1.

Scheme: 5

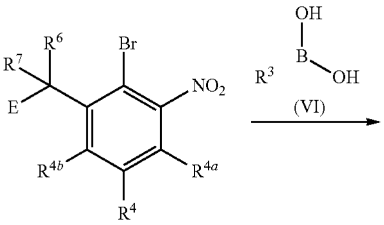

(VI)

(VII)

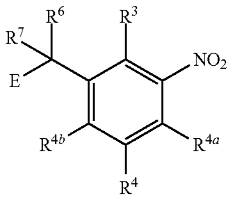

(V)

The compound of formula (V) wherein $R^3$ is preferably alkyl groups; can be obtained by palladium catalyzed cross coupling of corresponding alkyl boronic acid of formula (VI) with bromo derivative of formula (VII) in the presence of a base e.g. potassium carbonate or potassium phosphate by following the analogous procedure disclosed in US2017355679A1.

Scheme: 6

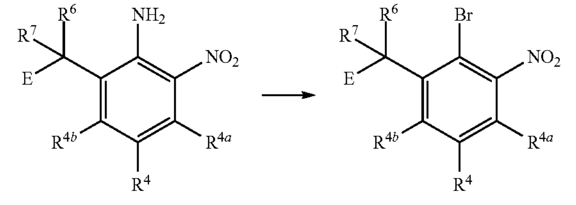

(VIII) (VII)

The corresponding halogen derivatives of formula (VII) can be obtained by sandmeyer reaction of corresponding aniline derivatives of formula (VIII) by following the analogous procedure disclosed in *J. Org. Chem.*, 1980, 45, 2570-2575. This approach provides various functionalization opportunities at this position by converting corresponding amino group to different halogens, nitrile, hydroxy, trifluoromethyl etc. as disclosed in *J. Fluorine Chem.*, 2001, 107, 31-34 and *Synthesis,* 2007, 81-84.

Scheme: 7

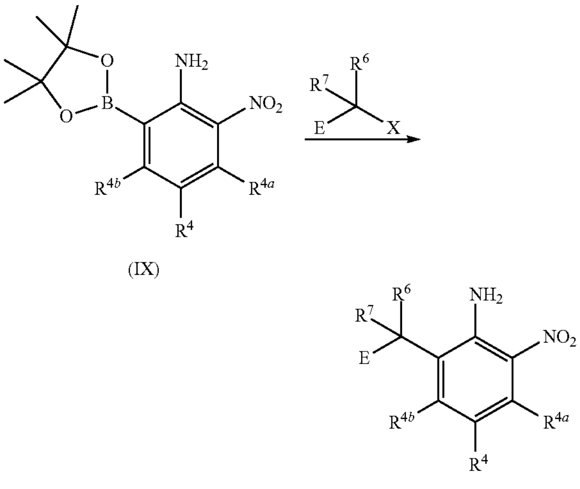

(IX)

(VIII)

The C-bridged derivative of formula (VIII) can be obtained from the boronate ester intermediate of formula (IX) by following suzuki coupling reaction with various benzyl, hetero aryl or alkyl bromides in the presence of palladium catalyst by following analogous procedure disclosed in WO2018069841.

Scheme: 8

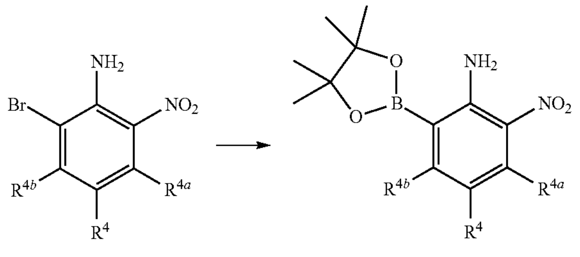

(X) (IX)

The boronate ester derivative of formula (IX) can be obtained from corresponding commercially available bromo derivative of formula (X) using bispinacolato diborane in the presence of palladium catalyst by following miyaura borylation reaction using suitable base as disclosed in WO 2016210234.

B. Synthesis of N-Bridged Amidine Derivative of Formula (Ib and Ic):

In one of the embodiment according to invention, the arylamidine of the formula (Ib) wherein $R^1$-$R^7$ are defined herein above, can be obtained by using the process described in following scheme 9-10.

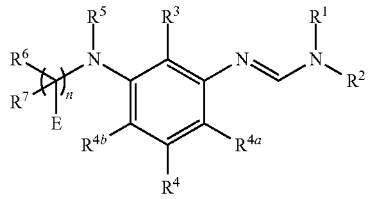

n = 0 (Ib); n = 1 (Ic)

Scheme: 9

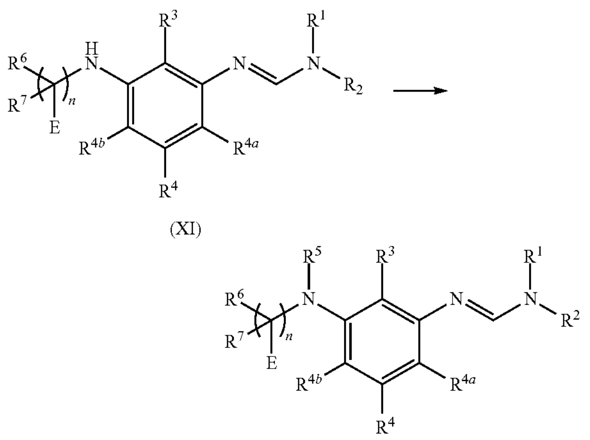

(XI)

(Ib, Ic)

The N-bridged amidine of formula (Ib), can be obtained by N-alkylation of amidine derivative of formula (XI) in the presence of suitable base and suitable alkyl halide, wherein $R^5$ is defined herein above, by following the analogous procedure disclosed in WO2018069842.

Scheme: 10

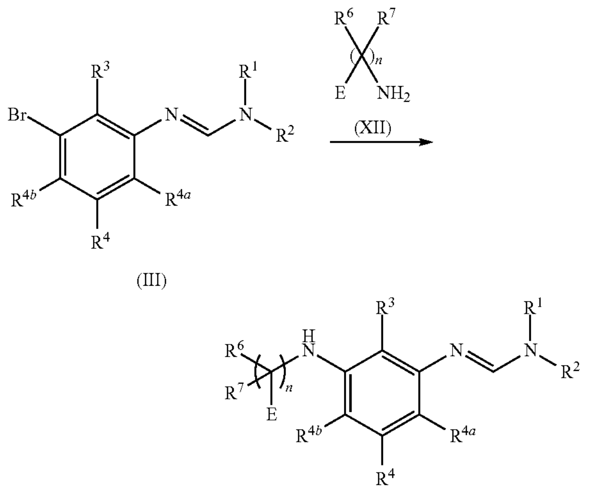

(III)

(XI)

The amidine derivative of formula (XI) prepared by palladium catalyzed cross coupling of corresponding amine derivatives of formula (XII) in the presence suitable base by following Buchwald-Hartwig coupling reaction as disclosed in *J. Med. Chem,* 2012, 55,19, 8538-48 and *J. Org. Chem.,* 2010, 75, 19, 6477-88.

C. Synthesis of O and S-Bridged Amidine Derivative of Formula (Id and Ie)

In one of the embodiment according to invention, the arylamidine of the formula (Id and Ie) wherein $R^1$-$R^7$ are defined herein above can be obtained by using the process described in following scheme 11-13.

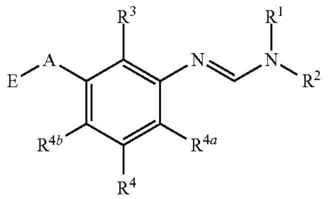

Id: A = O, Ie A = S

Scheme: 11

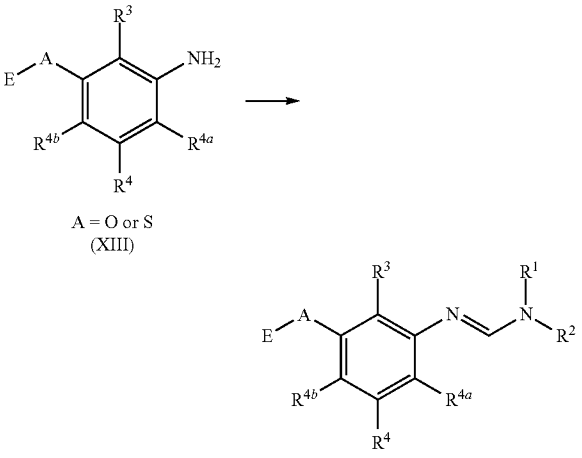

A = O or S
(XIII)

Id: A = O
Ie A = S

In one embodiment, the compound of formula (Id and Ie) can be prepared by treating the corresponding aniline derivatives of formula (XIII) with excess of trimethyl orthoformate using catalytic amount of p-toluenesulphonic acid (scheme 11). The resulting intermediate was heated with secondary amine ($HNR^1R^2$) in dioxane to obtain the desired amidine derivatives by following the analogous procedure as disclosed in US20110130282.

Scheme: 12

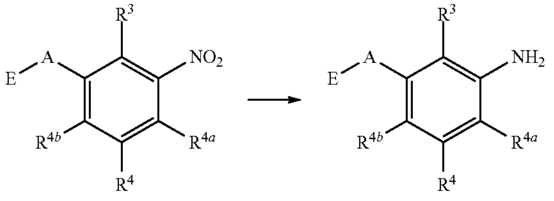

A = O or S
(XIV)

A = O or S
(XIII)

Amine derivative of formula (XIII) is a key intermediate prepared by reduction of nitro intermediate of formula (XIV) using iron and aq. ammonium chloride or stannous (II) chloride in hydrochloric acid in suitable solvent and temperature following the analogous procedure as disclosed in the US2006194801A1.

Scheme 13

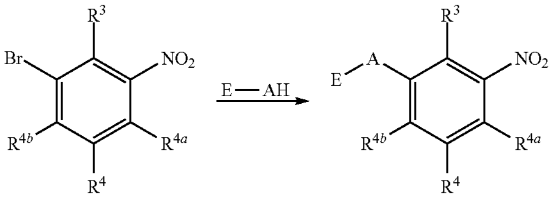

(XV)

A = O or S
(XIV)

Nitro derivative of formula (XIV) is an important intermediate and can be prepared by coupling reaction of halo derivative of formula (XV) and corresponding substituted phenols or thiophenols using suitable copper (I) reagent and solvent by following the analogous procedure disclosed in the WO2018069842.

D. Synthesis of Carbonyl-Bridged Amidine Derivative of Type (If)

In one of the embodiment according to invention, the formamidine derivative of the formula (If) can be obtained by using the process described in following scheme 14.

Scheme: 14

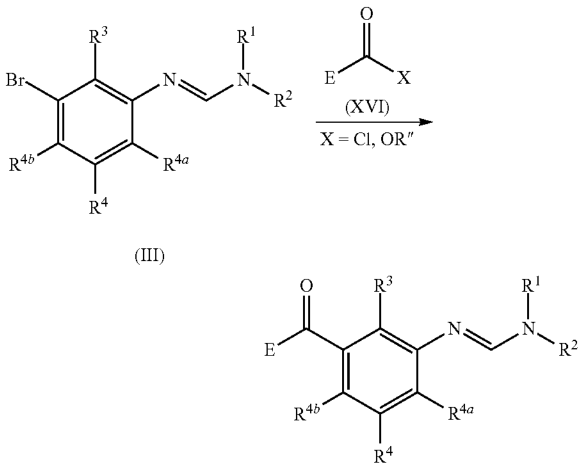

(III)

(If)

The amidine derivative of formula (If) prepared by acylation reaction using metal halogen exchange of compounds formula (III) in the presence of suitable lithiated/grignard reagents followed by the treatment with relative ester or wienreb amide derivatives of formula (XVI) and by following the analogous process as disclosed in *Angew. Chem. Int. Ed.,* 56(43), 13319-13323 and *J. Org. Chem.,* 67(11), 3585-3594; 2002.

E. Synthesis of Carbonyl Methyl-Bridged Amidine Derivative of Formula (Ig)

(Ig)

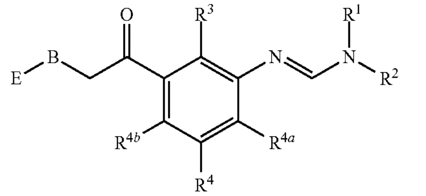

In one of the embodiment according to invention, the amidine derivative of the formula (Ig) wherein $R^1$-$R^7$ are defined herein above, wherein B is O, S, N can be obtained by a process described in following scheme 15.

Scheme: 15

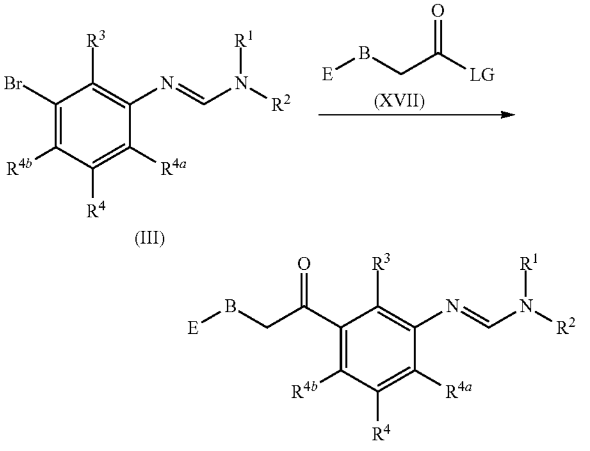

(III) (XVII) (Ig)

The amidine derivative of formula (Ig) prepared by using metal halogen exchange of compounds formula (III) in the presence of suitable lithiated/grignard reagents followed by treatment with relative ester or wienreb amid derivatives of formula (XVII) and by following the analogous process as disclosed in *Chem. Pharma. Bull.*, 2001, 49(2), 173-182, WO 2012029942 and *Eur. J. Med. Chem.*, 2013, 69, 244-261.

Scheme: 16

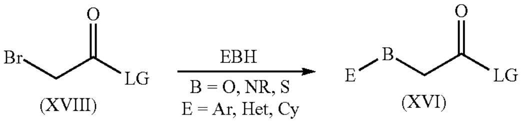

(XVIII) (XVI)

The key intermediate of formula (XVI) is prepared by alkylation reaction using ethyl bromoacetate with corresponding phenols, thiophenols and anilines in the presence of suitable base by following the analogous procedure as disclosed in *Tet. Lett.*, 2012, 53, 15, 2001-2004 and *J. Med. Chem.*, 2012, 55, 1, 515-527.

In one of the embodiment according to invention, the arylamidines of the formula (Ig) wherein $R^1$-$R^7$ are defined herein above and B is $CR^6R^7$ can be obtained by a process described in following scheme 17-20.

Scheme: 17

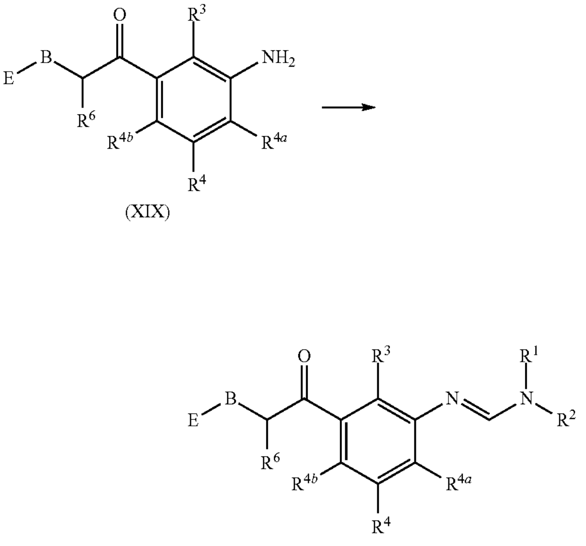

(XIX) (Ig)

B; $CR_6R_7$

The compound of formula (Ig) can be prepared by treating the corresponding aniline derivatives of formula (XIX) with excess of trimethyl orthoformate using catalytic amount of p-toluenesulphonic acid (scheme 17). The resulting intermediate was heated with secondary amine ($HNR^1R^2$) in dioxane to obtain the compound of formula (Ig) following the analogous procedure as disclosed in US20110130282.

Scheme: 18

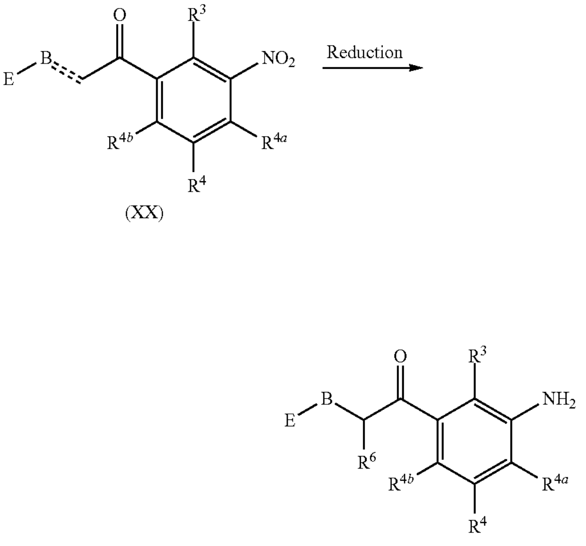

(XX) (XIX)

Amine derivative of formula (XIX) is a key intermediate prepared by reduction of nitro intermediate of formula (XX) using iron and aq. ammonium chloride or stannous (II) chloride in hydrochloric acid in suitable solvent and temperature following analogous procedure as disclosed in the US2006194801A1.

Scheme: 19

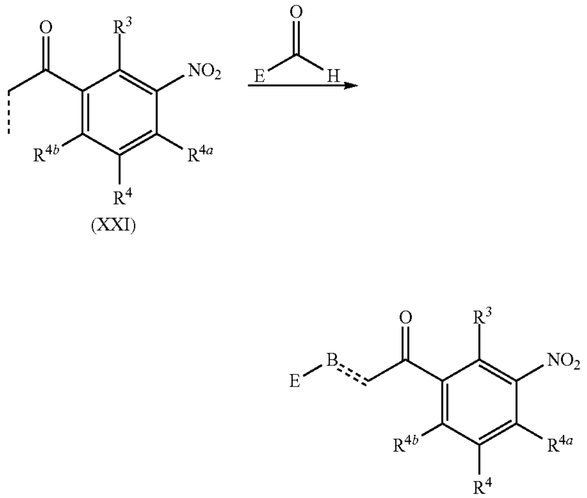

(XXI)

(XX)

Nitro intermediate of formula (XX) can be prepared by aldol condensation of ketone intermediate of formula (XXI) with corresponding aldehyde/ketone derivatives in the presence of suitable base e.g. aqueous sodium or potassium hydroxide following the analogous procedure as disclosed in *Synthesis,* 1980, 8, 647-650.

Scheme: 20

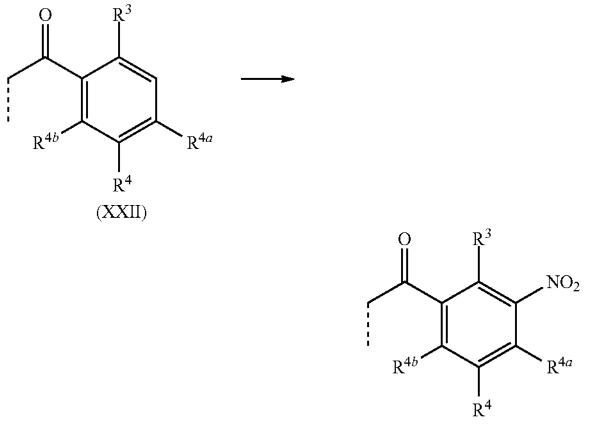

(XXII)

(XXI)

Nitro intermediate of formula (XXI) can be prepared by nitration of corresponding commercially available acetophenone following the analogous procedure disclosed in *J. Org. Chem.,* 1986, 51, 3439-3446.

F. Synthesis of 3-Bromoamidine Derivative of Formula (III):

In one of the embodiment according to invention, an important key intermediate arylamidine of the formula (III) wherein $R^1$-$R^4$ are defined herein above can be obtained by using the process described in following scheme 21.

Scheme: 21

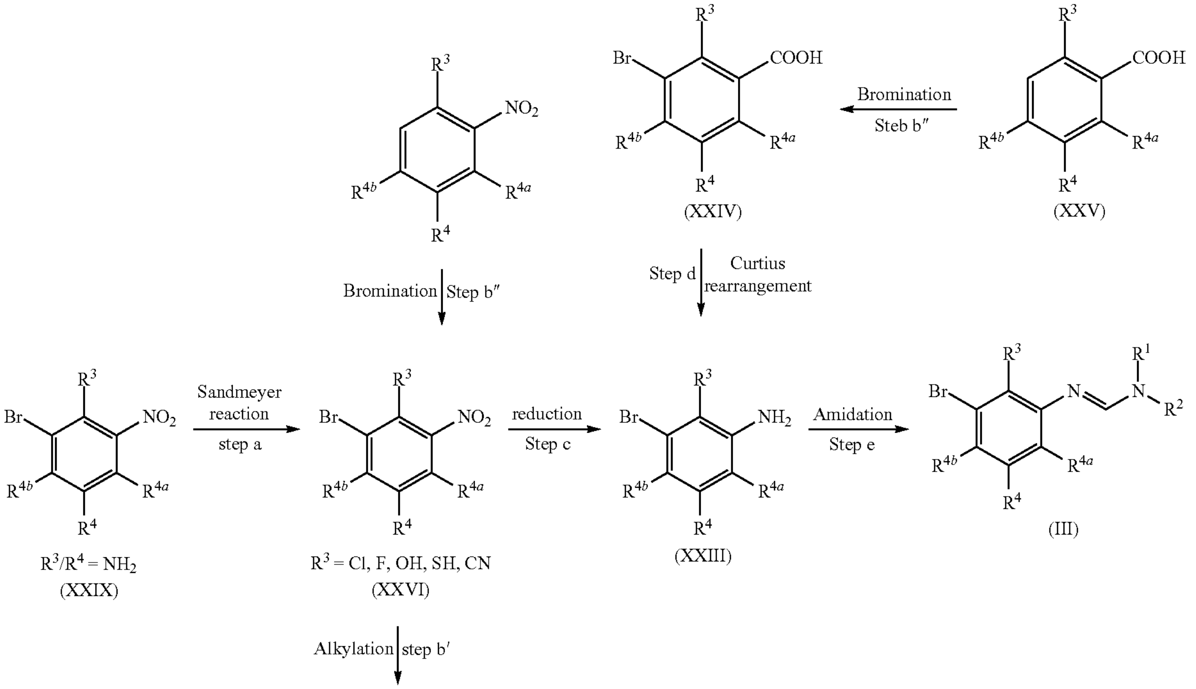

(XXIV) (XXV)

$R^3/R^4 = NH_2$
(XXIX)

$R^3$ = Cl, F, OH, SH, CN
(XXVI)

(XXIII)

(III)

-continued

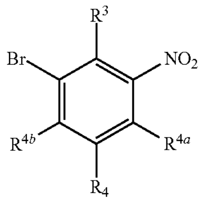

$R^3$ = OR", SR"
(XXVII)

The compound of formula (III) can be prepared by treating the corresponding aniline derivatives of formula (XXIII) in excess of trimethyl orthoformate using catalytic amount of p-toluenesulphonic acid (scheme 21, step e). The resulting intermediate was heated with secondary amine ($HNR^1R^2$) in dioxane to obtain the compound of formula (III) following analogous procedure as disclosed in US20110130282.

Aniline intermediate of formula (XXIII) can be obtained by one of the method as described in scheme 21.

In one embodiment, the aniline intermediate of formula (XXIII) obtained from corresponding substituted 3-bromobenzoic acid of formula (XXIV) by curtius rearrangement (scheme 21, step-d) in the presence of diphenylphosphoryl azide followed by acidic treatment by following the analogous procedure disclosed in *J. Am. Chem. Soc.,* 2005, 127, 16408 and *Org. Lett.,* 2012, 14, 608-611. The 3-bromo benzoic acid intermediate of formula (XXIV) can be obtained by bromination (scheme 21, step b") of commercially available 2,5-disubstituted benzoic acid (XXV) following literature method disclosed in *J. Org. Chem.,* 2013, 78, 2589-2599.

Aniline Intermediates of formula (XXIII) alternatively (Scheme 21, Step c) obtained from nitro intermediate of formula (XXVI) by reduction of corresponding nitro function of formula (XXVI) in the presence of suitable reducing agent e.g iron and aq. ammonium chloride or stannous (II) chloride in hydrochloric acid in suitable solvent following analogous procedure as disclosed in US2006194801 A1 and *J. Am. Chem. Soc.,* 2003, 125, 40, 12074-12075.

Nitro intermediate of formula (XXVI) can alternatively obtained from commercially available nitroaniline intermediate of formula (XXIX) by Sandmeyer reaction (scheme 21, step a) followed by radical-nucleophilic substitution as disclosed in literature *JOC,* 1980, 45, 2570-2575*; Synlett,* 2012, 23, 13, 1893-1896 and *Org Pro Res and Dev,* 2003, 7, 5, p. 762-768.

Nitro intermediate of formula (XXVI) where in $R^3/R^4$ group are preferably OH, SH can be alkylated by suitable alkylating agent (scheme 21, step b') to provide nitro intermediates of formula (XXVII) with suitable R" group.

Nitro intermediate of formula (XXVI) can alternatively obtained from commercially available nitrobenzene intermediate of formula (XXVIII) by bromination (scheme 21, step b") reaction to provide 3-bromo 2,5-disubstituted nitrobenzene derivative as disclosed in literature method *Chem Comm.* 2012, 48, 3442-3444*; Bio. Org. Med. Chem* 2014, 22, 1156-1162.

In one embodiment, the present invention provides use of compounds of formula (I) and compositions thereof, for controlling and/or preventing phytopathogenic fungi of agricultural crops and/or horticultural crops.

In another embodiment, of the present invention provides the use of compounds of formula (I) and compositions thereof for controlling rust diseases of agricultural crops and/or horticultural crops.

In preferred embodiment, the present invention provides use of compound of formula (I) and compositions thereof, that are particularly suitable for controlling and/or preventing against diseases of the agricultural crops such as cereals, corn, soybean and other leguminous plants; fruits and fruit trees; nuts and nut trees; citrus and citrus trees; any horticultural plants; oleaginous plants; coffee, tea, and other vegetables, and ornamentals.

In more preferred embodiment, the compounds of formula (I) may be used to treat several fungal pathogens. Non-limiting examples of pathogens of fungal diseases which can be treated in accordance with the invention include:

- diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator; Erysiphe* species, for example *Erysiphe cichoracearu;*
- diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* or *Phakopsora meibomiae; Puccinia* species, for example *Puccinia recondita, Puccinia graminis* or *Puccinia striiformis*, and *Puccinia melanocephala; Uromyces* species, for example *Uromyces appendiculatus;*
- In particular, *Cronartium ribicola* (White pine blister rust); *Gymnosporangium juniperi-virginianae* (Cedar-apple rust); *Hemileia vastatrix* (Coffee rust); *Phakopsora meibomiae* and *P. pachyrhizi* (Soybean rust); *Puccinia coronata* (Crown Rust of Oats and Ryegrass); *Puccinia graminis* (Stem rust of wheat and Kentucky bluegrass, or black rust of cereals); *Puccinia hemerocallidis* (Daylily rust); *Puccinia persistens* subsp. *triticina* (wheat rust or 'brown or red rust'); *Puccinia sorghi* (rust in corn); *Puccinia striiformis* ('Yellow rust' in cereals); *Puccinia melanocephala; Uromyces appendiculatus* (rust of beans); *Uromyces phaseoli* (Bean rust); *Puccinia melanocephala* ('Brown rust' in sugarcane); *Puccinia kuehnii* ('Orange rust' in sugarcane);
- diseases caused by pathogens from the group of the Oomycetes, for example *Albugo* species, for example *Albugo candido, Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;* leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidial form: *Drechslera*, syn: *Helminthosporium*) or *Cochliobolus miyabeanus; Colletotrichum* species, for example *Colletotrichum lindemuthanium, Colletotrichum capsici; Cycloconium* species, for example *Cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans; Magnaporthe* species, for example *Magnaporthe grisea; Microdochium* species, for example *Microdochium nivale; Mycosphaerella* species, for example *Mycosphaerella graminicola, Mycosphaerella arachidicola* or *Mycosphaerella fijiensis; Phaeosphaeria* species, for example *Phaeosphaeria nodorum; Pyrenophora* species, for example *Pyrenophora teres* or *Pyrenophora tritici repentis; Ramularia* species, for example *Ramularia collo-cygni* or *Ramularia areola; Rhynchosporium* species, for example *Rhynchosporium secalis; Septoria* species, for example *Septoria apii, Septoria tritici* or *Septoria lycopersici; Stagonospora* species, for example *Stagonospora nodorum; Typhula* species, for example *Typhula incarnata; Venturia* species, for example *Venturia inaequalis;* root and stem diseases caused, for example, by *Corticium* species, for example *Corticium graminearum; Fusarium* species, for example *Fusarium oxysporum; Gaeumannomyces* species, for example *Gaeumannomyces graminis; Plasmodiophora* species, for example *Plasmodiophora brassicae; Rhizoctonia* species, for example *Rhizoctonia solani; Sarocladium* species, for example *Sarocladium oryzae; Sclerotium* species, for example *Sclerotium oryzae; Tapesia* species, for example *Tapesia acuformis; Thielaviopsis* species, for example *Thielaviopsis basicola; Ganoderma* species, for example *Ganoderma lucidum;* ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Stagnospora* species, for example *Stagnospora nodorum;* diseases caused by smut fungi, for example *Sphacelotheca* species, for example *Sphacelotheca reiliana; Tilletia* species, for example *Tilletia caries* or *Tilletia controversa; Urocystis* species, for example *Urocystis occulta; Ustilago* species, for example *Ustilago nuda;* fruit rot caused, for example, by *Aspergillus* species, for example *Aspergillus flavus; Botrytis* species, for example *Botrytis cinerea; Penicillium* species, for example *Penicillium expansum* or *Penicillium purpurogenum; Rhizopus* species, for example *Rhizopus stolonifer; Selerotinia* species, for example *Selerotinia selerotiorum; Verticilium* species, for example *Verticilium alboatrum;* seed- and soil-borne rot and wilt diseases, and also diseases of seedlings, caused, for example, by *Alternaria* species, for example *Alternaria brassicicola; Aphanomyces* species, for example *Aphanomyces euteiches; Ascochyta* species, for example *Ascochyta lentis; Aspergillus* species, for example *Aspergillus flavus; Cladosporium* species, for example *Cladosporium herbarum; Cochliobolus* species, for example *Cochliobolus sativus* (conidial form: *Drechslera, Bipolaris* Syn: *Helminthosporium*); *Colletotrichum* species, for example *Colletotrichum coccodes; Fusarium* species, for example *Fusarium culmorum; Gibberella* species, for example *Gibberella zeae; Macrophomina* species, for example *Macrophomina phaseolina; Microdochium* species, for example *Microdochium nivale; Monographella* species, for example *Monographella nivalis; Penicillium* species, for example *Penicillium expansum; Phoma* species, for example *Phoma lingam; Phomopsis* species, for example *Phomopsis sojae; Phytophthora* species, for example *Phytophthora cactorum; Pyrenophora* species, for example *Pyrenophora graminea; Pyricularia* species, for example *Pyricularia oryzae; Pythium* species, for example *Pythium ultimum; Rhizoctonia* species, for example *Rhizoctonia solani; Rhizopus* species, for example *Rhizopus oryzae; Sclerotium* species, for example *Sclerotium rolfsii; Septoria* species, for example *Septoria nodorum*; Typhula species, for example *Typhula incarnata; Verticillium* species, for example *Verticillium dahliae;* cancers, galls and witches' broom caused, for example, by *Nectria* species, for example *Nectria galligena;* wilt diseases caused, for example, by *Monilinia* species, for example *Monilinia laxa;* deformations of leaves, flowers and fruits caused, for example, by *Exobasidium* species, for example *Exobasidium vexans; Taphrina* species, for example *Taphrina deformans;* degenerative diseases in woody plants, caused, for example, by *Esca* species, for example *Phaeomoniella ehlamydospora, Phaeoacremonium aleophilum* or *Fomitiporia mediterranea; Ganoderma* species, for example *Ganoderma boninense;* diseases of flowers and seeds caused, for example, by *Botrytis* species, for example *Botrytis cinerea;* diseases of plant tubers caused, for example, by *Rhizoctonia* species, for example *Rhizoctonia solani; Helminthosporium* species, for example *Helminthosporium solani;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora; Ralstonia* species, for example *Ralstonia solanacearum.*

Fungal diseases on roots and the stem base caused, for example, by black root rot (*Calonectria crotalariae*), charcoal rot (*Macrophomina phaseolina*), *Fusarium* blight or wilt, root rot, and pod and collar rot (*Fusarium oxysporum, Fusarium orthoceras, Fusarium semitectum, Fusarium equiseti*), *Mycoleptodiscus* root rot (*Mycoleptodiscus terrestris*), *Neocosmospora* (*Neocosmospora vasinfecta*), pod and stem blight (*Diaporthe phaseolorum*), stem canker (*Diaporthe phaseolorum* var. *caulivora*), *Phytophthora* rot (*Phy-*

*tophthora megasperma*), brown stem rot (*Phialophora gregata*), *Pythium* rot (*Pythium aphanidermatum, Pythium irregulare, Pythium debaryanum, Pythium myriotylum, Pythium ultimum*), *Rhizoctonia* root rot, stem decay, and damping-off (*Rhizoctonia solani*), *Sclerotinia* stem decay (*Sclerotinia sclerotiorum*), *Sclerotinia* southern blight (*Sclerotinia rolfsii*), *Thielaviopsis* root rot (*Thielaviopsis basicola*).

Plants which can be treated in accordance with the invention include the following: Rosaceae sp (for example pome fruits such as apples, pears, apricots, cherries, almonds and peaches), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Vitaceae sp. (for example grapes); Solanaceae sp. (for example tomatoes, peppers), Liliaceae sp., Asteraceae sp. (for example lettuce), Umbelliferae sp., Cruciferae sp., Chenopodiaceae sp., Cucurbitaceae sp. (for example cucumber), Alliaceae sp. (for example leek, onion), Papilionaceae sp. (for example peas); major crop plants, such as Poaceae/Gramineae sp. (for example maize, turf, cereals such as wheat, rye, rice, barley, oats, millet and triticale), Asteraceae sp. (for example sunflower), Brassicaceae sp. (for example white cabbage, red cabbage, broccoli, cauliflower, Brussels sprouts, pak choi, kohlrabi, radishes, and oilseed rape, mustard, horseradish and cress), Fabacae sp. (for example bean, peanuts), Papilionaceae sp. (for example soya bean), Solanaceae sp. (for example potatoes), Chenopodiaceae sp. (for example sugar beet, fodder beet, swiss chard, beetroot); Malvaceae (for example cotton); useful plants and ornamental plants for gardens and wooded areas; and genetically modified varieties of each of these plants.

More preference is given to controlling the following diseases of soya beans: Fungal diseases on leaves, stems, pods and seeds caused, for example, by *Altemaria* leaf spot (*Altemaria* spec. *atrans tenuissima*), Anthracnose (*Colletotrichum gloeosporoides dematium* var. *truncatum*), brown spot (*Septoria glycines*), *cercospora* leaf spot and blight (*Cercospora kikuchii*), *Choanephora* leaf blight (*Choanephora infundibulifera trispora* (Syn.)), *Dactuliophora* leaf spot (*Dactuliophora glycines*), downy mildew (*Peronospora manshurica*), *Drechslera* blight (*Drechslera glycini*), frogeye leaf spot (*Cercospora sojina*), *Leptosphaerulina* leaf spot (*Leptosphaerulina trifolii*), *Phyllosticta* leaf spot (*Phyllosticta* sojaecola), pod and stem blight (*Phomopsis sojae*), powdery mildew (*Microsphaera diffusa*), *Pyrenochaeta* leaf spot (*Pyrenochaeta glycines*), *Rhizoctonia* aerial, foliage, and web blight (*Rhizoctonia solani*), rust (*Phakopsora pachyrhizi, Phakopsora meibomiae*), scab (*Sphaceloma glycines*), *Stemphylium* leaf blight (*Stemphylium botryosum*), target spot (*Corynespora cassiicola*).

The present invention also relates to the use of compounds of formula I, the combinations or the compositions thereof for controlling or preventing the following plant diseases: *Puccinia* spp. (rusts) on various plants, for example, but not limited to *P. triticina* (brown or leaf rust), *P. striiformis* (stripe or yellow rust), *Puccinia melanocephala* (sugarcane rust), *P. hordei* (dwarf rust), *P. graminis* (stem or black rust) or *P. recondita* (brown or leaf rust) on cereals, such as e. g. wheat, barley or rye and Phakopsoraceae spp. on various plants, in particular *Phakopsora pachyrhizi* and *P. meibomiae* (soybean rust) on soybeans, *Hemileia vastatrix* (Coffee rust), *Uromyces appendiculatus, Uromyces fabae* and *Uromyces phaseoli* (rust of beans).

In one embodiment, the present invention provides use of compounds of formula (I) and compositions thereof, for controlling and/or preventing plant diseases caused by pathogens such as: *Pyricularia oryzae, Rhizoctonia solani, Botrytis cinerea, Alternaria solani, Colletotrichum capsici, Septoria lycopersici, Fusarium culmorum, Phakopsora pachyrhizi, Sphaerotheca fuliginea, Pseudoperonospora cubensis, Puccinia triticina, Septoria tritici, Phytopthora infestans, Plasmopara* viticola or *Uncinula* necator.

In a preferred embodiment, the present invention provides use of compounds of formula (I) and compositions thereof, for controlling and/or preventing plant diseases as: *Puccinia* spp. (rusts) on various plants, selected from, but not limited to *P. triticina* (brown or leaf rust), *P. striiformis* (stripe or yellow rust), *P. hordei* (dwarf rust), *P. graminis* (stem or black rust) or *P. recondita* (brown or leaf rust) on cereals, selected from wheat, barley or rye and Phakopsoraceae spp. on various plants, in particular *Phakopsora pachyrhizi* and *P. meibomiae* (soybean rust) on soybeans.

In more preferred embodiment, the present invention provides use of compounds of formula (I) and compositions thereof, for controlling and/or preventing phytopathogenic fungi such as *Phakopsora pachyrhizi, Phakopsora meibomiae*, of agricultural crops and or horticultural crops.

The present invention provides a method for controlling unwanted microorganisms, wherein compounds of the formula (I) are applied to the microorganisms and/or in their habitat.

The present invention further provides a method for protecting seed against unwanted microorganisms by using seed treated with at least one compound of the formula (I).

The compounds of the formula (I) can possess potent microbicidal activity and can be used for the control of unwanted microorganisms, such as fungi and bacteria, in crop protection and in the protection of such materials.

The compounds of the formula (I) possess fungicidal properties and can be used in crop protection, for example for control of Plasmodiophoromycetes, Oomycetes, Chytridiomycetes, Zygomycetes, Ascomycetes, Basidiomycetes and Deuteromycetes.

The compounds of the formula (I) can be used as bactericides in crop protection, for example, for control of Pseudomonadaceae, Rhizobiaceae, Enterobacteriaceae, Corynebacteriaceae and Streptomycetaceae.

The compounds of the formula (I) can be used for curative or protective control of phytopathogenic fungi. The present invention therefore also relates to curative and protective methods for controlling phytopathogenic fungi by the use of the active ingredients or compositions, which are applied to the seed, the plant or plant parts, the fruit or the soil in which the plants grow.

In one embodiment, the present invention provides a composition for controlling and/or preventing phytopathogenic microorganisms, comprising a compound of formula (I), isomers/structural isomers, stereo-isomers, diastereomers, enantiomers, tautomers, metal complexes, polymorphs, N-oxides, S-oxides or agriculturally acceptable salts thereof, and one or more inert carriers.

The present invention provides a composition wherein concentration of compound of formula (I) ranges from 10 to 90% by weight with respect to the total weight of the composition, preferably from 30 to 70% by weight with respect to the total weight of the composition.

The composition may additionally comprises one or more active compatible compound selected from fungicides, insecticides, nematicides, acaricides, biopesticides, herbicides, plant growth regulators, antibiotics, nutrients or fertilizers.

In one embodiment, the present invention provides a combination comprising the compound of formula (I), isomers/structural isomers, stereo-isomers, diastereomers, enantiomers, tautomers, metal complexes, polymorphs, N-oxides, S-oxides or agriculturally acceptable salts thereof and one or more active compatible compound selected from fungicides, insecticides, nematicides, acaricides, biopesticides, herbicides, plant growth regulators, antibiotics, nutrients or fertilizers.

According to the invention, as defined above a carrier is a natural or synthetic, organic or inorganic substance with which the active ingredients are mixed or combined for better applicability, in particular for application to plants or plant parts or seed. The carrier which may be solid or liquid is generally inert and should be suitable for use in agriculture.

Useful solid carriers include for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally, suitable is oligo- or polymers, for example those derived from vinylic monomers, from acrylic acid, from EO and/or PO alone or in combination with, for example, (poly) alcohols or (poly) amines. It is also possible to use lignin and its sulphonic acid derivatives, unmodified and modified celluloses, aromatic and/or aliphatic sulphonic acids and also their adducts with formaldehyde.

The active ingredients can be applied as such or converted to the customary formulations or in the form of their formulations or the use forms prepared therefrom, such as ready-to-use solutions, emulsions, water- or oil-based suspensions, powders, wettable powders, pastes, soluble powders, soluble tablets, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, nursery boxes, broadcasting, dusting, foaming, spreading-on and the like. It is also possible to deploy the active ingredients by the ultra-low volume method or to inject the active ingredient preparation or the active ingredient itself into the soil. It is also possible to treat the seed of the plants.

The active ingredients can be further converted to the nanoformulation with intent to further improve water solubility, thermal stability, bioavailability, sensory attributes and physiological performance.

Furthermore, the choice of the type of formulation will depend on the specific use.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The auxiliaries used may be those substances which are suitable for imparting particular properties to the composition itself and/or to preparations derived therefrom (for example spray liquors, seed dressings), such as certain technical properties and/or also particular biological properties. Typical auxiliaries include extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly) ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral, vegetable oils and methylated seed oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Compositions comprising compounds of the formula (I) may additionally comprise further components, for example surfactants. Suitable surfactants are emulsifiers and/or foam formers, dispersants or wetting agents having ionic or nonionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

The invention also relates to agrochemical compositions comprising an auxiliary and at least one compound of formula (I) according to the invention.

An agrochemical composition comprises a fungicidally effective amount of a compound of formula (I). The term "effective amount" denotes an amount of the composition or of the compounds of formula (I), which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound of formula (I) used.

The compounds of formula (I), their oxides and salts can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), cap rules (e.g. CS, ZC), pastes, pastilles, wettable powders or dusts (e.g. WP, SP, WS, DP, DS), pressings (e. g. BR, TB, DT), granules (e. g. WG, SG, GR, FG, GG, MG), insecticidal articles (e.g. LN), as well as gel formulations for the treatment of plant propagation materials such as seeds (e. g. GF). These and further compositions types are defined in the "Catalogue of pesticide formulation types and international coding system", Technical Monograph No. 2, 61 h Ed. May 2008, Croplife International.

The compositions are prepared in a known manner, such as described by Mollet and Grube mann, Formulation technology, Wiley VCH, Weinheim, 2001; or Knowles, New developments in crop protection product formulation, Agrow Reports DS243, TandF Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof.

Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers and Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugarbased surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity them selves, and which improve the biological performance of the compound of formula (I) on the target. Examples are surfactants, mineral or vegetable oils, and other auxiliaries. Further examples are listed by Knowles, Adjuvants and additives, Agrow Reports DS256, TandF Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin. Suitable anti-foaming agents are silicones, long chain alcohols, and salts of fatty acids. Suitable colorants (e. g. in red, blue, or green) are pigments of low water solubility and water soluble dyes. Examples are inorganic colorants (e. g. iron oxide, titan oxide, iron hexacyanoferrate) and organic colorants (e.g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound of formula (I) and 5-15 wt % wetting agent (e.g. alcohol alkoxylates) are dissolved in water and/or in a water-soluble solvent (e. g. alcohols) ad 100 wt %. The active substance dissolves upon dilution with water.

ii) Dispersible Concentrates (DC)

5-25 wt % of a compound of formula (I) and 1-10 wt % dispersant (e.g. polyvinyl pyrrolidone) are dissolved in organic solvent (e. g. cyclohexanone) ad 100 wt %. Dilution with water gives dispersion.

iii) Emulsifiable Concentrates (EC)

15-70 wt % of a compound of formula (I) and 5-10 wt % emulsifiers (e.g. calcium dodecylbenzenesulfonate and castor oil ethoxylate) are dissolved in water-insoluble organic solvent (e. g. aromatic hydro carbon) ad 100 wt %. Dilution with water gives an emulsion.

iv) Emulsions (EW, EO, ES)

5-40 wt % of a compound of formula (I) and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound of formula (I) are comminuted with addition of 2-10 wt % dispersants and wetting agents (e. g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-Dispersible Granules and Water-Soluble Granules (WG, SG)

50-80 wt % of a compound of formula (I) are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound of formula (I) are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound of formula (I) are comminuted with addition of 3-10 wt % dispersants (e.g. sodium lignosulfonate), 1-5 wt % thickener (e.g. carboxymethyl cellulose) and water ad 100 wt % to give a fine suspension of the active substance. Dilution with water gives a stable suspension of the active substance.

ix) Microemulsion (ME)

5-20 wt % of a compound of formula (I) are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound of formula (I), 0-40 wt % water insoluble organic solvent (e.g. aromatic hydrocarbon), 2-15 wt % acrylic monomers (e.g. methylmethacrylate, methacrylic acid and a di- or tri-acrylate) are dispersed into an aqueous solution of a protective colloid (e.g. polyvinyl alcohol). Radical polymerization results in the formation of poly(meth)acrylate microcapsules. Alternatively, an oil phase comprising 5-50 wt % of a compound of formula (I) according to the invention, 0-40 wt % water insoluble organic solvent (e. g. aromatic hydrocarbon), and an isocyanate monomer (e.g. diphenylmethene-4, 4'-diisocyanatae) are dispersed into an aqueous solution of a protective colloid (e. g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable Powders (DP, DS)

1-10 wt % of a compound of formula (I) is ground finely and mixed intimately with solid carrier (e.g. finely divided kaolin) ad 100 wt %.

xii) Granules (GR, FG)

0.5-30 wt % of a compound of formula (I) is ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound of formula (I) are dissolved in organic solvent (e.g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance.

The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The com positions in question give, after two-to-tenfold dilution, active substance concentrations of from 0.01 to 60% by weight, preferably from 0.1 to 40%, in the ready-to-use preparations. Application can be carried out before or during sowing. Methods for applying compound of formula (I) and compositions thereof, respectively, onto plant propagation material, especially seeds, include dressing, coating, pelleting, dusting, and soaking as well as in-furrow application methods. Preferably, compound of formula (I) or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions ac cording to the invention in a weight ratio of 1:100 to 100:1, preferably 1:10 to 10:1.

A pesticide is generally a chemical or biological agent (such as pesticidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term pesticides includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology to increase plant growth, biomass, yield or any other quality parameter of the harvestable goods of a crop plant.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides are typically created by growing and concentrating naturally occurring organisms and/or their metabolites including bacteria and other microbes, fungi, viruses, nematodes, proteins, etc. They are often considered to be important components of integrated pest management (IPM) programs.

Biopesticides fall into two major classes, microbial and biochemical pesticides:

1. Microbial pesticides consist of bacteria, fungi or viruses (and often include the metabolites that bacteria and fungi produce). entomopathogenic nematodes are also classed as microbial pesticides, even though they are multicellular.
2. Biochemical pesticides are naturally occurring substances that control pests or provide other crop protection uses as defined below, but are relatively non-toxic to mammals The user applies the composition according to the invention usually from a pre dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 500 liters, of the ready-to-use spray liquor are applied per hectare of agricultural useful area.

The present invention further relates to a composition for controlling unwanted microorganisms, comprising at least one of the compounds of the formula (I) and/or one or more active compatible compound selected from fungicides, bactericides, acaricides, insecticides, nematicides, herbicides, biopesticides, plant growth regulators, antibiotics, fertilizers and/or mixtures thereof.

Generally, a compound of the present invention is used in the form of a composition (e.g. formulation) containing a carrier. A compound of the invention and compositions thereof can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra-low volume (ulv) liquid, ultra-low volume (ulv) suspension, water dispersible granules or tablets, water dispersible powder for slurry treatment, water soluble granules or tablets, water soluble powder for seed treatment and wettable powder.

A formulation typically comprises a liquid or solid carrier and optionally one or more customary formulation auxiliaries, which may be solid or liquid auxiliaries, for example unepoxidized or epoxidized vegetable oils (for example epoxidized coconut oil, rapeseed oil or soya oil), antifoams, for example silicone oil, preservatives, clays, inorganic compounds, viscosity regulators, surfactant, binders and/or tackifiers. The composition may also further comprise a fertilizer, a micronutrient donor or other preparations which influence the growth of plants as well as comprising a combination containing the compound of the invention with one or more other biologically active agents, such as bactericides, fungicides, nematicides, plant activators, acaricides, and insecticides.

Accordingly, the present invention also makes available a composition comprising a compound of the invention and an agronomical carrier and optionally one or more customary formulation auxiliaries.

The compositions are prepared in a manner known per se, in the absence of auxiliaries for example by grinding, screening and/or compressing a solid compound of the present invention and in the presence of at least one auxiliary for example by intimately mixing and/or grinding the compound of the present invention with the auxiliary (auxiliaries). In the case of solid compounds of the invention, the grinding/milling of the compounds is to ensure specific particle size. These processes for the preparation of the compositions and the use of the compounds of the invention for the preparation of these compositions are also a subject of the invention.

The compositions comprise 0.1 to 99%, especially 0.1 to 95%, of compound according to the present invention and 1 to 99.9%, especially 5 to 99.9%, of at least one solid or liquid carrier, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Examples of foliar formulation types for pre-mix compositions are:

| | |
|---|---|
| GR: granules | EW: emulsions, oil in water |
| WP: wettable powders | ME: micro-emulsion |
| WG: water dispersable granules (powders) | SC: aqueous suspension concentrate |
| SG: water soluble granules | CS: aqueous capsule suspension |
| SL: soluble concentrates | OD: oil-based suspension concentrate, and |
| EC: emulsifiable concentrate | SE: aqueous suspo-emulsion. |

Whereas, examples of seed treatment formulation types for pre-mix compositions are:

| | |
|---|---|
| WS: wettable powders for seed treatment slurry | FS: suspension concentrates for seed treatment |
| LS: solution for seed treatment | WG: water dispersible granules, and |
| ES: emulsions for seed treatment | CS: aqueous capsule suspension. |

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries. Suitable carriers and adjuvants can be solid or liquid and are the substances ordinarily employed in formulation technology, e.g. natural or regenerated mineral substances, solvents, dispersants, wetting agents, tackifiers, thickeners, binders, or fertilizers.

Generally, a tank-mix formulation for foliar or soil application comprises 0.1 to 20%, especially 0.1 to 15%, of the desired ingredients, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation. Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be pre sized before coating. After coating, the seeds are typically dried and then transferred to a sizing machine for sizing. Such procedures are known in the art. The compounds of the present invention are particularly suited for use in soil and seed treatment applications.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

A compound of the formula (I) in a preferred embodiment, independent of any other embodiments, is in the form of a plant propagation material treating (or protecting) composition, wherein said plant propagation material protecting composition may comprises additionally a colouring agent. The plant propagation material protecting composition or mixture may also comprise at least one polymer from water-soluble and water-dispersible film-forming polymers that improve the adherence of the active ingredients to the treated plant propagation material, which polymer generally has an average molecular weight of at least 10,000 to about 100,000.

In one embodiment, the present invention provides a method for controlling or preventing infestation of useful plants by phytopathogenic microorganisms in agricultural crops and/or horticultural crops, wherein said compound of general formula (I), isomers/structural isomers, stereo-isomers, diastereomers, enantiomers, tautomers, metal complexes, polymorphs, N-oxides, S-oxides or agriculturally acceptable salts, composition or combination thereof, is applied to the plants, to the seeds of plants, to parts thereof or a locus thereof.

In another embodiment, the present invention provides a method for controlling or preventing phytopathogenic microorganisms in agricultural crops and/or horticultural crops using the compound of formula (I), isomers/structural isomers, stereo-isomers, diastereomers, enantiomers, tautomers, metal complexes, polymorphs, N-oxides, S-oxides or agriculturally acceptable salts, composition or combination thereof, which comprises a step of applying an effective dosage of the compound or the composition or the combination, in amounts ranging from 1 g to 2 kg per hectare of agricultural and/or horticultural crops.

In yet another embodiment, the present invention provides a method for combating phytopathogenic fungi, comprising treating plants, soil, seeds or materials to be protected with the compound of formula (I), isomers/structural isomers, stereo-isomers, diastereomers, enantiomers, tautomers, metal complexes, polymorphs, N-oxides, S-oxides or agriculturally acceptable salts, composition or combination thereof.

Examples of application methods for the compounds of the invention and compositions thereof, that is the methods of controlling pests in the agriculture, are spraying, atomizing, dusting, brushing on, dressing, scattering or pouring which are to be selected to suit the intended aims of the prevailing circumstances.

One method of application in agriculture is application to the foliage of the plants (foliar application), it being possible to select frequency and rate of application to match the danger of infestation with the pest or fungi in question. Alternatively, the active ingredient can reach the plants via the root system (systemic action), by applying the compound to the locus of the plants, for example by application of a liquid composition of the compound into the soil (by drenching), or by applying a solid form of the compound in the form of granules to the soil (soil application). In the case of paddy rice plants, such granules can be metered into the flooded paddy-field. The application of the compounds of the present invention to the soil is a preferred application method.

Typical rates of application per hectare is generally 1 to 2000 g of active ingredient per hectare, in particular 10 to 1000 g/ha, preferably 10 to 600 g/ha, such as 50 to 300 g/ha.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, other additional components may also be present, for example protective colloids, binders, adhesives, thickeners, thixotropic substances, penetrants, stabilizers, sequestering agents, complex formers. In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70% by weight.

The formulations described above can be used for controlling unwanted microorganisms, in which the compositions comprising compounds of the formula (I) are applied to the microorganisms and/or in their habitat.

Compounds of the formula (I) according to this invention, as well as salts, N-oxides, metal complexes, stereoisomers or polymorphs can be used as such or in formulations thereof and can be mixed with known mixing partners in order to broaden, for example, the activity spectrum or to prevent development of resistance. Useful mixing partners include, for example, known fungicides, insecticides, acaricides, nematicides, biopesticides and bactericides. A mixture with other known active ingredients, such as herbicides, or with fertilizers and growth regulators, safeners and/or semiochemicals, is also possible.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

The compound/s of Formula I, the combinations and the compositions thereof comprising them in the use as fungicides with other fungicides may result in an expansion of the fungicidal spectrum of activity being obtained or in a prevention of fungicide resistance development. Furthermore, in many cases, extraordinary effects are obtained.

This can be obtained by applying the compounds of Formula I and at least one further pesticidally active substance simultaneously, either jointly (e. g. as tank-mix) or separately, or in succession, wherein the time interval between the individual applications is selected to ensure that the active substance applied first still occurs at the site of action in a sufficient amount at the time of application of the further pesticidally active substance(s). The order of application is not essential for working of the present invention.

The known and reported active compounds such as fungicides, insecticides, nematicides, acaricides, biopesticides, herbicides, safeners, plant growth regulators, antibiotics, fertilizers and nutrients can be combined with at least one compound of Formula I of the present invention. For example, fungicides, insecticides, nematicides, acaricides, biopesticides, herbicides, safeners, plant growth regulators, antibiotics, fertilizers and nutrients disclosed and reported in WO2017076739 (A to 0) can be combined with compound of Formula I of the present invention. The present invention also relates to such combinations comprising the compound of the present invention and active compatible compounds reported in WO2017076739.

The fungicides, insecticides, nematicides, acaricides, biopesticides, herbicides, plant growth regulators, antibiotics, fertilizers and nutrients reported in WO2017076739, are not reproduced herein for the sake of brevity and are incorporated herein by way of reference as non-limiting examples to be combined with at least one compound of Formula I of the present invention.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

In one embodiment, the present invention provides a seed comprising compound of formula (I), agriculturally acceptable salts, isomers/structural isomers, stereo-isomers, diastereomers, enantiomers, tautomers, metal complexes, polymorphs, N-oxides or S-oxides thereof, wherein the amount of the compound of formula (I), isomers/structural isomers, stereo-isomers, diastereomers, enantiomers, tautomers, metal complexes, polymorphs, N-oxides, S-oxides or agriculturally acceptable salts thereof is from 0.1 g to 10 kg per 100 kg of seed.

The invention furthermore includes a method for treating seed, particularly seeds (dormant, primed, pregerminated or even with emerged roots and leaves) treated with at least one of the compounds of the formula (I) and compositions thereof. The inventive seeds are used in methods for protection of seeds and emerged plants from the seeds from phytopathogenic harmful fungi. In these methods, seed treated with at least one inventive active ingredient is used.

It is also desirable to optimize the amount of the active ingredient used so as to provide the best possible protection for the seeds, the germinating plants and emerged seedlings from attack by phytopathogenic fungi, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

The present invention therefore also relates to a method for protecting seeds, germinating plants and emerged seedlings against attack by animal pests and/or phytopathogenic harmful microorganisms by treating the seeds with an inventive composition. The invention also relates to the use of the compositions according to the invention for treating seeds for protecting the seeds, the germinating plants and emerged seedlings against animal pests and/or phytopathogenic microorganisms. The invention further relates to seeds which have been treated with an inventive composition for protection from animal pests and/or phytopathogenic microorganisms.

One of the advantages of the present invention is that the treatment of the seeds with these compositions not only protects the seed itself, but also the resulting plants after emergence, from animal pests and/or phytopathogenic harmful microorganisms. In this way, the immediate treatment of the crop at the time of sowing or shortly thereafter protect plants as well as seed treatment in prior to sowing. It is likewise considered to be advantageous that the inventive active ingredients or compositions can be used especially also for transgenic seed, in which case the plant which grows from this seed is capable of expressing a protein which acts against pests, herbicidal damage or abiotic stress. The treatment of such seeds with the inventive active ingredients or compositions, for example an insecticidal protein, can result in control of certain pests. Surprisingly, a further synergistic effect can be observed in this case, which additionally increases the effectiveness for protection against attack by pests, microorganisms, weeds or abiotic stress.

The compounds of the formula (I) are suitable for protection of seed of any plant variety which is used in agriculture, in the greenhouse, in forests or in horticulture. More particularly, the seed is that of cereals (such as wheat, barley, rye, millet and oats), oilseed rape, maize, cotton, soybean, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As described below, the treatment of transgenic seed with the inventive active ingredients or compositions is of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originate from *Bacillus* sp., in which case the gene product is effective against the European corn borer and/or the Western corn rootworm. Particularly preferably, the heterologous genes originate from *Bacillus thuringiensis.*

In the context of the present invention, the inventive composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pre-germinated seeds, or seeds sown on nursery trays, tapes or paper.

When treating the seeds, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

The compounds of the formula (I) can be applied directly, i.e. without containing any other components and without having been diluted. In general, it is preferable to apply the compositions to the seed in the form of a suitable formulation. Suitable formulations and methods for seed treatment are known to those skilled in the art. The compounds of the formula (I) can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

In the treatment of seeds to facilitate plantability seeds can be coated with polymer. The polymer coating is comprised of a binder, a wax and a pigment, and one or more stabilizers in an amount effective to stabilize the suspension. The binder can be a polymer selected from the group consisting of vinyl acetate-ethylene copolymer, vinyl acetate homopolymer, vinyl acetate-acrylic copolymer, vinylacrylic, acrylic, ethylene-vinyl chloride, vinyl ether maleic anhydride, or butadiene styrene. Other similar polymers can be used.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants. In this case, additional synergistic effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The compounds of the invention and compositions thereof are also suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds. The application of the compounds of the present invention to seeds is a preferred application method.

The application rate of the formulations usable in accordance with the invention can be varied within a relatively wide range. It is guided by the particular content of the active ingredients in the formulations and by the seeds. The application rates of each single active ingredient are generally between 0.001 and 15 g per kilogram of seed, preferably between 0.01 and 5 g per kilogram of seed.

When using the compounds of the formula (I) as fungicides, the application rates can be varied within a relatively wide range, depending on the kind of application. The application rate of the inventive active ingredients is:

- in the case of treatment of plant parts, for example leaves: from 0.1 to 10000 g/ha, preferably from 10 to 1000 g/ha, more preferably from 30 to 300 g/ha (in the case of application by watering or dripping, it is even possible to reduce the application rate, especially when inert substrates such as rockwool or perlite are used);
- in the case of seed treatment: from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed;
- in the case of soil treatment: from 0.1 to 10000 g/ha, preferably from 1 to 5000 g/ha.

These application rates are merely by way of example and are not limiting for the purposes of the invention.

In some cases, the compounds of the formula (I) can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (*Mycoplasma*-like organisms) and RLO (*Rickettsia*-like organisms).

The compounds of the formula (I) intervene in physiological processes of plants and can therefore also be used as plant growth regulators. Plant growth regulators may exert various effects on plants. The effect of the substances depends essentially on the time of application in relation to the developmental stage of the plant, the plant variety and also on the amounts of active ingredient applied to the plants or their environment and on the type of application. In each case, growth regulators should have a particular desired effect on the crop plants.

Growth regulating effects, comprise earlier germination, better emergence, more developed root system and/or improved root growth, increased ability of tittering, more productive tillers, earlier flowering, increased plant height and/or biomass, shorting of stems, improvements in shoot growth, number of kernels/ear, number of ears/$m^2$, number of stolons and/or number of flowers, enhanced harvest index, bigger leaves, less dead basal leaves, improved phyllotaxy, earlier maturation/earlier fruit finish, homogenous ripening, increased duration of grain filling, better fruit finish, bigger fruit/vegetable size, sprouting resistance and reduced lodging.

Increased or improved yield is referring to total biomass per hectare, yield per hectare, kernel/fruit weight, seed size and/or hectolitre weight as well as to improved product quality, comprising:

improved processability relating to size distribution (kernel, fruit, etc.), homogenous ripening, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

- further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;
- further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;
- and further comprising decreased undesired ingredients such as e.g. less mycotoxins, less aflatoxines, geosmin level, phenolic aromas, lacchase, polyphenol oxidases and peroxidases, nitrate content etc.

Plant growth-regulating compounds can be used, for example, to slow down the vegetative growth of the plants. Such growth depression is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, vegetative growth depression allows denser planting, and it is thus possible to achieve higher yields based on the soil surface. Another advantage of the smaller plants obtained in this way is that the crop is easier to cultivate and harvest.

Reduction of the vegetative plant growth may also lead to increased or improved yields because the nutrients and assimilates are of more benefit to flower and fruit formation than to the vegetative parts of the plants.

Alternatively, growth regulators can also be used to promote vegetative growth. This is of great benefit when harvesting the vegetative plant parts. However, promoting vegetative growth may also promote generative growth in that more assimilates are formed, resulting in more or larger fruits.

Furthermore, beneficial effects on growth or yield can be achieved through improved nutrient use efficiency, especially nitrogen (N)-use efficiency, phosphorus (P)-use efficiency, water use efficiency, improved transpiration, respiration and/or $CO_2$ assimilation rate, better nodulation, improved Ca-metabolism etc.

Likewise, growth regulators can be used to alter the composition of the plants, which in turn may result in an improvement in quality of the harvested products. Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Furthermore, growth regulators can modulate plant senescence, which may result in prolonged green leaf area duration, a longer grain filling phase, improved yield quality, etc.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"). In addition, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to synchronize maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

The compounds of the formula (I) also exhibit a potent strengthening effect in plants. Accordingly, they can be used for mobilizing the defences of the plant against attack by undesirable microorganisms.

Plant-strengthening (resistance-inducing) substances in the present context are substances capable of stimulating the defence system of plants in such a way that the treated plants, when subsequently inoculated with undesirable microorganisms, develop a high degree of resistance to these microorganisms.

Further, in context with the present invention plant physiology effects comprise the following: Abiotic stress tolerance, comprising tolerance to high or low temperatures, drought tolerance and recovery after drought stress, water use efficiency (correlating to reduced water consumption), flood tolerance, ozone stress and UV tolerance, tolerance towards chemicals like heavy metals, salts, pesticides etc.

Biotic stress tolerance comprising increased fungal resistance and increased resistance against nematodes, viruses and bacteria. In context with the present invention, biotic stress tolerance preferably comprises increased fungal resistance and increased resistance against nematodes.

Increased plant vigor, comprising plant health/plant quality and seed vigor, reduced stand failure, improved appearance, increased recovery after periods of stress, improved pigmentation (e.g. chlorophyll content, stay-green effects, etc.) and improved photosynthetic efficiency.

In addition, the compounds of the formula (I) can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

The compounds of the formula (I) can also be used in the protection of materials, for protection of industrial materials against attack and destruction by phytopathogenic fungi.

In addition, the compounds of the formula (I) can be used as antifouling compositions, alone or in combinations with other active ingredients.

Industrial materials in the present context are understood to mean inanimate materials which have been prepared for use in industry. For example, industrial materials which are to be protected by inventive compositions from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compounds of the formula (I) may prevent adverse effects, such as rotting, decay, discoloration, decoloration or formation of mould.

In the case of treatment of wood the compounds of the formula (I) may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition according to the invention; this includes for example direct application, spraying, dipping, injection or any other suitable means.

In addition, the compounds of the formula (I) can be used to protect objects which come into contact with saltwater or brackish water, especially hulls, screens, nets, buildings, moorings and signalling systems, from fouling.

The compounds of the formula (I) can also be employed for protecting storage goods. Storage goods are understood to mean natural substances of vegetable or animal origin or processed products thereof which are of natural origin, and for which long-term protection is desired.

Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive compositions may prevent adverse effects, such as rotting, decay, discoloration, decoloration or formation of mould.

Microorganisms capable of degrading or altering the industrial materials include, for example, bacteria, fungi, yeasts, algae and slime organisms. The compounds of the formula (I) preferably act against fungi, especially moulds, wood-discoloring and wood-destroying fungi (*Ascomycetes, Basidiomycetes, Deuteromycetes* and *Zygomycetes*), and against slime organisms and algae. Examples include microorganisms of the following genera: *Alternaria*, such as *Alternaria* tennis; *Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Setpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae.*

In addition, the compounds of the formula (I) also have very good antimycotic effects. They have a very broad antimycotic activity spectrum, especially against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The enumeration of these fungi by no means constitutes a restriction of the mycotic spectrum covered, and is merely of illustrative character.

The compounds can also be used to control important fungal pathogens in fish and crustacea farming, e.g. *Saprolegnia diclina* in trouts, *Saprolegnia parasitica* in crayfish.

The compounds of the formula (I) can therefore be used both in medical and non-medical applications.

The compounds of the formula (I) can be used as such, in the form of their formulations or the use forms prepared therefrom, such as ready-to-use solutions, suspensions, wettable powders, pastes, soluble powders, dusts and granules. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

It is possible to treat all plants and their parts in accordance with the invention, preferably with wild plant species and plant cultivars, or those obtained by conventional biological breeding methods, such as crossing or protoplast fusion, and also parts thereof. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as tobacco plants, with altered post-translational protein modification patterns.

The compounds of the present invention not only control undesired phytopathogenic microorganisms effectively but also show positive crop response such as plant growth enhancement effects like enhanced crop vigor, enhanced root growth, enhanced tolerant to drought, high salt, high temperature, chill, frost or light radiation, improved flowering, efficient water and nutrient utilization (such as improved nitrogen assimilation), enhanced quality plant product, more number of productive tillers, enhanced resistance to fungi, insects, pests and the like, which results in higher yields.

In one embodiment, the compounds of general formula (I) as disclosed in the present invention are used for the nonagronomic applications.

CHEMISTRY EXAMPLES

The following examples set forth the manner and process of making compounds of the present invention without being a limitation thereof and include the best mode contemplated by the inventors for carrying out the invention.

Example 1: Synthesis of 3-bromo Amidine Intermediates (III)

a) N'-(3-bromo-2,5-dimethylphenyl)-N-ethyl-N-methylformimidamide (III)

Step 1: Preparation of 3-bromo-2,5-dimethylbenzoic Acid (XXIV)

A mixture of 2,5-dimethylbenzoic acid (2 g, 13.3 mmol) and sulfuric acid (20 mL) was cooled to 0° C., N-bromosuccinimide (2.4 g, 13.3 mmol) was added to the reaction mixture and stirred at 0° C. for 1.5 h. After completion of the reaction, the reaction mixture was poured onto the crushed ice and extracted with ethyl acetate (50 mL). The ethyl acetate layer was washed with brine solution, dried over anhydrous sodium sulfate and evaporated under reduced pressure. The crude product was purified by column chromatography using 50% ethyl acetate in hexane as an eluent to obtain 3-bromo-2,5-dimethylbenzoic acid (1.6 g, 52% yield), LCMS (M−1): 229.00.

Step 2: Preparation of tert-butyl (3-bromo-2,5-dimethylphenyl)carbamate

A reaction mixture of 3-bromo-2,5-dimethylbenzoic acid (1 g, 4.3 mmol), triethylamine (1.5 mL, 10.9 mmol) and diphenylphosphoryl azide (1.8 g, 6.5 mmol) in anhydrous tert-butanol was heated at 80° C. for 6 h. After completion of the reaction, the reaction mixture was poured onto the crushed ice and extracted with ethyl acetate (50 mL). The ethyl acetate layer was washed with brine solution, dried over anhydrous sodium sulfate and evaporated under reduced pressure. The crude product was purified by column chromatography using 50% ethyl acetate in hexane as an eluent to obtain tert-butyl (3-bromo-2,5-dimethylphenyl) carbamate (0.9 g, 69% yield).

Step 3: Preparation of 3-bromo-2,5-dimethylaniline (XXIII)

To a solution of tert-butyl (3-bromo-2,5-dimethylphenyl) carbamate (1 g, 3.3 mmol) in dichloromethane (20 mL), trifluoroacetic acid (10 mL, 130 mmol) was added dropwise at 0° C. The reaction mixture was stirred at 25° C. for 6 h. After completion of the reaction, the reaction mixture was concentrated under reduced pressure. The crude residue was dissolved in dichloromethane (30 mL) and washed twice with saturated sodium bicarbonate solution (10 mL). The organic layer was separated, washed with brine solution then dried over anhydrous sodium sulfate and evaporated under reduced pressure. The crude product was purified by column chromatography using 50% ethyl acetate as an eluent to obtain 3-bromo-2,5-dimethylaniline (0.45 g, 2.2 mmol, 67% yield). $^1$H-NMR (400 MHz, DMSO-$d_6$) δ 6.59 (s, 1H), 6.42 (s, 1H), 5.10 (s, 2H), 2.11 (s, 3H), 2.09 (s, 3H).

Step 4: Preparation of N'-(3-bromo-2,5-dimethylphenyl)-N-ethyl-N-methylformimidamide (III)

To a stirred solution of 3-bromo-2,5-dimethylaniline (1.00 g, 5.0 mmol) in trimethyl orthoformate (15 mL), anhydrous p-toluenesulfonic acid monohydrate (0.05 g, 0.2 mmol) was added and the resulting reaction mixture was refluxed at 105° C. for 4 h. After completion of the reaction, the solvent was evaporated under reduced pressure. The crude product was dissolved in 1,4-dioxane (50 mL) under nitrogen atmosphere, followed by the addition of N-ethylmethylamine (0.9 mL, 10 mmol). The resulting reaction mixture was refluxed at 80° C. for 3 h. After completion of the reaction, the reaction mixture was concentrated under reduced pressure. The crude product was purified by column chromatography using 7% ethyl acetate in hexane as an eluent to obtain N'-(3-bromo-2,5-dimethylphenyl)-N-ethyl-N-methylformimidamide (1 g, 3.5 mmol, 71% yield). $^1$H-NMR (400 MHz, DMSO-$d_6$) δ 7.62 (brs, 1H), 6.96 (s, 1H), 6.59 (s, 1H), 3.40-3.31 (m, 2H), 2.91 (s, 3H), 2.22 (s, 3H), 2.18 (s, 3H), 1.11 (t, 3H); LCMS (M+1): 270.90.

b) N'-(3-bromo-5-fluoro-2-methylphenyl)-N-ethyl-N-methylformimidamide

Step 1: preparation of 1-bromo-5-fluoro-2-methyl-3-nitrobenzene

To a solution of 4-fluoro-1-methyl-2-nitrobenzene (2.00 g, 12.9 mmol) in trifluoroacetic acid (10 mL), sulfuric acid (3 mL) was added at 0° C. followed by N-bromosuccinimide (2.4 g, 13.3 mmol) was added to the reaction mixture and the reaction mixture was stirred at 0° C. for 1.5 h. After completion of the reaction, the reaction mixture was poured over crushed ice and extracted with ethyl acetate (50 mL). The ethyl acetate layer was washed with brine solution, dried over anhydrous sodium sulfate and evaporated under reduced pressure. The crude product was purified by column chromatography using 10% ethyl acetate in hexane as an eluent to obtain 1-bromo-5-fluoro-2-methyl-3-nitrobenzene (2.2 g, 9.4 mmol, 73% yield) as yellow liquid. $^1$H-NMR (400 MHz, $CDCl_3$) δ 7.57 (dd, 1H), 7.50 (dd, 1H), 2.52 (s, 3H); GCMS: 234.9.

Step 2: Preparation of 3-bromo-5-fluoro-2-methylaniline

To a stirred solution of 1-bromo-5-fluoro-2-methyl-3-nitrobenzene (1.0 g, 4.3 mmol) in aqueous ethanol (15 mL, 2:1), iron powder (1.7 g, 29.9 mmol) and ammonium chloride (1.1 g, 21.3 mmol) were added. The reaction mixture was heated at 80° C. for 2 h. After completion of the reaction, the reaction mixture was cooled to 25° C., filtered through celite bed and thoroughly washed with ethyl acetate. The combined filtrate was evaporated under reduced pressure. The crude product was neutralised with saturated aqueous sodium bicarbonate solution (25 mL) and extracted thrice with ethyl acetate (50 mL). The combined ethyl acetate layers were washed with water, brine solution and dried over anhydrous sodium sulfate, evaporated under reduced pressure to obtain the crude product, which was purified by column chromatography using 10% ethyl acetate in hexane as an eluent to obtain 3-bromo-5-fluoro-2-methylaniline (0.8 g, 3.8 mmol, 89% yield); GCMS: 202.9.

Step 3: Preparation of N'-(3-bromo-5-fluoro-2-methylphenyl)-N-ethyl-N-methylformimidamide To a stirred solution of 3-bromo-5-fluoro-2-methylaniline (1.0 g, 4.9 mmol) in 1,4-dioxane (10 mL), p-toluenesulfonic acid monohydrate (0.05 g, 0.2 mmol) and N-(dimethoxymethyl)-N-methylethanamine (1.6 g, 12.3 mmol) were added and the resulting reaction mixture was refluxed at 105° C. for 4 h. After completion of the reaction, the reaction mixture was concentrated under reduced pressure. The crude product was purified by column chromatography using 7% ethyl acetate in hexane as an eluent to obtain N'-(3-bromo-5-fluoro-2-methylphenyl)-N-ethyl-N-methylformimidamide (1 g, 3.5 mmol, 72% yield) as a brown liquid. $^1$H-NMR (400 MHz, DMSO-$d_6$) δ 7.75 (s, 1H), 7.01 (dd, 1H), 6.74-6.71 (m, 1H), 3.44-3.31 (m, 2H), 2.92 (s, 3H), 2.24 (s, 3H), 1.14-1.09 (m, 3H); LCMS (M+1): 274.80.

c) N'-(3-bromo-2-chloro-5-methylphenyl)-N-ethyl-N-methylformimidamide

Step 1: Preparation of 1-bromo-2-chloro-5-methyl-3-nitrobenzene

To a stirred mixture of 2-bromo-4-methyl-6-nitroaniline (2.0 g, 8.7 mmol), copper(I) chloride (1.7 g, 17.3 mmol) in acetonitrile (20 mL), tert-butyl nitrite (2.7 g, 26 mmol) was added dropwise at 0° C. After the completion of addition, the reaction mixture was allowed to stir at 25° C. for 1 h. After completion of the reaction, the reaction mixture was filtered through celite bed, washed with acetonitrile. The filtrate was concentrated under reduce pressure. The crude product was dissolved in ethyl acetate (50 mL), washed with aqueous ammonium chloride solution, brine solution and dried over anhydrous sodium sulphate. The solvent was evaporated under reduced pressure to obtain the crude product which was purified by column chromatography using 10% ethyl acetate as an eluent to obtain 1-bromo-2-chloro-5-methyl-3-nitrobenzene (1.6 g, 6.6 mmol, 76% yield). $^1$H-NMR (400 MHz, DMSO-$d_6$) δ 8.02-7.97 (1H), 7.94-7.90 (1H), 2.40-2.37 (3H); GCMS: 252.80.

Step 2: Preparation of 3-bromo-2-chloro-5-methylaniline

To a stirred solution of 1-bromo-2-chloro-5-methyl-3-nitrobenzene (1.00 g, 4 mmol) in aqueous ethanol (15 mL, 2:1), iron powder (1.6 g, 27.9 mmol) and ammonium chloride (1.1 g, 20 mmol) were added. The reaction mixture was heated at 80° C. for 2 h. After completion of the reaction, the reaction mixture was cooled to 25° C., filtered through celite bed and thoroughly washed with ethyl acetate. The combined filtrate was evaporated under reduced pressure. The crude product was neutralized with saturated aqueous sodium bicarbonate solution and extracted three times with ethyl acetate (50 mL). The combined organic layers were washed with water, brine solution, dried over anhydrous sodium sulfate, filtered and evaporated under reduced pressure to obtain the crude product, which was purified by column chromatography using 10% ethyl acetate as an eluent to obtain 3-bromo-2-chloro-5-methylaniline (0.8 g, 3.5 mmol, 89% yield) as a brown liquid. $^1$H-NMR (400 MHz, DMSO-$d_6$) δ 6.73-6.71 (m, 1H), 6.59-6.57 (m, 1H), 5.57 (s, 2H), 2.15 (s, 3H); LCMS (M+1): 222.00.

Step 3: Preparation of N'-(3-bromo-2-chloro-5-methylphenyl)-N-ethyl-N-methylformimidamide To a stirred solution of 3-bromo-2-chloro-5-methylaniline (1.0 g, 4.5 mmol) in 1,4-dioxane (10 mL), anhydrous p-toluenesulfonic acid monohydrate (0.04 g, 0.2 mmol) and N-(dimethoxymethyl)-N-methylethanamine (1.5 g, 11.3 mmol) were added and the resulting mixture was refluxed at 105° C. for 4 h. After completion of the reaction, the reaction mixture was concentrated under reduced pressure. The crude product was purified by column chromatography using 7% ethyl acetate in hexane as an eluent to obtain N'-(3-bromo-2-chloro-5-methylphenyl)-N-ethyl-N-methylformimidamide (0.9 g, 3.3 mmol, 73% yield) as a brown liquid. $^1$H-NMR (400 MHz, DMSO-$d_6$) δ 7.74 (s, 1H), 7.13-7.11 (m, 1H), 6.84-6.78 (m, 1H), 3.47-3.31 (m, 2H), 2.94 (s, 3H), 2.23 (s, 3H), 1.16-1.12 (m, 3H); LCMS (M+1): 290.80.

Example 2: Preparation of N'-(3-benzyl-2,5-dimethylphenyl)-N-ethyl-N-methylformimidamide a) Preparation of N'-(2,5-dimethyl-3-(4,4,5,5-tetramethyl-1,3,2-dioxaborolan-2-yl)phenyl)-N-ethyl-N-methylformimidamide A stirred mixture of N'-(3-bromo-2,5-dimethylphenyl)-N-ethyl-N-methylformimidamide (1.0 g, 3.7 mmol), bis(pinacol)diboron (1.9 g, 7.4 mmol), [1,1'-Bis(diphenylphosphino) ferrocene] dichloropalladium(II) dichloromethane [$PdCl_2$(dppf)-$CH_2Cl_2$] (0.2 g, 0.2 mmol) and potassium acetate (0.7 g, 7.4 mmol) in 1,4-dioxane (30 mL) was degassed for 5 min with nitrogen. The reaction mixture was stirred at 95° C. for 16 h under nitrogen atmosphere. After completion of the reaction, the reaction mixture was diluted with dichloromethane, filtered through celite bed, residue was washed with dichloromethane (100 mL). The combined filtrate was washed with brine solution, dried over anhydrous sodium sulfate. The volatiles were removed under reduced pressure. The crude product was purified by column chromatography using 10% ethyl acetate in hexane as an eluent to obtain N'-(2,5-dimethyl-3-(4,4,5,5-tetramethyl-1,3,2-dioxaborolan-2-yl)phenyl)-N-ethyl-N-methylformimidamide (0.8 g, 70% yield).

b) Preparation of N'-(3-benzyl-2,5-dimethylphenyl)-N-ethyl-N-methylformimidamide A mixture of N'-(2,5-dimethyl-3-(4,4,5,5-tetramethyl-1,3,2-dioxaborolan-2-yl)phenyl)-N-ethyl-N-methylformimidamide (0.5 g, 1.6 mmol), (bromomethyl)benzene (0.3 g, 1.6 mmol), $Pd(Ph_3p)_4$ [tetrakis(triphenylphosphine)palladium (0)] (0.09 g, 0.08 mmol) and potassium carbonate (0.5 g, 3.9 mmol) in dioxane:water (12 mL, 8:2) was degassed with nitrogen. The reaction mixture was stirred at 100° C. for 4 h under nitrogen atmosphere. After completion of the reaction, the reaction mixture was cooled to 25° C., filtered through celite bed. The filtrate was diluted with ethyl acetae and washed with brine, dried over anhydrous sodium sulfate and the solvent was removed under reduced pressure. The crude product was purified by column chromatography using 7% ethyl acetate in hexane as an eluent to obtain N'-(3-benzyl-2,5-dimethylphenyl)-N-ethyl-N-methylformimidamide (0.4 g, 63% yield).

Example 3: Preparation of N-ethyl-N'-(3-(3-fluorobenzyl)-2,5-dimethylphenyl)-N-methylformimidamide a) Preparation of 4-methyl-2-nitro-6-(4,4,5,5-tetramethyl-1,3,2-dioxaborolan-2-yl)aniline A stirred mixture of 2-bromo-4-methyl-6-nitroaniline (2.00 g, 8.7 mmol), bis(pinacol)diboron (4.4 g, 17.3 mmol), [1,1'-Bis(diphenylphosphino)ferrocene]dichloropalladium (II) dichloromethane [$PdCl_2$(dppf)-$CH_2Cl_2$] (0.35 g, 0.4 mmol) and potassium acetate (2.1 g, 21.6 mmol) in 1,4-dioxane (30 mL) was degassed with nitrogen. The reaction mixture was stirred at 95° C. for 16 h under nitrogen atmosphere. After completion of the reaction, the reaction mixture was diluted with dichloromethane filtered through celite bed, the residue was washed with dichloromethane (100 mL). The combined filtrate was washed with brine solution, dried over anhydrous sodium sulfate and the solvent was removed under reduced pressure. The crude product was purified by column chromatography using 10% ethyl acetate in hexane to obtain 4-methyl-2-nitro-6-(4,4,5,5-tetramethyl-1,3,2-dioxaborolan-2-yl)aniline (2. g, 7.3 mmol, 85% yield) as yellow solid. $^1$H-NMR (400 MHz, DMSO-$d_6$) δ 7.97 (d, 1H), 7.65 (d, 1H), 7.30 (s, 2H), 2.21 (s, 3H), 1.33 (s, 12H); GCMS: 278.2.

b) Preparation of 2-(3-fluorobenzyl)-4-methyl-6-nitroaniline

A mixture of 4-methyl-2-nitro-6-(4,4,5,5-tetramethyl-1,3,2-dioxaborolan-2-yl)aniline (2.0 g, 7.2 mmol), 1-(bromomethyl)-3-fluorobenzene (1.4 g, 7.2 mmol), tetrakis(triphenylphosphine)palladium(0) [$Pd(Ph_3P)_4$] (0.42 g, 0.4 mmol) and potassium carbonate (2.5 g, 17.9 mmol) in dioxane:water (35 mL, 8:2) was degassed with nitrogen. The reaction mixture was stirred at 100° C. for 4 h under nitrogen atmosphere. After completion of the reaction, the reaction mixture was cooled to 25° C., filtered through celite bed. The filtrate was diluted with ethyl acetate (200 mL) and washed with brine solution, dried over anhydrous sodium sulfate and the solvent was removed under reduced pressure. The crude product was purified by column chromatography using 10% ethyl acetate in hexane as an eluent to obtain 2-(3-fluorobenzyl)-4-methyl-6-nitroaniline (1.4 g, 5.2 mmol, 73% yield) as a yellow solid. $^1$H-NMR (400 MHz, DMSO-$d_6$) δ 7.74 (d, 1H), 7.35-7.29 (m, 1H), 7.14 (d, 1H), 7.09-7.00 (m, 3H), 3.98 (s, 2H), 2.16 (s, 3H); GCMS: 260.1.

c) Preparation of 2-bromo-1-(3-fluorobenzyl)-5-methyl-3-nitrobenzene

To a stirred mixture of 2-(3-fluorobenzyl)-4-methyl-6-nitroaniline (2.0 g, 8.3 mmol) copper(I) bromide (2.2 g, 15.4 mmol) in acetonitrile (20 mL), tert-butyl nitrite (2.4 g, 23.0 mmol) was added dropwise at 0° C. After complete addition, reaction mixture was allowed to stir at 25° C. for 1 h. After completion of the reaction, the reaction mixture was filtered through celite bed, washed with acetonitrile. The filtrate was concentrated under reduce pressure. The crude product was dissolved in ethyl acetate (50 mL), washed with aqueous ammonium chloride solution, brine solution and dried over anhydrous sodium sulphate. The solvent was removed under reduced pressure to obtain the crude product which was purified by column chromatography using 10% ethyl acetate in hexane as an eluent to obtain 2-bromo-1-(3-fluorobenzyl)-5-methyl-3-nitrobenzene (1.8 g, 5.5 mmol, 71% yield) as a yellow solid. $^1$H-NMR (400 MHz, DMSO-$d_6$) δ 7.68 (d, 1H), 7.49 (d, 1H), 7.37-7.31 (m, 1H), 7.07-7.01 (m, 3H), 4.17 (s, 2H), 2.32 (s, 3H); GCMS: 324.9.

d) Preparation of 3-(3-fluorobenzyl)-2,5-dimethylaniline

A mixture of 2-bromo-1-(3-fluorobenzyl)-5-methyl-3-nitrobenzene (2.0 g, 6.2 mmol), methylboronic acid (0.7 g, 12.3 mmol), $PdCl_2$(dppf)-$CH_2Cl_2$ adduct (0.5 g, 0.6 mmol) and potassium phosphate tribasic (3.3 g, 15.4 mmol) in dioxane:water (35 mL, 8:2) was degassed with nitrogen. The reaction mixture was stirred at 100° C. for 4 h under nitrogen atmosphere. After completion of the reaction, the reaction mixture was cooled to 25° C., filtered through celite bed. The filtrate was diluted with ethyl acetate (200 mL) and washed with brine solution, dried over anhydrous sodium sulfate and the solvent was removed under reduced pressure. The crude product was purified by column chromatography using 10% ethyl acetate in hexane as an eluent to obtain 1-(3-fluorobenzyl)-2,5-dimethyl-3-nitrobenzene (1.4 g, 5.5 mmol, 89% yield) as a yellow solid. $^1$H-NMR (400 MHz, DMSO-$d_6$) δ 7.55 (s, 1H), 7.36-7.30 (m, 2H), 7.05-7.00 (m, 1H), 6.96 (d, 2H), 4.08 (s, 2H), 2.32 (s, 3H), 2.18 (s, 3H); GCMS: 259.1.

e) Preparation of 3-(3-fluorobenzyl)-2,5-dimethylaniline

To a stirred solution of 1-(3-fluorobenzyl)-2,5-dimethyl-3-nitrobenzene (1 g, 3.8 mmol) in aqueous ethanol (15 mL, 2:1), iron powder (1.0 g, 19.2 mmol) and ammonium chloride (1.4 g, 27.0 mmol) were added. The reaction mixture was heated at 80° C. for 2 h. After completion of the reaction, the reaction mixture was cooled to 25° C., filtered through celite bed and thoroughly washed with ethyl acetate. The combined filtrate was evaporated under reduced pressure. The crude product was diluted with saturated aqueous sodium bicarbonate solution and extracted three times with ethyl acetate (50 mL). The combined organic layers were washed with water, brine, dried over anhydrous sodium sulfate, filtered and evaporated under reduced pressure to obtain a crude product, which was purified by column chromatography using 10% ethyl acetate in hexane as an eluent to obtain 3-(3-fluorobenzyl)-2,5-dimethylaniline (0.8 g, 3.4 mmol, 89% yield) as a brown liquid. $^1$H-NMR (400 MHz, DMSO-$d_6$) δ 7.32-7.27 (m, 1H), 7.00-6.95 (m, 2H), 6.88 (d, 1H), 6.38 (s, 1H), 6.26 (s, 1H), 4.69 (s, 2H), 3.86 (s, 2H), 2.12 (s, 3H), 1.85 (s, 3H); GCMS: 229.1.

f) Preparation of N-ethyl-N'-(3-(3-fluorobenzyl)-2,5-dimethylphenyl)-N-methylformimidamide To a stirred solution of 3-(3-fluorobenzyl)-2,5-dimethylaniline (1.0 g, 4.3 mmol) in 1,4-dioxane (10 ml), anhydrous p-toluenesulfonic acid monohydrate (0.04 g, 0.2 mmol) and N-(dimethoxymethyl)-N-methylethanamine (0.6 g, 4.3 mmol) were added and the resulting mixture was refluxed at 105° C. for 4 h. After completion of the reaction, the reaction mixture was concentrated under reduced pressure. The crude product was purified by column chromatography using 7% ethyl acetate in hexane as an eluent to obtain N-ethyl-N'-(3-(3-fluorobenzyl)-2,5-dimethylphenyl)-N-methylformimidamide (0.9 g, 3.1 mmol, 70% yield) as a brown liquid. $^1$H-NMR (400 MHz, DMSO-$d_6$) δ 7.57 (brs, 1H), 7.33-7.27 (m, 1H), 7.01-6.95 (m, 2H), 6.91-6.87 (m, 1H), 6.61 (s, 1H), 6.50 (s, 1H), 3.91 (s, 2H), 3.41-3.33 (m, 2H), 2.92 (s, 3H), 2.20 (s 3H), 2.04 (s, 3H), 1.12 (t, 3H); LCMS (M+1): 299.15.

Example 4: Preparation of N-ethyl-N'-(5-fluoro-2-methyl-3-(methyl(pyridin-2-yl)amino)phenyl)-N-methylformimidamide a) Preparation of 3-bromo-5-fluoro-2-methylaniline

To a stirred solution of 1-bromo-5-fluoro-2-methyl-3-nitrobenzene (10 g, 42.7 mmol) in aqueous ethanol (130 mL, 2:1), iron powder (23.9 g, 427 mmol) and ammonium chloride (22.9 g, 427 mmol) were added. The reaction mixture was heated at 80° C. for 2 h. After completion of the reaction, the reaction mixture was cooled to 25° C., filtered through celite bed and thoroughly washed with ethyl acetate (250 mL). The combined filtrate was evaporated under reduced pressure. The crude product was diluted with saturated aqueous sodium bicarbonate solution and extracted three times with ethyl acetate (150 mL). The combined organic layers were washed with water, brine solution, dried over anhydrous sodium sulfate, filtered and evaporated under reduced pressure to obtain the crude product, which was purified by column chromatography using 5% ethyl acetate in hexane as an eluent to obtain desired 3-bromo-5-fluoro-2-methylaniline (8 g, 39.0 mmol, 91% yield); GCMS: 202.9.

b) Preparation of N'-(3-bromo-5-fluoro-2-methylphenyl)-N-ethyl-N-methylformimidamide To a stirred solution of 3-bromo-5-fluoro-2-methylaniline (8 g, 39.2 mmol) in trimethyl orthoformate (50 mL), anhydrous p-toluenesulfonic acid monohydrate (0.75 g, 3.9 mmol) was added and the resulting mixture was refluxed at 105° C. for 4 h. After completion of the reaction, the reaction mixture was concentrated under reduced pressure. The crude product was dissolved in 1,4-dioxane (50 mL) under nitrogen atmosphere, followed by addition of N-ethylmethylamine (10.1 mL, 12 mmol). The resulting reaction mixture was refluxed at 80° C. for 3 h. After completion of the reaction, the reaction mixture was concentrated under reduced pressure. The crude product was purified by column chromatography using 7% ethyl acetate in hexane as an eluent to obtain N'-(3-bromo-5-fluoro-2-methylphenyl)-N-ethyl-N-methylformimidamide (8 g, 29.3 mmol, 75% yield). $^1$H-NMR (400 MHz, DMSO-$d_6$) δ 7.75-7.64 (m, 1H), 7.00 (dd, 1H), 6.77-6.71 (m, 1H), 3.46-3.33 (m, 2H), 3.01-2.92 (m, 3H), 2.25 (d, 3H), 1.13 (t, 3H); LCMS (M+1) 272.7.

c) Preparation of N-ethyl-N'-(5-fluoro-2-methyl-3-(pyridin-2-ylamino)phenyl)-N-methylformimidamide A stirred suspension of N'-(3-bromo-5-fluoro-2-methylphenyl)-N-ethyl-N-methylformimidamide (0.7 g, 2.5 mmol), pyridin-2-amine (0.3 g, 3.1 mmol), cesium carbonate (2.1 g, 6.4 mmol) in anhydrous toluene (10 mL) was degassed with nitrogen for 15 min. Palladium acetate (0.03 g, 0.1 mmol) and 2,2'-bis(diphenylphosphino)-1,1'-binaphthyl) (BINAP) (0.16 g, 0.3 mmol) were added and the reaction mixture was heated at 100° C. for 16 h under nitrogen atmosphere. After completion of the reaction, the reaction mixture was passed through celite, thoroughly washed with ethyl acetate (25 mL). The combined organic layers were washed twice with water (50 mL), once with brine solution (50 mL), dried over anhydrous sodium sulphate, filtered and concentrated under reduced pressure. The obtained crude product was purified by column chromatography using 40% ethyl acetate in hexane as an eluent to obtain N-ethyl-N'-(5-fluoro-2-methyl-3-(pyridin-2-ylamino)phenyl)-N-methylformimidamide (0.3 g, 1 mmol, 38% yield); LCMS: 286.95.

d) Preparation of N-ethyl-N'-(5-fluoro-2-methyl-3-(methyl(pyridin-2-yl)amino)phenyl)-N-methylformimidamide To a suspension of sodium hydride (0.06 g, 1.4 mmol) in N,N-dimethylformamide (5 mL) was added a solution of N-ethyl-N'-(5-fluoro-2-methyl-3-(pyridin-2-ylamino)phenyl)-N-methylformimidamide (0.2 g, 0.7 mmol) in N,N-dimethylformamide (3 mL) dropwise at 0-5° C. and the reaction mixture was allowed to stir for 15 min. After which methyl iodide (0.12 g, 1.4 mmol) was added dropwise and stirring was continued for 45 min. After completion of the reaction, the mixture was quenched in ice cold water, extracted two times with ethyl acetate (50 mL). The organic layer was washed twice with water (50 mL), followed by brine solution (50 mL), dried over anhydrous sodium sulphate, filtered and concentrated. The obtained crude product was purified by column chromatography using 10% ethyl acetate in hexane as an eluent to obtain N-ethyl-N'-(5-fluoro-2-methyl-3-(methyl(pyridin-2-yl)amino)phenyl)-N-methylformimidamide (0.16 g, 0.5 mmol, 74% yield); LCMS: 301.4.

Example 5: Synthesis of N'-(2-chloro-5-methyl-3-(methyl(pyridin-2-yl)amino)phenyl)-N-ethyl-N-methylformimidamide a) Preparation of 1-bromo-2-chloro-5-methyl-3-nitrobenzene To a solution of 2-bromo-4-methyl-6-nitroaniline (15 g, 64.9 mmol) in acetonitrile (150 mL), copper (I) chloride (9.6 g, 97 mmol) was added and the reaction mixture was stirred at 25° C. for 30 min. Then tert-butylnitrite (38.5 mL, 325 mmol) was added dropwise at 0° C. and the reaction mixture was slowly brought to 25° C. under continued stirring for 2 h. After completion of the reaction, the reaction mixture was quenched with aqueous ammonium chloride solution and extracted three times with ethyl acetate (200 mL). The combined organic layers were washed with brine solution (200 mL), dried over anhydrous sodium sulphate, filtered and concentrated under reduced pressure. The obtained crude product was purified by column chromatography using 10% ethyl acetate in hexane as an eluent to obtain 1-bromo-2-chloro-5-methyl-3-nitrobenzene (12 g, 48 mmol, 74% yield); GCMS: 251.0.

b) Preparation of 3-bromo-2-chloro-5-methylaniline

To a stirred solution of 1-bromo-2-chloro-5-methyl-3-nitrobenzene (13 g, 51.9 mmol) in aqueous ethanol (130 mL, 2:1), iron powder (29 g, 519 mmol) and ammonium chloride (27.8 g, 519 mmol) were added. The reaction mixture was heated at 80° C. for 2 h. After completion of the reaction, the reaction mixture was cooled to 25° C., filtered through celite bed and thoroughly washed with ethyl acetate. The combined filtrate was evaporated under reduced pressure. The crude product was diluted with saturated aqueous sodium bicarbonate solution and extracted three times with ethyl acetate (250 mL). The combined organic layers were washed with water, brine solution, dried over anhydrous sodium sulfate, filtered and evaporated under reduced pressure to obtain the crude product, which was purified by column chromatography using 10% ethyl acetate in hexane as an eluent to obtain 3-bromo-2-chloro-5-methylaniline (9.1 g, 41 mmol, 79% yield); GCMS: 220.9.

c) Preparation of N'-(3-bromo-2-chloro-5-methylphenyl)-N-ethyl-N-methylformimidamide To a stirred solution of 3-bromo-2-chloro-5-methylaniline (8.5 g, 38.5 mmol) in trimethyl orthoformate (50 mL), anhydrous p-toluenesulfonic acid monohydrate (0.7 g, 3.8 mmol) was added and the resulting mixture was refluxed at 105° C. for 4 h. After completion of the reaction, the reaction mixture was concentrated under reduced pressure. The crude product was dissolved in 1,4-dioxane (50 mL) under nitrogen atmosphere, followed by addition of N-ethylmethylamine (10.1 mL, 118 mmol). The resulting reaction mixture was refluxed at 80° C. for 3 h. After completion of the reaction, the reaction mixture was concentrated under reduced pressure. The crude product was purified by column chromatography using 7% ethyl acetate in hexane as an eluent to obtain N'-(3-bromo-2-chloro-5-methylphenyl)-N-ethyl-N-methylformimidamide (8.9 g, 31.4 mmol, 82% yield). $^1$H-NMR (400 MHz, DMSO-$d_6$) δ 7.74-7.63 (m, 1H), 7.12 (q, 1H), 6.80 (d, 1H), 3.47-3.30 (m, 4H), 3.03-2.94 (m, 3H), 2.22 (d, 3H), 1.15 (t, 3H); LCMS (M+1) 291.0.

d) Preparation of N'-(2-chloro-5-methyl-3-(pyridin-2-ylamino)phenyl)-N-ethyl-N-methylformimidamide A mixture of N'-(3-bromo-2-chloro-5-methylphenyl)-N-ethyl-N-methylformimidamide (0.7 g, 2.41 mmol), pyridin-2-amine (0.3 g, 3.1 mmol), cesium carbonate (2 g, 6.0 mmol) in anhydrous toluene (10 mL) was degassed with nitrogen. After which, palladium acetate (0.03 g, 0.1 mmol) and 2,2'-bis(diphenylphosphino)-1,1'-binaphthyl) (BINAP) (0.15 g, 0.2 mmol) were added and the reaction mixture was heated at 100° C. for 16 h under nitrogen atmosphere. After completion of the reaction, the reaction mixture was passed through celite and washed with ethyl acetate (50 mL). The combined organic layers were washed twice with water (50 mL), brine solution (50 mL), dried over anhydrous sodium sulphate, filtered and concentrated under reduced pressure. The obtained crude product was purified by column chromatography using 40% ethyl acetate in hexane as an eluent to obtain N'-(2-chloro-5-methyl-3-(pyridin-2-ylamino)phenyl)-N-ethyl-N-methylformimidamide (0.5 g, 40.8 mmol, 72% yield); LCMS: 303.4.

e) Preparation of N'-(2-chloro-5-methyl-3-(methyl(pyridin-2-yl)amino)phenyl)-N-ethyl-N-methylformimidamide To a suspension of sodium hydride (0.1 g, 1.7 mmol) in N,N-dimethylformamide (5 mL), a solution of N'-(2-chloro-5-methyl-3-(pyridin-2-ylamino)phenyl)-N-ethyl-N-methylformimidamide (0.3 g, 1.1 mmol) in N,N-dimethylformamide (3 mL) was added dropwise at 0-5° C. After stirring for 15 min, methyl iodide (0.2 g, 1.4 mmol) was added to the reaction mixture and stirring was continued for another 1 h. After completion of the reaction, the reaction mixture was quenched in ice-cold water, extracted twice with ethyl acetate (50 mL). The organic layer was washed twice with water (25 mL), brine solution (50 mL), dried over anhydrous sodium sulphate, filtered and concentrated under reduced pressure. The obtained crude product was purified by column chromatography using 10% ethyl acetate in hexane as an eluent to obtain N'-(2-chloro-5-methyl-3-(methyl(pyridin-2-yl)amino)phenyl)-N-ethyl-N-methylformimidamide (0.22 g, 0.7 mmol, 62% yield); LCMS: 317.40.

Example 6: Preparation of N'-(3-(2-(2-chloro-4-methoxyphenoxy)acetyl)-5-fluoro-2-methylphenyl)-N-ethyl-N-methylformimidamide a) Preparation of 2-chloro-N-methoxy-N-methylacetamide To a stirred solution of N,O-dimethylhydroxylamine hydrochloride (25 g, 256 mmol) in diethyl ether (50 mL) and water (50 mL), potassium carbonate (78 g, 564 mmol) was added followed by 2-chloroacetyl chloride (24.50 mL, 308 mmol). The reaction mixture was stirred at 25° C. for 16 h. After completion of the reaction, the reaction mixture was quenched with addition of water, mixture was extracted two times with 1,2-dichloromethane (250 mL). The combined organic layers were washed with water (100 mL), brine (100 mL), dried over sodium sulphate and evaporated under reduced pressure to obtain 2-chloro-N-methoxy-N-methylacetamide (25 g, 182 mmol, 71% yield).

b) Preparation of 2-(2-chloro-4-methoxyphenoxy)-N-methoxy-N-methylacetamide

To a stirred solution of 2-chloro-4-methoxyphenol (2.77 g, 17.45 mmol) in N,N-dimethylformamide (15 mL), potassium carbonate (4.02 g, 29.1 mmol) was added followed by addition of 2-chloro-N-methoxy-N-methylacetamide (2 g, 14.54 mmol) and the reaction mixture was stirred at 25° C. for 16 h. After completion of the reaction, the reaction mixture was quenched with ice water and extracted with three times with ethyl acetate (150 mL). The combined organic layers were washed with water, brine, dried over sodium sulphate and solvent was evaporated under reduced pressure to obtain 2-(2-chloro-4-methoxyphenoxy)-N-methoxy-N-methylacetamide (2.9 g, 11.17 mmol, 77% yield).

c) Preparation of N'-(3-(2-(2-chloro-4-methoxyphenoxy)acetyl)-5-fluoro-2-methylphenyl)-N-ethyl-N-methylformimidamide To a stirred solution of N'-(3-bromo-5-fluoro-2-methylphenyl)-N-ethyl-N-methylformimidamide (0.7 g, 2.56 mmol) in tetrahydrofuran (10 ml), n-butyl lithium (2.56 ml, 5.13 mmol) was added at −78° C. The reaction mixture was stirred at −78° C. for 1 h and then 2-(2-chloro-4-methoxyphenoxy)-N-methoxy-N-methylacetamide (0.799 g, 3.08 mmol) was added and the reaction mixture was allowed to stirred for 1 h at −78° C. After completion of the reaction, the reaction mixture was quenched with aqueous ammonium chloride and extracted three times with ethyl acetate (75 mL). The combined organic layers were washed with water (50 mL), brine and dried over anhydrous sodium sulphate; solvent was evaporated under reduced pressure. The crude product was further purified by prep. high-performance liquid chromatography to obtain N'-(3-(2-(2-chloro-4-methoxyphenoxy)acetyl)-5-fluoro-2-methylphenyl)-N-ethyl-N-methylformimidamide (0.116 g, 0.295 mmol, 11% yield).

Example 7: Preparation of N'-(2-chloro-5-methyl-3-((2-(trifluoromethyl)benzyl)amino)phenyl)-N-ethyl-N-methylformimidamide A stirred suspension of N'-(3-bromo-2-chloro-5-methylphenyl)-N-ethyl-N-methylformimidamide (0.7 g, 2.417 mmol), (2-(trifluoromethyl)phenyl)methanamine (0.441 mL, 3.14 mmol) and cesium carbonate (1.969 g, 6.04 mmol) in anhydrous toluene (10 mL) was degassed with nitrogen for 15 min. To this reaction mixture palladium acetate (0.027 g, 0.121 mmol) and 2,2'-bis(diphenylphosphino)-1,1'-binaphthyl) (BINAP) (0.151 g, 0.242 mmol) were added and the reaction mixture was heated at 100° C. for 16 h under nitrogen atmosphere. After completion of the reaction, the reaction mixture was passed through celite, thoroughly washed with ethyl acetate (25 mL). The combined organic layers were washed twice with water (50 mL), once with brine solution (50 mL), dried over anhydrous sodium sulphate, filtered and concentrated under reduced pressure. The obtained crude product was purified by column chromatography using 40% ethyl acetate in hexane as an eluent to obtain N'-(2-chloro-5-methyl-3-((2-(trifluoromethyl) benzyl)amino)phenyl)-N-ethyl-N-methylformimidamide (0.16 g, 0.417 mmol, 17% yield).

The following compounds in Table-I were obtained using analogous procedures as described in the schemes 1-21 or in the examples.

TABLE I

| Sr. No. | IUPAC Name | Analytical Data |
|---|---|---|
| 1 | N'-(2-chloro-5-methyl-3-(p-tolylamino)phenyl)-N-ethyl-N-methylformimidamide | $^1$H-NMR (400 MHz, DMSO-d6) δ 7.68 (s, 1H), 7.12 (s, 1H), 6.99-6.96 (m, 3H), 6.81 (s, 1H), 6.67 (d, 2H), 3.39-3.31 (m, 2H), 2.90 (s, 3H), 2.18 (s, 3H), 2.09 (s, 3H), 1.12 (t, 3H); LCMS (M + 1): 316.20 |
| 2 | N'-(2,5-dimethyl-3-(4-methylbenzyl)phenyl)-N-ethyl-N-methylformimidamide | $^1$H-NMR (400 MHz, DMSO-d6) δ 7.53 (brs, 1H), 7.05 (d, 2H), 6.97 (d, 2H), 6.55 (s, 1H), 6.44 (s, 1H), 3.81 (s, 2H), 3.35-3.28 (m, 2H), 2.89 (s, 3H), 2.23 (s, 3H), 2.16 (s, 3H), 2.02 (s, 3H), 1.09 (t, 3H); LCMS (M + 1): 295.40 |
| 3 | N'-(3-(3-chlorobenzyl)-2,5-dimethylphenyl)-N-ethyl-N-methylformimidamide | $^1$H-NMR (400 MHz, DMSO-d6) δ 7.56 (brs, 1H), 7.35-7.26 (m, 1H), 7.22-7.20 (m, 1H), 7.11 (s, 1H), 7.07 (d, 1H), 6.59 (s, 1H), 6.48 (s, 1H), 3.89 (s, 2H), 3.43-3.31 (m, 1H), 2.89 (s, 3H), 2.18 (s, 3H), 2.01 (s, 3H), 1.10 (t, 3H); LCMS (M + 1): 315.15 |
| 4 | N'-(2,5-dimethyl-3-(2-methylbenzyl)phenyl)-N-ethyl-N-methylformimidamide | $^1$H-NMR (400 MHz, DMSO-d6) δ 7.60 (s, 1H), 7.18 (d, 1H), 7.12-7.05 (m, 2H), 6.80-6.78 (m, 1H), 6.48 (s, 1H), 6.35 (s, 1H), 3.81 (s, 2H), 3.43-3.34 (m, 2H), 2.93 (s, 3H), 2.24 (s, 3H), 2.14 (s, 3H), 2.05 (s, 3H), 1.13 (t, 3H); LCMS (M + 1): 295.65 |

TABLE I-continued

| Sr. No. | IUPAC Name | Analytical Data |
|---|---|---|
| 5 | N-ethyl-N'-(3-(3-fluorobenzyl)-2,5-dimethylphenyl)-N-methylformimidamide | $^1$H-NMR (400 MHz, DMSO-d6) δ 7.57 (brs, 1H), 7.33-7.27 (m, 1H), 7.01-6.95 (m, 2H), 6.91-6.87 (m, 1H), 6.61 (s, 1H), 6.50 (s, 1H), 3.91 (s, 2H), 3.41-3.33 (m, 2H), 2.92 (s, 3H), 2.20 (s 3H), 2.04 (s, 3H), 1.12 (t, 3H); LCMS (M + 1): 299.15 |
| 6 | N-ethyl-N'-(3-((2-fluorophenyl)amino)-2,5-dimethylphenyl)-N-methylformimidamide | $^1$H-NMR (400 MHz, DMSO-d6) δ 7.74-7.41 (m, 1H), 7.14-7.09 (m, 1H), 7.03 (s, 1H), 6.97-6.93 (m, 1H), 6.76-6.71 (m, 1H), 6.67-6.63 (m, 1H), 6.47 (s, 1H), 6.37 (s, 1H), 3.41-3.34 (m, 2H), 2.93 (s, 3H), 2.17 (s, 3H), 2.02 (s, 3H), 1.13 (t, 3H); LCMS (M + 1): 300.40 |
| 7 | N-ethyl-N'-(3-((2-fluorophenyl)(methyl)amino)-2,5-dimethylphenyl)-N-methylformimidamide | $^1$H-NMR (400 MHz, DMSO-d6) δ 7.63 (m, 1H), 7.16-7.01 (m, 2H), 6.89-6.82 (m, 2H), 6.44 (s, 2H), 3.59-3.32 (m, 2H), 3.07 (s, 3H), 2.92 (s, 3H), 2.16 (s, 3H), 1.96 (s, 3H), 1.15-1.07 (m, 3H); LCMS (M + 1): 315.15 |
| 8 | N-ethyl-N'-(5-fluoro-2-methyl-3-(phenylamino)phenyl)-N-methylformimidamide | $^1$H-NMR (400 MHz, DMSO-d6) δ 7.72 (s, 1H), 7.41 (s, 1H), 7.23-7.18 (m, 2H), 6.93 (dd, 2H), 6.81-6.77 (m, 1H), 6.50 (dd, 1H), 6.32 (d, 1H), 3.44-3.32 (m, 2H), 2.94 (s, 3H), 2.08 (s, 3H), 1.14 (t, 3H); LCMS (M + 1): 285.85 |
| 9 | N'-(2-chloro-5-methyl-3-(phenylamino)phenyl)-N-ethyl-N-methylformimidamide | $^1$H-NMR (400 MHz, DMSO-d6) δ 7.73 (s, 1H), 7.39 (s, 1H), 7.22 (dd, 2H), 7.05-7.03 (m, 2H), 6.84 (t, 1H), 6.70 (s, 1H), 6.38 (s, 1H), 3.45-3.33 (m, 2H), 2.94 (S, 3H), 2.16 (S, 3H), 1.18-1.13 (m, 3H); LCMS (M + 1): 302.05 |
| 10 | N'-(2-chloro-5-methyl-3-(methyl(phenyl)amino)phenyl)-N-ethyl-N-methylformimidamide | $^1$H-NMR (400 MHz, DMSO-d6) δ 7.75 (s, 1H), 7.18-7.10 (m, 2H), 6.76-6.71 (m, 2H), 6.65 (t, 1H), 6.50 (dd, 2H), 3.45-3.34 (m, 2H), 3.14 (s, 3H), 2.94 (s, 3H), 2.24 (s, 3H), 1.18-1.13 (m, 3H); LCMS (M + 1): 316.00 |
| 11 | N-ethyl-N'-(5-fluoro-2-methyl-3-(methyl(phenyl)amino)phenyl)-N-methylformimidamide | $^1$H-NMR (400 MHz, DMSO-d6) δ 7.78 (s, 1H), 7.16-7.12 (m, 2H), 6.68-6.64 (m, 2H), 6.56-6.49 (m, 3H), 3.43-3.34 (m, 2H), 3.14 (s, 3H), 2.93 (S, 3H), 1.91 (s, 3H), 1.15 (t, 3H); LCMS (M + 1): 300.05 |
| 12 | N'-(2-chloro-5-methyl-3-(2-methylbenzyl)phenyl)-N-ethyl-N-methylformimidamide | $^1$H-NMR (400 MHz, DMSO-d6) δ 7.71 (bs, 1H), 7.20-7.17 (m, 1H), 7.15-7.08 (m, 2H), 6.90-6.87 (m, 1H), 6.67 (s, 1H), 6.41 (d, 1H), 3.96 (s, 2H), 3.43-3.32 (m, 2H), 2.92 (s, 3H), 2.23 (s, 3H), 2.15 (s, 3H), 1.16-1.12 (m, 3H); LCMS (M + 1): 314.85 |
| 13 | N'-(2-chloro-3-(2-chlorobenzyl)-5-methylphenyl)-N-ethyl-N-methylformimidamide | $^1$H-NMR (400 MHz, DMSO-d6) δ 7.71 (bs, 1H), 7.49-7.45 (m, 1H), 7.30-7.24 (m, 2H), 7.03-7.01 (m, 1H), 6.71 (s, 1H), 6.50 (s, 1H), 4.09 (s, 2H), 3.46-3.34 (m, 2H), 2.93 (s, 3H), 2.18 (s, 3H), 1.16-1.12 (m, 3H); LCMS (M + 1): 335.05 |
| 14 | N'-(2-chloro-3-(2-fluorobenzyl)-5-methylphenyl)-N-ethyl-N-methylformimidamide | $^1$H-NMR (400 MHz, DMSO-d6) δ 7.69 (bs, 1H), 7.30-7.24 (m, 1H), 7.20-7.06 (m, 3H), 6.69 (s, 1H), 6.61 (s, 1H), 4.01 (s, 2H), 3.43-3.34 (m, 3H), 2.92 (s, 3H), 2.19 (s, 3H), 1.15-1.11 (m, 3H); LCMS (M + 1): 319.45 |
| 15 | N-ethyl-N'-(5-fluoro-2-methyl-3-(o-tolylamino)phenyl)-N-methylformimidamide | $^1$H-NMR (400 MHz, DMSO-d6) δ 7.71 (s, 1H), 7.20-7.17 (m, 1H), 7.13-7.08 (m, 1H), 6.94-6.90 (m, 1H), 6.83-6.80 (m, 1H), 6.73 (d, 1H), 6.23 (d, 1H), 5.99-5.95 (m, 1H), 3.44-3.32(m, 2H), 2.94 (s, 3H), 2.16 (s, 3H), 2.06 (s, 3H), 1.14 (t, 3H); LCMS (M + 1): 300.45 |
| 16 | N-ethyl-N'-(5-fluoro-2-methyl-3-((4-((trifluoro-methyl)thio)phenyl)amino)phenyl)-N-methylformimidamide | $^1$H-NMR (400 MHz, DMSO-d6) δ 8.12 (s, 1H), 7.75 (S, 1H), 7.47-7.44 (m, 2H), 6.87-6.84 (m, 2H), 6.59 (dd, 1H), 6.52 (d, 1H), 3.45-3.32 (m, 2H), 2.94 (S, 3H), 2.05 (s, 3H), 1.14 (t, 3H); LCMS (M + 1): 386.45 |
| 17 | N'-(2-chloro-5-methyl-3-(3-methylbenzyl)phenyl)-N-ethyl-N-methylformimidamide | $^1$H-NMR (400 MHz, DMSO-d6) δ 7.67 (s, 1H), 7.15 (t, 1H), 7.00-6.96 (m, 3H), 6.69-6.65 (m, 2H), 3.96 (s, 2H), 3.46-3.31 (m, 2H), 2.92 (s, 3H), 2.25 (s, 3H), 2.19 (s, 3H), 1.13 (t, 3H); LCMS (M + 1): 315.40 |
| 18 | N'-(2-chloro-5-methyl-3-(4-methylbenzyl)phenyl)-N-ethyl-N-methylformimidamide | $^1$H-NMR (400 MHz, DMSO-d6) δ 7.66 (bs, 1H), 7.12-7.04 (m, 4H), 6.68-6.67 (m, 1H), 6.66-6.61 (m, 1H), 3.95 (m, 2H), 3.45-3.31 (m, 2H), 2.92 (s, 3H), 2.25 (s, 3H), 2.19 (s, 3H), 1.15-1.11 (m, 3H); LCMS (M + 1): 315.45 |
| 19 | N-ethyl-N'-(5-fluoro-3-((2-fluorophenyl)amino)-2-methylphenyl)-N-methylformimidamide | $^1$H-NMR (400 MHz, DMSO-d6) δ 7.72 (s, 1H), 7.21-7.15 (m, 2H), 7.05-7.02 (m, 1H), 6.92-6.86 (m, 2H), 6.36 (d, 1H), 6.24 (dd, 1H), 3.44-3.32 (m, 2H), 2.94 (s, 3H), 2.06 (s, 3H), 1.14 (t, 3H); LCMS (M + 1): 304.45 |
| 20 | N'-(3-((4-(tert-butyl)phenyl)amino)-5-fluoro-2-methylphenyl)-N-ethyl-N-methylformimidamide | $^1$H-NMR (400 MHz, DMSO-d6) δ 7.70 (s, 1H), 7.25-7.22 (m, 3H), 6.92-6.89 (m, 2H), 6.45 (dd, 1H), 6.25 (d, 1H), 3.44-3.32 (m, 2H), 2.94 (s, 3H), 2.08 (s, 3H), 1.26 (s, 9H), 1.16-1.10 (m, 3H); LCMS (M + 1): 342.65 |
| 21 | N'-(2-chloro-5-methyl-3-(2-(trifluoromethyl)benzyl)phenyl)-N-ethyl-N-methylformimidamide | $^1$H-NMR (400 MHz, DMSO-d6) δ 7.76-7.61 (m, 2H), 7.57 (t, 1H), 7.45 (t, 1H), 7.04 (d, 1H), 6.73 (s, 1H), 6.50-6.49 (m, 1H), 4.19 (s, 2H), 3.45-3.34 (m, 2H), 2.93 (s, 3H), 2.19 (s, 3H), 1.16-1.12 (m, 3H); LCMS (M + 1): 369.50 |
| 22 | N'-(2-chloro-3-(3-fluorobenzyl)-5-methylphenyl)-N-ethyl-N-methylformimidamide | $^1$H-NMR (400 MHz, DMSO-d6) δ 7.69 (bs, 1H), 7.35-7.29 (m, 1H), 7.04-6.96 (m, 3H), 6.74-6.73 (m, 1H), 6.68 (s, 1H), 4.03 (s, 2H), 3.43-3.34 (m, 2H), 2.92 (s, 3H), 2.21 (s, 3H), 1.15-1-11 (m, 3H); LCMS (M + 1): 319.55 |
| 23 | N'-(2-chloro-3-((2-fluorophenyl)amino)-5-methylphenyl)-N-ethyl-N-methylformimidamide | $^1$H-NMR (400 MHz, DMSO-d6) δ 7.65 (d, 1H), 7.24-7.19 (m, 1H), 7.13-7.09 (m, 3H), 7.01-6.97 (m, 1H), 6.37 (s, 2H), 3.44-3.33 (m, 2H), 2.97 (d, 3H), 2.15 (s, 3H), 1.18-1.13 (m, 3H); LCMS (M + 1): 320.20 |
| 24 | N'-(2-chloro-5-methyl-3-(o-tolylamino)phenyl)-N-ethyl-N-methylformimidamide | $^1$H-NMR (400 MHz, DMSO-d6) δ 7.70 (S, 1H), 7.23 (d, 1H), 7.16 (t, 1H), 7.06-6.98 (m, 2H), 6.69 (s, 1H), 6.25 (s, 1H), 6.12 (d, 1H), 3.44-3.33 (m, 2H), 2.94 (S, 3H), 2.17 (S, 3H), 2.10 (S, 3H), 1.17-1.13 (m, 3H); LCMS (M + 1): 316.15 |
| 25 | N'-(3-((4-(tert-butyl)phenyl)amino)-2-chloro-5-methylphenyl)-N-ethyl-N-methylformimidamide | $^1$H-NMR (400 MHz, DMSO-d6) δ 7.70 (S, 1H), 7.26 (d, 2H), 7.19 (s, 1H), 7.04-7.01 (m, 2H), 6.65 (d, 1H), 6.30 (s, 1H), 3.44-3.33 (m, 2H), 2.94 (S, 3H), 2.16 (s, 3H), 1.27 (s, 9H), 1.17-1.11 (m, 3H); LCMS (M + 1): 359.95 |

TABLE I-continued

| Sr. No. | IUPAC Name | Analytical Data |
| --- | --- | --- |
| 26 | N'-(2-chloro-5-methyl-3-((4-((trifluoro-methyl)thio)phenyl)amino)phenyl)-N-ethyl-N-methylformimidamide | $^1$H-NMR (400 MHz, DMSO-d6) δ 8.14 (s, 1H), 7.74 (S, 1H), 7.48-7.45 (m, 2H), 6.97-6.94 (m, 2H), 6.79 (d, 1H), 6.57 (s, 1H), 3.46-3.33 (m, 2H), 2.94 (S, 3H), 2.23 (s, 3H), 1.15 (t, 3H); LCMS (M + 1): 402.2 |
| 27 | N'-(2-chloro-3-(3-chlorobenzyl)-5-methylphenyl) methylformimidamide | $^1$H-NMR (400 MHz, DMSO-d6) δ 7.67 (bs, 1H), 7.30 (t, 1H), 7.24-7.21 (m, 1H), 7.19 (s, 1H), 7.14 (d, 1H), 6.74-6.73 (m, 1H), 6.67 (s, 1H), 4.00 (s, 2H), 3.40-3.31 (m, 2H), 2.91 (s, 3H), 2.18-2.23 (m, 3H), 1.13-1.09 (m, 3H); LCMS (M + 1): 336.05 |
| 28 | N'-(2-chloro-3-(3-methoxybenzyl)-5-methylphenyl)-N-ethyl-N-methylformimidamide | $^1$H-NMR (400 MHz, DMSO-d6) δ 7.62 (bs, 1H), 7.21-7.17 (m, 1H), 6.77-6.74 (m, 3H), 6.70 (d, 1H), 6.65 (s, 1H), 3.97 (s, 2H), 3.71 (s, 3H), 3.42-3.33 (m, 3H), 2.92 (s, 3H), 2.20 (s, 3H), 1.15-1.11 (m, 3H); LCMS (M + 1): 331.15 |
| 29 | N-ethyl-N'-(5-fluoro-3-((3-fluorophenyl)amino)-2-methylphenyl)-N-methylformimidamide | $^1$H-NMR (400 MHz, DMSO-d6) δ 7.73 (s, 2H), 7.17 (q, 1H), 6.66 (dd, 1H), 6.48-6.57 (m, 3H), 6.41 (d, 1H), 3.39 (d, 2H), 2.95 (d, 3H), 2.04 (s, 3H), 1.22-1.11 (m, 3H); LCMS (M + 1): 303.8 |
| 30 | N-ethyl-N'-(5-fluoro-3-((3-methoxyphenyl)amino)-2-methylphenyl)-N-methylformimidamide | $^1$H-NMR (400 MHz, DMSO-d6) δ 7.72 (s, 1H), 7.42 (s, 1H), 7.09 (t, 1H), 6.54-6.46 (m, 3H), 6.38-6.33 (m, 2H), 3.69 (s, 3H), 3.45-3.332 (m, 2H), 2.96 (d, 3H), 2.07 (s, 3H), 1.14 (t, 3H); LCMS (M + 1): 316.15 |
| 31 | N-ethyl-N'-(5-fluoro-2-methyl-3-(m-tolylamino)phenyl)-N-methylformimidamide | $^1$H-NMR (400 MHz, DMSO-d6) δ 7.73 (s, 2H), 7.17 (q, 1H), 6.66 (dd, 1H), 6.57-6.48 (m, 3H), 6.41 (d, 1H), 3.39 (d, 2H), 2.95 (d, 3H), 2.04 (s, 3H), 1.98 (s, 3H), 1.22-1.11 (m, 3H); LCMS (M + 1): 300.2 |
| 32 | N-ethyl-N'-(5-fluoro-3-((3-fluorophenyl)(methyl)amino)-2-methylphenyl)-N-methylformimidamide | $^1$H-NMR (400 MHz, DMSO-d6) δ 7.74 (d, 1H), 7.16-7.10 (m, 1H), 6.71 (d, 1H), 6.58 (dd, 1H), 6.46-6.41 (m, 1H), 6.27-6.23 (m, 2H), 3.46-3.36 (m, 2H), 3.15 (s, 3H), 2.97 (s, 3H), 1.91 (s, 3H), 1.15 (t, 3H); LCMS (M + 1): 318.15 |
| 33 | N'-(3-((3-chlorophenyl)(methyl)amino)-5-fluoro-2-methylphenyl)-N-ethyl-N-methylformimidamide | $^1$H-NMR (400 MHz, DMSO-d6) δ 7.75 (d, 1H), 7.14 (t, 1H), 6.73-6.66 (m, 2H), 6.58 (dd, 1H), 6.46-6.39 (m, 2H), 3.41 (dd, 2H), 3.15 (s, 3H), 2.98 (t, 3H), 1.91 (s, 3H), 1.15 (t, 3H); LCMS (M + 1): 334.15 |
| 34 | N'-(2-chloro-3-((3-chlorophenyl)amino)-5-methylphenyl)-N-ethyl-N-methylformimidamide | $^1$H-NMR (400 MHz, DMSO-d6) δ 7.75 (d, 2H), 7.14 (t, 1H), 6.73-6.66 (m, 3H), 6.58 (dd, 1H), 6.46-6.39 (m, 1H), 3.46-3.32 (m, 2H), 2.98 (S, 3H), 1.91 (s, 3H), 1.15 (t, 3H); LCMS (M + 1): 337.70 |
| 35 | N'-(2-chloro-3-((3-fluorophenyl)amino)-5-methylphenyl)-N-ethyl-N-methylformimidamide | $^1$H-NMR (400 MHz, DMSO-d6) δ 7.73-7.59 (m, 2H), 7.18 (q, 1H), 6.77 (dd, 1H), 6.73 (d, 1H), 6.68 (dt, 1H), 6.54 (td, 1H), 6.46 (s, 1H), 3.42-3.33(m, 2H), 2.95 (d, 3H), 2.19 (s, 3H), 1.13 (t, 3H); LCMS (M + 1): 320.2 |
| 36 | N'-(2-chloro-5-methyl-3-(m-tolylamino)phenyl)-N-ethyl-N-methylformimidamide | $^1$H-NMR (400 MHz, DMSO-d6) δ 7.71 (s, 1H), 7.26 (s, 1H), 7.14-7.08 (m, 1H), 6.90-6.81 (m, 2H), 6.67-6.65 (m, 2H), 6.36 (s, 1H), 3.45-3.33 (m, 2H), 2.97 (d, 3H), 2.25 (d, 3H), 2.17-2.15 (m, 3H), 1.15 (t, 3H); LCMS (M + 1): 316.15 |
| 37 | N'-(3-((3-chlorophenyl)amino)-5-fluoro-2-methylphenyl)-N-ethyl-N-methylformimidamide | $^1$H-NMR (400 MHz, DMSO-d6) δ 7.74 (S, 2H), 7.18 (t, 1H), 6.81-6.74 (m, 3H), 6.54 (dd, 1H), 6.46 (s, 1H), 3.46-3.32 (m, 2H), 2.94 (S, 3H), 2.04 (S, 3H), 1.16-1.12 (M, 3H); LCMS (M + 1): 320.40 |
| 38 | N-ethyl-N'-(5-fluoro-2-methyl-3-(methyl(m-tolyl)amino)phenyl)-N-methylformimidamide | $^1$H-NMR (400 MHz, DMSO-d6) δ 7.73 (d, 1H), 7.01 (t, 1H), 6.66 (d, 1H), 6.53-6.48 (m, 2H), 6.34 (s, 1H), 3.44-3.35 (m, 1H), 3.12 (s, 3H), 2.97 (d, 3H), 2.20 (d, 3H), 1.92 (s, 3H), 1.17-1.09 (m, 3H); LCMS (M + 1): 314.20 |
| 39 | N-ethyl-N'-(5-fluoro-3-((3-methoxyphenyl)(methyl)amino)-2-methylphenyl)-N-methylformimidamide | $^1$H-NMR (400 MHz, DMSO-d6) δ 7.75 (d, 1H), 7.14 (t, 1H), 6.73-6.66 (m, 2H), 6.58 (dd, 1H), 6.46-6.39 (m, 2H), 3.47-3.32 (m, 2H), 3.15 (s, 3H), 2.98 (d, 3H), 2.98 (S, 3H), 1.91 (s, 3H), 1.20-1.14 (m, 3H); LCMS (M + 1): 330.25 |
| 40 | N'-(2-chloro-3-((3-fluorophenyl)(methyl)amino)-5-methylphenyl)-N-ethyl-N-methylformimidamide | $^1$H-NMR (400 MHz, DMSO-d6) δ 7.77 (s, 1H), 7.09-7.13 (m, 1H), 6.74-6.80 (m, 1H), 6.41-6.45 (m, 1H), 6.22-6.27 (m, 2H), 3.33 (d, 3H), 3.19 (m, 3H), 3.15 (s, 3H), 2.97 (S, 3H), 1.14-1.23 (m, 3H); LCMS (M + 1): 334.15 |
| 41 | N'-(2-chloro-3-((3-chlorophenyl)(methyl)amino)-5-methylphenyl)-N-ethyl-N-methylformimidamide | $^1$H-NMR (400 MHz, DMSO-d6) δ 7.72 (d, 1H), 7.13 (t, 1H), 6.81-6.74 (m, 1H), 6.67 (d, 1H), 6.69-6.46 (m, 1H), 6.44-6.41 (m, 2H), 3.44-3.34 (m, 2H), 3.16 (s, 3H), 2.98 (d, 3H), 2.26 (s, 3H), 1.16 (t, 3H); LCMS (M + 1): 350.15 |
| 42 | N'-(2-chloro-3-((3-methoxyphenyl)amino)-5-methylphenyl)-N-ethyl-N-methylformimidamide | $^1$H-NMR (400 MHz, DMSO-d6) δ 7.64 (d, 1H), 7.36 (s, 1H), 7.09 (t, 1H), 6.71 (d, 1H), 6.60 (dd, 2H), 6.41-6.36 (m, 2H), 3.68 (s, 3H), 3.38 (d, 2H), 2.95 (d, 3H), 2.16 (s, 3H), 1.13 (t, 3H); LCMS (M + 1): 332.20 |
| 43 | N'-(2-chloro-5-methyl-3-(methyl(m-tolyl)amino)phenyl)-N-ethyl-N-methylformimidamide | $^1$H-NMR (400 MHz, DMSO-d6) δ 7.70 (d, 1H), 7.00 (t, 1H), 6.75-6.69 (m, 1H), 6.48 (d, 1H), 6.34 (s, 1H), 6.28 (d, 1H), 3.35-3.30 (m, 2H), 3.14 (d, 3H), 2.97 (d, 3H), 2.24 (s, 3H), 2.19 (s, 3H), 1.15 (t, 3H); LCMS (M + 1): 330.25 |
| 44 | N'-(2-chloro-3-(4-fluorobenzyl)-5-methylphenyl)-N-ethyl-N-methylformimidamide | $^1$H-NMR (400 MHz, DMSO-d6) δ 7.68 (brs, 1H), 7.23-7.19 (m, 2H), 7.12-7.06 (m, 2H), 6.71-6.70 (m, 1H), 6.61 (s, 1H), 3.99 (s, 2H), 3.42-3.32 (m, 3H), 2.92 (s, 3H), 2.20 (s, 3H), 1.15-1.13 (m, 3H); LCMS (M + 1): 319.15 |
| 45 | N'-(3-(2-bromobenzyl)-2-chloro-5-methylphenyl)-N-ethyl-N-methylformimidamide | $^1$H-NMR (400 MHz, DMSO-d6) δ 7.72-7.60 (m, 2H), 7.33-7.28 (m, 1H), 7.21-7.16 (m, 1H), 7.00 (d, 1H), 6.71 (s, 1H), 6.48 (s, 1H), 4.08 (s, 2H), 3.45-3.33 (m, 2H), 2.93 (s, 3H), 2.18 (s, 3H), 1.16-1.12 (m, 3H); LCMS (M + 1): 381.00 |

TABLE I-continued

| Sr. No. | IUPAC Name | Analytical Data |
|---|---|---|
| 46 | N'-(2-chloro-3-(4-cyanobenzyl)-5-methylphenyl)-N-ethyl-N-methylformimidamide | $^{1}$H-NMR (400 MHz, DMSO-d6) δ 7.76-7.73 (m, 2H), 7.69 (brs, 1H), 7.37 (d, 2H), 6.77 (d, 1H), 6.70 (s, 1H), 4.10 (s, 2H), 3.41-3.32 (m, 3H), 2.91 (s, 3H), 2.21 (s, 3H), 1.16-1.12 (m, 3H); LCMS (M + 1): 326.15 |
| 47 | N'-(2-chloro-3-(2-cyanobenzyl)-5-methylphenyl)-N-ethyl-N-methylformimidamide | $^{1}$H-NMR (400 MHz, DMSO-d6) δ 7.83-7.81 (m, 1H), 7.70-7.58 (m, 2H), 7.41 (t, 1H), 7.16 (d, 1H), 6.72 (s, 1H), 6.61 (s, 1H), 4.20 (s, 2H), 3.42-3.34 (m, 2H), 2.91 (s, 3H), 2.19 (s, 3H), 1.14-1.10 (m, 3H); LCMS (M + 1): 326.15 |
| 48 | N'-(2-chloro-3-(3-cyanobenzyl)-5-methylphenyl)-N-ethyl-N-methylformimidamide | $^{1}$H-NMR (400 MHz, DMSO-d6) δ 7.69-7.58 (m, 3H), 7.55-7.48 (m, 2H), 6.77 (d, 1H), 6.70 (s, 1H), 4.07 (s, 2H), 3.42-3.32 (m, 2H), 2.92 (S, 3H), 2.22 (s, 3H), 1.13 (t, 3H); LCMS (M + 1): 326.15 |
| 49 | N'-(2-chloro-3-((3-methoxyphenyl)(methyl)amino)-5-methylphenyl)-N-ethyl-N-methylformimidamide | $^{1}$H-NMR (400 MHz, DMSO-d6) δ 7.76 (s, 1H), 7.02 (t, 1H), 6.73 (d, 2H), 6.27 (d, 1H), 6.07-6.03 (m, 2H), 3.67 (s, 3H), 3.44-3.41 (m, 2H), 3.13 (s, 3H), 2.97 (d, 3H), 2.24 (s, 3H), 1.17-1.13 (m, 3H); LCMS (M + 1): 346.80 |
| 50 | N'-(2-chloro-5-methyl-3-(2-(trifluoromethoxy)benzyl)phenyl)-N-ethyl-N-methylformimidamide | $^{1}$H-NMR (400 MHz, DMSO-d6) δ 7.71 (brs, 1H), 7.40-7.34 (m, 2H), 7.33-7.28 (m, 1H), 7.11-7.08 (m, 1H), 6.71 (s, 1H), 6.59 (s, 1H), 4.05 (s, 2H), 3.43-3.33 (m, 2H), 2.92 (s, 3H), 2.19 (s, 3H), 1.15-1.10 (m, 3H); LCMS (M + 1): 385.35 |
| 51 | N'-(2-chloro-5-methyl-3-(4-(trifluoromethyl)benzyl)phenyl)-N-ethyl-N-methylformimidamide | $^{1}$H-NMR (400 MHz, DMSO-d6) δ 7.69-7.58 (m, 3H), 7.39 (d, 2H), 6.77 (d, 1H), 6.70 (s, 1H), 4.11 (s, 2H), 3.42-3.33 (m, 2H), 2.92 (s, 3H), 2.22 (s, 3H), 1.13 (t, 3H); LCMS (M + 1): 369.35 |
| 52 | N'-(2-chloro-5-methyl-3-(4-(trifluoromethoxy)benzyl)phenyl) -N-ethyl-N-methylformimidamide | $^{1}$H-NMR (400 MHz, DMSO-d6) δ 7.68 (brs, 1H), 7.31-7.26 (m, 4H), 6.76 (d, 1H), 6.68 (s, 1H), 4.04 (s, 2H), 3.42-3.32 (m, 2H), 2.92 (s, 3H), 2.21 (s, 3H), 1.13 (t, 3H); LCMS (M + 1): 385.35 |
| 53 | N'-(2-chloro-5-methyl-3-(3-(trifluoromethyl)benzyl)phenyl)-N-ethyl-N-methylformimidamide | $^{1}$H-NMR (400 MHz, DMSO-d6) δ 7.69-7.47 (m, 5H), 6.78 (d, 1H), 6.70 (s, 1H), 4.12 (s, 2H), 3.43-3.34 (m, 2H), 2.92 (s, 3H), 2.20 (d, 3H), 1.13 (t, 3H); LCMS (M + 1): 369.15 |
| 54 | N'-(2-chloro-3-(3-chloro-4-fluorobenzyl)-5-methylphenyl)-N-ethyl-N-methylformimidamide | $^{1}$H-NMR (400 MHz, DMSO-d6) δ 7.69 (brs, 1H), 7.37-7.30 (m, 2H), 7.20-7.16 (m, 1H), 6.75 (d, 1H), 6.69 (s, 1H), 4.00 (s, 2H), 3.41-3.34 (m, 2H), 2.92 (m, 3H), 2.22 (s, 3H), 1.13 (t, 3H); LCMS (M + 1): 353.15 |
| 55 | N'-(2-chloro-3-(3,5-dimethylbenzyl)-5-methylphenyl)-N-ethyl-N-methylformimidamide | $^{1}$H-NMR (400 MHz, DMSO-d6) δ 7.68 (brs, 1H), 6.80 (d, 3H), 6.68 (d, 1H), 6.64 (s, 1H), 3.92 (s, 2H), 3.42-3.34 (m, 2H), 2.93 (s, 3H), 2.21 (s, 6H), 2.19 (s, 3H), 1.14 (t, 3H); LCMS (M + 1): 329.40 |
| 56 | N'-(2-chloro-3-(3-chloro-2-fluorobenzyl)-5-methylphenyl)-N-ethyl-N-methylformimidamide | $^{1}$H-NMR (400 MHz, DMSO-d6) δ 7.68 (brs, 1H), 7.43 (t, 1H), 7.13 (t, 1H), 7.03 (t, 1H), 6.69 (s, 1H), 6.64 (s, 1H), 4.04 (s, 2H), 3.42-3.34 (m, 1H), 2.91 (s, 3H), 2.19 (s, 3H), 1.16-1.10 (m, 3H); LCMS (M + 1): 355.10 |
| 57 | N'-(2-chloro-3-(5-fluoro-2-methylbenzyl)-5-methylphenyl)-N-ethyl-N-methylformimidamide | $^{1}$H-NMR (400 MHz, DMSO-d6) δ 7.69 (brs, 1H), 7.05-7.02 (m, 1H), 6.95-6.86 (m, 2H), 6.66 (s, 1H), 6.39 (d, 1H), 3.91 (s, 2H), 3.41-3.34 (m, 2H), 2.92 (s, 3H), 2.21 (s, 3H), 2.14 (s, 3H), 1.12 (t, 3H); LCMS (M + 1): 333.15 |
| 58 | N'-(2-chloro-3-((3-isopropylphenyl)amino)-5-methylphenyl)-N-ethyl-N-methylformimidamide | $^{1}$H-NMR (400 MHz, DMSO-d6) δ 7.65 (d, 1H), 7.57 7.25 (s, 1H), 7.13-7.09 (t, 1H), 6.97 (t, 1H), 6.85-6.83 (d, 1H), 6.73-6.71 (d, 1H), 6.66 (s, 1H), 6.34 (s, 1H), 3.44-3.33 (m, 2H), 2.97 (d, 3H), 2.84-2.77 (m, 1H), 2.16 (s, 3H), 1.20-1.13 (m, 9H); LCMS (M + 1): 344.25 |
| 59 | N'-(2-chloro-3-((4-chlorophenyl)amino)-5-methylphenyl)-N-ethyl-N-methylformimidamide | $^{1}$H-NMR (400 MHz, DMSO-d6) δ 7.73-7.60 (m, 2H), 7.25-7.21 (m, 2H), 7.01-6.97 (m, 2H), 6.69-6.68 (m, 1H), 6.42 (s, 1H), 3.44-3.33 (m, 2H), 2.97 (d, 3H), 2.20 (d, 3H), 1.15 (t, 3H); LCMS (M + 1): 336.15 |
| 60 | N'-(2-chloro-3-((4-fluorophenyl)amino)-5-methylphenyl)-N-ethyl-N-methylformimidamide | $^{1}$H-NMR (400 MHz, DMSO-d6) δ 7.65 (d, 1H), 7.34 (s, 1H), 7.11-7.06 (m, 4H), 6.57 (d, 1H), 6.33 (s, 1H), 3.44-3.33 (m, 2H), 2.97 (d, 3H), 2.15 (s, 3H), 1.15 (t, 3H); LCMS (M + 1): 320.15 |
| 61 | N'-(2-chloro-3-((4-methoxyphenyl)amino)-5-methylphenyl)-N-ethyl-N-methylformimidamide | $^{1}$H-NMR (400 MHz, DMSO-d6) δ 7.68 (s, 1H), 7.08-7.05 (m, 2H), 7.01 (s, 1H), 6.90-6.87 (m, 2H), 6.41 (d, 1H), 6.21 (s, 1H), 3.74 (d, 3H), 3.44-3.32(m, 2H), 2.96 (d, 3H), 2.11 (s, 3H), 1.14 (t, 3H); LCMS (M + 1): 332.08 |
| 62 | N'-(2-chloro-3-((4-chlorophenyl)(methyl)amino)-5-methylphenyl)-N-ethyl-N-methylformimidamide | $^{1}$H-NMR (400 MHz, DMSO-d6) δ 7.70 (d, 1H), 7.18-7.14 (m, 2H), 6.78-6.73 (m, 2H), 6.50-6.46 (m, 2H), 3.45-3.32 (m, 2H), 3.16 (d, 3H), 2.97 (t, 3H), 2.25 (s, 3H), 1.18-1.13 (m, 3H); LCMS (M + 1): 350.15 |
| 63 | N'-(2-chloro-3-((3-isopropylphenyl)(methyl)amino)-5-methylphenyl)-N-ethyl-N-methylformimidamide | $^{1}$H-NMR (400 MHz, DMSO-d6) δ 7.76 (d, 1H), 7.02 (t, 1H), 6.74-6.70 (m, 2H), 6.56 (d, 1H), 6.44 (s, 1H), 6.24 (dd, 1H), 3.36 (m, 2H), 3.14 (s, 3H), 2.97 (m, 3H), 2.75 (t, 1H), 2.23 (s, 3H), 1.16 (d, 9H); LCMS (M + 1): 358.10 |
| 64 | N'-(2-chloro-3-((4-methoxyphenyl)(methyl)amino)-5-methylphenyl)-N-ethyl-N-methylformimidamide | $^{1}$H-NMR (400 MHz, DMSO-d6) δ 7.68 (d, 1H), 6.76 (d, 2H), 6.69-6.65 (m, 2H), 6.51-6.48 (m, 2H), 3.66 (s, 3H), 3.48-3.32 (m, 2H), 3.12 (d, 3H), 2.97 (m, 3H), 2.22 (s, 3H), 1.14 (d, 3H); LCMS (M + 1): 346.3 |
| 65 | N'-(2-chloro-3-(4-fluoro-2-methylbenzyl)-5-methylphenyl)-N-ethyl-N-methylformimidamide | $^{1}$H-NMR (400 MHz, DMSO-d6) δ 7.71 (brs, 1H), 7.07-7.03 (m, 1H), 6.93-6.87 (m, 2H), 6.68 (s, 1H), 6.41 (d, 1H), 3.93 (s, 2H), 3.45-3.32 (m, 2H), 2.94 (s, 3H), 2.245 (s, 3H), 2.16 (s, 3H), 1.14 (t, 3H); LCMS (M + 1): 333.20 |
| 66 | N'-(2-chloro-5-methyl-3-(pyridin-3-ylmethyl)phenyl)-N-ethyl-N-methylformimidamide | $^{1}$H-NMR (400 MHz, DMSO-d6) δ 8.48-8.39 (m, 2H), 7.68-7.54 (m, 2H), 7.31-7.28 (m, 1H), 6.76 (d, 1H), 6.68 (s, 1H), 4.03 (s, 2H), 3.42-3.34 (m, 2H), 2.92 (s, 3H), 2.20 (s, 3H), 1.17-1.08 (m, 3H); LCMS (M + 1): 302.15 |
| 67 | N'-(2-chloro-3-(3,4-difluorobenzyl)-5-methylphenyl)-N-ethyl-N-methylformimidamide | $^{1}$H-NMR (400 MHz, DMSO-d6) δ 7.68 (brs, 1H), 7.36-7.29 (m, 1H), 7.24-7.18 (m, 1H), 7.03-6.99 (m, 1H), 6.74 (d, 1H), 6.68 (s, 1H), 4.00 (s, 2H), 3.42-3.34 (m, 2H), 2.92 (s, 3H), 2.21 (s, 3H), 1.13 (t, 3H); LCMS (M + 1): 337.20 |

TABLE I-continued

| Sr. No. | IUPAC Name | Analytical Data |
|---|---|---|
| 68 | N'-(2-chloro-3-(4-fluoro-3-methylbenzyl)-5-methylphenyl)-N-ethyl-N-methylformimidamide | $^1$H-NMR (400 MHz, DMSO-d6) δ 7.68 (brs, 1H), 7.10-7.08 (m, 1H), 7.05-7.00 (m, 2H), 6.70 (d, 1H), 6.66 (s, 1H), 3.95 (s, 2H), 3.42-3.34 (m, 2H), 2.92 (s, 3H), 2.20 (s, 3H), 2.18 (s, 3H), 1.13 (t, 3H); LCMS (M + 1): 333.25 |
| 69 | N'-(2-chloro-3-((4-fluorophenyl)(methyl)amino)-5-methylphenyl)-N-ethyl-N-methylformimidamide | $^1$H-NMR (400 MHz, DMSO-d6) δ 7.74 (S, 1H), 7.00-6.95 (m, 2H), 6.73 (d, 2H), 6.51-6.47 (m, 2H), 3.43-3.33 (m, 2H), 3.14 (s, 3H), 2.93 (s, 3H), 2.22 (s, 3H), 1.24-1.14 (m, 3H) |
| 70 | N'-(3-benzyl-2-chloro-5-methylphenyl)-N-ethyl-N-methylformimidamide | $^1$H-NMR (400 MHz, DMSO-d6) δ 7.67 (brs, 1H), 7.30-7.26 (m, 2H), 7.20-7.16 (m, 3H), 6.71 (s, 1H), 6.66 (s, 1H), 4.01 (s, 2H), 3.52-3.36 (s, 2H), 2.92 (s, 3H), 2.20 (s, 3H), 1.13 (t, 3H); LCMS (M + 1): 301.05 |
| 71 | N'-(2-chloro-3-(3,5-difluoro-4-methoxybenzyl)-5-methylphenyl)-N-ethyl-N-methylformimidamide | $^1$H-NMR (400 MHz, DMSO-d6) δ 7.69 (brs, 1H), 6.96-6.89 (m, 2H), 6.76 (d, 1H), 6.70 (s, 1H), 3.95 (s, 2H), 3.87 (s, 3H), 3.42-3.33 (m, 2H), 2.92 (s, 3H), 2.22 (s, 3H), 1.14 (t, 3H); LCMS (M + 1): 368.95 |
| 72 | N'-(2-chloro-3-((3,4-difluorophenyl)amino)-5-methylphenyl)-N-ethyl-N-methylformimidamide | $^1$H-NMR (400 MHz, DMSO-d6) δ 7.65 (s, 1H), 7.32-7.26 (m, 1H), 7.19 (t, 1H), 7.08-7.01 (m, 2H), 6.31 (s, 1H), 6.16 (s, 1H), 3.44-3.33 (m, 2H), 2.96 (s, 3H), 2.12 (s, 3H), 1.15 (t, 3H); LCMS (M + 1): 338.05 |
| 73 | N'-(3-((3,4-difluorophenyl)amino)-5-fluoro-2-methylphenyl)-N-ethyl-N-methylformimidamide | $^1$H-NMR (400 MHz, DMSO-d6) δ 7.74-7.62 (m, 2H), 7.27-7.19 (m, 1H), 6.86-6.77 (m, 1H), 6.68-6.64 (m, 1H), 6.52-6.48 (m, 1H), 6.40 (d, 1H), 3.46-3.32 (m, 2H), 2.96 (s, 3H), 2.06 (s, 3H), 1.14 (t, 3H); LCMS (M + 1): 322 |
| 74 | N'-(2-chloro-3-((3,5-difluorophenyl)(methyl)amino)-5-methylphenyl)-N-ethyl-N-methylformimidamide | $^1$H-NMR (400 MHz, DMSO-d6) δ 7.73 (d, 1H), 6.84-6.77 (m, 2H), 6.39 (t, 1H), 6.07-6.05 (m, 2H), 3.48-3.30 (m, 2H), 3.18 (d, 3H), 2.98 (s, 3H), 2.27 (s, 3H), 1.18-1.10 (m, 3H); LCMS (M + 1): 352.4 |
| 75 | N'-(2-chloro-3-((2,4-difluorophenyl)amino)-5-methylphenyl)-N-ethyl-N-methylformimidamide | $^1$H-NMR (400 MHz, DMSO-d6) δ 7.72-7.61 (m, 2H), 7.29-7.21 (m, 1H), 6.96-6.93 (m, 1H), 6.81-6.77 (m, 1H), 6.69-6.67 (m, 1H), 6.44 (s, 1H), 3.48-3.32 (m, 2H), 2.96 (s, 3H), 2.21 (s, 3H), 1.14 (s, 3H); LCMS (M + 1): 338.05 |
| 76 | N'-(3-((2,4-difluorophenyl)amino)-5-fluoro-2-methylphenyl)-N-ethyl-N-methylformimidamide | $^1$H-NMR (400 MHz, DMSO-d6) δ 7.67 (d, 1H), 7.29-7.23 (m, 1H), 7.13 (s, 1H), 7.01-6.96 (m, 2H), 6.29 (d, 1H), 6.08-6.05 (m, 1H), 3.44-3.30 (m, 2H), 2.96 (d, 3H), 2.07 (s, 3H), 1.14 (t, 3H); LCMS (M + 1): 322.15 |
| 77 | N'-(3-((3,5-difluorophenyl)amino)-5-fluoro-2-methylphenyl)-N-ethyl-N-methylformimidamide | $^1$H-NMR (400 MHz, DMSO-d6) δ 8.07 (s, 1H), 7.70 (d, 1H), 6.59 (dd, 1H), 6.52 (d, 1H), 6.46-6.41 (m, 1H), 6.39-6.34 (m, 2H), 3.45 (m, 2H), 2.97 (d, 3H), 2.05 (s, 3H), 1.15 (t, 3H); LCMS (M + 1): 322.05 |
| 78 | N'-(2-chloro-3-((3,5-difluorophenyl)amino)-5-methylphenyl)-N-ethyl-N-methylformimidamide | $^1$H-NMR (400 MHz, DMSO-d6) δ 8.10 (d, 1H), 7.75-7.62 (m, 1H), 6.78 (d, 1H), 6.58 (s, 1H), 6.50-6.45(m, 3H), 3.47-3.33 (m, 2H), 3.01-2.93 (m, 3H), 2.23 (s, 3H), 1.17-1.12 (t, 3H); LCMS (M + 1): 337.95 |
| 79 | N'-(3-benzyl-5-chloro-2-methylphenyl)-N-ethyl-N-methylformimidamide | $^1$H-NMR (400 MHz, DMSO-d6) δ 7.69 (brs, 1H), 7.31-7.27 (m, 2H), 7.21-7.17 (m, 1H), 7.15-7.13 (m, 2H), 6.76 (s, 2H), 3.93 (s, 2H), 3.41-3.38 (m, 2H), 2.91 (s, 3H), 2.09 (s, 3H), 1.12 (t, 3H); LCMS (M + 1): 310.00 |
| 80 | N'-(3-((2,4-difluorophenyl)(methyl)amino)-5-fluoro-2-methylphenyl)-N-ethyl-N-methylformimidamide | $^1$H-NMR (400 MHz, DMSO-d6) δ 7.67 (d, 1H), 7.21-7.15 (m, 1H), 7.01-6.88 (m, 2H), 6.52-6.44 (m, 2H), 3.43-3.33 (m, 2H), 3.07 (s, 3H), 2.95 (d, 3H), 1.89 (s, 3H), 1.15-1.10 (m, 3H); LCMS (M + 1): 336.2 |
| 81 | N'-(2-chloro-3-((3,4-difluorophenyl)(methyl)amino)-5-methylphenyl)-N-ethyl-N-methylformimidamide | $^1$H-NMR (400 MHz, DMSO-d6) δ 7.76 (d, 1H), 7.20-7.13 (m, 1H), 6.80-6.74 (m, 2H), 6.49-6.43 (m, 1H), 6.21-6.16 (m, 1H), 3.48-3.33 (m, 2H), 3.14 (d, 3H), 2.96 (s, 3H), 2.25 (s, 3H), 1.18-1.13 (m, 3H); LCMS (M + 1): 352.45 |
| 82 | N'-(2-chloro-3-((2,4-difluorophenyl)(methyl)amino)-5-methylphenyl)-N-ethyl-N-methylformimidamide | $^1$H-NMR (400 MHz, DMSO-d6) δ 7.62 (d, 1H), 7.15-7.09 (m, 1H), 6.98-6.90 (m, 2H), 6.56 (s, 2H), 3.39-3.33 (m, 2H), 3.09 (s, 3H), 2.94 (s, 3H), 2.20 (s, 3H), 1.14-1.08 (m, 3H); LCMS (M + 1): 352.0 |
| 83 | N'-(3-((3,4-difluorophenyl)(methyl)amino)-5-fluoro-2-methylphenyl)-N-ethyl-N-methylformimidamide | $^1$H-NMR (400 MHz, DMSO-d6) δ 7.69 (d, 1H), 7.16-7.08 (m, 1H), 6.66 (d, 1H), 6.53 (d, 1H), 6.44-6.41 (m, 1H), 6.13 (t, 1H), 3.43-3.31 (m, 2H), 3.09 (s, 3H), 2.94 (s, 3H), 1.87 (s, 3H), 1.12-1.05 (m, 3H); LCMS (M + 1): 336.0 |
| 84 | N'-(3-((3,5-difluorophenyl)(methyl)amino)-5-fluoro-2-methylphenyl)-N-ethyl-N-methylformimidamide | $^1$H-NMR (400 MHz, DMSO-d6) δ 7.73 (d, 1H), 6.72 (t, 1H), 6.59 (dd, 1H), 6.37 (t, 1H), 6.04 (d, 2H), 3.46-3.34 (m, 2H), 3.16 (d, 3H), 2.96 (s, 3H), 1.90 (s, 3H), 1.15-1.08 (m, 3H); LCMS (M + 1): 336.45 |
| 85 | N'-(2-chloro-5-methyl-3-(pyridin-2-ylamino)phenyl)-N-ethyl-N-methylformimidamide | $^1$H-NMR (400 MHz, DMSO-d6) δ 8.09 (d, 1H), 8.02 (s, 1H), 7.64 (d, 1H), 7.53 (d, 1H), 7.37 (d, 1H), 6.89 (d, 1H), 6.72 (d, 1H), 6.46 (s, 1H), 3.46-3.35 (m, 2H), 2.95 (s, 3H), 2.21 (s, 3H), 1.13 (t, 3H); LCMS (M + 1): 303.4 |
| 86 | N'-(2-chloro-5-methyl-3-((3-methylpyridin-2-yl)amino)phenyl)-N-ethyl-N-methylformimidamide | $^1$H-NMR (400 MHz, DMSO-d6) δ 8.00 (dd, 1H), 7.72-7.61 (m, 1H), 7.48-7.46 (m, 1H), 7.20 (s, 1H), 6.74 (dd, 1H), 6.46 (s, 1H), 3.46-3.33 (m, 2H), 3.02 (d, 3H), 2.96 (s, 3H), 2.25 (s, 3H), 2.23 (s, 3H), 1.13 (t, 3H); LCMS (M + 1): 317.45 |
| 87 | N'-(5-chloro-3-(4-fluoro-3,5-dimethylbenzyl)-2-methylphenyl)-N-ethyl-N-methylformimidamide | $^1$H-NMR (400 MHz, DMSO-d6) δ 7.70 (brs, 1H), 6.83 (d, 2H), 6.75 (d, 2H), 3.83 (s, 2H), 3.49-3.34 (m, 2H), 2.91 (s, 3H), 2.17 (s, 3H), 2.16 (s, 3H), 2.09 (s, 3H), 1.13 (t, 3H); LCMS (M + 1): 347.50 |
| 88 | N'-(5-chloro-2-methyl-3-(2-methylbenzyl)phenyl)-N-ethyl-N- | $^1$H-NMR (400 MHz, DMSO-d6) δ 7.73 (brs, 1H), 7.22-7.19 (m, 1H), 7.16-7.09 (m, 2H), 6.86-6.84 (m, 1H), 6.77 (s, 1H), 6.44 (d, 1H), 3.87 (s, 2H), |

TABLE I-continued

| Sr. No. | IUPAC Name | Analytical Data |
|---|---|---|
| | methylformimidamide | 3.43-3.33 (m, 2H), 2.93 (s, 3H), 2.22 (s, 3H), 2.11 (s, 3H), 1.14 (t, 3H); LCMS (M + 1): 315.20 |
| 89 | N'-(5-chloro-3-(2-chlorobenzyl)-2-methylphenyl)-N-ethyl-N-methylformimidamide | $^1$H-NMR (400 MHz, DMSO-d6) δ 7.73 (BRS, 1H), 7.51-7.47 (m, 1H), 7.31-7.25 (m, 2H), 7.04-7.00 (m, 1H), 6.80 (s, 1H), 6.54 (d, 1H), 4.01 (s, 2H), 3.43-3.30 (m, 2H), 2.93 (S, 3H), 2.09 (s, 3H), 1.15-1.11 (M, 3H); LCMS (M + 1): 335.15 |
| 90 | N'-(3-(2-bromobenzyl)-5-chloro-2-methylphenyl)-N-ethyl-N-methylformimidamide | $^1$H-NMR (400 MHz, DMSO-d6) δ 7.74-7.63 (m, 2H), 7.33 (t, 1H), 7.21 (t, 1H), 7.01 (d, 1H), 6.80 (s, 1H), 6.52 (d, 1H), 4.00 (s, 2H), 3.43-3.30 (m, 2H), 2.93 (S, 3H), 2.10 (S, 3H), 1.14 (t, 3H); LCMS (M + 1): 381.05 |
| 91 | N'-(2-chloro-3-(2,6-difluorobenzyl)-5-methylphenyl)-N-ethyl-N-methylformimidamide | $^1$H-NMR (400 MHz, DMSO-d6) δ 7.70 (brs, 1H), 7.43-7.37 (m, 1H), 7.16-7.10 (m, 2H), 6.66 (s, 1H), 6.32 (s, 1H), 4.02 (s, 2H), 3.45-3.32 (m, 2H), 2.94 (s, 3H), 2.14 (s, 3H), 1.14 (t, 3H); LCMS (M + 1): 337.00 |
| 92 | N'-(2-chloro-3-(2-chloro-6-fluorobenzyl)-5-methylphenyl)-N-ethyl-N-methylformimidamide | $^1$H-NMR (400 MHz, DMSO-d6) δ 7.71 (brs, 1H), 7.46-7.39 (m, 2H), 7.32-7.27 (m, 1H), 6.66 (s, 1H), 6.04 (s, 1H), 4.12 (s, 2H), 3.45-3.32 (m, 2H), 2.95 (s, 3H), 2.10 (s, 3H), 1.15 (t, 3H); LCMS (M + 1): 354.90 |
| 93 | N'-(3-(4-bromobenzyl)-2-chloro-5-methylphenyl)-N-ethyl-N-methylformimidamide | $^1$H-NMR (400 MHz, DMSO-d6) δ 7.68 (brs, 1H), 7.48-7.45 (m, 2H), 7.14 (d, 2H), 6.73-6.68 (m, 2H), 3.98 (s, 2H), 3.43-3.32 (m, 2H), 2.92 (s, 3H), 2.21 (s, 3H), 1.13 (t, 3H); LCMS (M + 1): 380.85 |
| 94 | N'-(5-chloro-2-methyl-3-(3-methylbenzyl)phenyl)-N-ethyl-N-methylformimidamide | $^1$H-NMR (400 MHz, DMSO-d6) δ 7.71 (brs, 1H), 7.19-7.15 (m, 1H), 7.01 (d, 1H), 6.95 (d, 1H), 6.92 (s, 1H), 6.75 (d, 2H), 3.89 (s, 2H), 3.42-3.33 (m, 2H), 2.91 (s, 3H), 2.27 (sz, 3H), 2.10 (s, 3H), 1.16-1.12 (m, 3H); LCMS (M + 1): 316.90 |
| 95 | N-ethyl-N'-(5-fluoro-2-methyl-3-(pyridin-2-ylamino)phenyl)-N-methylformimidamide | $^1$H-NMR (400 MHz, DMSO-d6) δ 8.10-8.07 (m, 2H), 7.68 (d, 1H), 7.55-7.50 (m, 1H), 7.19-7.14 (m, 1H), 6.82-6.79 (m, 1H), 6.72-6.68 (m, 1H), 6.41 (d, 1H), 3.56-3.31 (m, 2H), 2.97 (s, 3H), 2.11 (s, 3H), 1.14 (t, 3H); LCMS (M + 1): 286.95 |
| 96 | N'-(3-((3-chloro-5-fluorophenyl)amino)-5-fluoro-2-methylphenyl)-N-ethyl-N-methylformimidamide | $^1$H-NMR (400 MHz, DMSO-d6) δ 8.06 (s, 1H), 7.69 (d, 1H), 6.62 (dt, 1H), 6.56 (dd, 2H), 6.52 (d, 1H), 6.45 (dt, 1H), 3.46-3.33 (m, 2H), 2.95 (s, 3H), 2.02 (s, 3H), 1.14 (t, 3H); LCMS (M + 1): 337.95 |
| 97 | N'-(2-chloro-3-((3-chloro-5-fluorophenyl)amino)-5-methylphenyl)-N-ethyl-N-methylformimidamide | $^1$H-NMR (400 MHz, DMSO-d6) δ 8.10 (s, 1H), 7.67 (d, 1H), 6.74 (d, 1H), 6.68-6.63 (m, 2H), 6.57-6.52 (m, 2H), 3.46-3.33 (m, 2H), 2.96 (s, 3H), 2.21 (s, 3H), 1.13 (t, 3H); LCMS (M + 1): 354.35 |
| 98 | N'-(3-((5-chloro-2-methylphenyl)(methyl)amino)-5-fluoro-2-methylphenyl)-N-ethyl-N-methylformimidamide | $^1$H-NMR (400 MHz, DMSO-d6) δ 7.78-7.59 (m, 1H), 7.15 (dd, 1H), 7.02-6.99 (m, 1H), 6.96 (t, 1H), 6.54-6.44 (m, 1H), 6.23-6.19 (m, 1H), 3.33 (d, 2H), 3.01-2.92 (m, 6H), 1.98 (d, 3H), 1.89-1.85 (m, 3H), 1.13 (d, 3H); LCMS (M + 1): 348.45 |
| 99 | N'-(2-chloro-3-((3-chloro-5-fluorophenyl)(methyl)amino)-5-methylphenyl)-N-ethyl-N-methylformimidamide | $^1$H-NMR (400 MHz, DMSO-d6) δ 7.73 (d, 1H), 6.79-6.77 (m, 2H), 6.60 (dt, 1H), 6.23 (t, 2H), 3.48-3.23 (m, 2H), 3.17 (s, 3H), 2.98 (s, 3H), 2.27 (s, 3H), 1.16 (t, 3H); LCMS (M + 1): 368.15 |
| 100 | N'-(2-chloro-3-((5-chloro-2-methylphenyl)amino)-5-methylphenyl)-N-ethyl-N-methylformimidamide | $^1$H-NMR (400 MHz, DMSO-d6) δ 7.67 (m1H), 7.18 (dd, 1H), 6.96-6.89 (m, 1H), 6.76 (d, 1H), 6.43-6.31 (m, 1H), 3.45-3.33 (m, 3H), 2.97 (d, 1H), 2.52-2.50 (m, 3H), 2.34 (s, 3H), 2.21-2.08 (m, 3H), 1.15 (t, 3H); LCMS (M + 1): 350.20 |
| 101 | N'-(5-chloro-3-(3-chlorobenzyl)-2-methylphenyl)-N-ethyl-N-methylformimidamide | $^1$H-NMR (400 MHz, DMSO-d6) δ 7.71 (brs, 1H), 7.33 (t, 1H), 7.26 (d, 1H), 7.18 (s, 1H), 7.11 (d, 1H), 6.81-6.79 (m, 2H), 3.96 (s, 2H), 3.48-3.34 (m, 2H), 2.92 (d, 3H), 2.07 (s, 3H), 1.13 (s, 3H); LCMS (M + 1): 336.95 |
| 102 | N'-(5-chloro-3-(3-fluorobenzyl)-2-methylphenyl)-N-ethyl-N-methylformimidamide | $^1$H-NMR (400 MHz, DMSO-d6) δ 7.71 (brs, 1H), 7.36-7.31 (m, 1H), 7.05-6.93 (m, 3H), 6.80-6.78 (m, 2H), 3.96 (s, 2H), 3.42-3.33 (m, 2H), 2.95 (s, 3H), 2.07 (s, 3H), 1.13 (t, 3H); LCMS (M + 1): 319.35 |
| 103 | N'-(5-chloro-3-(2-fluorobenzyl)-2-methylphenyl)-N-ethyl-N-methylformimidamide | $^1$H-NMR (400 MHz, DMSO-d6) δ 7.69 (brs, 1H), 7.29-7.24 (m, 1H), 7.20-7.15 (m, 1H), 7.13-7.09 (mz, 1H), 7.04 (td, 1H), 6.76 (s, 1H), 6.65 (d, 1H), 3.92 (s, 2H), 3.40-3.32 (m, 2H), 2.90 (s, 3H), 2.09 (s, 3H), 1.11 (t, 3H); LCMS (M + 1): 319.45 |
| 104 | N'-(5-chloro-3-(2-cyanobenzyl)-2-methylphenyl)-N-ethyl-N-methylformimidamide | $^1$H-NMR (400 MHz, DMSO-d6) δ 7.84 (dd, 1H), 7.72-7.60 (m, 2H), 7.43 (td, 1H), 7.15 (d, 1H), 6.81-6.78 (m, 1H), 6.60 (d, 1H), 4.13 (s, 2H), 3.42-3.32 (s, 2H), 2.91 (s, 3H), 2.08 (s, 3H), 1.12 (t, 3H); LCMS (M + 1): 326.50 |
| 105 | N'-(5-chloro-2-methyl-3-(4-methylbenzyl)phenyl)-N-ethyl-N-methylformimidamide | $^1$H-NMR (400 MHz, DMSO-d6) δ 7.67 (brs, 1H), 7.07 (d, 2H), 6.99 (d, 2H), 6.72-6.71 (m, 2H), 3.85 (s, 2H), 3.39-3.31 (m, 2H), 2.89 (s, 3H), 2.24 (s, 3H), 2.06 (s, 3H), 1.10 (t, 3H); LCMS (M + 1): 321.50 |
| 106 | N'-(3-((3-chloro-5-fluorophenyl)(methyl)amino)-5-fluoro-2-methylphenyl)-N-ethyl-N-methylformimidamide | $^1$H-NMR (400 MHz, DMSO-d6) δ 7.74 (d, 1H), 6.73 (t, 1H), 6.61-6.56 (m, 2H), 6.20 (d, 2H), 3.46-3.34 (m, 2H), 3.14 (s, 3H), 2.96 (s, 3H), 1.90 (s, 3H), 1.16-1.07 (m, 3H); LCMS (M + 1): 352.45 |
| 107 | N'-(2-chloro-5-methyl-3-(methyl(pyridin-2-yl)amino)phenyl)-N-ethyl-N-methylformimidamide | $^1$H-NMR (400 MHz, DMSO-d6) δ 8.11 (d, 1H), 7.72 (d, 1H), 7.36-7.40 (m, 1H), 6.80 (d, 2H), 6.62-6.59 (m, 1H), 6.10 (d, 1H), 3.28-3.46 (m, 2H), 2.98 (s, 3H), 2.26 (s, 3H), 1.16 (t, 3H), 1.17-1.10 (m, 3H); LCMS (M + 1): 317.4 |
| 108 | N'-(2-chloro-5-methyl-3-(methyl(3-methylpyridin-2-yl)amino)phenyl)-N-ethyl-N-methylformimidamide | $^1$H-NMR (400 MHz, DMSO-d6) δ 7.61 (d, 1H), 7.07 (d, 1H), 6.97-6.93 (m, 2H), 6.52 (d, 1H), 6.27 (d, 1H), 3.39-3.31 (m, 2H), 3.02 (d, 3H), 2.92 (s, 3H), 2.11 (s, 3H), 1.78 (s, 3H), 1.11-1.05 (m, 3H); LCMS (M + 1): 331.45 |
| 109 | N-ethyl-N'-(5-fluoro-2-methyl-3-(methyl(pyridin-2-yl)amino)phenyl)-N-methylformimidamide | $^1$H-NMR (400 MHz, DMSO-d6) δ 8.14-8.12 (m, 1H), 7.74 (d, 1H), 7.41-7.36 (m, 1H), 6.73 (d, 1H), 6.65-6.59 (m, 2H), 6.08 (d, 1H), 3.46-3.34 (m, 2H), 3.25 (s, 3H), 2.98 (d, 3H), 1.91 (s, 3H), 1.17-1.09 (m, 3H); LCMS (M + 1): 300.38 |

TABLE I-continued

| Sr. No. | IUPAC Name | Analytical Data |
|---|---|---|
| 110 | N'-(2-chloro-3-((5-chloro-2-methylphenyl)(methyl)amino)-5-methylphenyl)-N-ethyl-N-methylformimidamide | $^1$H-NMR (400 MHz, DMSO-d6) δ 7.61 (d, 1H), 7.07 (d, 1H), 6.97-6.93 (m, 2H), 6.52 (d, 1H), 6.27 (d, 1H), 3.39-3.31 (m, 2H), 3.02 (d, 3H), 2.92 (d, 3H), 2.11 (d, 3H), 1.78 (s, 3H),, 1.05-1.11 (m, 3H); LCMS (M + 1): 364.3 |
| 111 | N'-(2-chloro-3-((3-fluoro-5-methylphenyl)amino)-5-methylphenyl)-N-ethyl-N-methylformimidamide | $^1$H-NMR (400 MHz, DMSO-d6) δ 7.61-7.72 (m, 2H), 6.73 (d, 1H), 6.60 (s, 1H), 6.49 (d, 2H), 6.40 (d, 1H), 3.46 (m, 2H), 2.97 (d, 3H), 2.21 (d, 6H), 1.15 (t, 3H); LCMS (M + 1): 333.8 |
| 112 | N'-(2-chloro-3-((5-chloro-3-methylpyridin-2-yl)amino)-5-methylphenyl)-N-ethyl-N-methylformimidamide | $^1$H-NMR (400 MHz, DMSO-d6) δ 7.98 (t, 1H), 7.76 (d, 1H), 7.62-7.58 (m, 1H), 7.44 (d, 1H), 7.38-7.36 (m, 1H), 6.54 (s, 1H), 3.35-3.45 (m, 2H), 2.97 (d, 3H), 2.26 (d, 6H), 1.15 (t, 3H); LCMS (M + 1): 351.27 |
| 113 | N'-(3-((2-chloro-5-methylphenyl)amino)-5-fluoro-2-methylphenyl)-N-ethyl-N-methylformimidamide | $^1$H-NMR (400 MHz, DMSO-d6) δ 7.70 (d, 1H), 7.27 (d, 1H), 6.96 (s, 1H), 6.69-6.66 (m, 1H), 6.54 (d, 1H), 6.46 (d, 1H), 6.36 (dd, 1H), 3.47-3.30 (m, 5H), 2.97 (d, 3H), 2.18 (s, 3H), 2.01 (s, 3H), 1.15 (t, 3H); LCMS (M + 1): 333.8 |
| 114 | N-ethyl-N'-(5-fluoro-3-((3-fluoro-5-methylphenyl)amino)-2-methylphenyl)-N-methylformimidamide | $^1$H-NMR (400 MHz, DMSO-d6) δ 7.70 (d, 2H), 6.56 (d, 1H), 6.53 (d, 1H), 6.43 (d, 1H), 6.38 (s, 1H), 6.35 (d, 1H), 3.47-3.33 (m, 2H), 3.01-2.93-(m, 3H), 2.19 (s, 3H), 2.05 (d, 3H), 1.15-1.13 (m, 3H); LCMS (M + 1): 317.38 |
| 115 | N'-(2-chloro-3-((2-chloro-5-methylphenyl)amino)-5-methylphenyl)-N-ethyl-N-methylformimidamide | $^1$H-NMR (400 MHz, DMSO-d6) δ 7.68 (d, 1H), 7.32 (d, 1H), 6.88-6.84 (m, 2H), 6.76 (dd, 1H), 6.54 (d, 1H), 6.46 (s, 1H), 3.46-3.30 (m, 2H), 2.98 (d, 3H), 2.23 (s, 3H), 2.19 (s, 3H), 1.15 (t, 3H); LCMS (M + 1): 350.28 |
| 116 | N'-(3-((5-chloro-2-methylphenyl)amino)-5-fluoro-2-methylphenyl)-N-ethyl-N-methylformimidamide | $^1$H-NMR (400 MHz, DMSO-d6) δ 7.76 (s, 1H), 7.15 (d, 1H), 7.00 (s, 1H), 6.82 (dd, 1H), 6.51 (d, 1H), 6.44 (s, 1H), 6.23 (dd, 1H), 3.47-3.30 (m, 2H), 2.97 (d, 3H), 2.17 (s, 3H), 2.00 (s, 3H), 1.15 (t, 3H); LCMS (M + 1): 333.83 |
| 117 | N'-(3-((2-chloro-5-methylphenyl)(methyl)amino)-5-fluoro-2-methylphenyl)-N-ethyl-N-methylformimidamide | $^1$H-NMR (400 MHz, DMSO-d6) δ 7.64 (d, 1H), 7.27 (d, 1H), 6.87 (dd, 1H), 6.82 (s, 1H), 6.45 (d, 1H), 6.33 (dd, 1H), 3.37 (d, 2H), 3.04 (d, 3H), 2.92 (d, 3H), 2.22 (s, 3H), 1.85 (s, 3H), 1.10 (t, 3H); LCMS (M + 1): 347.86 |
| 118 | N'-(2-chloro-3-((5-chloro-3-methylpyridin-2-yl)(methyl)amino)-5-methylphenyl)-N-ethyl-N-methylformimidamide | $^1$H-NMR (400 MHz, DMSO-d6) δ 8.15 (d, 1H), 7.67 (d, 1H), 7.49-7.48 (m, 1H), 6.65 (d, 1H), 6.27 (d, 1H), 3.46-3.34 (m, 2H), 3.13 (d, 3H), 2.96 (d, 3H), 2.12 (s, 3H), 1.60 (d, 3H), 1.13 (t, 3H); LCMS (M + 1): 365.3 |
| 119 | N-ethyl-N'-(5-fluoro-3-((3-fluoro-5-methylphenyl)(methyl)amino)-2-methylphenyl)-N-methylformimidamide | $^1$H-NMR (400 MHz, DMSO-d6) δ 7.75 (d, 1H), 6.71 (d, 1H), 6.56 (dd, 1H), 6.28 (d, 1H), 6.11 (s, 1H), 6.04-6.00 (m, 1H), 3.30-3.47 (m, 2H), 3.13 (s, 3H), 2.98 (d, 3H), 2.18 (s, 3H), 1.92 (s, 3H), 1.16 (t, 3H); LCMS (M + 1): 331.0 |
| 120 | N'-(2-chloro-3-((2-chloro-5-methylphenyl)(methyl)amino)-5-methylphenyl)-N-ethyl-N-methylformimidamide | $^1$H-NMR (400 MHz, DMSO-d6) δ 7.70 (s, 1H), 7.24 (d, 1H), 6.92 (s, 1H), 6.86 (d, 1H), 6.54 (s, 1H), 6.41 (d, 1H), 3.38 (d, 2H), 3.09 (s, 3H), 2.95 (d, 3H), 2.26 (s, 3H), 2.17 (s, 3H), 1.13 (t, 3H); LCMS (M + 1): 364.3 |
| 121 | N-ethyl-N'-(5-fluoro-3-((2-fluoro-6-methylphenyl)amino)-2-methylphenyl)-N-methylformimidamide | $^1$H-NMR (400 MHz, DMSO-d6) δ 7.69 (s, 1H), 7.21-7.01 (m, 3H), 6.67 (d, 1H), 6.07 (d, 1H), 5.43-5.40 (m, 1H), 3.30-3.49 (m, 2H), 2.95 (s, 3H), 2.17 (s, 6H), 1.14 (t, 3H); LCMS (M + 1): 317.38 |
| 122 | N-ethyl-N'-(5-fluoro-3-((2-fluoro-3-methylphenyl)amino)-2-methylphenyl)-N-methylformimidamide | $^1$H-NMR (400 MHz, DMSO-d6) δ 7.75-7.61 (m, 1H), 7.12 (s, 1H), 6.94-6.90 (m, 1H), 6.79-6.77 (m, 1H), 6.71-6.66 (m, 1H), 6.36-6.32 (m, 1H), 6.23-6.26 (m, 1H), 3.31-3.48 (m, 2H), 2.91-3.03 (m, 3H), 2.26-2.22 (m, 3H), 2.08 (dd, 3H), 1.16-1.12 (m, 3H); LCMS (M + 1): 317.38 |
| 123 | N'-(2-chloro-3-((2-fluoro-3-methylphenyl)amino)-5-methylphenyl)-N-ethyl-N-methylformimidamide | $^1$H-NMR (400 MHz, DMSO-d6) δ 7.64 (d, 1H), 6.95 (t, 2H), 6.92-6.88 (m, 1H), 6.86-6.82 (m, 1H), 6.37 (d, 2H), 3.46-3.33 (m, 2H), 2.95 (d, 3H), 2.23 (d, 3H), 2.14 (s, 3H), 1.13 (t, 3H); LCMS (M + 1): 333.8 |
| 124 | N'-(5-chloro-3-(4-fluorobenzyl)-2-methylphenyl)-N-ethyl-N-methylformimidamide | $^1$H-NMR (400 MHz, DMSO-d6) δ 7.69 (brs, 1H), 7.18-7.08 (m, 4H), 6.77 (s, 2H), 3.92 (s, 2H), 3.42-3.30 (m, 2H), 2.91 (s, 3H), 2.05 (s, 3H), 1.14-1.10 (m, 3H); LCMS (M + 1): 319.10 |
| 125 | N'-(3-(4-bromobenzyl)-5-chloro-2-methylphenyl)-N-ethyl-N-methylformimidamide | $^1$H-NMR (400 MHz, DMSO-d6) δ 7.70 (brs, 1H), 7.48 (d, 2H), 7.09 (d, 2H), 6.78 (s, 2H), 3.92 (s, 2H), 3.41-3.30 (m, 2H), 2.91 (s, 3H), 2.07 (s, 3H), 1.16-1.11 (m, 3H); LCMS (M + 1): 381.00 |
| 126 | N'-(5-chloro-3-(4-chlorobenzyl)-2-methylphenyl)-N-ethyl-N-methylformimidamide | $^1$H-NMR (400 MHz, DMSO-d6) δ 7.70(brs, 1H), 7.34 (d, 2H), 7.15 (d, 2H), 6.78 (s, 2H), 3.93 (s, 2H), 3.42-3.33 (m, 3H), 2.89 (s, 3H), 2.06 (s, 3H), 1.14-1.09 (m, 3H); LCMS (M + 1): 335.05 |
| 127 | N'-(5-chloro-2-methyl-3-(3-(trifluoromethyl)benzyl)phenyl)-N-ethyl-N-methylformimidamide | $^1$H-NMR (400 MHz, DMSO-d6) δ 7.76-7.51 (m, 4H), 7.42 (d, 1H), 6.86-6.74 (m, 2H), 4.05 (s, 2H), 3.41-3.311 (m, 2H), 2.91 (s, 3H), 2.08 (s, 3H), 1.17-1.05 (m, 3H); LCMS (M + 1): 369.75 |
| 128 | N'-(5-chloro-3-(4-fluoro-3-methylbenzyl)-2-methylphenyl)-N-ethyl-N-methylformimidamide | $^1$H-NMR (400 MHz, DMSO-d6) δ 7.69 (brs, 1H), 7.06-7.01 (m, 2H), 6.97-6.93 (m, 1H), 6.75 (s, 2H), 3.87 (s, 2H), 3.42-3.31 (m, 2H), 2.91 (s, 3H), 2.19 (s, 3H), 2.08 (s, 3H), 1.14-1.09 (m, 3H); LCMS (M + 1): 333.15 |
| 129 | N'-(5-chloro-3-(3,4-difluorobenzyl)-2-methylphenyl)-N-ethyl-N-methylformimidamide | $^1$H-NMR (400 MHz, DMSO-d6) δ 7.70 (brs, 1H), 7.37-7.30 (m, 1H), 7.18 (m, 1H), 6.97-6.94 (m, 1H), 6.82-6.73 (m, 2H), 3.94 (s, 2H), 3.42-3.30 (m, 2H), 2.91 (s, 3H), 2.07 (s, 3H), 1.14-1.11 (m, 3H); LCMS (M + 1): 337.70 |
| 130 | N'-(5-chloro-3-(3-chloro-4-fluorobenzyl)-2-methylphenyl)-N-ethyl-N-methylformimidamide | $^1$H-NMR (400 MHz, DMSO-d6) δ 7.71 (brs, 1H), 7.35-7.30 (m, 2H), 7.14-7.10 (m, 1H), 6.81-6.78 (m, 2H), 3.94 (s, 2H), 3.42-3.30 (m, 2H), 2.91 (s, 3H), 2.07 (s, 3H), 1.14-1.11 (m, 3H); LCMS (M + 1): 354.65 |

TABLE I-continued

| Sr. No. | IUPAC Name | Analytical Data |
|---|---|---|
| 131 | N'-(5-chloro-3-(4-chloro-3-fluorobenzyl)-2-methylphenyl)-N-ethyl-N-methylformimidamide | $^1$H-NMR (400 MHz, DMSO-d6) δ 7.71 (brs, 1H), 7.49 (t, 1H), 7.17 (d, 1H), 6.98 (d, 1H), 6.82-6.79 (m, 2H), 3.96 (s, 2H), 3.41-3.30 (m, 2H), 2.91 (s, 3H), 2.06 (s, 3H), 1.12-1.06 (m, 3H); LCMS (M + 1): 353.05 |
| 132 | N-ethyl-N'-(5-fluoro-2-methyl-3-((3-(trifluoromethyl)pyridin-2-yl)amino)phenyl)-N-methylformimidamide | $^1$H-NMR (400 MHz, DMSO-d6) δ 8.23-8.25 (m, 1H), 7.92 (q, 1H), 7.84 (d, 1H), 7.76-7.64 (m, 1H), 6.86-6.78 (m, 2H), 6.60-6.54 (m, 1H), 3.46-3.31 (m, 2H), 2.93-3.01 (m, 3H), 1.96 (s, 3H), 1.14 (t, 3H); LCMS (M + 1): 355.10 |
| 133 | N'-(2-chloro-3-((2-fluoro-6-methylphenyl)amino)-5-methylphenyl)-N-ethyl-N-methylformimidamide | $^1$H-NMR (400 MHz, DMSO-d6) δ 7.57-7.73 (m, 1H), 7.19 (td, 1H), 7.13-7.09 (m, 2H), 6.68 (s, 1H), 6.13 (s, 1H), 5.59 (s, 1H), 3.47-3.35 (m, 2H), 2.95 (d, 3H), 2.16 (t, 3H), 2.04 (d, 3H), 1.13 (t, 3H); LCMS (M + 1): 334.50 |
| 134 | N'-(2-chloro-3-((4-chloro-2-fluorophenyl)amino)-5-methylphenyl)-N-ethyl-N-methylformimidamide | $^1$H-NMR (400 MHz, DMSO-d6) δ 7.67 (d, 1H), 7.42-7.38 (m, 1H), 7.33 (d, 1H), 7.15 (dt, 1H), 7.01-6.97 (m, 1H), 6.44-6.39 (m, 2H), 3.59-3.30 (m, 2H), 2.97 (d, 3H), 2.16 (d, 3H), 1.15 (t, 3H); LCMS (M + 1): 350.24 |
| 135 | N'-(2-chloro-5-methyl-3-((3-(trifluoromethyl)pyridin-2-yl)amino)phenyl)-N-ethyl-N-methylformimidamide | $^1$H-NMR (400 MHz, DMSO-d6) δ 8.36 (t, 1H), 8.01-74.98 (m, 1H), 7.77 (d, 1H), 7.36 (d, 1H), 6.96 (dd, 1H), 6.62 (s, 1H), 3.46-3.30 (m, 2H), 2.98 (d, 3H), 2.26 (s, 3H), 1.15 (t, 3H); LCMS (M + 1): 370.8 |
| 136 | N'-(3-((4-chloro-2-fluorophenyl)amino)-5-fluoro-2-methylphenyl)-N-ethyl-N-methylformimidamide | $^1$H-NMR (400 MHz, DMSO-d6) δ 7.68 (d, 1H), 7.41-7.35 (m, 2H), 7.10 (dq, 1H), 6.78 (t, 1H), 6.42 (d, 1H), 6.30 (d, 1H), 3.44-3.30 (m, 2H), 2.97 (d, 3H), 2.04 (s, 3H), 1.14 (t, 3H); LCMS (M + 1): 337.79 |
| 137 | N'-(2-chloro-3-((3-chloro-5-(trifluoromethyl)phenyl)amino)-5-methylphenyl)-N-ethyl-N-methylformimidamide | $^1$H-NMR (400 MHz, DMSO-d6) δ 8.33 (d, 1H), 7.71 (d, 1H), 7.07-7.05 (m, 2H), 7.00-6.99 (m, 1H), 6.77 (d, 1H), 6.62 (d, 1H), 3.47-3.31 (m, 2H), 2.98 (d, 3H), 2.24 (s, 3H), 1.15 (t, 3H); LCMS (M + 1): 405.85 |
| 138 | N'-(2-chloro-3-((2-fluoro-6-methylphenyl)(methyl)amino)-5-methylphenyl)-N-ethyl-N-methylformimidamide | $^1$H-NMR (400 MHz, DMSO-d6) δ 7.64-7.63 (m, 1H), 7.09 (td, 1H), 7.02-6.97 (m, 2H), 6.56 (d, 1H), 6.39-6.38 (m, 1H), 3.39-3.30 (m, 2H), 3.17-3.15 (m, 3H), 2.97-2.88 (m, 3H), 2.22 (s, 3H), 2.13 (s, 3H), 1.14 (t, 3H); LCMS (M + 1): 347.86 |
| 139 | N'-(2-chloro-3-((2-fluoro-3-methylphenyl)(methyl)amino)-5-methylphenyl)-N-ethyl-N-methylformimidamide | $^1$H-NMR (400 MHz, DMSO-d6) δ 7.70 (s, 1H), 6.96 (t, 1H), 6.83-6.75 (m, 2H), 6.59-6.55 (m, 2H), 3.44-3.30 (m, 2H), 3.11 (s, 3H), 2.92 (s, 3H), 2.19 (s, 3H), 2.14 (s, 3H), 1.14 (t, 3H); LCMS (M + 1): 348.40 |
| 140 | N'-(3-((4-chloro-2-fluorophenyl)(methyl)amino)-5-fluoro-2-methylphenyl)-N-ethyl-N-methylformimidamide | $^1$H-NMR (400 MHz, DMSO-d6) δ 7.65 (d, 1H), 6.98-6.75 (m, 3H), 6.59-6.55 (m, 2H), 3.44-3.30 (m, 2H), 2.92-3.11 (m, 3H), 2.50-2.55 (m, 3H), 2.15-2.19 (m, 6H), 1.13-1.35 (m, 3H); LCMS (M + 1): 347.86 |
| 141 | N-ethyl-N'-(5-fluoro-3-(2-fluorobenzyl)-2-methylphenyl)-N-methylformimidamide | $^1$H-NMR (400 MHz, DMSO-d6) δ 7.71 (brs, 1H), 7.31-7.25 (m, 1H), 7.22-7.17 (m, 1H), 7.15-7.11 (m, 1H), 7.08-7.04 (m, 1H), 6.58 (d, 1H), 6.45-6.42 (m, 1H), 3.94 (s, 2H), 3.43-3.30 (m, 2H), 2.91 (s, 3H), 2.09 (s, 3H), 1.15-1.11 (m, 3H); LCMS (M + 1): 303.40 |
| 142 | N'-(3-(2-chlorobenzyl)-5-fluoro-2-methylphenyl)-N-ethyl-N-methylformimidamide | $^1$H-NMR (400 MHz, DMSO-d6) δ 7.72 (brs, 1H), 7.52-7.47 (m, 1H), 7.30-7.26 (m, 2H), 7.03-7.00 (m, 1H), 6.60 (d, 1H), 6.33-6.30 (m, 1H), 4.01 (s, 2H), 3.44-3.31 (m, 2H), 2.93 (s, 3H), 2.07 (s, 3H), 1.14 (t, 3H); LCMS (M + 1): 319.35 |
| 143 | N-ethyl-N'-(5-fluoro-2-methyl-3-(2-(trifluoromethyl)benzyl)phenyl)-N-methylformimidamide | $^1$H-NMR (400 MHz, DMSO-d6) δ 7.77-7.55 (m, 2H), 7.58 (t, 1H), 7.45 (t, 1H), 7.04 (d, 1H), 6.63 (d, 1H), 6.34 (dd, 1H), 4.10 (s, 2H), 3.43-3.31 (m, 2H), 2.93 (s, 3H), 2.03 (s, 3H), 1.17-1.12 (m, 3H); LCMS (M + 1): 353.40 |
| 144 | N'-(3-(3-chlorobenzyl)-5-fluoro-2-methylphenyl)-N-ethyl-N-methylformimidamide | $^1$H-NMR (400 MHz, DMSO-d6) δ 7.71 (brs, 1H), 7.32 (t, 1H), 7.27-7.24 (m, 1H), 7.20-7.17 (m, 1H), 7.11 (d, 1H), 6.59 (d, 2H), 3.96 (s, 2H), 3.42-3.31 (m, 3H), 2.92 (s, 3H), 2.06 (s, 3H), 1.13 (t, 3H); LCMS (M + 1): 318.95 |
| 145 | N-ethyl-N'-(5-fluoro-3-((2-fluoro-6-methylphenyl)(methyl)amino)-2-methylphenyl)-N-methylformimidamide | $^1$H-NMR (400 MHz, DMSO-d6) δ 7.67-7.53 (m, 1H), 7.13-7.08 (m, 1H), 7.04-7.00 (m, 2H), 6.47 (dd, 1H), 6.34-6.27 (m, 1H), 3.40-3.29 (m, 2H), 3.13-3.10 (m, 3H), 2.99-2.83 (m, 3H), 2.10-2.04 (m, 3H), 1.58 (s, 3H), 1.11-1.05 (m, 3H); LCMS (M + 1): 331.41 |
| 146 | N-ethyl-N'-(5-fluoro-2-methyl-3-(3-methylbenzyl)phenyl)-N-methylformimidamide | $^1$H-NMR (400 MHz, DMSO-d6) δ 7.69 (brs, 1H), 7.17 (t, 1H), 7.01-6.91 (m, 3H), 6.56-6.51 (m, 2H), 3.89 (s, 2H), 3.47-3.32 (m, 2H), 2.92 (s, 3H), 2.26 (s, 3H), 2.08 (s, 3H), 1.13 (t, 3H); LCMS (M + 1): 299.15 |
| 147 | N-ethyl-N'-(5-fluoro-3-(3-fluorobenzyl)-2-methylphenyl)-N-methylformimidamide | $^1$H-NMR (400 MHz, DMSO-d6) δ 7.70 (brs, 1H), 7.35-7.30 (m, 1H), 7.04-6.93 (m, 3H), 6.58 (d, 2H), 3.96 (s, 2H), 3.42-3.31 (m, 2H), 2.92 (s, 3H), 2.06 (s, 3H), 1.13 (t, 3H); LCMS (M + 1): 302.95 |
| 148 | N-ethyl-N'-(5-fluoro-2-methyl-3-(2-methylbenzyl)phenyl)-N-methylformimidamide | $^1$H-NMR (400 MHz, DMSO-d6) δ 7.72 (brs, 1H), 7.20 (d, 1H), 7.16-7.09 (m, 2H), 6.86-6.84 (m, 1H), 6.57 (d, 1H), 6.22-6.19 (m, 1H), 3.87 (s, 2H), 3.44-3.30 (m, 2H), 2.93 (sz, 3H), 2.22 (s, 3H), 2.10 (s, 3H), 1.14 (t, 3H); LCMS (M + 1): 299.10 |
| 149 | N'-(3-benzyl-5-fluoro-2-methylphenyl)-N-ethyl-N-methylformimidamide | $^1$H-NMR (400 MHz, DMSO-d6) δ 7.69 (brs, 1H), 7.31-7.27 (m, 2H), 7.21-7.13 (m, 3H), 6.57-6.52 (m, 2H), 3.94 (s, 2H), 3.42-3.30 (m, 2H), 2.92 (s, 3H), 2.08 (s, 3H), 1.13 (t, 3H); LCMS (M + 1): 285.10 |
| 150 | N'-(2-chloro-3-(4-methoxybenzyl)-5-methylphenyl)-N-ethyl-N-methylformimidamide | $^1$H-NMR (400 MHz, DMSO-d6) δ 7.65 (brs, 1H), 7.10-7.07 (m, 2H), 6.82 (d, 2H), 6.65 (d, 1H), 6.62-6.58 (m, 1H), 3.91 (s, 2H), 3.69 (s, 3H), 3.44-3.31 (m, 2H), 2.90 (s, 3H), 2.17 (s, 3H), 1.11 (t, 3H); LCMS (M + 1): 330.95 |
| 151 | N'-(3-(2-bromobenzyl)-5-fluoro-2-methylphenyl)-N-ethyl-N-methylformimidamide | $^1$H-NMR (400 MHz, DMSO-d6) δ 7.68-7.61 (m, 2H), 7.30 (t, 1H), 7.17 (t, 1H), 7.03-7.01 (m, 1H), 6.54 (dd, 1H), 6.28 (dd, 1H), 4.01 (s, 2H), 3.41-3.35 (m, 2H), 2.96 (s, 3H), 2.08 (s, 3H), 1.15 (t, 3H); LCMS (M + 1): 364.95 |

TABLE I-continued

| Sr. No. | IUPAC Name | Analytical Data |
|---|---|---|
| 152 | N-ethyl-N'-(5-fluoro-3-((2-fluoro-3-methylphenyl)(methyl)amino)-2-methylphenyl)-N-methylformimidamide | $^1$H-NMR (400 MHz, DMSO-d6) δ 7.74-7.62 (m, 1H), 6.98-6.94 (m, 1H), 6.86-6.82 (m, 1H), 6.71 (td, 1H), 6.50-6.43 (m, 2H), 3.45-3.30 (m, 2H), 3.08 (s, 3H), 3.01-2.91 (m, 3H), 2.17 (d, 3H), 1.92-1.90 (m, 3H), 1.15-1.09 (m, 3H); LCMS (M + 1): 332.3 |
| 153 | N-ethyl-N'-(5-fluoro-2-methyl-3-(methyl(3-(trifluoromethyl)pyridin-2-yl)amino)phenyl)-N-methylformimidamide | $^1$H-NMR (400 MHz, DMSO-d6) δ 8.55 (d, 1H), 7.99 (dd, 1H), 7.69 (d, 1H), 7.13 (dd, 1H), 6.60-6.54 (m, 1H), 6.12 (dd, 1H), 3.46-3.30 (m, 2H), 3.19 (s, 3H), 2.94 (s, 3H), 2.01 (s, 3H), 1.14 (t, 3H); LCMS (M + 1): 369.95 |
| 154 | N'-(5-chloro-2-methyl-3-(m-tolylamino)phenyl)-N-ethyl-N-methylformimidamide | $^1$H-NMR (400 MHz, DMSO-d6) δ 7.67 (d, 1H), 7.35 (d, 1H), 7.08 (t, 1H), 6.70-6.67 (m, 3H), 6.62 (d, 1H), 6.52 (s, 1H), 3.43-3.30 (m, 2H), 2.96 (d, 3H), 2.23 (s, 3H), 2.07 (s, 3H), 1.14 (t, 3H); LCMS (M + 1): 316.1 |
| 155 | N'-(5-chloro-2-methyl-3-(phenylamino)phenyl)-N-ethyl-N-methylformimidamide | $^1$H-NMR (400 MHz, DMSO-d6) δ 7.73-7.61 (m, 1H), 7.42 (s, 1H), 7.23-7.18 (m, 2H), 6.89 (dd, 2H), 6.82-6.78 (m, 1H), 6.71 (d, 1H), 6.53-6.51 (m, 1H), 3.47-3.29 (m, 2H), 3.02-2.91 (m, 3H), 2.09 (d, 3H), 1.13 (dd, 3H); LCMS (M + 1): 302.8 |
| 156 | N'-(2-chloro-3-((4-chloro-2-fluorophenyl)(methyl)amino)-5-methylphenyl)-N-ethyl-N-methylformimidamide | $^1$H-NMR (400 MHz, DMSO-d6) δ 7.72-7.59 (m, 1H), 7.26 (dd, 1H), 7.17-7.14 (m, 1H), 6.94 (t, 1H), 6.63-6.59 (m, 2H), 3.46-3.30 (m, 2H), 3.16-3.11 (m, 3H), 3.02-2.92 (m, 3H), 2.20 (s, 3H), 1.17-1.10 (m, 3H); LCMS (M + 1): 370.7 |
| 157 | N'-(2-chloro-5-methyl-3-(methyl(3-(trifluoromethyl)pyridin-2-yl)amino)phenyl)-N-ethyl-N-methylformimidamide | $^1$H-NMR (400 MHz, DMSO-d6) δ 8.54-8.52 (m, 1H), 7.99-7.96 (m, 1H), 7.65 (d, 1H), 7.14-7.11 (m, 1H), 6.66 (s, 1H), 6.39 (d, 1H), 3.36-3.32 (m, 2H), 3.25 (s, 3H), 2.96 (d, 3H), 2.15 (s, 3H), 1.14 (t, 3H); LCMS (M + 1): 385.83 |
| 158 | N'-(2-chloro-3-((3-chloro-5-(trifluoro-methyl)phenyl)(methyl)amino)-5-methylphenyl)-N-ethyl-N-methylformimidamide | $^1$H-NMR (400 MHz, DMSO-d6) δ 7.81-7.68 (m, 1H), 7.01 (s, 1H), 6.87-6.85 (m, 1H), 6.81-6.79 (m, 1H), 6.67-6.62 (m, 2H), 3.47-3.30 (m, 2H), 3.23 (s, 3H), 3.02-2.95 (m, 3H), 2.29 (d, 3H), 1.18-1.12 (m, 3H); LCMS (M + 1): 418.25 |
| 159 | N'-(5-chloro-2-methyl-3-(methyl(phenyl)amino)phenyl)-N-ethyl-N-methylformimidamide | $^1$H-NMR (400 MHz, DMSO-d6) δ 7.80 (s, 1H), 7.17-7.12 (m, 2H), 6.85 (s, 1H), 6.75 (d, 1H), 6.67 (t, 1H), 6.49 (d, 2H), 3.54-3.33 (m, 2H), 3.21-3.14 (m, 3H), 2.97 (d, 3H), 1.94 (s, 3H), 1.16 (t, 3H); LCMS (M + 1): 316.05 |
| 160 | N'-(5-chloro-2-methyl-3-(methyl(m-tolyl)amino)phenyl)-N-ethyl-N-methylformimidamide | $^1$H-NMR (400 MHz, DMSO-d6) δ 7.82-7.68 (m, 1H), 7.00-7.00 (m, 1H), 6.85-6.80 (m, 1H), 6.73 (d, 1H), 6.50-6.48 (m, 1H), 6.34 (s, 1H), 6.27 (dd, 1H), 3.48-3.29 (m, 2H), 3.15-3.12 (m, 3H), 3.02-2.93 (m, 3H), 2.22-2.18 (m, 3H), 1.95 (d, 3H), 1.19-1.10 (m, 3H); LCMS (M + 1): 330.1 |
| 161 | N'-(3-((3-chloro-5-(triiluoromethyl)phenyl)amino)-5-fluoro-2-methylphenyl)-N-ethyl-N-methylformimidamide | $^1$H-NMR (400 MHz, DMSO-d6) δ 8.27 (s, 1H), 7.78-7.66 (m, 1H), 7.05 (s, 1H), 6.98-6.94 (m, 2H), 6.63-6.53 (m, 2H), 3.49-3.30 (m, 2H), 3.01-2.95 (m, 3H), 2.04 (s, 3H), 1.15 (t, 3H); LCMS (M + 1): 388.0 |
| 162 | N'-(5-chloro-3-((4-methoxyphenyl)amino)-2-methylphenyl)-N-ethyl-N-methylformimidamide | $^1$H-NMR (400 MHz, DMSO-d6) δ 7.70 (s, 1H), 7.05 (s, 1H), 6.98-6.94 (m, 2H), 6.90-6.86 (m, 2H), 6.47 (t, 1H), 6.37 (s, 1H), 3.73 (d, 3H), 3.38 (d, 2H), 2.96 (d, 3H), 2.09 (s, 3H), 1.14 (t, 3H); LCMS (M + 1): 332.0 |
| 163 | N'-(5-chloro-3-((3-chlorophenyl)amino)-2-methylphenyl)-N-ethyl-N-methylformimidamide | $^1$H-NMR (400 MHz, DMSO-d6) δ 7.75-7.63 (m, 2H), 7.18-7.14 (m, 1H), 6.76-6.72 (m, 4H), 6.63 (s, 1H), 3.46-3.33 (m, 2H), 2.95 (d, 3H), 2.03 (s, 3H), 1.13 (t, 3H); LCMS (M + 1): 336.12 |
| 164 | N'-(3-((3-bromophenyl)amino)-5-chloro-2-methylphenyl)-N-ethyl-N-methylformimidamide | $^1$H-NMR (400 MHz, DMSO-d6) δ 7.80-7.65 (m, 2H), 7.15-7.10 (m, 1H), 6.95-6.88 (m, 2H), 6.80-6.75 (m, 2H), 6.66-6.63 (m, 1H), 3.47-3.30 (m, 2H), 3.01-2.94 (m, 3H), 2.10-2.02 (m, 3H), 1.16-1.10 (m, 3H); LCMS (M + 1): 381.85 |
| 165 | N'-(5-chloro-3-((2-fluorophenyl)amino)-2-methylphenyl)-N-ethyl-N-methylformimidamide | $^1$H-NMR (400 MHz, DMSO-d6) δ 7.76-7.62 (m, 1H), 7.25 (s, 1H), 7.21-7.16 (m, 1H), 7.07-7.03 (m, 1H), 6.93-6.89 (m, 1H), 6.88-6.82 (m, 1H), 6.58-6.54 (m, 1H), 6.46 (t, 1H), 3.48-3.30 (m, 2H), 3.03-2.94 (m, 3H), 2.10-2.05 (m, 3H), 1.14 (t 3H); LCMS (M + 1): 320.1 |
| 166 | N'-(5-chloro-3-((3-fluorophenyl)amino)-2-methylphenyl)-N-ethyl-N-methylformimidamide | $^1$H-NMR (400 MHz, DMSO-d6) δ 7.80-7.64 (m, 2H), 7.22-7.16 (m, 1H), 6.77 (d, 1H), 6.68-6.63 (m, 2H), 6.55-6.50 (m, 2H), 33.49-3.30 (m, 2H), 3.04-2.90 (m, 3H), 2.09-2.02 (m, 3H), 1.16-1.10 (m, 3H); LCMS (M + 1): 319.95 |
| 167 | N'-(5-chloro-3-((4-methoxyphenyl)(methyl)amino)-2-methylphenyl)-N-ethyl-N-methylformimidamide | $^1$H-NMR (400 MHz, DMSO-d6) δ 7.72 (dd, 1H), 6.80-6.75 (m, 3H), 6.69 (d, 1H), 6.51 (td, 2H), 3.67 (s, 3H), 3.45-3.29 (m, 2H), 3.09 (d, 3H), 3.02-2.91 (m, 3H), 1.93 (t, 3H), 1.17-1.10 (m, 3H); LCMS (M + 1): 345.9 |
| 168 | N'-(3-(2-cyanobenzyl)-5-fluoro-2-methylphenyl)-N-ethyl-N-methylformimidamide | $^1$H-NMR (400 MHz, DMSO-d6) δ 7.86-7.84 (m, 1H), 7.73-7.62 (m, 2H), 7.46-7.43 (m, 1H), 7.17 (d, 1H), 6.63 (d, 1H), 6.39 (dd, 1H), 4.15 (s, 2H), 3.43-3.31 (m, 2H), 2.93 (m, 3H), 2.09 (s, 3H), 1.14 (t, 3H); LCMS (M + 1): 310.40 |
| 169 | N'-(2-chloro-3-((2,3-dihydrobenzo[b][1,4]dioxin-6-yl)amino)-5-methylphenyl)-N-ethyl-N-methylformimidamide | $^1$H-NMR (400 MHz, DMSO-d6) δ 7.61 (d, 1H), 7.02 (s, 1H), 6.74 (dd, 1H), 6.59-6.56 (m, 2H), 6.49 (d, 1H), 6.23 (s, 1H), 4.19 (td, 4H), 3.37 (d, 2H), 2.94 (d, 3H), 2.11 (s, 3H), 1.12 (t, 3H); LCMS (M + 1): 360.7 |
| 170 | N-ethyl-N'-(5-fluoro-2-methyl-3-(2-(trifluoromethoxy)benzyl)phenyl)-N-methylformimidamide | $^1$H-NMR (400 MHz, DMSO-d6) δ 7.72 (brs, 1H), 7.41-7.37 (m, 2H), 7.35-7.29 (m, 1H), 7.07 (d, 1H), 6.61 (d, 1H), 6.43 (dd, 1H), 3.97 (s, 2H), 3.43-3.30 (m, 2H), 2.93 (s, 3H), 2.04 (s, 3H), 1.13 (t, 3H); LCMS (M + 1): 369.15 |

TABLE I-continued

| Sr. No. | IUPAC Name | Analytical Data |
|---|---|---|
| 171 | N-ethyl-N'-(5-fluoro-2-methyl-3-(4-methylbenzyl)phenyl)-N-methylformimidamide | $^1$H-NMR (400 MHz, DMSO-d6) δ 7.68 (brs, 1H), 7.09 (d, 2H), 7.02 (d, 2H), 6.55-6.49 (m, 2H), 3.48-3.26 (sm, 2H), 2.91 (s, 3H), 2.26 (s, 3H), 2.08 (s, 3H), 1.12 (t, 3H); LCMS (M + 1): 299.20 |
| 172 | N'-(3-(4-chlorobenzyl)-5-fluoro-2-methylphenyl)-N-ethyl-N-methylformimidamide | $^1$H-NMR (400 MHz, DMSO-d6) δ 7.69 (brs, 1H), 7.35-7.23 (m, 2H), 7.15 (d, 2H), 6.56 (d, 2H), 3.93 (s, 2H), 3.50-3.26 (m, 2H), 2.91 (s, 3H), 2.05 (s, 3H), 1.13 (t, 3H); LCMS (M + 1): 319.10 |
| 173 | N-ethyl-N'-(5-fluoro-2-methyl-3-(3-(trifluoromethoxy)benzyl)phenyl)-N-methylformimidamide | $^1$H-NMR (400 MHz, DMSO-d6) δ 7.70 (brsz, 1H), 7.42 (t, 1H), 7.20-7.13 (m, 3H), 6.59 (d, 2H), 4.00 (s, 2H), 3.42-3.31 (m, 2H), 2.91 (s, 3H), 2.06 (s, 3H), 1.12 (t, 3H); LCMS (M + 1): 369.30 |
| 174 | N'-(3-(3-cyanobenzyl)-5-fluoro-2-methylphenyl)-N-ethyl-N-methylformimidamide | $^1$H-NMR (400 MHz, DMSO-d6) δ 7.70-7.60 (m, 3H), 7.53-7.46 (m, 2H), 6.60 (d, 2H), 4.01 (s, 2H), 3.42-3.32 (m, 2H), 2.91 (s, 3H), 2.06 (s, 3H), 1.13 (t, 3H); LCMS (M + 1): 310.15 |
| 175 | N'-(3-(4-bromobenzyl)-5-fluoro-2-methylphenyl)-N-ethyl-N-methylformimidamide | $^1$H-NMR (400 MHz, DMSO-d6) δ 7.69 (brs, 1H), 7.58-7.4 (m, 2H), 7.10 (d, 2H), 6.59-6.55 (m, 2H), 3.91 (s, 2H), 3.42-3.32 (m, 2H), 2.91 (s, 3H), 2.05 (s, 3H), 1.12 (t, 3H); LCMS (M + 1): 364.55 |
| 176 | N-ethyl-N'-(5-fluoro-2-methyl-3-(4-(trifluorometh-oxy)benzyl)phenyl)-N-methylformimidamide | $^1$H-NMR (400 MHz, DMSO-d6) δ 7.69 (brs, 1H), 7.29-7.24 (m, 4H), 6.58 (d, 2H), 3.97 (s, 2H), 3.41-3.33 (m, 2H), 2.91 (s, 3H), 2.06 (s, 3H), 1.12 (t, 3H); LCMS (M + 1): 369.20 |
| 177 | N'-(2-chloro-3-((2-(difluoromethoxy)phenyl)amino)-5-methylphenyl)-N-ethyl-N-methylformimidamide | $^1$H-NMR (400 MHz, DMSO-d6) δ 7.66 (d, 1H), 7.337.20 (d, 1H), 7.17-7.11 (m, 3H), 6.98-6.93 (m, 1H), 6.79 (s, 1H), 6.57 (d, 1H), 6.41 (s, 1H), 3.43-3.33 (m, 2H), 2.96 (d, 3H), 2.17 (s, 3H), 1.13 (t, 3H); LCMS (M + 1): 368.4 |
| 178 | N'-(5-chloro-3-((2-fluorophenyl)(methyl)amino)-2-methylphenyl)-N-ethyl-N-methylformimidamide | $^1$H-NMR (400 MHz, DMSO-d6) δ 7.75-7.63 (m, 1H), 7.12-7.07 (m, 2H), 6.98-6.91 (m, 2H), 6.72-6.69 (m, 1H), 6.62 (d, 1H), 3.46-3.29 (m, 2H), 3.10 (s, 3H), 3.00-2.92 (m, 3H), 1.97 (s, 3H), 1.16-1.10 (m, 3H); LCMS (M + 1): 333.95 |
| 179 | N'-(5-chloro-3-((3-fluorophenyl)(methyl)amino)-2-methylphenyl)-N-ethyl-N-methylformimidamide | $^1$H-NMR (400 MHz, DMSO-d6) δ 7.73 (d, 1H), 7.14-7.09 (m, 1H), 6.86 (d, 1H), 6.77 (d, 1H), 6.44-6.40 (m, 1H), 6.25-6.21 (m, 2H), 3.46-3.34 (m, 2H), 3.15 (d, 3H), 3.00-2.92 (m, 3H), 1.91 (s, 3H), 1.15-1.08 (m, 3H); LCMS (M + 1): 334.1 |
| 180 | N'-(5-chloro-3-((3-chlorophenyl)(methyl)amino)-2-methylphenyl)-N-ethyl-N-methylformimidamide | $^1$H-NMR (400 MHz, DMSO-d6) δ 7.74 (d, 1H), 7.12 (t, 1H), 6.87 (d, 1H), 6.77 (d, 1H), 6.67-6.65 (m, 1H), 6.43 (t, 1H), 6.37 (dd, 1H), 3.46-3.35 (m, 2H), 3.16-3.13 (m, 3H), 3.00-2.92 (m, 3H), 1.91 (s, 3H), 1.14 (t, 3H); LCMS (M + 1): 349.95 |
| 181 | N'-(2-chloro-5-methyl-3-((2-(trifluoro-methyl)benzyl)amino)phenyl)-N-ethyl-N-methylformimidamide | $^1$H-NMR (400 MHz, DMSO-d6) δ 7.70 (d, 1H), 7.62-7.51 (m, 2H), 7.45 (d, 1H), 7.41 (t, 1H), 6.01 (s, 1H), 5.91 (t, 1H), 5.78 (d, 1H), 4.51 (d, 2H), 3.41 (d, 2H), 2.89 (s, 3H), 1.98 (s, 3H), 1.09 (t, 3H); LCMS (M + 1): 384.05 |
| 182 | N-ethyl-N'-(5-fluoro-3-((4-fluoro-3-methylbenzyl)amino)-2-methylphenyl)-N-methylformimidamide | $^1$H-NMR (400 MHz, DMSO-d6) δ 7.59 (s, 1H), 7.22 (d, 1H), 7.17-7.13 (m, 1H), 7.06-7.02 (m, 1H), 5.89 (d, 1H), 5.79-5.75 (m, 1H), 5.73-5.70 (m, 1H), 4.24 (d, 2H), 3.46-3.35 (m, 1H), 3.28 (d, 1H), 2.90 (s, 3H), 2.19 (d, 3H), 2.03 (s, 3H), 1.10 (t, 3H); LCMS (M + 1): 332.15 |
| 183 | N'-(5-chloro-3-((3-chlorobenzyl)amino)-2-methylphenyl)-N-ethyl-N-methylformimidamide | $^1$H-NMR (400 MHz, DMSO-d6) δ 7.64 (s, 1H), 7.38-7.26 (m, 4H), 6.15 (s, 1H), 6.00 (d, 1H), 5.84 (t, 1H), 4.35 (d, 2H), 3.37 (d, 2H), 2.92 (s, 3H), 2.08 (s, 3H), 1.12 (t, 3H); LCMS (M + 1): 349.95 |
| 184 | N'-(2-chloro-3-((2,3-dihydrobenzo[b][1,4]dioxin-6-yl)(methyl)amino)-5-methylphenyl)-N-ethyl-N-methylformimidamide | $^1$H-NMR (400 MHz, DMSO-d6) δ 7.66 (d, 1H), 6.69-6.61 (m, 3H), 6.00-5.98 (m, 2H), 4.15-4.10 (m, 4H), 3.46-3.35 (m, 2H), 3.08-3.04 (m, 3H), 2.98-2.88 (m, 3H), 2.21 (s, 3H), 1.18-1.08 (m, 3H); LCMS (M + 1): 374.1 |
| 185 | N'-(5-chloro-2-methyl-3-(o-tolylamino)phenyl)-N-ethyl-N-methylformimidamide | $^1$H-NMR (400 MHz, DMSO-d6) δ 7.72-7.70 (m, 1H), 7.19 (d, 1H), 7.11 (td, 1H), 6.92 (td, 1H), 6.80-6.77 (m, 2H), 6.44 (s, 1H), 6.19-6.18 (m, 1H), 3.46-3.30 (m, 2H), 3.01-2.91 (m, 3H), 2.16 (s, 3H), 2.08 (d, 3H), 1.14 (t, 3H); LCMS (M + 1): 315.9 |
| 186 | N'-(2-chloro-5-methyl-3-(pyrimidin-2-ylamino)phenyl)-N-ethyl-N-methylformimidamide | $^1$H-NMR (400 MHz, DMSO-d6) δ 8.44-8.39 (m, 3H), 7.73-7.61 (m, 1H), 7.37 (d, 1H), 6.84-6.82 (m, 1H), 6.58-6.55 (m, 1H), 3.03-2.94 (m, 2H), 2.55-2.50 (m, 3H), 2.25 (s, 3H), 1.15 (t, 3H); LCMS (M + 1): 303.8 |
| 187 | N-ethyl-N'-(5-fluro-2-methyl-3-(pyrimidin-2-ylamino)phenyl)-N-methylformimidamide | $^1$H-NMR (400 MHz, DMSO-d6) δ 8.68 (s, 1H), 8.44-8.38 (m, 2H), 7.75-7.63 (m, 1H), 7.01 (dd, 1H), 6.77 (t, 1H), 6.49 (d, 1H), 3.52-3.28 (m, 2H), 2.97 (d, 3H), 2.08 (s, 3H), 1.14 (t, 3H); LCMS (M + 1): 303.8 |
| 188 | N-ethyl-N'-(5-fluoro-2-methyl-3-(4-(trifluoromethyl)benzyl)phenyl)-N-methylformimidamide | $^1$H-NMR (400 MHz, DMSO-d6) δ 7.66-7.55 (m, 3H), 7.31 (d, 2H), 6.57-6.55 (m, 2H), 4.00 (s, 2H), 3.41-3.31 (m, 2H), 2.86 (s, 3H), 2.01 (s, 3H), 1.08 (t, 3H); LCMS (M + 1): 353.40 |
| 189 | N'-(2-bromo-3-(3-fluorobenzyl)-5-methylphenyl)-N-ethyl-N-methylformimidamide | $^1$H-NMR (400 MHz, DMSO-d6) δ 7.60 (brs, 1H), 7.30 (t, 6.4Hz, 1H), 7.02-6.94 (m, 3H), 6.71 (d, 1H), 6.65 (s, 1H), 4.05 (s, 2H), 3.42-3.13 (m, 2H), 2.86 (s, 3H), 2.18 (s, 3H), 1.12 (t, 3H); LCMS (M + 1): 364.80 |
| 190 | N-ethyl-N'-(3-(3-fluorobenzyl)-5-methyl-2-(methylthio)phenyl)-N-methylformimidamide | $^1$H-NMR (400 MHz, DMSO-d6) δ 7.62 (brs, 1H), 7.28 (t, 1H), 7.02-6.90 (m, 3H), 6.71 (d, 1H), 6.55 (s, 1H), 4.17 (s, 2H), 3.46-3.31 (m, 2H), 2.93 (s, 3H), 2.19 (s, 3H), 2.16 (s, 3H), 1.12 (t, 3H); LCMS (M + 1): 331.20 |
| 191 | N'-(5-chloro-2-methyl-3-(methyl(o-tolyl)amino)phenyl)-N-ethyl-N-methylformimidamide | $^1$H-NMR (400 MHz, DMSO-d6) δ 7.73 (s, 1H), 7.18-7.13 (m, 2H), 6.96-6.94 (m, 2H), 6.64 (s, 1H), 6.40 (t, 1H), 3.43-3.33 (m, 2H), 2.95 (d, 6H), 1.96 (d, 6H), 1.12 (d, 3H); LCMS (M + 1): 330.1 |
| 192 | N'-(2-chloro-5-methyl-3-(methyl(pyrimidin-2-yl)amino)phenyl)-N-ethyl-N-methylformimidamide | $^1$H-NMR (400 MHz, DMSO-d6) δ 8.44-8.39 (m, 1H), 7.73-7.61 (m, 1H), 7.37 (d, 1H), 6.84-6.82 (m, 2H), 6.58-6.55 (m, 1H), 3.67 (s, 3H), 3.03-2.94 (m, 2H), 2.55-2.50 (m, 3H), 2.25 (s, 3H), 1.15 (t, 3H); LCMS (M + 1): 317.75 |

TABLE I-continued

| Sr. No. | IUPAC Name | Analytical Data |
|---|---|---|
| 193 | N-ethyl-N'-(5-fluoro-2-methyl-3-(pyrazin-2-ylamino)phenyl)-N-methylformimidamide | $^1$H-NMR (400 MHz, DMSO-d6) δ 8.58 (s, 1H), 8.26 (t, 1H), 8.06-8.04 (m, 1H), 7.89 (t, 1H), 7.74-7.61 (m, 1H), 7.15 (dd, 1H), 6.48 (d, 1H), 3.46-3.30 (m, 2H), 2.97 (d, 3H), 2.11 (d, 3H), 1.15 (t, 3H); LCMS (M + 1): 288.1 |
| 194 | N'-(2-chloro-5-methyl-3-(pyrazin-2-ylamino)phenyl)-N-ethyl-N-methylformimidamide | $^1$H-NMR (400 MHz, DMSO-d6) δ 8.63 (s, 1H), 8.30 (t, 1H), 8.07-8.06 (m, 1H), 7.92-7.91 (m, 1H), 7.74 (s, 1H), 7.32 (s, 1H), 6.56 (s, 1H), 3.46-3.33 (m, 2H), 2.98 (d, 3H), 2.24 (s, 3H), 1.15 (t, 3H); LCMS (M + 1): 304.1 |
| 195 | N'-(2-chloro-5-methyl-3-((1-(pyrazin-2-yl)propan-2-yl)amino)phenyl)-N-ethyl-N-methylformimidamide | $^1$H-NMR (400 MHz, DMSO-d6) δ 8.59-8.57 (m, 2H), 8.47 (d, 1H), 7.56 (d, 1H), 6.18 (s, 1H), 6.03 (s, 1H), 4.84 (d, 1H), 3.97-3.90 (m, 1H), 3.42-3.32 (m, 2H), 3.11 (q, 1H), 2.91-2.99 (m, 4H), 2.16 (d, 3H), 1.10-1.19 (m, 6H); LCMS (M + 1): 345.85 |
| 196 | N'-(2-chloro-5-methyl-3-(((5-methylpyrazin-2-yl)methyl)amino)phenyl)-N-ethyl-N-methylformimidamide | $^1$H-NMR (400 MHz, DMSO-d6) δ 8.49 (d, 1H), 8.45 (s, 1H), 7.63-7.53 (m, 1H), 6.07 (d, 2H), 5.89 (t, 1H), 4.45 (d, 2H), 3.38 (d, 1H), 3.28 (s, 1H), 2.92 (d, 3H), 2.45 (s, 3H), 2.10 (d, 3H), 1.11 (t, 3H); LCMS (M + 1): 332.15 |
| 197 | N-ethyl-N'-(5-fluoro-2-methyl-3-((1-(pyrazin-2-yl)propan-2-yl)amino)phenyl)-N-methylformimidamide | $^1$H-NMR (400 MHz, DMSO-d6) δ 8.57 (q, 1H), 8.55 (d, 1H), 8.45 (d, 1H), 7.59 (s, 1H), 6.04 (dd, 1H), 5.91 (d, 1H), 4.75 (d, 1H), 3.83 (dt, 1H), 3.33-3.35 (m, 1H), 3.29-3.24 (m, 1H), 3.09 (q, 1H), 2.87 (dd, 4H), 1.93-1.88 (m, 3H), 1.15 (d, 3H), 1.10 (t, 3H); LCMS (M + 1): 330.15 |
| 198 | N-ethyl-N'-(5-fluoro-2-methyl-3-(((5-methylpyrazin-2-yl)methyl)amino)phenyl)-N-methylformimidamide | $^1$H-NMR (400 MHz, DMSO-d6) δ 8.47 (s, 1H), 8.44 (d, 1H), 7.62-7.53 (m, 1H), 5.94 (d, 1H), 5.86-5.81 (m, 2H), 4.41 (d, 2H), 3.37 (d, 1H), 3.21-3.30 (1H), 2.90 (s, 3H), 2.45 (s, 3H), 2.04 (s, 3H), 1.10 (t, 3H); LCMS (M + 1): 316.4 |
| 199 | N-ethyl-N'-(5-fluoro-2-methyl-3-(methyl(pyrazin-2-yl)amino)phenyl)-N-methylformimidamide | $^1$H-NMR (400 MHz, DMSO-d6) δ 8.10 (q, 1H), 7.81-7.62 (m, 2H), 7.52 (s, 1H), 6.78-6.70 (m, 2H), 3.34-3.35 (m, 2H), 3.28 (d, 3H), 2.96 (d, 3H), 1.94-1.87 (m, 3H), 1.16-1.10 (m, 3H); LCMS (M + 1): 302.15 |
| 200 | N-ethyl-N'-(5-fluoro-2-methyl-3-(methyl(pyrimidin-2-yl)amino)phenyl)-N-methylformimidamide | $^1$H-NMR (400 MHz, DMSO-d6) δ 8.31 (s, 2H), 7.71 (d, 1H), 6.67-6.60 (m, 3H), 3.46-3.33 (m, 2H), 3.31 (s, 3H), 2.95 (d, 3H), 1.87 (d, 3H), 1.13 (t, 3H); LCMS (M + 1): 301.85 |
| 201 | N-ethyl-N'-(5-fluoro-2-methyl-3-(3-(trifluoromethyl)benzyl)phenyl)-N-methylformimidamide | $^1$H-NMR (400 MHz, DMSO-d6) δ 7.70 (brs, 1H), 7.57-7.51 (m, 3H), 7.44 (d, 1H), 6.60 (d, 2H), 4.05 (s, 2H), 3.42-3.31 (m, 2H), 2.91 (s, 3H), 2.06 (s, 3H), 1.12 (t, 3H); LCMS (M + 1): 353.50 |
| 202 | N'-(3-(4-cyanobenzyl)-5-fluoro-2-methylphenyl)-N-ethyl-N-methylformimidamide | $^1$H-NMR (400 MHz, DMSO-d6) δ 7.76-7.74 (m, 2H), 7.69 (brs, 1H), 7.33 (d, 2H), 6.60 (d, 2H), 4.04 (s, 2H), 3.42-3.33 (m, 2H), 2.92 (s, 3H), 2.04 (s, 3H), 1.13 (t, 3H); LCMS (M + 1): 310.45 |
| 203 | N-ethyl-N'-(5-fluoro-3-(4-fluoro-3-methylbenzyl)-2-methylphenyl)-N-methylformimidamide | $^1$H-NMR (400 MHz, DMSO-d6) δ 7.69 (brs, 1H), 7.05-7.01 (m, 2H), 6.97-6.94 (m, 1H), 6.57-6.51 (m, 2H), 3.87 (s, 2H), 3.41-3.32 (m, 2H), 2.91 (s, 3H), 2.19 (d, 3H), 2.07 (s, 3H), 1.12 (t, 3H); LCMS (M + 1): 317.50 |
| 204 | N-ethyl-N'-(5-fluoro-3-(4-fluorobenzyl)-2-methylphenyl)-N-methylformimidamide | $^1$H-NMR (400 MHz, DMSO-d6) δ 7.66 (brs, 1H), 7.16-7.12 (m, 2H), 7.11-7.05 (m, 2H), 6.61-6.51 (m, 2H), 3.90 (s, 2H), 3.40-3.30 (m, 2H), 2.89 (s, 3H), 2.04 (s, 3H), 1.10 (t, 3H); LCMS (M + 1): 303.20 |
| 205 | N'-(3-(3-bromobenzyl)-5-fluoro-2-methylphenyl)-N-ethyl-N-methylformimidamide | $^1$H-NMR (400 MHz, DMSO-d6) δ 7.68 (brs, 1H), 7.39-7.36 (m, 1H), 7.30 (d, 1H), 7.24 (t, 1H), 7.13 (d, 1H), 6.57 (d, 2H), 3.93 (s, 2H), 3.40-3.31 (m, 2H), 2.86 (s, 3H), 2.04 (s, 3H), 1.11 (t, 3H); LCMS (M + 1): 364.50 |
| 206 | N'-(3-(4-chloro-3-fluorobenzyl)-5-fluoro-2-methylphenyl)-N-ethyl-N-methylformimidamide | $^1$H-NMR (400 MHz, DMSO-d6) δ 7.68 (brs, 1H), 7.47 (t, 1H), 7.15 (d, 1H), 6.97 (d, 1H), 6.57 (d, 2H), 3.94 (s, 2H), 3.40-3.31 (m, 1H), 2.89 (s, 3H), 2.03 (s, 3H), 1.11 (t, 3H); LCMS (M + 1): 337.10 |
| 207 | N'-(3-benzyl-2,5-dimethylphenyl)-N-ethyl-N-methylformimidamide | $^1$H-NMR (400 MHz, DMSO-d6) δ 7.53 (brs, 1H), 7.26-7.22 (m, 2H), 7.16-7.09 (m, 3H), 6.58 (s, 1H), 6.46 (s, 1H), 3.87 (s, 2H), 3.48-3.33 (m, 2H), 2.89 (s, 3H), 2.17 (s, 3H), 2.03 (s, 3H), 1.09 (t, 3H); LCMS (M + 1): 281.50 |
| 208 | N'-(2,5-dimethyl-3-(3-methylbenzyl)phenyl)-N-ethyl-N-methylformimidamide | $^1$H-NMR (400 MHz, DMSO-d6) δ 7.53 (brs, 1H), 7.12 (t, 1H), 6.96-6.87 (m, 3H), 6.57 (s, 1H), 6.45 (s, 1H), 3.82 (s, 2H), 3.49-3.32 (m, 21H), 2.89 (s, 3H), 2.23 (s, 3H), 2.17 (s, 3H), 2.03 (s, 3H), 1.10 (t, 3H); LCMS (M + 1): 295.50 |
| 209 | N'-(2-bromo-5-methyl-3-(2-methylbenzyl)phenyl)-N-ethyl-N-methylformimidamide | $^1$H-NMR (400 MHz, DMSO-d6) δ 7.70 (s, 1H), 7.19 (dd, 1H), 7.15-7.08 (m, 2H), 6.88-6.86 (m, 1H), 6.66 (s, 1H), 6.40 (d, 1H), 3.98 (s, 2H), 3.44-3.33 (m, 2H), 2.95 (s, 3H), 2.27 (s, 3H), 2.15 (s, 3H), 1.15 (t, 3H); LCMS (M + 1): 360.50 |
| 210 | N'-(2-chloro-5-methyl-3-(methyl(pyrazin-2-yl)amino)phenyl)-N-ethyl-N-methylformimidamide | $^1$H-NMR (400 MHz, DMSO-d6) δ 8.10 (q, 1H), 7.81 (d, 1H), 7.72 (d, 1H), 7.52 (d, 1H), 6.84 (d, 2H), 3.46-3.34 (m, 2H), 3.27 (d, 3H), 2.96 (d, 3H), 2.26 (s, 3H), 1.18-1.10 (m, 3H); LCMS (M + 1): 317.85 |
| 211 | N'-(5-chloro-2-methyl-3-(pyrazin-2-ylamino)phenyl)-N-ethyl-N-methylformimidamide | $^1$H-NMR (400 MHz, DMSO-d6) δ 8.60 (s, 1H), 8.25-8.23 (m, 1H), 8.06-8.04 (m, 1H), 7.90-7.88 (m, 1H), 7.76-7.63 (m, 1H), 7.32 (d, 1H), 6.68-6.65 (m, 1H), 3.48-3.31 (m, 2H), 3.03-2.91 (m, 3H), 2.14-2.09 (m, 3H), 1.16-1.11 (m, 3H); LCMS (M + 1): 304.00 |
| 212 | N'-(5-chloro-2-methyl-3-(pyrimidin-2-ylamino)phenyl)-N-ethyl-N-methylformimidamide | $^1$H-NMR (400 MHz, DMSO-d6) δ 8.72 (s, 1H), 8.37 (d, 2H), 7.66 (d, 1H), 7.14 (d, 1H), 6.75 (t, 1H), 6.67 (s, 1H), 3.41-3.35 (m, 2H), 2.95 (d, 3H), 2.06 (s, 3H), 1.12 (t, 3H); LCMS (M + 1): 304.1 |
| 213 | N'-(5-chloro-2-methyl-3-(methyl(pyrazin-2-yl)amino)phenyl)-N-ethyl-N-methylformimidamide | $^1$H-NMR (400 MHz, DMSO-d6) δ 8.12-8.10 (m, 1H), 7.83-7.72 (m, 2H), 7.55 (d, 1H), 6.97-6.92 (m, 2H), 3.47-3.35 (m, 2H), 3.31 (d, 3H), 2.99 (d, 3H), 1.96 (d, 3H), 1.16 (t, 3H); LCMS (M + 1): 318.4 |
| 214 | N'-(5-chloro-2-methyl-3-(methyl(pyrimidin-2- | $^1$H-NMR (400 MHz, DMSO-d6) δ 8.33 (s, 2H), 7.73 (d, 1H), 6.87-6.85 (m, 2H), 6.70-6.67 (m, 1H), 3.45-3.33 (m, 2H), 2.97-2.91 (m, 3H), 3.02-2.90 |

TABLE I-continued

| Sr. No. | IUPAC Name | Analytical Data |
| --- | --- | --- |
| | yl)amino)phenyl)-N-ethyl-N-methylformimidamide | (m, 3H), 1.89 (s, 3H), 1.20-1.13 (m, 3H); LCMS (M + 1): 317.8 |
| 215 | N'-(3-(2-bromo-4-fluorobenzyl)-2-chloro-5-methylphenyl)-N-ethyl-N-methylformimidamide | $^1$H-NMR (400 MHz, DMSO-d6) δ 7.70-7.58 (m, 2H), 7.19 (td, 1H), 7.02 (dd, 1H), 6.70 (s, 1H), 6.45 (d, 1H), 4.03 (s, 2H), 3.43-3.31 (m, 2H), 2.92 (s, 3H), 2.16 (s, 3H), 1.14-1.06(m, 3H); LCMS (M + 1): 399.05 |
| 216 | N'-(3-(4-bromo-3-methylbenzyl)-2-chloro-5-methylphenyl)-N-ethyl-N-methylformimidamide | $^1$H-NMR (400 MHz, DMSO-d6) δ 7.66 (brs, 1H), 7.45 (d, 1H), 7.17 (d, 1H), 6.90 (dd, 1H), 6.69 (d, 1H), 6.65 (s, 1H), 3.93 (s, 3H), 3.41-3.31 (m, 2H), 2.90 (s, 3H), 2.27 (s, 3H), 2.19 (s, 3H), 1.11 (t, 3H); LCMS (M + 1): 395.05 |
| 217 | N'-(3-(4-bromo-2-fluorobenzyl)-2-chloro-5-methylphenyl)-N-ethyl-N-methylformimidamide | $^1$H-NMR (400 MHz, DMSO-d6) δ 7.69 (s, 1H), 7.52 (dd, 1H), 7.34 (dd, 1H), 7.02 (t, 1H), 6.70 (s, 1H), 6.63 (d, 1H), 3.98 (s, 2H), 3.44-3.33 (m, 2H), 2.93 (s 3H), 2.20 (s, 3H), 1.13 (t, 3H); LCMS (M + 1): 398.85 |
| 218 | N'-(2-chloro-3-(4-fluoro-3-(trifluoromethyl)benzyl)-5-methylphenyl)-N-ethyl-N-methylformimidamide | $^1$H-NMR (400 MHz, DMSO-d6) δ 7.69-7.58 (m, 2H), 7.54-7.50 (m, 1H), 7.44-7.40 (m, 1H), 6.78-6.70 (m, 2H), 4.08 (s, 2H), 3.43-3.33 (m, 2H), 2.92 (s, 3H), 2.22 (s, 3H), 1.13 (t, 3H); LCMS (M + 1): 388.20 |
| 219 | N-ethyl-N'-(3-(2-fluorobenzyl)-2,5-dimethylphenyl)-N-methylformimidamide | $^1$H-NMR (400 MHz, DMSO-d6) δ 7.56 (brs, 1H), 7.26-7.21 (m, 1H), 7.18-7.13 (m, 1H), 7.11-7.05 (m, 1H), 7.03-6.96 (m, 1H), 6.49 (d, 2H), 3.86 (s, 2H), 3.43-3.32 (m, 2H), 2.90 (s, 3H), 2.15 (s, 3H), 2.04 (s, 3H), 1.10 (t, 3H); LCMS (M + 1): 299.45 |
| 220 | N'-(3-(2-chlorobenzyl)-2,5-dimethylphenyl)-N-ethyl-N-methylformimidamide | $^1$H-NMR (400 MHz, DMSO-d6) δ 7.56 (brs, 1H), 7.44-7.40 (m, 1H), 7.23-7.17 (m, 1H), 6.90-6.84 (m, 1H), 6.47 (s, 1H), 6.39 (s, 1H), 3.91 (s, 3H), 3.42-3.29 (m, 2H), 2.88 (s, 3H), 2.12 (s, 3H), 1.99 (s, 3H), 1.08 (t, 3H); LCMS (M + 1): 316.05 |
| 221 | N'-(3-(2-bromobenzyl)-2,5-dimethylphenyl)-N-ethyl-N-methylformimidamide | $^1$H-NMR (400 MHz, DMSO-d6) δ 7.63-7.59 (m, 1H), 7.26 (td, 1H), 7.15 (td, 1H), 6.89 (dd, 1H), 6.50 (s, 1H), 6.40 (s, 1H), 3.92 (m, 2H), 3.46-3.32 (3H), 2.90 (s, 3H), 2.14 (s, 3H), 2.01 (s, 3H), 1.11 (t, 3H); LCMS (M + 1): 359.40 |
| 222 | N-ethyl-N'-(3-(4-fluorobenzyl)-2,5-dimethylphenyl)-N-methylformimidamide | $^1$H-NMR (400 MHz, DMSO-d6) δ 7.72-7.40 (1H), 7.15-7.06 (m, 4H), 6.59 (s, 1H), 6.48 (s, 1H), 3.87 (s, 2H), 3.42-3.33 (m, 2H), 2.91 (s, 3H), 2.19 (s, 3H), 2.04 (s, 3H), 1.11 (t, 3H); LCMS (M + 1): 299.40 |
| 223 | N'-(3-(4-bromobenzyl)-2,5-dimethylphenyl)-N-ethyl-N-methylformimidamide | $^1$H-NMR (400 MHz, DMSO-d6) δ 7.59-7.45 (m, 3H), 7.09 (d, 2H), 6.61 (s, 1H), 6.51 (s, 1H), 3.88 (s, 2H), 3.48-3.27 (m, 2H), 2.94 (s, 3H), 2.22 (s, 3H), 2.05 (s, 3H), 1.14 (t, 3H); LCMS (M + 1): 361.15 |
| 224 | N'-(3-(4-chlorobenzyl)-2,5-dimethylphenyl)-N-ethyl-N-methylformimidamide | $^1$H-NMR (400 MHz, DMSO-d6) δ 7.64-7.52 (m, 1H) 7.33-7.30 (m, 2H), 7.14-7.11 (m, 2H), 6.59 (s, 1H), 6.49 (s, 1H), 3.88 (s, 2H), 3.46-3.33 (m, 2H), 2.91 (s, 3H), 2.19 (s, 3H), 2.03 (s, 3H), 1.11 (t, 3H); LCMS (M + 1): 315.05 |
| 225 | N'-(3-(benzo[d]thiazol-6-ylamino)-5-fluoro-2-methylphenyl)-N-ethyl-N-methylformimidamide | $^1$H-NMR (400 MHz, DMSO-d6) δ 9.06 (d, 1H), 7.90 (dd, 1H), 7.73 (d, 2H), 7.46 (t, 1H), 7.15 (dd, 1H), 6.57 (dd, 1H), 6.39 (s, 1H), 3.35 (d, 2H), 2.98 (d, 3H), 2.09 (s, 3H), 1.15 (t, 3H); LCMS (M + 1): 343.25 |
| 226 | N'-(2-chloro-3-((6-ethylpyridin-2-yl)amino)-5-methylphenyl)-N-ethyl-N-methylformimidamide | $^1$H-NMR (400 MHz, DMSO-d6) δ 7.90 (s, 1H), 7.66 (d, 1H), 7.55-7.54 (m, 1H), 7.46 (dd, 1H), 6.74 (d, 1H), 6.63 (d, 1H), 6.45 (s, 1H), 3.46-3.32 (m, 2H), 2.97 (d, 3H), 2.62 (q, 2H), 2.23 (s, 3H), 1.23 (t, 3H), 1.15 (t, 3H); LCMS (M + 1): 332.85 |
| 227 | N-ethyl-N'-(3-((6-ethylpyridin-2-yl)amino)-5-fluoro-2-methylphenyl)-N-methylformimidamide | $^1$H-NMR (400 MHz, DMSO-d6) δ 7.97 (s, 1H), 7.67 (d, 1H), 7.46-7.41 (m, 1H), 7.31-7.25 (m, 1H), 6.63-6.57 (m, 2H), 6.38 (d, 1H), 3.51-3.32 (m, 2H), 2.97 (d, 3H), 2.60 (q, 2H), 2.12 (s, 3H), 1.24-1.19 (m, 3H), 1.14 (t, 3H); LCMS (M + 1): 332.85 |
| 228 | N'-(3-(benzo[d]thiazol-6-ylamino)-2-chloro-5-methylphenyl)-N-ethyl-N-methylformimidamide | $^1$H-NMR (400 MHz, DMSO-d6) δ 9.10 (d, 1H), 7.91 (dd, 1H), 7.76-7.60 (m, 3H), 7.27-7.19 (m, 1H), 6.76-6.75 (m, 1H), 6.44 (s, 1H), 3.45-3.33 (m, 2H), 2.98 (d, 3H), 2.20 (s, 3H), 1.15 (t, 3H); LCMS (M + 1): 359.35 |
| 229 | N'-(3-(2-chloro-5-fluorobenzyl)-5-fluoro-2-methylphenyl)-N-ethyl-N-methylformimidamide | $^1$H-NMR (400 MHz, DMSO-d6) δ 7.73 (brs, 1H), 7.55 (dd, 1H), 7.17 (t, 1H), 6.81 (dd, 1H), 6.63 (d, 1H), 6.35 (dd, 1H), 4.00 (s, 2H), 3.50-3.32 (m, 2H), 2.93 (s, 3H), 2.07 (s, 3H), 1.14 (t, 3H); LCMS (M + 1): 338.00 |
| 230 | N'-(3-(2-bromo-4-fluorobenzyl)-5-fluoro-2-methylphenyl)-N-ethyl-N-methylformimidamide | $^1$H-NMR (400 MHz, DMSO-d6) δ 7.76-7.60 (m, 2H), 7.23-7.18 (m, 1H), 7.05-7.01 (m, 1H), 6.62-6.59 (m, 1H), 6.29 (dd, 1H), 3.97 (s, 2H), 3.50-3.31 (m, 2H), 2.93 (s, 3H), 2.07 (s, 3H), 1.17-1.09 (m, 3H); LCMS (M + 1): 383.00 |
| 231 | N-ethyl-N'-(5-fluoro-3-(5-fluoro-2-methylbenzyl)-2-methylphenyl)-N-methylformimidamide | $^1$H-NMR (400 MHz, DMSO-d6) δ 7.73 (brs, 1H), 7.25-7.22 (m, 1H), 6.96 (td, 1H), 6.59 (dd, 2H), 6.27 (dd, 1H), 3.88 (s, 2H), 3.50-3.33 (m, 2H), 2.94 (s, 3H), 2.20 (s, 3H), 2.07 (s, 3H), 1.14 (t, 3H); LCMS (M + 1): 317.30 |
| 232 | N'-(3-(4-bromo-3-methylbenzyl)-5-fluoro-2-methylphenyl)-N-ethyl-N-methylformimidamide | $^1$H-NMR (400 MHz, DMSO-d6) δ 7.69 (brs, 1H), 7.47 (d, 1H), 7.14 (d, 1H), 6.88 (dd, 1H), 6.58-6.53 (m, 2H), 3.87 (s, 2H), 3.42-3.32 (m, 2H), 2.93 (s, 3H), 2.30 (s, 3H), 2.06 (s, 3H), 1.12 (t, 3H); LCMS (M + 1): 378.25 |
| 233 | N'-(3-(2-bromo-5-fluorobenzyl)-5-fluoro-2-methylphenyl)-N-ethyl-N-methylformimidamide | $^1$H-NMR (400 MHz, DMSO-d6) δ 7.79-7.63 (m, 2H), 7.12-7.07 (m, 1H), 6.79 (dd, 1H), 6.63 (d, 1H), 6.33 (dd, 1H), 3.99 (s, 2H), 3.51-3.33 (m, 2H), 2.94 (s, 3H), 2.06 (s, 3H), 1.14 (t, 3H); LCMS (M + 1): 383.15 |
| 234 | N-ethyl-N'-(5-fluoro-3-(4-fluoro-3-(trifluoromethyl)benzyl)-2-methylphenyl)-N-methylformimidamide | $^1$H-NMR (400 MHz, DMSO-d6) δ 7.73-7.54 (m, 2H), 7.49-7.39 (m, 2H), 6.59 (d, 2H), 4.02 (s, 2H), 3.49-3.31 (m, 2H), 2.93 (s, 3H), 2.06 (s, 3H), 1.12 (t, 3H); LCMS (M + 1): 371.50 |
| 235 | N-ethyl-N'-(5-fluoro-3-(3-fluoro-5-methylbenzyl)-2-methylphenyl)-N-methylformimidamide | $^1$H-NMR (400 MHz, DMSO-d6) δ 7.69 (brs, 1H), 6.86-6.82 (m, 2H), 6.72 (d, 1H), 6.56 (d, 2H), 3.91 (s, 2H), 3.50-3.38 (m, 2H), 2.952(s, 3H), 2.27 (s, 3H), 2.07 (s, 3H), 1.13 (t, 3H); LCMS (M + 1): 317.50 |

TABLE I-continued

| Sr. No. | IUPAC Name | Analytical Data |
|---|---|---|
| 236 | N'-(3-(4-bromo-2-fluorobenzyl)-5-fluoro-2-methylphenyl)-N-ethyl-N-methylformimidamide | $^1$H-NMR (400 MHz, DMSO-d6) δ 7.70 (brs, 1H), 7.53 (dd, 1H), 7.35 (dd, 1H), 7.00 (t, 1H), 6.63-6.54 (m, 1H), 6.46 (dd, 1H), 3.91 (s, 2H), 3.54-3.32 (m, 2H), 2.952 (s, 3H), 2.07 (s, 3H), 1.13 (t, 3H); LCMS (M + 1): 382.30 |
| 237 | N-ethyl-N'-(5-fluoro-3-(3-fluoro-5-methoxybenzyl)-2-methylphenyl)-N-methylformimidamide | $^1$H-NMR (400 MHz, DMSO-d6) δ 7.69 (brs, 1H), 6.67-6.63 (m, 1H), 6.58-6.54 (m, 3H), 6.51-6.48 (m, 1H), 3.91 (s, 2H), 3.74 (s, 3H), 3.48-3.38 (m, 2H), 2.92 (s, 3H), 2.07 (s, 3H), 1.13 (t, 3H); LCMS (M + 1): 333.55 |
| 238 | N'-(3-(benzo[d]thiazol-6-yl(methyl)amino)-5-fluoro-2-methylphenyl)-N-ethyl-N-methylformimidamide | $^1$H-NMR (400 MHz, DMSO-d6) δ 8.98 (s, 1H), 7.79-7.68 (m, 2H), 7.23 (d, 1H), 6.71-6.66 (m, 1H), 6.60 (ddd, 2H), 3.46-3.34 (m, 2H), 3.21 (s, 3H), 2.96 (d, 3H), 1.92 (s, 3H), 1.14 (t, 3H); LCMS (M + 1): 357.3 |
| 239 | N-ethyl-N'-(3-((6-ethylpyridin-2-yl)(methyl)amino)-5-fluoro-2-methylphenyl)-N-methylformimidamide | $^1$H-NMR (400 MHz, DMSO-d6) δ 7.72 (d, 1H), 7.26 (dd, 1H), 6.70 (d, 1H), 6.61 (dd, 1H), 6.45 (d, 1H), 5.82 (d, 1H), 3.34-3.47 (m, 2H), 3.27 (s, 3H), 2.96 (d, 3H), 2.60 (q, 2H), 1.89 (s, 3H), 1.22 (q, 3H), 1.13 (t, 3H); LCMS (M + 1): 329.35 |
| 240 | N'-(3-(benzo[d]thiazol-6-yl(methyl)amino)-2-chloro-5-methylphenyl)-N-ethyl-N-methylformimidamide | $^1$H-NMR (400 MHz, DMSO-d6) δ 8.98 (s, 1H), 7.78-7.65 (m, 2H), 7.23 (d, 1H), 6.77 (d, 2H), 6.61 (dd, 2H), 3.44-3.34 (m, 2H), 3.21 (s, 3H), 2.96 (d, 3H), 2.24 (s, 3H), 1.14 (t, 3H); LCMS (M + 1): 374.05 |
| 241 | N-ethyl-N'-(5-fluoro-2-methyl-3-(4-(methylthio)benzyl)phenyl)-N-methylformimidamide | $^1$H-NMR (400 MHz, DMSO-d6) δ 7.69 (s, 1H), 7.21-7.16 (m, 2H), 7.08 (d, 2H), 6.56-6.52 (m, 2H), 3.89 (s, 2H), 3.48-3.33 (m, 2H), 2.92 (s, 3H), 2.44 (s, 3H), 2.06 (s, 3H), 1.12 (t, 3H); LCMS (M + 1): 331.55 |
| 242 | N'-(3-(benzo[d]thiazol-6-ylamino)-5-chloro-2-methylphenyl)-N-ethyl-N-methylformimidamide | $^1$H-NMR (400 MHz, DMSO-d6) δ 9.04-9.10 (m, 1H), 7.89-7.96 (m, 1H), 7.71-7.77 (m, 1H), 7.42 (d, 1H), 7.12 (dd, 1H), 6.78 (d, 1H), 6.61 (s, 1H), 3.45-3.33 (m, 3H), 3.01-2.94 (m, 3H), 2.10 (s, 3H), 1.15 (t, 3H); LCMS (M + 1): 360.1 |
| 243 | N'-(5-chloro-3-((6-ethylpyridin-2-yl)amino)-2-methylphenyl)-N-ethyl-N-methylformimidamide | $^1$H-NMR (400 MHz, DMSO-d6) δ 8.01 (s, 1H), 7.72-7.71 (m, 1H), 7.47-7.46 (m, 1H), 7.44-7.42 (m, 1H), 6.60-6.55 (m, 3H), 3.46-3.30 (m, 2H), 3.00-2.94 (m, 3H), 2.59 (q, 2H) 2.12 (s, 3H), 1.23-1.18 (m, 3H), 1.14 (t, 3H); LCMS (M + 1): 332.1 |
| 244 | N'-(5-chloro-2-methyl-3-(2-(trifluoromethyl)benzyl)phenyl)-N-ethyl-N-methylformimidamide | $^1$H-NMR (400 MHz, DMSO-d6) δ 7.69 (s, 1H), 7.3-7.36 (m, 1H), 7.33-7.30 (m, 1H), 7.26-7.21 (m, 1H), 7.12 (d, 1H), 6.79-6.77 (m, 2H), 3.93 (s, 2H), 3.39-3.32 (m, 2H), 2.89 (s, 3H), 2.05 (s, 3H), 1.11 (t, 3H); LCMS (M + 1): 370.15 |
| 245 | N'-(3-(3-bromobenzyl)-5-chloro-2-methylphenyl)-N-ethyl-N-methylformimidamide | $^1$H-NMR (400 MHz, DMSO-d6) δ 7.75-7.61 (m, 2H), 7.58-7.52 (m, 1H), 7.44 (t, 1H), 7.02 (d, 1H), 6.81-6.78 (m, 1H), 6.54 (d, 1H), 4.08 (s, 2H), 3.42-3.34 (m, 2H), 2.90 (s, 3H), 2.01 (s, 3H), 1.12 (t, 3H); LCMS (M + 1): 381.10 |
| 246 | N'-(5-chloro-3-(4-cyanobenzyl)-2-methylphenyl)-N-ethyl-N-methylformimidamide | $^1$H-NMR (400 MHz, DMSO-d6) δ 7.74-7.72 (m, 2H), 7.63 (s, 1H), 7.31 (d, 2H), 6.81-6.78 (m, 2H), 4.02 (s, 2H), 3.91-3.36 (m, 2H), 2.89 (s, 3H), 2.03 (s, 3H), 1.10 (t, 3H); LCMS (M + 1): 326.45 |
| 247 | N'-(5-chloro-2-methyl-3-(2-(trifluoromethoxy)benzyl)phenyl)-N-ethyl-N-methylformimidamide | $^1$H-NMR (400 MHz, DMSO-d6) δ 7.70 (s, 1H), 7.36-7.33 (m, 2H), 7.32-7.27 (m, 1H), 7.06-7.04 (m, 1H), 6.79 (s, 1H), 6.64 (d, 1H), 3.95 (s, 2H), 3.46-3.32 (m, 2H), 2.90 (s, 3H), 2.03 (s, 3H), 1.11 (t, 3H); LCMS (M + 1): 386.15 |
| 248 | N'-(5-chloro-2-methyl-3-(pyridin-3-ylmethyl)phenyl)-N-ethyl-N-methylformimidamide | $^1$H-NMR (400 MHz, DMSO-d6) δ 8.41-8.38 (m, 2H), 7.69 (s, 1H), 7.49 (d, 1H), 7.30-7.28 (m, 1H), 6.79 (s, 2H), 3.95 (s, 2H), 3.98-3.32 (m, 2H), 2.89 (s, 3H), 2.07 (s, 3H), 1.11 (t, 3H); LCMS (M + 1): 302.45 |
| 249 | N'-(5-chloro-2-methyl-3-(4-(trifluoromethyl)benzyl)phenyl)-N-ethyl-N-methylformimidamide | $^1$H-NMR (400 MHz, DMSO-d6) δ 7.69-7.54 (m, 3H), 7.33 (d, 2H), 6.82-6.78 (m, 2H), 4.03 (s, 2H), 3.39-3.31 (m, 2H), 2.89 (s, 3H), 2.04 (s, 3H), 1.10 (d, 3H); LCMS (M + 1): 370.10 |
| 250 | N'-(5-chloro-3-(3-cyanobenzyl)-2-methylphenyl)-N-ethyl-N-methylformimidamide | $^1$H-NMR (400 MHz, DMSO-d6) δ 7.69-7.58 (m, 3H), 7.51-7.44 (m, 2H), 6.81-6.78 (m, 2H), 3.99 (s, 2H), 3.40-3.32 (m, 2H), 2.90 (s, 3H), 2.05 (s, 3H), 1.11 (t, 3H); LCMS (M + 1): 326.20 |
| 251 | N'-(5-chloro-2-methyl-3-(3-(trifluoromethoxy)benzyl)phenyl)-N-ethyl-N-methylformimidamide | $^1$H-NMR (400 MHz, DMSO-d6) δ 7.69 (s, 1H), 7.44-7.36 (m, 1H), 7.18-7.11 (m, 3H), 6.80-6.77 (m, 2H), 3.98 (s, 2H), 3.95-3.31 (m, 2H), 2.89 (s, 3H), 2.05 (s, 3H), 1.11 (t, 3H); LCMS (M + 1): 386.00 |
| 252 | N'-(5-chloro-2-methyl-3-(4-(methylthio)benzyl)phenyl)-N-ethyl-N-methylformimidamide | $^1$H-NMR (400 MHz, DMSO-d6) δ 7.69 (s, 1H), 7.21-7.17 (m, 2H), 7.08 (d, 2H), 6.76 (s, 2H), 3.89 (s, 2H), 3.41-3.32 (m, 2H), 2.92 (s, 3H), 2.44 (s, 3H), 2.08 (s, 3H), 1.12 (t, 3H); LCMS (M + 1): 348.10 |
| 253 | N'-(5-chloro-3-((6-ethylpyridin-2-yl)(methyl)amino)-2-methylphenyl)-N-ethyl-N-methylformimidamide | $^1$H-NMR (400 MHz, DMSO-d6) δ 7.75 (d, 1H), 7.30-7.26 (m, 1H), 6.89 (d, 1H), 6.84-6.83 (m, 1H), 6.49-6.46 (m, 1H), 5.84 (d, 1H), 3.46-3.35 (m, 2H), 3.31 (d, 3H), 2.94-3.02 (m, 3H), 2.62 (q, 2H), 1.93 (s, 3H), 1.22 (t, 3H), 1.15 (t, 3H); LCMS (M + 1): 346.0 |
| 254 | N-ethyl-N'-(5-fluoro-3-((3-fluoro-4-methoxyphenyl)amino)-2-methylphenyl)-N-methylformimidamide | $^1$H-NMR (400 MHz, DMSO-d6) δ 7.64 (d, 1H), 7.28 (s, 1H), 7.03 (t, 1H), 6.79 (dd, 1H), 6.72 (dt, 1H), 6.38 (dd, 1H), 6.26 (d, 1H), 3.76 (s, 3H), 3.40 (d, 2H), 2.94 (d, 3H), 2.05 (s, 3H), 1.12 (t, 3H); LCMS (M + 1): 334.4 |
| 255 | N'-(2-chloro-3-((3-fluoro-4-methoxyphenyl)amino)-5-methylphenyl)-N-ethyl-N-methylformimidamide | $^1$H-NMR (400 MHz, DMSO-d6) δ 7.70 (s, 1H), 7.29 (s, 1H), 7.09-7.04 (m, 1H), 6.93 (dd, 1H), 6.85 (d, 1H), 6.57 (d, 1H), 6.32 (s, 1H), 3.79 (s, 3H), 3.42-3.33 (m, 2H), 2.94 (s, 3H), 2.15 (s, 3H), 1.15 (t, 3H); LCMS (M + 1): 351.0 |
| 256 | N'-(5-chloro-3-((3-fluoro-4-methoxyphenyl)amino)-2-methylphenyl)-N-ethyl-N-methylformimidamide | $^1$H-NMR (400 MHz, DMSO-d6) δ 7.72 (d, 1H), 7.30 (s, 1H), 7.06 (t, 1H), 6.78 (dd, 1H), 6.72 (dq, 1H), 6.61 (d, 1H), 6.49-6.47 (m, 1H), 3.77 (d, 3H), 3.43-3.31 (m, 2H), 3.01-2.93 (m, 3H), 2.07 (s, 3H), 1.16-1.11 (m, 3H); LCMS (M + 1): 350.35 |
| 257 | N-ethyl-N'-(5-fluoro-3-((3-fluoro-4-methoxyphenyl)(methyl)amino)- | $^1$H-NMR (400 MHz, DMSO-d6) δ 7.71 (d, 1H), 6.96 (t, 1H), 6.64 (d, 1H), 6.52 (dd, 1H), 6.36 (dd, 1H), 6.22-6.19 (m, 1H), 3.71 (s, 3H), 3.35-3.44 (m, |

TABLE I-continued

| Sr. No. | IUPAC Name | Analytical Data |
|---|---|---|
| | 2-methylphenyl)-N-methylformimidamide | 2H), 3.09 (s, 3H), 2.95 (d, 3H), 1.90 (s, 3H), 1.13 (t, 3H); LCMS (M + 1): 348.0 |
| 258 | N'-(2-chloro-3-((3-fluoro-4-methoxyphenyl)(methyl)amino)-5-methylphenyl)-N-ethyl-N-methylformimidamide | $^1$H-NMR (400 MHz, DMSO-d6) δ 7.67 (d, 1H), 6.95 (t, 1H), 6.73-6.68 (m, 2H), 6.33 (dd, 1H), 6.21 (dt, 1H), 3.71 (s, 3H), 3.38 (dt, 2H), 3.11 (d, 3H), 2.95 (d, 3H), 2.25 (d, 3H), 1.13 (t, 3H); LCMS (M + 1): 364.15 |
| 259 | N-ethyl-N'-(5-fluoro-2-methyl-3-(3-nitrobenzyl)phenyl)-N-methylformimidamide | $^1$H-NMR (400 MHz, DMSO-d6) δ 8.06-8.03 (m, 1H), 7.96 (s, 1H), 7.69-7.55 (m, 3H), 6.63-6.58 (m, 2H), 4.08 (s, 2H), 3.47-3.32 (m, 2H), 2.89 (s, 3H), 2.05 (s, 3H), 1.21-1.09 (m, 3H); LCMS (M + 1): 330.45 |
| 260 | N-ethyl-N'-(5-fluoro-2-methyl-3-(pyridin-3-ylmethyl)phenyl)-N-methylformimidamide | $^1$H-NMR (400 MHz, DMSO-d6) δ 8.41-8.35 (m, 2H), 7.67 (s, 1H), 7.49 (d, 1H), 7.29 (dd, 1H), 6.56 (d, 2H), 3.94 (s, 2H), 3.40-3.35 (m, 2H), 2.90 (s, 3H), 2.05 (s, 3H), 1.10 (t, 3H); LCMS (M + 1): 286.20 |
| 261 | N-ethyl-N'-(3-(4-fluorobenzyl)-5-methoxy-2-methylphenyl)-N-methylformimidamide | $^1$H-NMR (400 MHz, DMSO-d6) δ 7.59 (s, 1H), 7.15-7.11 (m, 2H), 7.09-7.04 (m, 2H), 6.35 (d, 1H), 6.25 (d, 1H), 3.86 (s, 2H), 3.67 (s, 3H), 3.47-3.31 (m, 2H), 2.89 (s, 3H), 1.98 (s, 3H), 1.10 (t, 3H); LCMS (M + 1): 315.45 |
| 262 | N-ethyl-N'-(5-methoxy-2-methyl-3-(2-methylbenzyl)phenyl)-N-methylformimidamide | $^1$H-NMR (400 MHz, DMSO-d6) δ 7.63 (s, 1H), 7.18-7.15 (m, 1H), 7.11-7.04 (m, 2H), 6.80-6.78 (m, 1H), 6.26 (d, 1H), 6.08 (d, 1H), 3.81 (s, 2H), 3.61 (s, 3H), 3.43-3.31 (m, 2H), 2.92 (s, 3H), 2.22 (s, 3H), 2.06 (s, 3H), 1.12 (t, 3H); LCMS (M + 1): 311.45 |
| 263 | N-ethyl-N'-(5-methoxy-2-methyl-3-(4-methylbenzyl)phenyl)-N-methylformimidamide | $^1$H-NMR (400 MHz, DMSO-d6) δ 7.58 (s, 1H), 7.05 (d, 2H), 6.99 (d, 2H), 6.33 (d, 1H), 6.24 (d, 1H), 3.82 (s, 2H), 3.66 (s, 3H), 3.48-3.32 (m, 2H), 2.89 (s, 3H), 2.23 (s, 3H), 1.99 (s, 3H), 1.10 (t, 3H); LCMS (M + 1): 311.40 |
| 264 | N'-(3-(3-chlorobenzyl)-5-methoxy-2-methylphenyl)-N-ethyl-N-methylformimidamide | $^1$H-NMR (400 MHz, DMSO-d6) δ 7.61 (s, 1H), 7.29 (t, 1H), 7.23-7.20 (m, 1H), 7.12 (d, 1H), 7.09 (d, 1H), 6.38 (d, 1H), 6.27 (d, 1H), 3.89 (s, 2H), 3.68 (s, 3H), 3.49-3.32 (m, 1H), 2.89 (s, 3H), 1.98 (s, 3H), 1.12-1.08 (m, 3H); LCMS (M + 1): 332.00 |
| 265 | N'-(3-(2-chlorobenzyl)-5-methoxy-2-methylphenyl)-N-ethyl-N-methylformimidamide | $^1$H-NMR (400 MHz, DMSO-d6) δ 7.64 (s, 1H), 7.47-7.44 (m, 1H), 7.26-7.20 (m, 2H), 6.95-6.93 (m, 1H), 6.31 (d, 1H), 6.17 (d, 1H), 3.94 (s, 2H), 3.64 (s, 3H), 3.45-3.31 (m, 2H), 2.91 (s, 3H), 1.98 (s, 3H), 1.11 (t, 3H); LCMS (M + 1): 331.10 |
| 266 | N-ethyl-N'-(3-(2-fluorobenzyl)-5-methoxy-2-methylphenyl)-N-methylformimidamide | $^1$H-NMR (400 MHz, DMSO-d6) δ 7.61 (s, 1H), 7.27-7.21 (m, 1H), 7.18-7.13 (m, 1H), 7.10-7.06 (m, 1H), 7.02-6.97 (m, 1H), 6.27 (s, 2H), 3.87 (s, 2H), 3.64 (s, 3H), 3.46-3.31 (m, 2H), 2.90 (s, 3H), 2.01 (s, 3H), 1.11 (t, 3H); LCMS (M + 1): 315.35 |
| 267 | N'-(5-chloro-3-((3-fluoro-4-methoxyphenyl)(methyl)amino)-2-methylphenyl)-N-ethyl-N-methylformimidamide | $^1$H-NMR (400 MHz, DMSO-d6) δ 7.72 (d, 1H), 6.96 (t, 1H), 6.81 (d, 1H), 6.72 (s, 1H), 6.36 (dd, 1H), 6.20 (d, 1H), 3.70 (d, 3H), 3.44-3.34 (m, 2H), 3.08 (s, 3H), 2.95 (d, 3H), 1.92 (s, 3H), 1.23-1.12 (m, 3H); LCMS (M + 1): 364.1 |
| 268 | N-ethyl-N'-(5-methoxy-3-((2-methoxyphenyl)amino)-2-methylphenyl)-N-methylformimidamide | $^1$H-NMR (400 MHz, DMSO-d6) δ 7.64 (s, 1H), 6.95-6.92 (m, 1H), 6.78-6.69 (m, 3H), 6.35 (s, 1H), 6.31 (d, 1H), 6.10 (d, 1H), 3.82 (s, 3H), 3.64 (s, 3H), 3.35 (s, 2H), 2.92 (s, 3H), 1.97 (s, 3H), 1.12 (t, 3H); LCMS (M + 1): 328.35 |
| 269 | N-ethyl-N'-(3-((3-fluoro-4-methoxyphenyl)amino)-5-methoxy-2-methylphenyl)-N-methylformimidamide | $^1$H-NMR (400 MHz, DMSO-d6) δ 7.58 (d, 1H), 7.16 (s, 1H), 6.98 (t, 1H), 6.68 (dd, 1H), 6.62 (dt, 1H), 6.26 (d, 1H), 6.05 (d, 1H), 3.74 (s, 3H), 3.63 (s, 3H), 3.45 (s, 1H), 3.25-3.30 (1H), 2.92 (s, 3H), 1.98 (s, 3H), 1.12 (t, 3H); LCMS (M + 1): 346.35 |
| 270 | N-ethyl-N'-(5-methoxy-3-((2-methoxyphenyl)(methyl)amino)-2-methylphenyl)-N-methylformimidamide | $^1$H-NMR (400 MHz, DMSO-d6) δ 7.57 (d, 1H), 6.98-6.92 (m, 2H), 6.77-6.73 (m, 1H), 6.58-6.56 (m, 1H), 6.28 (d, 1H), 6.11 (s, 1H), 3.74-3.71 (m, 3H), 3.67 (d, 3H), 3.38 (d, 1H), 3.27 (d, 1H), 3.00 (d, 3H), 2.86 (s, 3H), 1.66 (d, 3H), 1.29-1.19 (m, 1H), 1.15-1.07 (m, 3H); LCMS (M + 1): 342.4 |
| 271 | N-ethyl-N'-(3-((3-fluoro-4-methoxyphenyl)(methyl)amino)-5-methoxy-2-methylphenyl)-N-methylformimidamide | $^1$H-NMR (400 MHz, DMSO-d6) δ 7.65 (d, 1H), 6.94 (t, 1H), 6.34-6.26 (m, 1H), 6.18 (dt, 1H), 3.69 (d, 6H), 3.38-3.33 (m, 2H), 3.07 (d, 3H), 2.93 (d, 3H), 1.85 (s, 3H), 1.22 (s, 2H), 1.14-1.08 (m, 3H); LCMS (M + 1): 360.55 |
| 272 | N-ethyl-N'-(5-methoxy-2-methyl-3-((6-(trifluoromethyl)pyridin-2-yl)amino)phenyl)-N-methylformimidamide | $^1$H-NMR (400 MHz, DMSO-d6) δ 8.62 (d, 1H), 7.72-7.68 (m, 1H), 7.07 (dd, 2H), 6.85-6.83 (m, 1H), 6.79 (t, 1H), 6.25 (s, 1H), 3.71 (d, 3H), 3.32 (s, 2H), 2.94 (s, 3H), 2.03 (s, 3H), 1.14 (t, 3H); LCMS (M + 1): 367.0 |
| 273 | N-ethyl-N'-(5-fluoro-2-methyl-3-((6-(trifluoromethyl)pyridin-2-yl)amino)phenyl)-N-methylformimidamide | $^1$H-NMR (400 MHz, DMSO-d6) δ 8.67 (s, 1H), 7.75-7.62 (m, 2H), 7.11 (d, 1H), 7.06 (dd, 1H), 6.96 (d, 1H), 6.49 (d, 1H), 3.40 (d, 2H), 2.95 (d, 3H), 2.08 (s, 3H), 1.13 (t, 3H); LCMS (M + 1): 354.95 |
| 274 | N'-(5-chloro-2-methyl-3-((6-(trifluoromethyl)pyridin-2-yl)amino)phenyl)-N-ethyl-N-methylformimidamide | $^1$H-NMR (400 MHz, DMSO-d6) δ 8.69 (d, 1H), 7.74-7.63 (m, 2H), 7.23 (d, 1H), 7.11 (d, 1H), 7.03 (d, 1H), 6.92 (d, 1H), 6.69 (s, 1H), 3.43-3.34 (m, 2H), 2.95 (d, 3H), 2.08 (s, 3H), 1.13 (t, 3H); LCMS (M + 1): 370.95 |
| 275 | N'-(2-chloro-3-((4-fluoro-3-methoxyphenyl)amino)-5-methylphenyl)-N-ethyl-N-methylformimidamide | $^1$H-NMR (400 MHz, DMSO-d6) δ 7.63 (d, 1H), 7.30 (s, 1H), 7.04 (dd, 1H), 6.88 (dd, 1H), 6.63 (d, 1H), 6.58-6.55 (m, 1H), 6.32 (s, 1H), 3.76 (s, 3H), 3.40 (d, 2H), 2.95 (d, 3H), 2.15 (s, 3H), 1.13 (t, 3H); LCMS (M + 1): 349.95 |
| 276 | N-ethyl-N'-(3-((4-fluoro-3-methoxyphenyl)amino)-5-methoxy-2-methylphenyl)-N-methylformimidamide | $^1$H-NMR (400 MHz, DMSO-d6) δ 7.60 (d, 1H), 7.21 (s, 1H), 6.96 (dd, 1H), 6.67 (dd, 1H), 6.34 (td, 2H), 6.05 (d, 1H), 3.72 (d, 3H), 3.63 (s, 3H), 3.42 (d, 1H), 2.92 (s, 3H), 1.98 (d, 3H), 1.22 (s, 1H), 1.12 (t, 3H); LCMS (M + 1): 346.0 |
| 277 | N-ethyl-N'-(3-(3-fluorobenzyl)-5-methoxy-2-methylphenyl)-N-methylformimidamide | $^1$H-NMR (400 MHz, DMSO-d6) δ 7.62 (s, 1H), 7.33-7.28 (m, 1H), 7.02-6.97 (m, 2H), 6.93-6.89 (m, 1H), 6.39 (d, 1H), 6.29 (d, 1H), 3.92 (s, 2H), 3.69 (s, 3H), 3.42-3.31 (s, 2H), 2.91 (s, 3H), 2.00 (s, 3H), 1.12 (t, 3H); LCMS (M + 1): 315.25 |

TABLE I-continued

| Sr. No. | IUPAC Name | Analytical Data |
|---|---|---|
| 278 | N-ethyl-N'-(5-methoxy-2-methyl-3-(3-methylbenzyl)phenyl)-N-methylformimidamide | $^{1}$H-NMR (400 MHz, DMSO-d6) δ 7.61(brs, 1H), 7.15 (t, 1H), 6.99-6.95 (m, 2H), 6.91 (d, 1H), 6.36 (d, 1H), 6.27 (d, 1H), 3.84 (s, 2H), 3.68 (s, 3H), 3.40-3.31 (m, 2H), 2.92 (s, 3H), 2.25 (s, 3H), 2.02 (s, 3H), 1.12 (t, 3H); LCMS (M + 1): 311.25 |
| 279 | N'-(3-(4-chlorobenzyl)-5-methoxy-2-methylphenyl)-N-ethyl-N-methylformimidamide | $^{1}$H-NMR (400 MHz, DMSO-d6) δ 7.61 (s, 1H), 7.34-7.30 (m, 2H), 7.15-7.12 (m, 2H), 6.37 (d, 1H), 6.28 (d, 1H), 3.89 (s, 2H), 3.68 (s, 3H), 3.42-3.31 (m, 2H), 2.91 (s, 3H), 1.99 (s, 3H), 1.12 (t, 3H); LCMS (M + 1): 331.05 |
| 280 | N-ethyl-N'-(5-methoxy-2-methyl-3-(3-nitrobenzyl)phenyl)-N-methylformimidamide | $^{1}$H-NMR (400 MHz, DMSO-d6) δ 8.07-8.04 (m, 1H), 7.97-7.95 (m, 1H), 7.65-7.56 (m, 3H), 6.44 (d, 1H), 6.32 (d, 1H), 4.06 (s, 2H), 3.69 (s, 3H), 3.46-3.31 (m, 2H), 2.91 (s, 3H), 2.01 (s, 3H), 1.12 (t, 3H); LCMS (M + 1): 342.10 |
| 281 | N-ethyl-N'-(3-(5-fluoro-2-methylbenzyl)-5-methoxy-2-methylphenyl)-N-methylformimidamide | $^{1}$H-NMR (400 MHz, DMSO-d6) δ 7.67 (s, 1H), 7.23-7.20 (m, 1H), 6.93 (td, 1H), 6.53 (dd, 1H), 6.32 (s, 1H), 6.15 (d, 1H), 3.83 (s, 2H), 3.66 (s, 3H), 3.48-3.31 (m, 2H), 2.94 (s, 3H), 2.23 (s, 3H), 2.00 (s, 3H), 1.14 (t, 3H); LCMS (M + 1): 329.00 |
| 282 | N'-(3-(3-chloro-4-fluorobenzyl)-5-methoxy-2-methylphenyl)-N-ethyl-N-methylformimidamide | $^{1}$H-NMR (400 MHz, DMSO-d6) δ 7.68 (s, 1H), 6.90-6.81 (m, 2H), 6.72 (d, 1H), 6.56 (d, 2H), 3.91 (s, 2H), 3.42-3.33 (m, 2H), 2.92 (s, 3H), 2.68 (s, 3H), 2.09 (s, 3H), 1.13 (t, 3H); LCMS (M + 1): 350.90 |
| 283 | N'-(2-chloro-5-methyl-3-((6-(trifluoromethyl)pyridin-2-yl)amino)phenyl)-N-ethyl-N-methylformimidamide | $^{1}$H-NMR (400 MHz, DMSO-d6) δ 8.72 (s, 1H), 7.77-7.73 (m, 2H), 7.28 (d, 1H), 7.15 (d, 1H), 7.02 (d, 1H), 6.59-6.57 (m, 1H), 3.45-3.30 (m, 2H), 3.02-2.95 (m, 3H), 2.23 (s, 3H), 1.15 (t, 3H); LCMS (M + 1): 370.9 |
| 284 | N-ethyl-N'-(3-((4-fluoro-3-methoxyphenyl)(methyl)amino)-5-methoxy-2-methylphenyl)-N-methylformimidamide | $^{1}$H-NMR (400 MHz, DMSO-d6) δ 7.71-7.69 (m, 1H), 6.92 (dd, 1H), 6.35 (s, 1H), 6.30-6.27 (m, 2H), 5.87 (td, 1H), 3.73-3.69 (m, 6H), 3.44-3.32 (m, 2H), 3.13 (s, 3H), 3.01-2.92 (m, 3H), 1.90-1.88 (m, 3H), 1.17-1.12 (m, 3H); LCMS (M + 1): 360.05 |
| 285 | N-ethyl-N'-(5-methoxy-2-methyl-3-(methyl(6-(trifluoromethyl)pyridin-2-yl)amino)phenyl)-N-methylformimidamide | $^{1}$H-NMR (400 MHz, DMSO-d6) δ 7.63-7.74 (m, 1H), 7.54-7.58 (m, 2H), 7.00-7.02 (m, 1H), 6.44-6.46 (m, 2H), 6.24 (d, 1H), 3.72 (s, 3H), 3.48-3.28 (m, 2H), 3.03-2.90 (m, 3H), 1.90-1.87 (m, 3H), 1.31-1.23 (m, 2H), 1.09-1.16 (m, 3H); LCMS (M + 1): 381.05 |
| 286 | N'-(3-(3,4-difluorobenzyl)-5-methoxy-2-methylphenyl)-N-ethyl-N-methylformimidamide | $^{1}$H-NMR (400 MHz, DMSO-d6) δ 7.61 (s, 1H), 7.35-7.28 (m, 1H), 7.14-7.11 (m, 1H), 6.95-6.93 (m, 1H), 6.38 (d, 1H), 6.29 (s, 1H), 3.89 (s, 2H), 3.69 (s, 3H), 3.45-3.32 (m, 2H), 2.92 (s, 3H), 2.00 (s, 3H), 1.12 (t, 3H); LCMS (M + 1): 333.40 |
| 287 | N'-(3-(4-bromobenzyl)-5-methoxy-2-methylphenyl)-N-ethyl-N-methylformimidamide | $^{1}$H-NMR (400 MHz, DMSO-d6) δ 7.61 (s, 1H), 7.46-7.44 (m, 1H), 7.08 (d, 2H), 6.37 (d, 1H), 6.28 (d, 1H), 3.87 (s, 2H), 3.68 (s, 4H), 3.47-3.33 (m, 2H), 2.91 (s, 3H), 1.99 (s, 3H), 1.12 (t, 3H); LCMS (M + 1): 376.15 |
| 288 | N'-(2-chloro-3-((4-fluoro-3-methoxyphenyl)(methyl)amino)-5-methylphenyl)-N-ethyl-N-methylformimidamide | $^{1}$H-NMR (400 MHz, DMSO-d6) δ 7.67 (d, 1H), 6.91 (dd, 1H), 6.73-6.69 (m, 2H), 6.30 (dd, 1H), 5.88 (td, 1H), 3.73 (s, 3H), 3.46-3.33 (m, 2H), 3.13 (s, 3H), 2.95 (d, 3H), 2.22 (s, 3H), 1.22 (s, 2H), 1.13 (t, 3H); LCMS (M + 1): 363.8 |
| 289 | N'-(5-chloro-2-methyl-3-(methyl(6-(trifluoromethyl)pyridin-2-yl)amino)phenyl)-N-ethyl-N-methylformimidamide | $^{1}$H-NMR (400 MHz, DMSO-d6) δ 7.83-7.72 (m, 1H), 7.61 (t, 1H), 7.06 (d, 1H), 6.97-6.93 (m, 2H), 6.28 (t, 1H), 3.48-3.31 (m, 2H), 3.29 (s, 3H), 3.03-2.92 (m, 3H), 1.93 (s, 3H), 1.24 (s, 1H), 1.18-1.11 (m, 3H); LCMS (M + 1): 369.0 |
| 290 | N'-(2-chloro-5-methyl-3-(methyl(6-(trifluoromethyl)pyridin-2-yl)amino)phenyl)-N-ethyl-N-methylformimidamide | $^{1}$H-NMR (400 MHz, DMSO-d6) δ 7.74 (d, 1H), 7.62-7.57 (m, 1H), 7.07-7.04 (m, 1H), 6.88-6.84 (m, 2H), 6.28 (d, 1H), 3.48-3.32 (m, 2H), 3.29 (s, 3H), 2.98 (d, 3H), 2.28 (s, 3H), 1.18-1.12 (m, 3H); LCMS (M + 1): 384.75 |
| 291 | N-ethyl-N'-(5-fluoro-2-methyl-3-(methyl(6-(trifluoromethyl)pyridin-2-yl)amino)phenyl)-N-methylformimidamide | $^{1}$H-NMR (400 MHz, DMSO-d6) δ 7.69-7.88 (1H), 7.59 (d, 1H), 7.06-7.04 (m, 1H), 6.73 (dd, 2H), 6.26 (s, 1H), 3.49-3.31 (m, 3H), 2.98 (d, 3H), 1.92 (d, 3H), 1.25 (d, 2H), 1.15 (d, 3H); LCMS (M + 1): 369.0 |
| 292 | N-ethyl-N'-(3-(3-fluoro-5-methylbenzyl)-5-methoxy-2-methylphenyl)-N-methylformimidamide | $^{1}$H-NMR (400 MHz, DMSO-d6) δ 7.61 (s, 1H), 6.80 (d, 2H), 6.66 (d, 1H), 6.36 (d, 1H), 6.27 (d, 1H), 3.85 (s, 2H), 3.67 (s, 3H), 3.45-3.37 (s, 1H), 2.90 (s, 3H), 2.25 (s, 3H), 1.99 (s, 3H), 1.10 (t, 3H); LCMS (M + 1): 328.80 |
| 293 | N'-(3-(2-chloro-5-fluorobenzyl)-5-methoxy-2-methylphenyl)-N-ethyl-N-methylformimidamide | $^{1}$H-NMR (400 MHz, DMSO-d6) δ 7.65-7.49 (m, 2H), 7.12 (td, 1H), 6.70 (dd, 1H), 6.31 (s, 1H), 6.21-6.19 (m, 1H), 3.93 (s, 2H), 3.65 (s, 3H), 3.47-3.31 (m, 2H), 2.91 (s, 3H), 1.97 (s, 3H), 1.11 (t, 3H); LCMS (M + 1): 348.80 |
| 294 | N'-(3-(2-bromobenzyl)-5-methoxy-2-methylphenyl)-N-ethyl-N-methylformimidamide | $^{1}$H-NMR (400 MHz, DMSO-d6) δ 7.63-7.54 (m, 2H), 7.27 (t, 1H), 7.15 (t, 1H), 6.92 (d, 1H), 6.29 (s, 1H), 6.16 (d, 1H), 3.93 (s, 2H), 3.64 (s, 3H), 3.46-3.33 (m, 2H), 2.91 (s, 3H), 1.99 (d, 3H), 1.11(t, 3H); LCMS (M + 1): 374.75 |
| 295 | N-ethyl-N'-(5-methoxy-2-methyl-3-(4-(trifluoromethyl)benzyl)phenyl)-N-methylformimidamide | $^{1}$H-NMR (400 MHz, DMSO-d6) δ 7.64-7.43 (m, 3H), 7.33 (d, 2H), 6.39 (d, 1H), 6.28 (d, 1H), 3.98 (s, 2H), 3.68 (s, 3H), 3.42-3.32 (m, 2H), 2.89 (s, 3H), 1.98 (s, 3H), 1.10 (t, 3H); LCMS (M + 1): 365.30 |
| 296 | N-ethyl-N'-(5-methoxy-2-methyl-3-(3-(trifluoromethyl)benzyl)phenyl)-N-methylformimidamide | $^{1}$H-NMR (400 MHz, DMSO-d6) δ 7.61-7.47 (m, 4H), 7.41 (d, 1H), 6.39 (d, 1H), 6.29 (s, 1H), 3.99 (s, 2H), 3.68 (s, 3H), 3.47-3.31 (m, 2H), 2.89 (s, 3H), 1.99 (s, 3H), 1.10 (t, 3H); LCMS (M + 1): 364.80 |

TABLE I-continued

| Sr. No. | IUPAC Name | Analytical Data |
|---|---|---|
| 297 | N'-(5-cyano-3-(3-fluorobenzyl)-2-methylphenyl)-N-ethyl-N-methylformimidamide | $^1$H-NMR (400 MHz, DMSO-d6) δ 7.75 (s, 1H), 7.34-7.28 (m, 1H), 7.18 (s, 1H), 7.18-7.14 (m, 1H), 7.07-6.93 (m, 3H), 4.00 (s, 2H), 3.43-3.32 (m, 2H), 2.89 (m, 3H), 2.15 (s, 3H), 1.17-1.10 (m, 3H); LCMS (M + 1): 309.80 |
| 298 | N'-(3-benzyl-5-methoxy-2-methylphenyl)-N-ethyl-N-methylformimidamide | $^1$H-NMR (400 MHz, DMSO-d6) δ 7.58 (s, 1H), 7.27-7.22 (m, 2H), 7.16-7.10 (m, 3H), 6.35 (d, 1H), 6.25 (d, 1H), 3.88 (s, 2H), 3.65 (s, 3H), 3.45-3.29 (m, 2H), 2.90 (s, 3H), 1.99 (s, 3H), 1.11 (t, 3H); LCMS (M + 1): 297.30 |
| 299 | N-ethyl-N'-(5-methoxy-2-methyl-3-(2-(trifluoromethoxy)benzyl)phenyl)-N-methylformimidamide | $^1$H-NMR (400 MHz, DMSO-d6) δ 7.56-7.63 (m, 1H), 7.37-7.25 (m, 3H), 7.01 (d, 1H), 6.29-6.26 (m, 2H), 3.91 (s, 2H), 3.65 (s, 3H), 3.43-3.34 (m, 2H), 2.90 (s, 3H), 1.96 (s, 3H), 1.11 (t, 3H); LCMS (M + 1): 381.35 |
| 300 | N-ethyl-N'-(5-methoxy-2-methyl-3-((2-(trifluoromethoxy)phenyl)amino)phenyl)-N-methylformimidamide | $^1$H-NMR (400 MHz, DMSO-d6) δ 7.62 (d, 1H), 7.26 (s, 1H), 7.22 (d, 1H), 7.11-7.07 (m, 1H), 6.75-6.71 (m, 1H), 6.53 (dd, 1H), 6.27 (d, 1H), 6.24 (s, 1H), 3.67 (s, 3H), 3.36 (d, 2H), 2.92 (s, 3H), 1.91 (s, 3H), 1.12 (t, 3H); LCMS (M + 1): 381.8 |
| 301 | N'-(5-chloro-2-methyl-3-((2-(trifluoromethoxy)phenyl)amino)phenyl)-N-ethyl-N-methylformimidamide | $^1$H-NMR (400 MHz, DMSO-d6) δ 7.69 (d, 1H), 7.42 (s, 1H), 7.26 (dt, 1H), 7.17-7.13 (m, 1H), 6.83 (td, 1H), 6.67-6.59 (m, 3H), 3.43-3.34 (m, 2H), 2.95 (d, 3H), 1.98 (s, 3H), 1.13 (t, 3H); LCMS (M + 1): 385.8 |
| 302 | N'-(2-chloro-5-methyl-3-((2-(trifluoromethoxy)phenyl)amino)phenyl)-N-ethyl-N-methylformimidamide | $^1$H-NMR (400 MHz, DMSO-d6) δ 7.66 (d, 1H), 7.31 (dt, 1H), 7.24-7.20 (m, 1H), 7.13 (s, 1H), 7.00-6.92 (m, 2H), 6.55 (d, 1H), 6.48 (s, 1H), 3.43-3.33 (m, 2H), 2.96 (d, 3H), 2.18 (s, 3H), 1.22 (s, 1H), 1.13 (t, 3H); LCMS (M + 1): 385.7 |
| 303 | N-ethyl-N'-(5-fluoro-2-methyl-3-((2-(trifluoromethoxy)phenyl)amino)phenyl)-N-methylformimidamide | $^1$H-NMR (400 MHz, DMSO-d6) δ 7.68 (d, 1H), 7.37 (s, 1H), 7.26 (dt, 1H), 7.17-7.13 (m, 1H), 6.83 (td, 1H), 6.66 (dd, 1H), 6.47 (d, 1H), 6.38 (dd, 1H), 3.43-3.33 (m, 2H), 2.95 (d, 3H), 1.98 (s, 3H), 1.13 (t, 3H); LCMS (M + 1): 369.8 |
| 304 | N'-(3-(2-(2-chloro-4-methoxyphenoxy)acetyl)-5-fluoro-2-methylphenyl)-N-ethyl-N-methylformimidamide | $^1$H-NMR (400 MHz, DMSO-d6) δ 7.74 (s, 1H), 7.22 (dd, 1H), 7.03 (d, 1H), 7.00 (d, 1H), 6.90 (d, 1H), 6.82 (dd, 1H), 5.35 (s, 2H), 3.71 (s, 3H), 3.45-3.34 (m, 2H), 2.93 (s, 3H), 2.16 (s, 3H), 1.13 (t, 3H); LCMS (M + 1): 392.80 |
| 305 | N-ethyl-N'-(5-methoxy-2-methyl-3-(3-(trifluoromethoxy)benzyl)phenyl)-N-methylformimidamide | $^1$H-NMR (400 MHz, DMSO-d6) δ 7.60 (s, 1H), 7.39 (t, 1H), 7.15-7.09 (m, 3H), 6.38 (d, 1H), 6.27 (d, 1H), 3.94 (s, 2H), 3.67 (s, 3H), 3.46-3.32 (m, 1H), 2.89 (s, 3H), 1.99 (s, 3H), 1.10 (t, 3H); LCMS (M + 1): 381.35 |
| 306 | N'-(3-(3-cyanobenzyl)-5-methoxy-2-methylphenyl)-N-ethyl-N-methylformimidamide | $^1$H-NMR (400 MHz, DMSO-d6) δ 7.66-7.44 (m, 5H), 6.39 (d, 1H), 6.29 (s, 1H), 3.95 (s, 2H), 3.68 (s, 3H), 3.43-3.32 (m, 2H), 2.89 (s, 3H), 1.98 (s, 3H), 1.10 (t, 3H); LCMS (M + 1): 322.30 |
| 307 | N-ethyl-N'-(5-methoxy-2-methyl-3-(2-(trifluoromethyl)benzyl)phenyl)-N-methylformimidamide | $^1$H-NMR (400 MHz, DMSO-d6) δ 7.74 (d, 1H), 7.67 (s, 1H), 7.55 (t, 1H), 7.43 (t, 1H), 7.00 (d, 1H), 6.33 (s, 1H), 6.21 (d, 1H), 4.07 (s, 2H), 3.67 (s, 3H), 3.48-3.31 (m, 2H), 2.92 (s, 3H), 1.95 (s, 3H), 1.13 (t, 3H); LCMS (M + 1): 364.80 |
| 308 | N'-(3-benzyl-5-cyano-2-methylphenyl)-N-ethyl-N-methylformimidamide | $^1$H-NMR (400 MHz, DMSO-d6) δ 7.60 (s, 1H), 7.31-7.28 (m, 2H), 7.22-7.17 (m, 1H), 7.16-7.13 (m, 4H), 4.00 (s, 2H), 3.45-3.33 (m, 2H), 2.92 (s, 3H), 2.18 (s, 3H), 1.14 (t, 3H); LCMS (M + 1): 291.80 |
| 309 | N'-(5-cyano-3-(3-cyanobenzyl)-2-methylphenyl)-N-ethyl-N-methylformimidamide | $^1$H-NMR (400 MHz, DMSO-d6) δ 7.77-7.66 (m, 2H), 7.63-7.62 (m, 1H), 7.53-7.47 (m, 2H), 7.23 (d, 1H), 7.17 (d, 1H), 4.07 (s, 2H), 3.45-3.33 (m, 2H), 2.92 (m, 3H), 2.16 (s, 3H), 1.14 (t, 3H); LCMS (M + 1): 316.80 |
| 310 | N'-(5-cyano-3-(4-fluorobenzyl)-2-methylphenyl)-N-ethyl-N-methylformimidamide | $^1$H-NMR (400 MHz, DMSO-d6) δ 7.74 (s, 1H), 7.24-7.06 (m, 6H), 3.96 (s, 2H), 3.42-3.31 (m, 2H), 2.91 (s, 3H), 2.15 (s, 3H), 1.13 (t, 3H); LCMS (M + 1): 310.3 |
| 311 | N'-(3-(4-chlorobenzyl)-5-cyano-2-methylphenyl)-N-ethyl-N-methylformimidamide | $^1$H-NMR (400 MHz, DMSO-d6) δ 7.74 (s, 1H), 7.34-7.30 (m, 2H), 7.16-7.12 (m, 4H), 3.97 (s, 2H), 3.42-3.32 (m, 2H), 2.90 (s, 3H), 2.14 (s, 3H), 1.14-1.10 (m, 3H); LCMS (M + 1): 326.05 |
| 312 | N'-(5-cyano-2-methyl-3-(3-nitrobenzyl)phenyl)-N-ethyl-N-methylformimidamide | $^1$H-NMR (400 MHz, DMSO-d6) δ 8.09-8.03 (m, 1H), 7.98 (d, 1H), 7.76 (s, 1H), 7.61-7.56 (m, 2H), 7.25 (d, 1H), 7.17 (d, 1H), 4.15 (s, 2H), 3.43-3.32 (m, 2H), 2.91 (s, 3H), 2.15 (s, 3H), 1.14-1.07 (m, 3H); LCMS (M + 1): 337.30 |
| 313 | N'-(3-(3-bromobenzyl)-5-cyano-2-methylphenyl)-N-ethyl-N-methylformimidamide | $^1$H-NMR (400 MHz, DMSO-d6) δ 7.75 (s, 1H), 7.38 (d, 1H), 7.32 (s, 1H), 7.24 (t, 1H), 7.19-7.11 (m, 3H), 3.99 (s, 2H), 3.43-3.32 (m, 2H), 2.91 (s, 3H), 2.14 (s, 3H), 1.12 (t, 3H); LCMS (M + 1): 371.70 |
| 314 | N'-(5-cyano-2-methyl-3-(2-(trifluoromethoxy)benzyl)phenyl)-N-ethyl-N-methylformimidamide | $^1$H-NMR (400 MHz, DMSO-d6) δ 7.77 (s, 1H), 7.40-7.28 (m, 3H), 7.17 (d, 1H), 7.04 (d, 2H), 4.01 (s, 2H), 3.44-3.33 (m, 2H), 2.91 (s, 3H), 2.12 (s, 3H), 1.13 (t, 3H); LCMS (M + 1): 375.75 |

* Compound names generated using Chemdraw Professional 17.1

As described herein the compounds of general formula (I) show fungicidal activities which are exerted with respect to numerous phytopathogenic fungi which attacks on important agricultural crops. The compounds of the present invention were assessed for their activity as described in the following tests:

Biological Test Examples, In Vitro Test

Example 1: *Pyricularia oryzae* (Rice Blast)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification each plate was seeded with a 5 mm size mycelial disc taken from the periphery of an actively growing virulent culture plate. Plates were incubated in growth chambers at 25° C. temperature and 60% relative humidity for seven days and then the radial growth was measured and compared to that of the untreated control.

| Compounds | | | | | | | | | | | |
|---|---|---|---|---|---|---|---|---|---|---|---|
| | | | | | | | | | 1 | 2 | 3 |
| 4 | 5 | 6 | 7 | 8 | 9 | 10 | 12 | 13 | 14 | 15 | 16 |
| 17 | 18 | 19 | 20 | 21 | 22 | 23 | 24 | 25 | 28 | 29 | 30 |
| 31 | 32 | 33 | 34 | 35 | 36 | 37 | 38 | 39 | 40 | 41 | 42 |
| 44 | 45 | 46 | 47 | 48 | 49 | 50 | 51 | 52 | 54 | 55 | 56 |
| 57 | 58 | 59 | 60 | 61 | 64 | 65 | 66 | 67 | 68 | 69 | 70 |
| 71 | 72 | 73 | 75 | 76 | 77 | 78 | 79 | 80 | 82 | 83 | 86 |
| 87 | 88 | 89 | 90 | 91 | 92 | 93 | 94 | 96 | 97 | 98 | 100 |
| 101 | 102 | 103 | 104 | 105 | 107 | 108 | 111 | 112 | 113 | 114 | 115 |
| 116 | 117 | 118 | 119 | 120 | 121 | 122 | 123 | 124 | 125 | 126 | 127 |
| 128 | 129 | 130 | 131 | 133 | 134 | 135 | 136 | 137 | 138 | 139 | 140 |
| 141 | 142 | 143 | 144 | 145 | 146 | 147 | 148 | 149 | 150 | 151 | 152 |
| 154 | 155 | 157 | 159 | 160 | 161 | 162 | 163 | 164 | 165 | 166 | 167 |
| 168 | 169 | 170 | 171 | 172 | 173 | 174 | 175 | 176 | 177 | 178 | 179 |
| 181 | 182 | 183 | 185 | 188 | 189 | 190 | 191 | 201 | 202 | 203 | 204 |
| 205 | 206 | 207 | 208 | 213 | 214 | 216 | 217 | 218 | 219 | 220 | 221 |
| 222 | 223 | 224 | 225 | 228 | 229 | 230 | 231 | 232 | 233 | 234 | 235 |
| 236 | 237 | 238 | 240 | 241 | 242 | 243 | 244 | 245 | 246 | 247 | 248 |
| 249 | 250 | 251 | 252 | 253 | 254 | 255 | 259 | 261 | 262 | 263 | 264 |
| 265 | 266 | 267 | 271 | 272 | 273 | 274 | 275 | 276 | 286 | 287 | 288 |
| 289 | 290 | 291 | 292 | 293 | 294 | 295 | 296 | 297 | 298 | 299 | 300 |
| 301 | 302 | 303 | 304 | 305 | 306 | 307 | 308 | 309 | 310 | 311 | 313 |

at 300 ppm gave a minimum of 70% control in these tests when compared to the untreated check which showed extensive disease development.

Example 2: *Rhizoctonia solani* (Rice Sheath Blight/Potato Black Scurf)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification each plate was seeded with a 5 mm size mycelial disc taken from the periphery of an actively growing virulent culture plate. Plates were incubated in growth chambers at 25° C. temperature and 60% relative humidity for seven days and then the radial " " growth was measured and compared to that of the untreated control.

| Compounds | | | | | | | | | | | |
|---|---|---|---|---|---|---|---|---|---|---|---|
| | | | | | | | | | | 1 | 2 |
| 3 | 4 | 5 | 6 | 7 | 9 | 11 | 12 | 13 | 14 | 15 | 16 |
| 17 | 18 | 19 | 20 | 21 | 22 | 23 | 24 | 25 | 26 | 27 | 28 |
| 29 | 30 | 31 | 34 | 35 | 37 | 38 | 42 | 44 | 45 | 46 | 48 |
| 50 | 51 | 52 | 54 | 55 | 56 | 58 | 59 | 60 | 61 | 64 | 65 |
| 67 | 68 | 69 | 70 | 71 | 72 | 73 | 75 | 76 | 77 | 79 | 80 |
| 82 | 83 | 84 | 87 | 88 | 89 | 90 | 91 | 92 | 93 | 94 | 96 |
| 98 | 100 | 102 | 103 | 104 | 105 | 113 | 124 | 125 | 126 | 127 | 128 |
| 129 | 130 | 131 | 133 | 134 | 135 | 136 | 138 | 140 | 141 | 142 | 143 |
| 144 | 145 | 146 | 147 | 148 | 149 | 150 | 151 | 152 | 154 | 161 | 162 |
| 163 | 164 | 165 | 167 | 168 | 169 | 170 | 171 | 172 | 173 | 174 | 175 |
| 176 | 177 | 178 | 181 | 182 | 183 | 185 | 188 | 189 | 190 | 191 | 201 |

-continued

| Compounds | | | | | | | | | | | |
|---|---|---|---|---|---|---|---|---|---|---|---|
| 202 | 203 | 204 | 205 | 206 | 207 | 208 | 209 | 213 | 214 | 216 | 217 |
| 218 | 219 | 220 | 221 | 222 | 223 | 224 | 229 | 230 | 231 | 232 | 233 |
| 234 | 235 | 236 | 237 | 239 | 241 | 242 | 243 | 244 | 245 | 246 | 247 |
| 253 | 254 | 255 | 259 | 260 | 261 | 262 | 263 | 264 | 265 | 266 | 273 |
| 274 | 275 | 276 | 286 | 287 | 292 | 293 | 294 | 295 | 296 | 298 | 299 |
| 300 | 301 | 302 | 303 | 305 | 306 | 307 | 308 | 311 | | | |

at 300 ppm gave a minimum of 70% control in these tests when compared to the untreated check which showed extensive disease development.

Example 3: *Botrytis cinerea* (Gray Mold)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification each plate was seeded with a 5 mm size mycelial disc taken from the periphery of an actively growing virulent culture plate. Plates were incubated in growth chambers at 22° C. temperature and 90% relative humidity for seven days and then the radial growth was measured and compared to that of the untreated control.

| Compounds | | | | | | | | | | | |
|---|---|---|---|---|---|---|---|---|---|---|---|
| | | | | | | | | | | 2 | 3 |
| 4 | 5 | 8 | 9 | 10 | 11 | 12 | 13 | 14 | 15 | 16 | 17 |
| 18 | 19 | 20 | 21 | 22 | 24 | 25 | 26 | 27 | 29 | 31 | 32 |
| 33 | 34 | 35 | 37 | 38 | 40 | 41 | 42 | 43 | 44 | 45 | 46 |
| 50 | 51 | 52 | 54 | 55 | 56 | 57 | 58 | 59 | 60 | 62 | 63 |
| 65 | 67 | 68 | 70 | 71 | 72 | 73 | 76 | 77 | 79 | 80 | 81 |
| 83 | 84 | 87 | 88 | 89 | 90 | 91 | 92 | 93 | 94 | 96 | 98 |
| 100 | 102 | 103 | 105 | 106 | 110 | 117 | 118 | 119 | 122 | 123 | 124 |
| 125 | 126 | 128 | 129 | 133 | 134 | 136 | 140 | 141 | 142 | 143 | 144 |
| 145 | 146 | 147 | 148 | 149 | 150 | 151 | 152 | 159 | 160 | 161 | 163 |
| 164 | 166 | 170 | 171 | 172 | 173 | 174 | 175 | 176 | 178 | 179 | 181 |
| 182 | 183 | 185 | 188 | 191 | 201 | 202 | 203 | 204 | 205 | 206 | 207 |
| 208 | 213 | 216 | 217 | 220 | 221 | 222 | 223 | 224 | 229 | 230 | 231 |
| 232 | 233 | 235 | 236 | 237 | 244 | 245 | 246 | 247 | 259 | 261 | 262 |
| 263 | 264 | 265 | 273 | 274 | 286 | 287 | 288 | 292 | 293 | 294 | 295 |
| 296 | 297 | 299 | 301 | 302 | 303 | 305 | 307 | 308 | 310 | 311 | |

at 300 ppm gave a minimum of 70% control in these tests when compared to the untreated check which showed extensive disease development.

Example 4: *Alternaria solani* (Early Blight of Tomato/Potato)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification each plate was seeded with a 5 mm size mycelial disc taken from the periphery of an actively growing virulent culture plate. Plates were incubated in growth chambers at 25° C. temperature and 60% relative humidity for seven days and then the radial growth was measured and compared to that of the untreated control.

| Compounds | | | | | | | | | | | |
|---|---|---|---|---|---|---|---|---|---|---|---|
| | | | | | | | | | | 1 | 2 |
| 3 | 4 | 5 | 6 | 7 | 8 | 9 | 10 | 11 | 12 | 13 | 14 |
| 15 | 16 | 17 | 18 | 19 | 20 | 21 | 22 | 23 | 24 | 25 | 26 |
| 27 | 28 | 29 | 30 | 31 | 32 | 33 | 34 | 35 | 36 | 37 | 38 |
| 39 | 40 | 41 | 42 | 43 | 44 | 45 | 46 | 47 | 48 | 49 | 50 |
| 51 | 52 | 53 | 54 | 55 | 56 | 57 | 58 | 59 | 60 | 61 | 62 |
| 63 | 64 | 65 | 66 | 67 | 68 | 69 | 70 | 71 | 72 | 73 | 74 |
| 75 | 76 | 77 | 78 | 79 | 80 | 81 | 82 | 83 | 84 | 85 | 86 |
| 87 | 88 | 89 | 90 | 91 | 92 | 93 | 94 | 96 | 98 | 100 | 101 |
| 102 | 103 | 104 | 105 | 106 | 108 | 110 | 112 | 113 | 114 | 115 | 116 |
| 117 | 118 | 119 | 120 | 121 | 123 | 124 | 125 | 126 | 127 | 128 | 129 |
| 130 | 131 | 133 | 136 | 137 | 138 | 140 | 142 | 143 | 144 | 145 | 146 |
| 147 | 148 | 149 | 150 | 151 | 152 | 153 | 154 | 155 | 156 | 157 | 159 |
| 160 | 161 | 162 | 163 | 164 | 165 | 166 | 167 | 168 | 169 | 170 | 171 |
| 172 | 173 | 174 | 175 | 176 | 177 | 178 | 179 | 180 | 181 | 182 | 183 |
| 185 | 188 | 189 | 190 | 191 | 201 | 202 | 203 | 204 | 205 | 206 | 207 |
| 208 | 209 | 213 | 214 | 216 | 217 | 218 | 219 | 220 | 221 | 222 | 223 |
| 224 | 225 | 226 | 227 | 228 | 229 | 230 | 231 | 232 | 233 | 234 | 235 |
| 236 | 237 | 238 | 239 | 240 | 241 | 242 | 243 | 244 | 245 | 246 | 247 |
| 253 | 254 | 255 | 259 | 260 | 261 | 262 | 263 | 264 | 265 | 266 | 268 |
| 269 | 271 | 272 | 273 | 274 | 275 | 276 | 286 | 287 | 288 | 289 | 290 |
| 291 | 292 | 293 | 294 | 295 | 296 | 297 | 298 | 299 | 300 | 301 | 302 |
| 303 | 304 | 305 | 306 | 307 | 308 | 310 | | | | | |

at 300 ppm gave a minimum of 70% control in these tests when compared to the untreated check which showed extensive disease development.

Example 5: *Colletotrichum capsici* (Anthracnose)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification each plate was seeded with a 5 mm size mycelial disc taken from the periphery of an actively growing virulent culture plate. Plates were incubated in growth chambers at 25° C. temperature and 60% relative humidity for seven days and then the radial growth was measured and compared to that of the untreated control.

| Compounds | | | | | | | | | | | |
|---|---|---|---|---|---|---|---|---|---|---|---|
| | | | | | | | | | | 1 | 2 |
| 3 | 4 | 5 | 7 | 9 | 11 | 12 | 13 | 14 | 15 | 16 | 17 |
| 18 | 19 | 20 | 21 | 23 | 24 | 25 | 26 | 27 | 31 | 34 | 35 |
| 36 | 37 | 38 | 39 | 40 | 41 | 44 | 45 | 46 | 48 | 50 | 51 |
| 56 | 58 | 59 | 60 | 61 | 62 | 65 | 67 | 68 | 71 | 73 | 75 |
| 77 | 79 | 88 | 89 | 90 | 91 | 92 | 93 | 94 | 96 | 98 | 100 |
| 101 | 102 | 103 | 105 | 112 | 113 | 114 | 115 | 116 | 118 | 120 | 123 |
| 124 | 125 | 126 | 128 | 129 | 131 | 133 | 139 | 143 | 144 | 150 | 152 |
| 156 | 161 | 162 | 163 | 171 | 172 | 181 | 183 | 189 | 190 | 201 | 203 |
| 204 | 207 | 208 | 209 | 213 | 216 | 217 | 219 | 220 | 221 | 222 | 223 |
| 224 | 225 | 226 | 233 | 235 | 236 | 244 | 245 | 246 | 254 | 255 | 263 |
| 275 | 287 | | | | | | | | | | |

at 300 ppm gave a minimum of 70% control in these tests when compared to the untreated check which showed extensive disease development.

Example 6: *Septoria lycopersici/Corynespora cassicola* (CORYCA) (Leaf Spot of Tomato)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification each plate was seeded with a 5 mm size mycelial disc taken from the periphery of an actively growing virulent culture plate. Plates were incubated in growth chambers at 25° C. temperature and 70% relative humidity for seven days and then the radial growth was measured and compared to that of the untreated control.

| Compounds | | | | | | | | | | | |
|---|---|---|---|---|---|---|---|---|---|---|---|
| | | | | | | | | | | 2 | 3 |
| 4 | 5 | 6 | 9 | 10 | 11 | 12 | 13 | 14 | 15 | 16 | 17 |
| 18 | 19 | 20 | 22 | 23 | 24 | 25 | 29 | 30 | 31 | 35 | 36 |
| 37 | 38 | 43 | 44 | 50 | 51 | 52 | 54 | 55 | 56 | 58 | 59 |
| 60 | 67 | 70 | 72 | 73 | 76 | 77 | 79 | 84 | 89 | 91 | 92 |
| 94 | 96 | 100 | 101 | 103 | 112 | 113 | 114 | 115 | 116 | 117 | 118 |
| 119 | 120 | 121 | 123 | 124 | 125 | 126 | 128 | 129 | 130 | 131 | 133 |
| 136 | 138 | 140 | 141 | 142 | 143 | 144 | 145 | 146 | 147 | 148 | 149 |
| 151 | 159 | 161 | 162 | 163 | 164 | 165 | 166 | 188 | 189 | 191 | 201 |
| 203 | 204 | 205 | 206 | 207 | 208 | 209 | 213 | 214 | 216 | 217 | 219 |
| 220 | 221 | 222 | 223 | 224 | 226 | 235 | 236 | 237 | 243 | 259 | 261 |
| 262 | 263 | 264 | 265 | 266 | 271 | 272 | 273 | 274 | 275 | 276 | 286 |
| 287 | 291 | 292 | 293 | 294 | 295 | 296 | 297 | 299 | 300 | 301 | 302 |
| 303 | 305 | 307 | 308 | | | | | | | | |

at 300 ppm gave a minimum of 70% control in these tests when compared to the untreated check which showed extensive disease development.

Example 7: *Fusarium culmorum* (Foot Rot of Cereals)

Compounds were dissolved in 0.3% dimethyl sulfoxide and then added to potato dextrose agar medium just prior to dispensing it into petri dishes. 5 mL medium with the compound in the desired concentration was dispensed into 60 mm sterile petri-plates. After solidification each plate was seeded with a 5 mm size mycelial disc taken from the periphery of an actively growing virulent culture plate. Plates were incubated in growth chambers at 25° C. temperature and 60% relative humidity for seven days and then the radial growth was measured and compared to that of the untreated control.

| Compounds | | | | | | | | | | | |
|---|---|---|---|---|---|---|---|---|---|---|---|
| | | | | | | | | | | 1 | 2 |
| 3 | 4 | 5 | 12 | 13 | 17 | 18 | 20 | 25 | 26 | 35 | 44 |
| 46 | 51 | 52 | 54 | 55 | 56 | 59 | 73 | 77 | 87 | 88 | 105 |
| 112 | 116 | 120 | 124 | 125 | 126 | 129 | 142 | 162 | 163 | 164 | 188 |
| 190 | 204 | 207 | 208 | 214 | 220 | 221 | 222 | 223 | 224 | 236 | 246 |
| 261 | 262 | 263 | 264 | 265 | 266 | 271 | 275 | 286 | 287 | 292 | 293 |
| 294 | 295 | 299 | 305 | 307 | | | | | | | |

at 300 ppm gave a minimum of 70% control in these tests when compared to the untreated check which showed extensive disease development.

Biological Test Examples In Vivo on Plants

Example A: *Pyricularia oryzae* Test in Rice

Compounds were dissolved in 2% dimethyl sulfoxide/acetone and then mixed with water containing an emulsifier to a calibrated spray volume of 50 mL. This 50 mL spray solution was poured into spray bottles for further applications.

To test the preventive activity of compounds, healthy young rice seedlings/plants, raised in the greenhouse, were sprayed with the active compound preparation at the stated application rates inside spray cabinets using hollow cone nozzles. One day after treatment, the plants were inoculated with a spore suspension (sterile water) containing $1.4 \times 10^6$ *Pyricularia oryzae* inoculum. The inoculated plants were then kept in a greenhouse chamber at 24° C. temperature and 95% relative humidity for disease expression.

A visual assessment of the compound's performance was carried out by rating the disease severity (0-100% scale) on treated plants 3, 7, 10 and 15 days after application. Efficacy (% control) of the compounds was calculated by comparing the disease rating in the treatments with the one of the untreated control. The treated plants were also assessed for plant compatibility by recording symptoms like necrosis, chlorosis & stunting. Compounds 50 51 52 54 55 94 178 180 181 277 at 500 ppm gave a minimum of 70% control in these tests when compared to the untreated check which showed extensive disease development.

Example B: *Botrytis cinera* Test in Tomato

Compounds were dissolved in 2% dimethyl sulfoxide/acetone and then mixed with water containing an emulsifier to a calibrated spray volume of 50 mL. This 50 mL spray solution was poured into spray bottles for further applications.

To test the preventive activity of compounds, healthy young bean/chili plants, raised in the greenhouse, were sprayed with active compound preparation at the stated application rates inside the spray cabinets using hollow cone nozzles. One day after treatment, the plants were inoculated with a spore suspension (2% Malt) containing $1.2 \times 10^6$ *Botrytis cinerea* inoculum. The inoculated plants were then kept in a greenhouse chamber at 18-20° C. temperature and 90-100% relative humidity for disease expression.

A visual assessment of the compound's performance was carried out by rating the disease severity (0-100% scale) on treated plants 3, 7, 10 and 15 days after application. Efficacy (% control) of the compounds was calculated by comparing the disease rating in the treatment with the one in the untreated control. The treated plants were also assessed for plant compatibility by recording symptoms like necrosis, chlorosis and stunting. Compounds 27 36 39 45 49 192 258 263 264 269 282 at 500 ppm gave a minimum of 70% control in these tests when compared to the untreated check which showed extensive disease development.

Example C: *Phakopsora pachyrhizi* Test in Soybean

Compounds were dissolved in 2% dimethyl sulfoxide/acetone and then mixed with water containing emulsifier to a calibrated spray volume of 50 mL. This 50 mL spray solution was poured into spray bottles for further applications.

To test the preventive activity of compounds, healthy young Soybean plants raised in the greenhouse were sprayed with the active compound preparation at the stated application rates inside the spray cabinets using hollow cone nozzles. One day after treatment, the plants were inoculated with a suspension containing $2\times10^5$ *Phakopsora pachyrhizi* conidia. The inoculated plants were then kept in a greenhouse chamber at 22-24° C. temperature and 80-90% relative humidity for disease expression.

A visual assessment of the compound's performance was carried out by rating the disease severity (0-100% scale) on treated plants 3, 7, 10 and 15 days after application. Efficacy (% control) of the compounds was calculated by comparing the disease rating in the treatment with the one of the untreated control. The sprayed plants were also assessed for plant compatibility by recording symptoms like necrosis, chlorosis and stunting.

| Compounds | | | | | | | | | | | |
|---|---|---|---|---|---|---|---|---|---|---|---|
| | | | | | 14 | 16 | 17 | 18 | 20 | 21 | 22 |
| 23 | 26 | 28 | 29 | 30 | 31 | 32 | 33 | 34 | 36 | 38 | 39 |
| 40 | 41 | 42 | 43 | 44 | 45 | 50 | 51 | 52 | 53 | 54 | 55 |
| 56 | 57 | 58 | 59 | 60 | 65 | 66 | 67 | 68 | 69 | 70 | 71 |
| 77 | 79 | 80 | 81 | 84 | 85 | 86 | 87 | 88 | 89 | 90 | 91 |
| 92 | 93 | 94 | 95 | 98 | 100 | 101 | 102 | 103 | 104 | 105 | 109 |
| 111 | 113 | 114 | 115 | 116 | 117 | 119 | 120 | 121 | 122 | 123 | 124 |
| 125 | 126 | 127 | 128 | 129 | 130 | 131 | 133 | 134 | 143 | 144 | 145 |
| 146 | 147 | 148 | 149 | 150 | 151 | 152 | 153 | 155 | 156 | 157 | 159 |
| 160 | 161 | 178 | 179 | 181 | 182 | 183 | 184 | 185 | 187 | 188 | 189 |
| 190 | 191 | 192 | 193 | 194 | 195 | 196 | 201 | 202 | 203 | 204 | 205 |
| 206 | 207 | 208 | 209 | 210 | 211 | 214 | 215 | 216 | 217 | 218 | 219 |
| 220 | 221 | 222 | 223 | 224 | 229 | 230 | 231 | 232 | 233 | 234 | 235 |
| 236 | 237 | 239 | 242 | 253 | 255 | 259 | 261 | 262 | 263 | 264 | 266 |
| 270 | 273 | 274 | 275 | 276 | 277 | 278 | 279 | 281 | 282 | 284 | 286 |
| 287 | 294 | 295 | 296 | 297 | 298 | 299 | 300 | 301 | | | |

at 500 ppm gave a minimum of 70% control in these tests when compared to the untreated check which showed extensive disease development Having described the invention with reference to certain preferred aspects, other aspects will become apparent to one skilled in the art from consideration of the specification. It will be apparent to those skilled in the art that many modifications, both to materials and methods, may be practiced without departing from the scope of the invention.

The invention claimed is:

1. A compound of formula (I),

Formula (I)

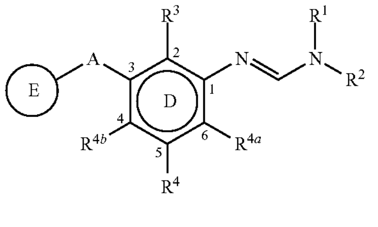

wherein, $R^1$ is selected from the group consisting of $C_1$-$C_{12}$-alkyl, $C_2$-$C_{12}$-alkenyl, $C_2$-$C_{12}$-alkynyl, $C_1$-$C_{12}$-haloalkyl, $C_1$-$C_{12}$-alkoxy, $C_3$-$C_8$-cycloalkyl and $C_4$-$C_8$-cycloalkylalkyl;

$R^2$ is selected from $C_2$-$C_{12}$-alkyl; or $R^1$ and $R^2$ together with the atoms to which they are attached or together with further atoms selected from the group consisting of C, N, O, $S(O)_m$ and optionally including 1 to 3 ring members selected from the group consisting of C(═O) or C(═S) may form a three to seven membered non aromatic ring, which for its part may be substituted by one or more groups selected from the group consisting of X, CN, R', OR', SR', $N(R')_2$, COOR' and $CON(R')_2$;

$R^3$ is selected from the group consisting of X, cyano, $C_1$-$C_{12}$-alkyl, $C_2$-$C_{12}$-alkenyl, $C_2$-$C_{12}$-alkynyl, $C_1$-$C_{12}$-haloalkyl, N(R'R'''), OR'', $S(O)_nR'''$, (C═O)—R'' and $C_3$-$C_8$-cycloalkyl;

$R^4$ is selected from the group consisting of X, cyano, $C_1$-$C_{12}$-alkyl, $C_2$-$C_{12}$-alkenyl, $C_2$-$C_{12}$-alkynyl, $C_1$-$C_{12}$-haloalkyl, N(R'R'''), OR'', $S(O)_nR'''$, (C═O)—R'', $C_3$-$C_8$-cycloalkyl and $C_7$-$C_{12}$-aralkyl;

$R^{4a}$ and $R^{4b}$ are independently selected from the group consisting of hydrogen, X, and $C_1$-$C_4$-alkyl;

A represents —{[C($R^6R^7$)]$_{0-2}$—(B)$_{0-1}$}— wherein B represents $NR^5$ or $CR^6R^7$; or A represents —{[B—C($R^6R^7$)]—C(═Y)}— wherein B represent O, S, $NR^5$ or $CR^6R^7$; and Y represents O or S;

$R^5$ is selected from the group consisting of hydrogen, and $C_1$-$C_8$-alkyl;

$R^6$ and $R^7$ are independently selected from the group consisting of hydrogen, X, cyano, $C_1$-$C_8$-alkyl, and $C_1$-$C_8$-haloalkyl;

$R^6$ and $R^7$ together with the atom to which they are attached or together with further atoms selected from the group consisting of C, N, O, $S(O)_m$ and optionally including 1 to 3 ring members selected from the group consisting of C(═O) or C(═S) may form a three to six membered ring, which for its part may be substituted by one or more groups selected from the group consisting of X, CN, R', OR', SR', $N(R')_2$, COOR' and $CON(R')_2$;

ring E is selected from the group consisting of fused or non-fused $C_3$-$C_{18}$-carbocyclyl and $C_3$-$C_{18}$-heterocyclyl, which may optionally be substituted by one or more groups of $R^8$;

$R^8$ is selected from the group consisting of hydrogen, X, cyano, nitro, $C_1$-$C_{12}$-alkyl, $C_2$-$C_{12}$-alkenyl, $C_2$-$C_{12}$- alkynyl, $C_1$-$C_{12}$-haloalkyl, $C_2$-$C_{12}$-haloalkenyl, $C_2$-$C_{12}$-haloalkynyl, $C_3$-$C_8$-cycloalkyl, $C_4$-$C_8$-cycloalkenyl, $C_4$-$C_8$-cycloalkynyl, $C_7$-$C_{19}$-aralkyl, $C_5$-$C_{12}$-bicycloalkyl, $C_6$-$C_{10}$-aryl, $C_3$-$C_6$-heterocyclyl, SCN, $SF_5$, N(R'R'''), OR'', $S(O)_nR'''$, (C═O)—R''', $C_1$-$C_8$-alkyl-$S(O)_nR''$, $C_1$-$C_8$-alkyl-(C═O)—R'', CR'═NR'', —$S(R^9)$═$N(R^{10})$, —$S(R^9)(O)$═$N(R^{10})$, $S(R^9)_2$═N—, $S(R^9)_2(O)$═N— and $S(R^9)_2(O)$═N—C($R^{6a}R^{7a}$)—; wherein one or more carbon atoms in cyclic ring may be replaced by heteroatoms selected from the group consisting of N, O, $S(O)_m$ and optionally including 1 to 3 ring members selected from the group consisting of C(═O) and C(═S);

$R^{6a}$ and $R^{7a}$ are independently selected from the group consisting of hydrogen, X, cyano, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $(NR'')_2$, OR'', $S(O)_nR'''$, (C═O)—R'' and $C_3$-$C_8$-cycloalkyl; or $R^{6a}$ and $R^{7a}$ together with the atom to which they are attached or together with further atoms selected from the group consisting of C, N, O, $S(O)_m$ and optionally including 1 to 3 ring members selected from the group consisting of C(═O) and C(═S), may form a three to six membered ring, which for its part may be substituted by one or more group selected from the group consisting of X, CN, R', OR', SR', $N(R')_2$, COOR' and $CON(R')_2$; or $R^{6a}$ and $R^{7a}$ together with the atom to which they are attached may form a group of ═O or ═S;

$R^9$ is independently selected from the group consisting of $C_1$-$C_8$-alkyl and $C_3$-$C_8$-cycloalkyl;

$R^{10}$ is selected from the group consisting of hydrogen, cyano, $C_1$-$C_8$-alkyl, $C_2$-$C_8$-alkenyl, $C_2$-$C_8$-alkynyl, (C═O)—R'', $S(O)_nR'''$ and $C_3$-$C_8$-cycloalkyl; or $R^9$ and $R^{10}$ together with the atom to which they are attached or together with further atoms selected from the group consisting of C, N, O, $S(O)_m$ and optionally including 1 to 3 ring members selected from the group consisting of C(═O) or C(═S) may form a three to seven membered ring, which for its part may be substituted by one or more groups selected from the group consisting of X, CN, R', OR', SR', $N(R')_2$, COOR' and $CON(R')_2$; or $R^8$ and $R^9$ or $R^{10}$ together with the atom to which they are attached or together with further atoms selected from the group consisting of C, N, O, $S(O)_m$ and optionally including 1 to 3 ring members selected from the group consisting of C(═O) or C(═S) may form a three to seven membered ring, which for its part may be substituted by one or more groups selected from the group consisting of X, CN, R', OR', SR', $N(R')_2$, COOR' and $CON(R')_2$;

$R^5$ or $R^6$ or $R^7$ and $R^8$ or two $R^8$ together with the atoms to which they are attached or together with further atoms selected from the group consisting of C, N, O, $S(O)_m$ and optionally including 1 to 3 ring members selected from the group consisting of C(═O) or C(═S), may form a three to ten membered ring, which for its part may be substituted by one or more groups selected from the group consisting of X, CN, R', OR', SR', $N(R')_2$, COOR' and $CON(R')_2$;

X represents halogen;

R' is selected from the group consisting of hydrogen, $C_1$-$C_8$-alkyl and $C_3$-$C_8$-cycloalkyl; wherein alkyl and cycloalkyl group may be optionally substituted by one or more X;

R'' is selected from the group consisting of hydrogen, $C_1$-$C_8$-alkyl, $C_1$-$C_8$-haloalkyl, $C_3$-$C_8$-cycloalkyl, $N(R')_2$, and OR';

R''' is selected from R'';

n represents integer 0, 1 or 2;

m represents an integer 0, 1 or 2;

or agriculturally acceptable salts, stereo-isomers, polymorphs, or N-oxides thereof.

2. The compound of formula (I) as claimed in claim 1, wherein $R^1$ is selected from the group consisting of $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_3$-$C_5$-cycloalkyl and $C_4$-$C_8$-cycloalkylalkyl;

$R^2$ is selected from $C_2$-$C_6$-alkyl;

$R^3$ and $R^4$ are independently selected from the group consisting of X, cyano, $C_1$-$C_6$-alkyl, $C_2$-$C_6$-alkenyl, $C_2$-$C_6$-alkynyl, $C_1$-$C_6$-haloalkyl, N(R'R'''), OR'', $S(O)_nR'''$, (C═O)—R'' and $C_3$-$C_8$-cycloalkyl;

$R^5$ is selected from the group consisting of hydrogen and $C_1$-$C_6$-alkyl;

$R^6$ and $R^7$ are independently selected from the group consisting of hydrogen, X, cyano, $C_1$-$C_4$-alkyl, and $C_1$-$C_4$-haloalkyl;

ring E is selected from the group consisting of fused or non-fused $C_3$-$C_{10}$-carbocyclyl and $C_5$-$C_{10}$-heterocyclyl, which may optionally be substituted by one or more groups of $R^8$;

or agriculturally acceptable salts, stereo-isomers, polymorphs, or N-oxides thereof.

3. The compound of formula (I) as claimed in claim 1, wherein said $R^1$ and $R^2$ is selected from the group consisting of $C_1$-$C_6$-alkyl, $C_2$-$C_6$-alkenyl, $C_3$-$C_5$-cycloalkyl, and $C_4$-$C_8$-cycloalkylalkyl;

$R^2$ is selected from $C_2$-$C_6$-alkyl;

$R^3$ and $R^4$ are independently selected from the group consisting of X, cyano, $C_1$-$C_6$-alkyl, $C_2$-$C_6$-alkenyl, $C_2$-$C_6$-alkynyl, $C_1$-$C_6$-haloalkyl, $C_3$-$C_5$-cycloalkyl and OR'';

$R^5$ is selected from the group consisting of hydrogen and $C_1$-$C_6$-alkyl;

$R^6$ and $R^7$ are independently selected from the group consisting of hydrogen, X, cyano, $C_1$-$C_4$-alkyl, and $C_1$-$C_4$-haloalkyl;

ring E is selected from cyclopropyl, cyclobutyl, phenyl, napthalenyl, furyl, thienyl, pyrrolyl, isoxazolyl, thiazolyl, isothiazolyl, thiadiazolyl, pyrazolyl, oxazolyl, imidazolyl, oxadiazolyl, triazolyl, pyridinyl, pyridazinyl, pyrimidinyl, pyrazinyl, triazinyl, indolyl, benzimidazolyl, indazolyl, benzofuranyl, benzothiophenyl, benzothiazolyl, benzoxazolyl, quinolinyl, isoquinolinyl, iquinazolinyl, cinnonyl, indolizinyl, pyrazolo[1,5-a]pyridinyl, imidazo[1,2-a]pyridinyl, pyrrolo[1,2-a]pyrimidinyl, pyrazolo[1,5-a]pyrimidinyl, imidazo[1,2-a]pyrimidinyl, pyrrolo[1,2-a]pyrazinyl, pyrazolo[1,5-a]pyrazinyl, imidazo[1,2-a]pyrazinyl substituted with one or more $R^8$;

or agriculturally acceptable salts, stereo-isomers, polymorphs, or N-oxides thereof.

4. The compound of formula (I) as claimed in claim 1, wherein said compound of formula (I) is selected from the group consisting of N'-(2-chloro-5-methyl-3-(p-tolylamino)phenyl)-N-ethyl-N-methylformimidamide, N'-(2,5-dimethyl-3-(4-methylbenzyl)phenyl)-N-ethyl-N-methylformimidamide, N'-(3-(3-chlorobenzyl)-2,5-dimethylphenyl)-N-ethyl-N-methylformimidamide, N'-(2,5-dimethyl-3-(2-methylbenzyl)phenyl)-N-ethyl-N-methylformimidamide, N-ethyl-N'-(3-(3-fluorobenzyl)-2,5-dimethylphenyl)-N-methylformimidamide, N-ethyl-N'-(3-((2-fluorophenyl)amino)-2,5-dimethylphenyl)-N-methylformimidamide, N-ethyl-N'-(3-((2-fluorophenyl)(methyl)amino)-2,5-dimethylphenyl)-N-methylformimidamide, N-ethyl-N'-(5-fluoro-2-methyl-3-(phenylamino)phenyl)-N-methylformimidamide, N'-(2-chloro-5-methyl-3-(phenylamino)phenyl)-N-ethyl-N-methylformimidamide, N'-(2-chloro-5-methyl-3-(methyl(phenyl)amino)phenyl)-N-ethyl-N-methylformimidamide, N-ethyl-N'-(5-fluoro-2-methyl-3-(methyl(phenyl)amino)phenyl)-N-methylformimidamide, N'-(2-chloro-5-methyl-3-(2-methylbenzyl)phenyl)-N-ethyl-N-methylformimidamide, N'-(2-chloro-3-(2-chlorobenzyl)-5-methylphenyl)-N-ethyl-N-methylformimidamide, N'-(2-chloro-3-(2-fluorobenzyl)-5-methylphenyl)-N-ethyl-N-methylformimidamide, N-ethyl-N'-(5-fluoro-2-methyl-3-(o-tolylamino)phenyl)-N-methylformimidamide, N-ethyl-N'-(5-fluoro-2-methyl-3-((4-((trifluoromethyl)thio)phenyl)amino)phenyl)-N-methylformimidamide, N'-(2-chloro-5-methyl-3-(3-methylbenzyl)phenyl)-N-ethyl-N-methylformimidamide, N'-(2-chloro-5-methyl-3-(4-methylbenzyl)phenyl)-N-ethyl-N-methylformimidamide, N-ethyl-N'-(5-fluoro-3-((2-fluorophenyl)amino)-2-methylphenyl)-N-methylformimidamide, N'-(3-((4-(tert-butyl)phenyl)amino)-5-fluoro-2-methylphenyl)-N-ethyl-N-methylformimidamide, N'-(2-chloro-5-methyl-3-(2-(trifluoromethyl)benzyl)phenyl)-N-ethyl-N-methylformimidamide, N'-(2-chloro-3-(3-fluorobenzyl)-5-methylphenyl)-N-ethyl-N-methylformimidamide, N'-(2-chloro-3-((2-fluorophenyl)amino)-5-methylphenyl)-N-ethyl-N-methylformimidamide, N'-(2-chloro-5-methyl-3-(o-tolylamino)phenyl)-N-ethyl-N-methylformimidamide, N'-(3-((4-(tert-butyl)phenyl)amino)-2-chloro-5-methylphenyl)-N-ethyl-N-methylformimidamide, N'-(2-chloro-5-methyl-3-((4-((trifluoromethyl)thio)phenyl)amino)phenyl)-N-ethyl-N-methylformimidamide, N'-(2-chloro-3-(3-chlorobenzyl)-5-methylphenyl)-N-ethyl-N-methylformimidamide, N'-(2-chloro-3-(3-methoxybenzyl)-5-methylphenyl)-N-ethyl-N-methylformimidamide, N-ethyl-N'-(5-fluoro-3-((3-fluorophenyl)amino)-2-methylphenyl)-N-methylformimidamide, N-ethyl-N'-(5-fluoro-3-((3-methoxyphenyl)amino)-2-methylphenyl)-N-methylformimidamide, N-ethyl-N'-(5-fluoro-2-methyl-3-(m-tolylamino)phenyl)-N-methylformimidamide, N-ethyl-N'-(5-fluoro-3-((3-fluorophenyl)(methyl)amino)-2-methylphenyl)-N-methylformimidamide, N'-(3-((3-chlorophenyl)(methyl)amino)-5-fluoro-2-methylphenyl)-N-ethyl-N-methylformimidamide, N'-(2-chloro-3-((3-chlorophenyl)amino)-5-methylphenyl)-N-ethyl-N-methylformimidamide, N'-(2-chloro-3-((3-fluorophenyl)amino)-5-methylphenyl)-N-ethyl-N-methylformimidamide, N'-(2-chloro-5-methyl-3-(m-tolylamino)phenyl)-N-ethyl-N-methylformimidamide, N'-(3-((3-chlorophenyl)amino)-5-fluoro-2-methylphenyl)-N-ethyl-N-methylformimidamide, N-ethyl-N'-(5-fluoro-2-methyl-3-(methyl(m-tolyl)amino)phenyl)-N-methylformimidamide, N-ethyl-N'-(5-fluoro-3-((3-methoxyphenyl)(methyl)amino)-2-methylphenyl)-N-methylformimidamide, N'-(2-chloro-3-((3-fluorophenyl)(methyl)amino)-5-methylphenyl)-N-ethyl-N-methylformimidamide, N'-(2-chloro-3-((3-chlorophenyl)(methyl)amino)-5-methylphenyl)-N-ethyl-N-methylformimidamide, N'-(2-chloro-3-((3-methoxyphenyl)amino)-5-methylphenyl)-N-ethyl-N-methylformimidamide, N'-(2-chloro-5-methyl-3-(methyl(m-tolyl)amino)phenyl)-N-ethyl-N-methylformimidamide, N'-(2-chloro-3-(4-fluorobenzyl)-5-methylphenyl)-N-ethyl-N-methylformimidamide, N'-(3-(2-bromobenzyl)-2-chloro-5-methylphenyl)-N-ethyl-N-methylformimidamide, N'-(2-chloro-3-(4-cyanobenzyl)-5-methylphenyl)-N-ethyl-N-methylformimidamide, N'-(2-chloro-3-(2-cyanobenzyl)-5-methylphenyl)-N-ethyl-N-methylformimidamide, N'-(2-chloro-3-(3-cyanobenzyl)-5-methylphenyl)-N-ethyl-N-methylformimidamide, N'-(2-chloro-3-((3-methoxyphenyl)(methyl)amino)-5-methylphenyl)-N-ethyl-N-methylformimidamide, N'-(2-chloro-5-methyl-3-(2-(trifluoromethoxy)benzyl)phenyl)-N-ethyl-N-methylformimidamide, N'-(2-chloro-5-methyl-3-(4-(trifluoromethyl)benzyl)phenyl)-N-ethyl-N-methylformimidamide, N'-(2-chloro-5-methyl-3-(4-(trifluoromethoxy)benzyl)phenyl)-N-ethyl-N-methylformimidamide, N'-(2-chloro-5-methyl-3-(3-(trifluoromethyl)benzyl)phenyl)-N-ethyl-N-methylformimidamide, N'-(2-chloro-3-(3-chloro-4-fluorobenzyl)-5-methylphenyl)-N-ethyl-N-methylformimidamide, N'-(2-chloro-3-(3,5-dimethylbenzyl)-5-methylphenyl)-N-ethyl-N-methylformimidamide, N'-(2-chloro-3-(3-chloro-2-fluorobenzyl)-5-methylphenyl)-N-ethyl-N-methylformimidamide, N'-(2-chloro-3-(5-fluoro-2-methylbenzyl)-5-methylphenyl)-N-ethyl-N-methylformimidamide, N'-(2-chloro-3-((3-isopropylphenyl)amino)-5-methylphenyl)-N-ethyl-N-methylformimidamide, N'-(2-chloro-3-((4-chlorophenyl)amino)-5-methylphenyl)-N-ethyl-N-methylformimidamide, N'-(2-chloro-3-((4-fluorophenyl)amino)-5-methylphenyl)-N-ethyl-N-methylformimidamide, N'-(2-chloro-3-((4-methoxyphenyl)amino)-5-methylphenyl)-N-ethyl-N-methylformimidamide, N'-(2-chloro-3-((4-chlorophenyl)(methyl)amino)-5-methylphenyl)-N-ethyl-N-methylformimidamide, N'-(2-chloro-3-((3-isopropylphenyl)(methyl)amino)-5-methylphenyl)-N-ethyl-N-methylformimidamide, N'-(2-chloro-3-((4-methoxyphenyl)(methyl)amino)-5-methylphenyl)-N-ethyl-N-methylformimidamide, N'-(2-chloro-3-(4-fluoro-2-methylbenzyl)-5-methylphenyl)-N-ethyl-N-methylformimidamide, N'-(2-chloro-5-methyl-3-(pyridin-3-ylmethyl)phenyl)-N-ethyl-N-methylformimidamide, N'-(2-chloro-3-(3,4-difluorobenzyl)-5-methylphenyl)-N-ethyl-N-methylformimidamide, N'-(2-chloro-3-(4-fluoro-3-methylbenzyl)-5-methylphenyl)-N-ethyl-N-methylformimidamide, N'-(2-chloro-3-((4-fluorophenyl)(methyl)amino)-5-methylphenyl)-N-ethyl-N-methylformimidamide, N'-(3-benzyl-2-chloro-5-methylphenyl)-N-ethyl-N-methylformimidamide, N'-(2-chloro-3-(3,5-difluoro-4-methoxybenzyl)-5-methylphenyl)-N-ethyl-N-methylformimidamide, N'-(2-chloro-3-((3,4-difluorophenyl)amino)-5-methylphenyl)-N-ethyl-N-methylformimidamide, N'-(3-((3,4-difluorophenyl)amino)-5-fluoro-2-methylphenyl)-N-ethyl-N-methylformimidamide, N'-(2-chloro-3-((3,5-difluorophenyl)(methyl)amino)-5-methylphenyl)-N-ethyl-N-methylformimidamide, N'-(2-chloro-3-((2,4-difluorophenyl)amino)-5-methylphenyl)-N-ethyl-N-methylformimidamide, N'-(3-((2,4-difluorophenyl)amino)-5-fluoro-2-methylphenyl)-N-ethyl-N-methylformimidamide, N'-(3-((3,5-difluorophenyl)amino)-5-fluoro-2-methylphenyl)-N-ethyl-N-methylformimidamide, N'-(2-chloro-3-((3,5-difluorophenyl)amino)-5-methylphenyl)-N-ethyl-N-methylformimidamide, N'-(3-benzyl-5-chloro-2-methylphenyl)-N-ethyl-N-methylformimidamide, N'-(3-((2,4-difluorophenyl)(methyl)amino)-5-fluoro-2-methylphenyl)-N-ethyl-N-methylformimidamide, N'-(2-chloro-3-((3,4-difluorophenyl)(methyl)amino)-5-methylphenyl)-N-ethyl-N-methylformimidamide, N'-(2-chloro-3-((2,4-difluorophenyl)(methyl)amino)-5-methylphenyl)-N-ethyl-N-methylformimidamide, N'-(3-((3,4-difluorophenyl)(methyl)amino)-5-fluoro-2-methylphenyl)-N-ethyl-N-methylformimidamide, N'-(3-((3,5-difluorophenyl)(methyl)amino)-5-fluoro-2-methylphenyl)-N-ethyl-N-methylformimidamide, N'-(2-chloro-5-methyl-3-(pyridin-2-ylamino)phenyl)-N-ethyl-N-methylformimidamide, N'-(2-chloro-5-methyl-3-((3-methylpyridin-2-yl)amino)phenyl)-N-ethyl-N-methylformimidamide, N'-(5-chloro-3-(4-fluoro-3,5-dimethylbenzyl)-2-methylphenyl)-N-ethyl-N-methylformimidamide, N'-(5-chloro-2-methyl-3-(2-methylbenzyl)phenyl)-N-ethyl-N-methylformimidamide, N'-(5-chloro-3-(2-chlorobenzyl)-2-methylphenyl)-N-ethyl-N-methylformimidamide, N'-(3-(2-bromobenzyl)-5-chloro-2-methylphenyl)-N-ethyl-N-methylformimidamide, N'-(2-chloro-3-(2,6-difluorobenzyl)-5-methylphenyl)-N-ethyl-N-methylformimidamide, N'-(2-chloro-3-(2-chloro-6-fluorobenzyl)-5-methyl phenyl)-N-ethyl-N-methylformimidamide, N'-(3-(4-bromobenzyl)-2-chloro-5-methylphenyl)-N-ethyl-N-methylformimidamide, N'-(5-chloro-2-methyl-3-(3-methylbenzyl)phenyl)-N-ethyl-N-methylformimidamide, N-ethyl-N'-(5-fluoro-2-methyl-3-(pyridin-2-ylamino)phenyl)-N-methylformimidamide, N'-(3-((3-chloro-5-fluorophenyl)amino)-5-fluoro-2-methylphenyl)-N-ethyl-N-methylformimidamide, N'-(2-chloro-3-((3-chloro-5-fluorophenyl)amino)-5-methylphenyl)-N-ethyl-N-methylformimidamide, N'-(3-((5-chloro-2-methylphenyl)(methyl)amino)-5-fluoro-2-methylphenyl)-N-ethyl-N-methylformimidamide, N'-(2-chloro-3-((3-chloro-5-fluorophenyl)(methyl)amino)-5-methylphenyl)-N-ethyl-N-methylformimidamide, N'-(2-chloro-3-((5-chloro-2-methylphenyl)amino)-5-methylphenyl)-N-ethyl-N-methylformimidamide, N'-(5-chloro-3-(3-chlorobenzyl)-2-methylphenyl)-N-ethyl-N-methylformimidamide, N'-(5-chloro-3-(3-fluorobenzyl)-2-methylphenyl)-N-ethyl-N-methylformimidamide, N'-(5-chloro-3-(2-fluorobenzyl)-2-methylphenyl)-N-ethyl-N-methylformimidamide, N'-(5-chloro-3-(2-cyanobenzyl)-2-methylphenyl)-N-ethyl-N-methylformimidamide, N'-(5-chloro-2-methyl-3-(4-methylbenzyl)phenyl)-N-ethyl-N-methylformimidamide, N'-(3-((3-chloro-5-fluorophenyl)(methyl)amino)-5-fluoro-2-methylphenyl)-N-ethyl-N-methylformimidamide, N'-(2-chloro-5-methyl-3-(methyl(pyridin-2-yl)amino)phenyl)-N-ethyl-N-methylformimidamide, N'-(2-chloro-5-methyl-3-(methyl(3-methylpyridin-2-yl)amino)phenyl)-N-ethyl-N-methylformimidamide, N-ethyl-N'-(5-fluoro-2-methyl-3-(methyl(pyridin-2-yl)amino)phenyl)-N-methylformimidamide, N'-(2-chloro-3-((5-chloro-2-methylphenyl)(methyl)amino)-5-methylphenyl)-N-ethyl-N-methylformimidamide, N'-(2-chloro-3-((3-fluoro-5-methylphenyl)amino)-5-methylphenyl)-N-ethyl-N-methylformimidamide, N'-(2-chloro-3-((5-chloro-3-methylpyridin-2-yl)amino)-5-methylphenyl)-N-ethyl-N-methylformimidamide, N'-(3-((2-chloro-5-methylphenyl)amino)-5-fluoro-2-methylphenyl)-N-ethyl-N-methylformimidamide, N-ethyl-N'-(5-fluoro-3-((3-fluoro-5-methylphenyl)amino)-2-methylphenyl)-N-methylformimidamide, N'-(2-chloro-3-((2-chloro-5-methylphenyl)amino)-5-methylphenyl)-N-ethyl-N-methylformimidamide, N'-(3-((5-chloro-2-methylphenyl)amino)-5-fluoro-2-methylphenyl)-N-ethyl-N-methylformimidamide, N'-(3-((2-chloro-5-methylphenyl)(methyl)amino)-5-fluoro-2-methylphenyl)-N-ethyl-N-methylformimidamide, N'-(2-chloro-3-((5-chloro-3-methylpyridin-2-yl)(methyl)amino)-5-methylphenyl)-N-ethyl-N-methylformimidamide, N-ethyl-N'-(5-fluoro-3-((3-fluoro-5-methylphenyl)(methyl)amino)-2-methylphenyl)-N-methylformimidamide, N'-(2-chloro-3-((2-chloro-5-methylphenyl)(methyl)amino)-5-methylphenyl)-N-ethyl-N-methylformimidamide, N-ethyl-N'-(5-fluoro-3-((2-fluoro-6-methylphenyl)amino)-2-methylphenyl)-N-methylformimidamide, N-ethyl-N'-(5-fluoro-3-((2-fluoro-3-methylphenyl)amino)-2-methylphenyl)-N-methylformimidamide, N'-(2-chloro-3-((2-fluoro-3-methylphenyl)amino)-5-methylphenyl)-N-ethyl-N-methylformimidamide, N'-(5-chloro-3-(4-fluorobenzyl)-2-methylphenyl)-N-ethyl-N-methylformimidamide, N'-(3-(4-bromobenzyl)-5-chloro-2-methylphenyl)-N-ethyl-N-methylformimidamide, N'-(5-chloro-3-(4-chlorobenzyl)-2-methylphenyl)-N-ethyl-N-methylformimidamide, N'-(5-chloro-2-methyl-3-(3-(trifluoromethyl)benzyl)phenyl)-N-ethyl-N-methylformimidamide, N'-(5-chloro-3-(4-fluoro-3-methylbenzyl)-2-methylphenyl)-N-ethyl-N-methylformimidamide, N'-(5-chloro-3-(3,4-difluorobenzyl)-2-methylphenyl)-N-ethyl-N-methylformimidamide, N'-(5-chloro-3-(3-chloro-4-fluorobenzyl)-2-methylphenyl)-N-ethyl-N-methylformimidamide, N'-(5-chloro-3-(4-chloro-3-fluorobenzyl)-2-methylphenyl)-N-ethyl-N-methylformimidamide, N-ethyl-N'-(5-fluoro-2-methyl-3-((3-(trifluoromethyl)pyridin-2-yl)amino)phenyl)-N-methylformimidamide, N'-(2-chloro-3-((2-fluoro-6-methylphenyl)amino)-5-methylphenyl)-N-ethyl-N-methylformimidamide, N'-(2-chloro-3-((4-chloro-2-fluorophenyl)amino)-5-methylphenyl)-N-ethyl-N-methylformimidamide, N'-(2-chloro-5-methyl-3-((3-(trifluoromethyl)pyridin-2-yl)amino)phenyl)-N-ethyl-N-methylformimidamide, N'-(3-((4-chloro-2-fluorophenyl)amino)-5-fluoro-2-methylphenyl)-N-ethyl-N-methylformimidamide, N'-(2-chloro-3-((3-chloro-5-(trifluoromethyl)phenyl)amino)-5-methylphenyl)-N-ethyl-N-methylformimidamide, N'-(2-chloro-3-((2-fluoro-6-methylphenyl)(methyl)amino)-5-methylphenyl)-N-ethyl-N-methylformimidamide, N'-(2-chloro-3-((2-fluoro-3-methylphenyl)(methyl)amino)-5-methylphenyl)-N-ethyl-N-methylformimidamide, N'-(3-((4-chloro-2-fluorophenyl)(methyl)amino)-5-fluoro-2-methylphenyl)-N-ethyl-N-methylformimidamide, N-ethyl-N'-(5-fluoro-3-(2-fluorobenzyl)-2-methylphenyl)-N-methylformimidamide, N'-(3-(2-chlorobenzyl)-5-fluoro-2-methylphenyl)-N-ethyl-N-methylformimidamide, N-ethyl-N'-(5-fluoro-2-methyl-3-(2-(trifluoromethyl)benzyl)phenyl)-N-methylformimidamide, N'-(3-(3-chlorobenzyl)-5-fluoro-2-methylphenyl)-N-ethyl-N-methylformimidamide, N-ethyl-N'-(5-fluoro-3-((2-fluoro-6-methylphenyl)(methyl)amino)-2-methylphenyl)-N-methylformimidamide, N-ethyl-N'-(5-fluoro-2-methyl-3-(3-methylbenzyl)phenyl)-N-methylformimidamide, N-ethyl-N'-(5-fluoro-3-(3-fluorobenzyl)-2-methylphenyl)-N-methylformimidamide, N-ethyl-N'-(5-fluoro-2-methyl-3-(2-methylbenzyl)phenyl)-N-methylformimidamide, N'-(3-benzyl-5-fluoro-2-methylphenyl)-N-ethyl-N-methylformimidamide, N'-(2-chloro-3-(4-methoxybenzyl)-5-methylphenyl)-N-ethyl-N-methylformimidamide, N'-(3-(2-bromobenzyl)-5-fluoro-2-methylphenyl)-N-ethyl-N-methylformimidamide, N-ethyl-N'-(5-fluoro-3-((2-fluoro-3-methylphenyl)(methyl)amino)-2-methylphenyl)-N-methylformimidamide, N-ethyl-N'-(5-fluoro-2-methyl-3-(methyl(3-(trifluoromethyl)pyridin-2-yl)amino)phenyl)-N-methylformimidamide, N'-(5-chloro-2-methyl-3-(m-tolylamino)phenyl)-N-ethyl-N-methylformimidamide, N'-(5-chloro-2-methyl-3-(phenylamino)phenyl)-N-ethyl-N-methylformimidamide, N'-(2-chloro-3-((4-chloro-2-fluorophenyl)(methyl)amino)-5-methylphenyl)-N-ethyl-N-methylformimidamide, N'-(2-chloro-5-methyl-3-(methyl(3-(trifluoromethyl)pyridin-2-yl)amino)phenyl)-N-ethyl-N-methylformimidamide, N'-(2-chloro-3-((3-chloro-5-(trifluoromethyl)phenyl)(methyl)amino)-5-methylphenyl)-N-ethyl-N-methylformimidamide, N'-(5-chloro-2-methyl-3-(methyl(phenyl)amino)phenyl)-N-ethyl-N-methylformimidamide, N'-(5-chloro-2-methyl-3-(methyl(m-tolyl)amino)phenyl)-N-ethyl-N-methylformimidamide, N'-(3-((3-chloro-5-(trifluoromethyl)phenyl)amino)-5-fluoro-2-methylphenyl)-N-ethyl-N-methylformimidamide, N'-(5-chloro-3-((4-methoxyphenyl)amino)-2-methylphenyl)-N-ethyl-N-methylformimidamide, N'-(5-chloro-3-((3-chlorophenyl)amino)-2-methylphenyl)-N-ethyl-N-methylformimidamide, N'-(3-((3-bromophenyl)amino)-5-chloro-2-methylphenyl)-N-ethyl-N-methylformimidamide, N'-(5-chloro-3-((2-fluorophenyl)amino)-2-methylphenyl)-N-ethyl-N-methylformimidamide, N'-(5-chloro-3-((3-fluorophenyl)amino)-2-methylphenyl)-N-ethyl-N-methylformimidamide, N'-(5-chloro-3-((4-methoxyphenyl)(methyl)amino)-2-methylphenyl)-N-ethyl-N-methylformimidamide, N'-(3-(2-cyanobenzyl)-5-fluoro-2-methylphenyl)-N-ethyl-N-methylformimidamide, N'-(2-chloro-3-((2,3-dihydrobenzo[b][1,4]dioxin-6-yl)amino)-5-methylphenyl)-N-ethyl-N-methylformimidamide, N-ethyl-N'-(5-fluoro-2-methyl-3-(2-(trifluoromethoxy)benzyl)phenyl)-N-methylformimidamide, N-ethyl-N'-(5-fluoro-2-methyl-3-(4-methylbenzyl)phenyl)-N-methylformimidamide, N'-(3-(4-chlorobenzyl)-5-fluoro-2-methylphenyl)-N-ethyl-N-methylformimidamide, N-ethyl-N'-(5-fluoro-2-methyl-3-(3-(trifluoromethoxy)benzyl)phenyl)-N-methylformimidamide, N'-(3-(3-cyanobenzyl)-5-fluoro-2-methylphenyl)-N-ethyl-N-methylformimidamide, N'-(3-(4-bromobenzyl)-5-fluoro-2-methylphenyl)-N-ethyl-N-methylformimidamide, N-ethyl-N'-(5-fluoro-2-methyl-3-(4-(trifluoromethoxy)benzyl)phenyl)-N-methylformimidamide, N'-(2-chloro-3-((2-(difluoromethoxy)phenyl)amino)-5-methylphenyl)-N-ethyl-N-methylformimidamide, N'-(5-chloro-3-((2-fluorophenyl)(methyl)amino)-2-methylphenyl)-N-ethyl-N-methylformimidamide, N'-(5-chloro-3-((3-fluorophenyl)(methyl)amino)-2-methylphenyl)-N-ethyl-N-methylformimidamide, N'-(5-chloro-3-((3-chlorophenyl)(methyl)amino)-2-methylphenyl)-N-ethyl-N-methylformimidamide, N'-(2-chloro-5-methyl-3-((2-(trifluoromethyl)benzyl)amino)phenyl)-N-ethyl-N-methylformimidamide, N-ethyl-N'-(5-fluoro-3-((4-fluoro-3-methylbenzyl)amino)-2-methylphenyl)-N-methylformimidamide, N'-(5-chloro-3-((3-chlorobenzyl)amino)-2-methylphenyl)-N-ethyl-N-methylformimidamide, N'-(2-chloro-3-((2,3-dihydrobenzo[b][1,4]dioxin-6-yl)(methyl)amino)-5-methylphenyl)-N-ethyl-N-methylformimidamide, N'-(5-chloro-2-methyl-3-(o-tolylamino)phenyl)-N-ethyl-N-methylformimidamide, N'-(2-chloro-5-methyl-3-(pyrimidin-2-ylamino)phenyl)-N-ethyl-N-methylformimidamide, N-ethyl-N'-(5-fluoro-2-methyl-3-(pyrimidin-2-ylamino)phenyl)-N-methylformimidamide, N-ethyl-N'-(5-fluoro-2-methyl-3-(4-(trifluoromethyl)benzyl)phenyl)-N-methylformimidamide, N'-(2-bromo-3-(3-fluorobenzyl)-5-methylphenyl)-N-ethyl-N-methylformimidamide, N-ethyl-N'-(3-(3-fluorobenzyl)-5-methyl-2-(methylthio)phenyl)-N-methylformimidamide, N'-(5-chloro-2-methyl-3-(methyl(o-tolyl)amino)phenyl)-N-ethyl-N-methylformimidamide, N'-(2-chloro-5-methyl-3-(methyl(pyrimidin-2-yl)amino)phenyl)-N-ethyl-N-methylformimidamide, N-ethyl-N'-(5-fluoro-2-methyl-3-(pyrazin-2-ylamino)phenyl)-N-methylformimidamide, N'-(2-chloro-5-methyl-3-(pyrazin-2-ylamino)phenyl)-N-ethyl-N-methylformimidamide, N'-(2-chloro-5-methyl-3-((1-(pyrazin-2-yl)propan-2-yl)amino)phenyl)-N-ethyl-N-methylformimidamide, N'-(2-chloro-5-methyl-3-(((5-methylpyrazin-2-yl)methyl)amino)phenyl)-N-ethyl-N-methylformimidamide, N-ethyl-N'-(5-fluoro-2-methyl-3-((1-(pyrazin-2-yl)propan-2-yl)amino)phenyl)-N-methylformimidamide, N-ethyl-N'-(5-fluoro-2-methyl-3-(((5-methylpyrazin-2-yl)methyl)amino)phenyl)-N-methylformimidamide, N-ethyl-N'-(5-fluoro-2-methyl-3-(methyl(pyrazin-2-yl)amino)phenyl)-N-methylformimidamide, N-ethyl-N'-(5-fluoro-2-methyl-3-(methyl(pyrimidin-2-yl)amino)phenyl)-N-methylformimidamide, N-ethyl-N'-(5-fluoro-2-methyl-3-(3-(trifluoromethyl)benzyl)phenyl)-N-methylformimidamide, N'-(3-(4-cyanobenzyl)-5-fluoro-2-methylphenyl)-N-ethyl-N-methylformimidamide, N-ethyl-N'-(5-fluoro-3-(4-fluoro-3-methylbenzyl)-2-methylphenyl)-N-methylformimidamide, N-ethyl-N'-(5-fluoro-3-(4-fluorobenzyl)-2-methylphenyl)-N-methylformimidamide, N'-(3-(3-bromobenzyl)-5-fluoro-2-methylphenyl)-N-ethyl-N-methylformimidamide, N'-(3-(4-chloro-3-fluorobenzyl)-5-fluoro-2-methylphenyl)-N-ethyl-N-methylformimidamide, N'-(3-benzyl-2,5-dimethylphenyl)-N-ethyl-N-methylformimidamide, N'-(2,5-dimethyl-3-(3-methylbenzyl)phenyl)-N-ethyl- N-methylformimidamide, N'-(2-bromo-5-methyl-3-(2-methylbenzyl)phenyl)-N-ethyl-N-methylformimidamide, N'-(2-chloro-5-methyl-3-(methyl(pyrazin-2-yl)amino)phenyl)-N-ethyl-N-methylformimidamide, N'-(5-chloro-2-methyl-3-(pyrazin-2-ylamino)phenyl)-N-ethyl-N-methylformimidamide, N'-(5-chloro-2-methyl-3-(pyrimidin-2-ylamino)phenyl)-N-ethyl-N-methylformimidamide, N'-(5-chloro-2-methyl-3-(methyl(pyrazin-2-yl)amino)phenyl)-N-ethyl-N-methylformimidamide, N'-(5-chloro-2-methyl-3-(methyl(pyrimidin-2-yl)amino)phenyl)-N-ethyl-N-methylformimidamide, N'-(3-(2-bromo-4-fluorobenzyl)-2-chloro-5-methylphenyl)-N-ethyl-N-methylformimidamide, N'-(3-(4-bromo-3-methylbenzyl)-2-chloro-5-methylphenyl)-N-ethyl-N-methylformimidamide, N'-(3-(4-bromo-2-fluorobenzyl)-2-chloro-5-methylphenyl)-N-ethyl-N-methylformimidamide, N'-(2-chloro-3-(4-fluoro-3-(trifluoromethyl)benzyl)-5-methylphenyl)-N-ethyl-N-methylformimidamide, N-ethyl-N'-(3-(2-fluorobenzyl)-2,5-dimethylphenyl)-N-methylformimidamide, N'-(3-(2-chlorobenzyl)-2,5-dimethylphenyl)-N-ethyl-N-methylformimidamide, N'-(3-(2-bromobenzyl)-2,5-dimethylphenyl)-N-ethyl-N-methylformimidamide, N-ethyl-N'-(3-(4-fluorobenzyl)-2,5-dimethylphenyl)-N-methylformimidamide, N'-(3-(4-bromobenzyl)-2,5-dimethylphenyl)-N-ethyl-N-methylformimidamide, N'-(3-(4-chlorobenzyl)-2,5-dimethylphenyl)-N-ethyl-N-methylformimidamide, N'-(3-(benzo[d]thiazol-6-ylamino)-5-fluoro-2-methylphenyl)-N-ethyl-N-methylformimidamide, N'-(2-chloro-3-((6-ethylpyridin-2-yl)amino)-5-methylphenyl)-N-ethyl-N-methylformimidamide, N-ethyl-N'-(3-((6-ethylpyridin-2-yl)amino)-5-fluoro-2-methylphenyl)-N-methylformimidamide, N'-(3-(benzo[d]thiazol-6-ylamino)-2-chloro-5-methylphenyl)-N-ethyl-N-methylformimidamide, N'-(3-(2-chloro-5-fluorobenzyl)-5-fluoro-2-methylphenyl)-N-ethyl-N-methylformimidamide, N'-(3-(2-bromo-4-fluorobenzyl)-5-fluoro-2-methylphenyl)-N-ethyl-N-methylformimidamide, N-ethyl-N'-(5-fluoro-3-(5-fluoro-2-methylbenzyl)-2-methylphenyl)-N-methylformimidamide, N'-(3-(4-bromo-3-methylbenzyl)-5-fluoro-2-methylphenyl)-N-ethyl-N-methylformimidamide, N'-(3-(2-bromo-5-fluorobenzyl)-5-fluoro-2-methylphenyl)-N-ethyl-N-methylformimidamide, N-ethyl-N'-(5-fluoro-3-(4-fluoro-3-(trifluoromethyl)benzyl)-2-methylphenyl)-N-methylformimidamide, N-ethyl-N'-(5-fluoro-3-(3-fluoro-5-methylbenzyl)-2-methylphenyl)-N-methylformimidamide, N'-(3-(4-bromo-2-fluorobenzyl)-5-fluoro-2-methylphenyl)-N-ethyl-N-methylformimidamide, N-ethyl-N'-(5-fluoro-3-(3-fluoro-5-methoxybenzyl)-2-methylphenyl)-N-methylformimidamide, N'-(3-(benzo[d]thiazol-6-yl(methyl)amino)-5-fluoro-2-methylphenyl)-N-ethyl-N-methylformimidamide, N-ethyl-N'-(3-((6-ethylpyridin-2-yl)(methyl)amino)-5-fluoro-2-methylphenyl)-N-methylformimidamide, N'-(3-(benzo[d]thiazol-6-yl(methyl)amino)-2-chloro-5-methylphenyl)-N-ethyl-N-methylformimidamide, N-ethyl-N'-(5-fluoro-2-methyl-3-(4-(methylthio)benzyl)phenyl)-N-methylformimidamide, N'-(3-(benzo[d]thiazol-6-ylamino)-5-chloro-2-methylphenyl)-N-ethyl-N-methylformimidamide, N'-(5-chloro-3-((6-ethylpyridin-2-yl)amino)-2-methylphenyl)-N-ethyl-N-methylformimidamide, N'-(5-chloro-2-methyl-3-(2-(trifluoromethyl)benzyl)phenyl)-N-ethyl-N-methylformimidamide, N'-(3-(3-bromobenzyl)-5-chloro-2-methylphenyl)-N-ethyl-N-methylformimidamide, N'-(5-chloro-3-(4-cyanobenzyl)-2-methylphenyl)-N-ethyl-N-methylformimidamide, N'-(5-chloro-2-methyl-3-(2-(trifluoromethoxy)benzyl)phenyl)-N-ethyl-N-methylformimidamide, N'-(5-chloro-2-methyl-3-(pyridin-3-ylmethyl)phenyl)-N-ethyl-N-methylformimidamide, N'-(5-chloro-2-methyl-3-(4-(trifluoromethyl)benzyl)phenyl)-N-ethyl-N-methylformimidamide, N'-(5-chloro-3-(3-cyanobenzyl)-2-methylphenyl)-N-ethyl-N-methylformimidamide, N'-(5-chloro-2-methyl-3-(3-(trifluoromethoxy)benzyl)phenyl)-N-ethyl-N-methylformimidamide, N'-(5-chloro-2-methyl-3-(4-(methylthio)benzyl)phenyl)-N-ethyl-N-methylformimidamide, N'-(5-chloro-3-((6-ethylpyridin-2-yl)(methyl)amino)-2-methylphenyl)-N-ethyl-N-methylformimidamide, N-ethyl-N'-(5-fluoro-3-((3-fluoro-4-methoxyphenyl)amino)-2-methylphenyl)-N-methylformimidamide, N'-(2-chloro-3-((3-fluoro-4-methoxyphenyl)amino)-5-methylphenyl)-N-ethyl-N-methylformimidamide, N'-(5-chloro-3-((3-fluoro-4-methoxyphenyl)amino)-2-methylphenyl)-N-ethyl-N-methylformimidamide, N-ethyl-N'-(5-fluoro-3-((3-fluoro-4-methoxyphenyl)(methyl)amino)-2-methylphenyl)-N-methylformimidamide, N'-(2-chloro-3-((3-fluoro-4-methoxyphenyl)(methyl)amino)-5-methylphenyl)-N-ethyl-N-methylformimidamide, N-ethyl-N'-(5-fluoro-2-methyl-3-(3-nitrobenzyl)phenyl)-N-methylformimidamide, N-ethyl-N'-(5-fluoro-2-methyl-3-(pyridin-3-ylmethyl)phenyl)-N-methylformimidamide, N-ethyl-N'-(3-(4-fluorobenzyl)-5-methoxy-2-methylphenyl)-N-methylformimidamide, N-ethyl-N'-(5-methoxy-2-methyl-3-(2-methylbenzyl)phenyl)-N-methylformimidamide, N-ethyl-N'-(5-methoxy-2-methyl-3-(4-methylbenzyl)phenyl)-N-methylformimidamide, N'-(3-(3-chlorobenzyl)-5-methoxy-2-methylphenyl)-N-ethyl-N-methylformimidamide, N'-(3-(2-chlorobenzyl)-5-methoxy-2-methylphenyl)-N-ethyl-N-methylformimidamide, N-ethyl-N'-(3-(2-fluorobenzyl)-5-methoxy-2-methylphenyl)-N-methylformimidamide, N'-(5-chloro-3-((3-fluoro-4-methoxyphenyl)(methyl)amino)-2-methylphenyl)-N-ethyl-N-methylformimidamide, N-ethyl-N'-(5-methoxy-3-((2-methoxyphenyl)amino)-2-methylphenyl)-N-methylformimidamide, N-ethyl-N'-(3-((3-fluoro-4-methoxyphenyl)amino)-5-methoxy-2-methylphenyl)-N-methylformimidamide, N-ethyl-N'-(5-methoxy-3-((2-methoxyphenyl)(methyl)amino)-2-methylphenyl)-N-methylformimidamide, N-ethyl-N'-(3-((3-fluoro-4-methoxyphenyl)(methyl)amino)-5-methoxy-2-methylphenyl)-N-methylformimidamide, N-ethyl-N'-(5-methoxy-2-methyl-3-((6-(trifluoromethyl)pyridin-2-yl)amino)phenyl)-N-methylformimidamide, N-ethyl-N'-(5-fluoro-2-methyl-3-((6-(trifluoromethyl)pyridin-2-yl)amino)phenyl)-N-methylformimidamide, N'-(5-chloro-2-methyl-3-((6-(trifluoromethyl)pyridin-2-yl)amino)phenyl)-N-ethyl-N-methylformimidamide, N'-(2-chloro-3-((4-fluoro-3-methoxyphenyl)amino)-5-methylphenyl)-N-ethyl-N-methylformimidamide, N-ethyl-N'-(3-((4-fluoro-3-methoxyphenyl)amino)-5-methoxy-2-methylphenyl)-N-methylformimidamide, N-ethyl-N'-(3-(3-fluorobenzyl)-5-methoxy-2-methylphenyl)-N-methylformimidamide, N-ethyl-N'-(5-methoxy-2-methyl-3-(3-methylbenzyl)phenyl)-N-methylformimidamide, N'-(3-(4-chlorobenzyl)-5-methoxy-2-methylphenyl)-N-ethyl-N-methylformimidamide, N-ethyl-N'-(5-methoxy-2-methyl-3-(3-nitrobenzyl)phenyl)-N-methylformimidamide, N-ethyl-N'-(3-(5-fluoro-2-methylbenzyl)-5-methoxy-2-methylphenyl)-N-methylformimidamide, N'-(3-(3-chloro-4-fluorobenzyl)-5-methoxy-2-methylphenyl)-N-ethyl-N-methylformimidamide, N'-(2-chloro-5-methyl-3-((6-(trifluoromethyl)pyridin-2-yl)amino)phenyl)-N-ethyl-N-methylformimidamide, N-ethyl-N'-(3-((4-fluoro-3-methoxyphenyl)(methyl)amino)-5-methoxy-2-methylphenyl)-N-methylformimidamide, N-ethyl-N'-(5-methoxy-2-methyl-3-(methyl(6-(trifluoromethyl) pyridin-2-yl)amino)phenyl)-N-methylformimidamide, N'-(3-(3,4-difluorobenzyl)-5-methoxy-2-methylphenyl)-N-ethyl-N-methylformimidamide, N'-(3-(4-bromobenzyl)-5-methoxy-2-methylphenyl)-N-ethyl-N-methylformimidamide, N'-(2-chloro-3-((4-fluoro-3-methoxyphenyl)(methyl)amino)-5-methylphenyl)-N-ethyl-N-methylformimidamide, N'-(5-chloro-2-methyl-3-(methyl(6-(trifluoromethyl)pyridin-2-yl) amino)phenyl)-N-ethyl-N-methylformimidamide, N'-(2-chloro-5-methyl-3-(methyl(6-(trifluoromethyl) pyridin-2-yl)amino)phenyl)-N-ethyl-N-methylformimidamide, N-ethyl-N'-(5-fluoro-2-methyl-3-(methyl(6-(trifluoromethyl)pyridin-2-yl)amino) phenyl)-N-methylformimidamide, N-ethyl-N'-(3-(3-fluoro-5-methylbenzyl)-5-methoxy-2-methylphenyl)-N-methylformimidamide, N'-(3-(2-chloro-5-fluorobenzyl)-5-methoxy-2-methylphenyl)-N-ethyl-N-methylformimidamide, N'-(3-(2-bromobenzyl)-5-methoxy-2-methylphenyl)-N-ethyl-N-methylformimidamide, N-ethyl-N'-(5-methoxy-2-methyl-3-(4-(trifluoromethyl)benzyl)phenyl)-N-methylformimidamide, N-ethyl-N'-(5-methoxy-2-methyl-3-(3-(trifluoromethyl)benzyl)phenyl)-N-methylformimidamide, N'-(5-cyano-3-(3-fluorobenzyl)-2-methylphenyl)-N-ethyl-N-methylformimidamide, N'-(3-benzyl-5-methoxy-2-methylphenyl)-N-ethyl-N-methylformimidamide, N-ethyl-N'-(5-methoxy-2-methyl-3-(2-(trifluoromethoxy)benzyl)phenyl)-N-methylformimidamide, N-ethyl-N'-(5-methoxy-2-methyl-3-((2-(trifluoromethoxy)phenyl)amino)phenyl)-N-methylformimidamide, N'-(5-chloro-2-methyl-3-((2-(trifluoromethoxy) phenyl)amino)phenyl)-N-ethyl-N-methylformimidamide, N'-(2-chloro-5-methyl-3-((2-(trifluoromethoxy)phenyl)amino)phenyl)-N-ethyl-N-methylformimidamide, N-ethyl-N'-(5-fluoro-2-methyl-3-((2-(trifluoromethoxy)phenyl)amino)phenyl)-N-methylformimidamide, N'-(3-(2-(2-chloro-4-methoxyphenoxy)acetyl)-5-fluoro-2-methylphenyl)-N-ethyl-N-methylformimidamide, N-ethyl-N'-(5-methoxy-2-methyl-3-(3-(trifluoromethoxy)benzyl) phenyl)-N-methylformimidamide, N'-(3-(3-cyanobenzyl)-5-methoxy-2-methylphenyl)-N-ethyl-N-methylformimidamide, N-ethyl-N'-(5-methoxy-2-methyl-3-(2-(trifluoromethyl)benzyl)phenyl)-N-methylformimidamide, N'-(3-benzyl-5-cyano-2-methylphenyl)-N-ethyl-N-methylformimidamide, N'-(5-cyano-3-(3-cyanobenzyl)-2-methylphenyl)-N-ethyl-N-methylformimidamide, N'-(5-cyano-3-(4-fluorobenzyl)-2-methylphenyl)-N-ethyl-N-methylformimidamide, N'-(3-(4-chlorobenzyl)-5-cyano-2-methylphenyl)-N-ethyl-N-methylformimidamide, N'-(5-cyano-2-methyl-3-(3-nitrobenzyl)phenyl)-N-ethyl-N-methylformimidamide, N'-(3-(3-bromobenzyl)-5-cyano-2-methylphenyl)-N-ethyl-N-methylformimidamide and N'-(5-cyano-2-methyl-3-(2-(trifluoromethoxy)benzyl)phenyl)-N-ethyl-N-methylformimidamide.

5. A process for preparing the compound of formula (I) as claimed in claim 1, wherein said process comprises at least one of the following steps (a) to (h):

a) converting a compound of formula (XXVI) or (XXIV) to a compound of formula (XXIII) according to the reaction scheme as depicted below:

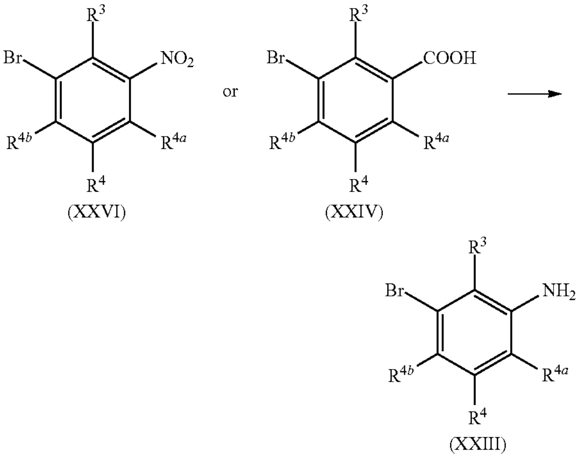

(XXVI) or (XXIV) (XXIII)

b) reacting a compound of formula (XXIII) with a suitable secondary amine ($HNR^1R^2$) to obtain a compound of formula (III) according to the reaction scheme as depicted below:

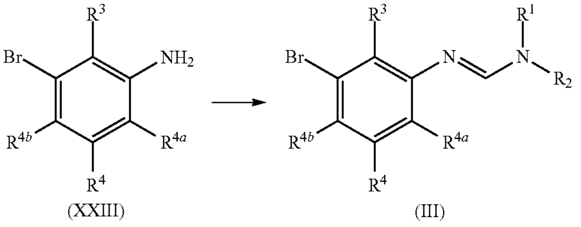

(XXIII) (III)

c) reacting a compound of formula (III) with compound of formula (XII), (XVI), (XVII) or (XXXI) to obtain the compound of formula (I) according to the reaction scheme as depicted below:

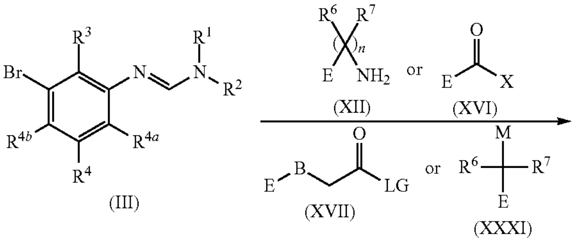

(III) (XII) or (XVI) (XVII) or (XXXI)

-continued

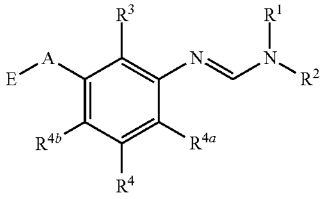

(I)

d) converting a compound of formula (III) to a compound of formula (II) according to the reaction scheme as depicted below:

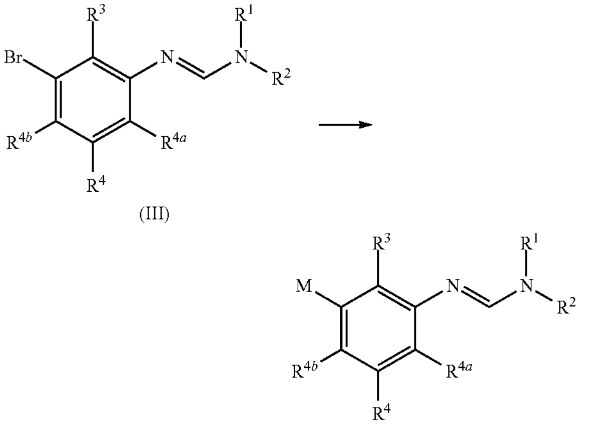

(III)

(II)

e) reacting a compound of formula (II) with a compound of formula (XXX) to obtain a compound of formula (I) according to the reaction scheme as depicted below:

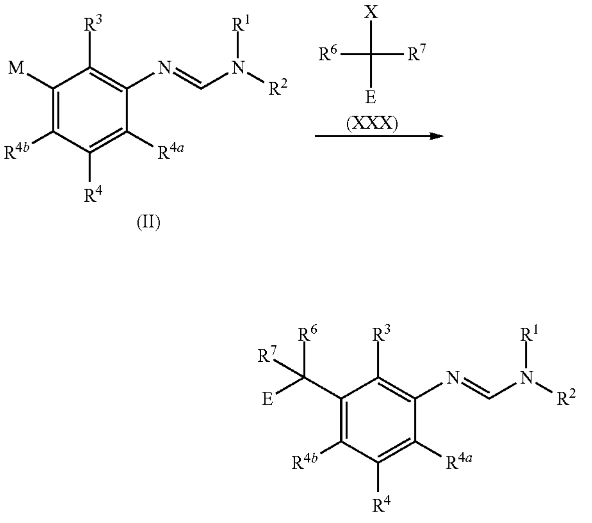

(II)

(XXX)

(I)

f) reacting a compound of formula (XV) with compound of formula (XII), (XVI), (XVII) or (XXXI) to obtain a compound of formula (XIV) according to the reaction scheme as depicted below:

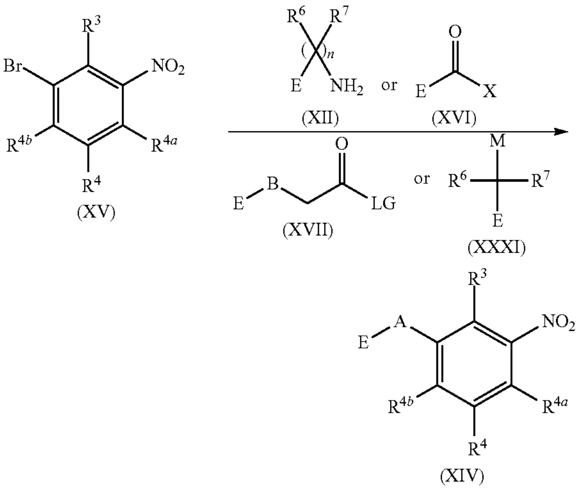

(XV)

(XII) or (XVI)

(XVII) or (XXXI)

(XIV)

g) converting a compound of formula (XIV) to a compound of formula (XIII) according to the reaction scheme as depicted below:

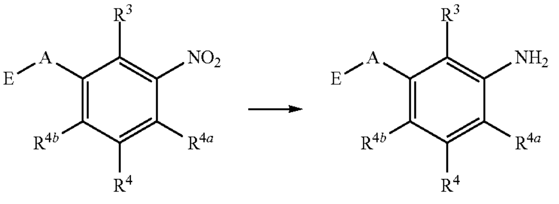

(XIV)

(XIII)

h) reacting a compound of formula (XIII) with a suitable secondary amine ($HNR^1R^2$) to obtain a compound of formula (I) according to the reaction scheme as depicted below:

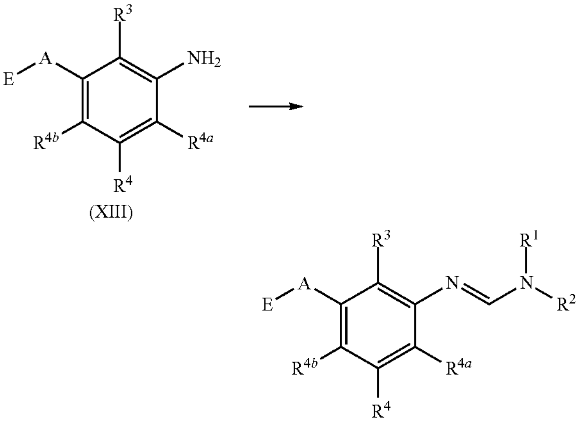

(XIII)

(I)

where in the above reaction schemes, M is selected from the group consisting of lithium derivative, boronic ester, boronic acid, MgX and ZnX.

6. A composition for controlling and/or preventing phytopathogenic microorganisms, comprising a compound of formula (I), stereo-isomers, polymorphs, N-oxides, or agriculturally acceptable salts thereof, as claimed in claim 1 and one or more inert carriers.

7. The composition as claimed in claim 6, wherein said composition may additionally comprises one or more active compatible compound selected from fungicides, insecticides, nematicides, acaricides, biopesticides, herbicides, plant growth regulators, antibiotics, nutrients or fertilizers.

8. The composition as claimed in claim 6, wherein the concentration of compound of formula (I) ranges from 10 to 90% by weight with respect to the total weight of the composition.

9. A combination comprising the compound of formula (I), stereo-isomers, polymorphs, N-oxides, or agriculturally acceptable salts thereof as claimed in claim 1 and one or more active compatible compound selected from fungicides, insecticides, nematicides, acaricides, biopesticides, herbicides, plant growth regulators, antibiotics, nutrients or fertilizers.

10. A process for controlling or preventing agricultural crops and/or horticultural crops against phytopathogenic microorganisms, the process comprising:

applying the compound of formula (I), stereo-isomers, polymorphs, N-oxides, or agriculturally acceptable salts thereof as claimed in claim 1 to the agricultural crops and/or horticultural crops.

11. A process for controlling rust diseases of agricultural crops and/or horticultural crops, the process comprising:

applying the compound of formula (I) according to claim 1 to the agricultural crops and/or horticultural crops.

12. The process according to claim 11, wherein said rust diseases of crops are *Hemileia vastatrix* (Coffee rust), *Uromyces appendiculatus/fabae/phaseoli* (rust of beans) *Puccinia* spp. (rusts) on various plants selected from *P. triticina* (brown or leaf rust), *P. striiformis* (stripe or yellow rust), *P. hordei*(dwarf rust), *P. graminis* (stem or black rust) or *P. recondita* (brown or leaf rust) on cereals selected from wheat, barley or rye and *Phakopsora* spp. on various plants.

13. The process according to claim 10, wherein phytopathogenic microorganisms are selected from *Phakopsora pachyrhizi, Phakopsora meibomiae*, of agricultural crops and/or horticultural crops.

14. The process as claimed in claim 10, wherein said agricultural crops are cereals, corn, rice, soybean and other leguminous plants, fruits and fruit trees, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and other vegetables, and ornamentals.

15. A seed comprising compound of formula (I), agriculturally acceptable salts, stereo-isomers, polymorphs, or N-oxides thereof as claimed in claim 1, wherein the amount of the compound of formula (I), stereo-isomers, diastereomers, enantiomers, tautomers, polymorphs, N-oxides, or agriculturally acceptable salts thereof is from 0.1 g to 1 kg per 100 kg of seed.

16. A method for controlling or preventing infestation of useful plants by phytopathogenic microorganisms in agricultural crops and/or horticultural crops, wherein said compound of formula (I), stereo-isomers, polymorphs, N-oxides, or agriculturally acceptable salts thereof as claimed in claim 1, is applied to the plants, to parts thereof or to a locus thereof.

17. A method for controlling or preventing infestation of useful plants by phytopathogenic microorganisms in agricultural crops and/or horticultural crops, wherein the compound of formula (I), stereo-isomers, polymorphs, N-oxides, or agriculturally acceptable salts thereof as claimed in claim 1, is applied to the seeds of plants.

18. A method for controlling or preventing phytopathogenic microorganisms in agricultural crops and/or horticultural crops using the compound of formula (I), stereo-isomers, polymorphs, N-oxides, or agriculturally acceptable salts thereof as claimed in claim 1, which comprises a step of applying an effective dosage of the compound or the composition or the combination, in amounts ranging from 1 g to 2 kg per hectare of agricultural and/or horticultural crops.

19. A method for combating phytopathogenic fungi, comprising treating plants, soil, seeds or materials to be protected with the compound of formula (I), stereo-isomers, polymorphs, N-oxides, or agriculturally acceptable salts thereof as claimed in claim 1.

20. A compound of formula (A),

Formula (A)

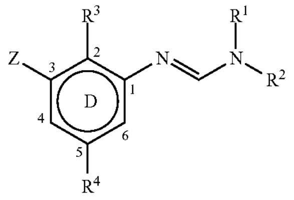

wherein,

Z represent OH, $NH_2$, SH, X, or leaving group;

$R^1$ is selected from the group consisting of $C_1$-$C_{12}$-alkyl, $C_2$-$C_{12}$-alkenyl, $C_2$-$C_{12}$-alkynyl, $C_1$-$C_{12}$-haloalkyl, and $C_3$-$C_8$-cycloalkyl;

$R^2$ is selected from $C_2$-$C_{12}$-alkyl;

$R^3$ is selected from the group consisting of X, cyano, $C_1$-$C_{12}$-alkyl, $C_2$-$C_{12}$-alkenyl, $C_2$-$C_{12}$-alkynyl, $C_1$-$C_{12}$-haloalkyl, N(R'R'''), OR'', $S(O)_nR'''$, (C═O)—R'' and $C_3$-$C_8$-cycloalkyl;

$R^4$ is selected from the group consisting of X, cyano, $C_1$-$C_{12}$-alkyl, $C_2$-$C_{12}$-alkenyl, $C_2$-$C_{12}$-alkynyl, $C_1$-$C_{12}$-haloalkyl, N(R'R'''), OR'', $S(O)_nR'''$, (C═O)—R'', $C_3$-$C_8$-cycloalkyl and $C_7$-$C_{12}$-aralkyl.

21. A compound selected from the group consisting of 2-chloro-5-methyl-$N^1$-(p-tolyl)benzene-1,3-diamine, 2,5-dimethyl-3-(4-methylbenzyl)aniline, 3-(3-chlorobenzyl)-2,5-dimethylaniline, 2,5-dimethyl-3-(2-methylbenzyl)aniline, 3-(3-fluorobenzyl)-2,5-dimethylaniline, $N^1$-(2-fluorophenyl)-2,5-dimethylbenzene-1,3-diamine, $N^1$-(2-fluorophenyl)-$N^1$,2,5-trimethylbenzene-1,3-diamine, 5-fluoro-2-methyl-$N^1$-phenylbenzene-1,3-diamine, 2-chloro-5-methyl-$N^1$-phenylbenzene-1,3-diamine, 2-chloro-$N^1$,5-dimethyl-$N^1$-phenylbenzene-1,3-diamine, 5-fluoro-$N^1$,2-dimethyl-$N^1$-phenylbenzene-1,3-diamine, 2-chloro-5-methyl-3-(2-methylbenzyl)aniline, 2-chloro-3-(2-chlorobenzyl)-5-methylaniline, 2-chloro-3-(2-fluorobenzyl)-5-methylaniline, 5-fluoro-2-methyl-$N^1$-(o-tolyl)benzene-1,3-diamine, 5-fluoro-2-methyl-$N^1$-(4-((trifluoromethyl)thio)phenyl)benzene-1,3-diamine, 2-chloro-5-methyl-3-(3-methylbenzyl) aniline, 2-chloro-5-methyl-3-(4-methylbenzyl)aniline, 5-fluoro-$N^1$-(2-fluorophenyl)-2-methylbenzene-1,3-diamine, $N^1$-(4-(tert-butyl)phenyl)-5-fluoro-2-methylbenzene-1,3-diamine, 2-chloro-5-methyl-3-(2-(trifluoromethyl) benzyl)aniline, 2-chloro-3-(3-fluorobenzyl)-5-methylaniline, 2-chloro-$N^1$-(2-fluorophenyl)-5-methylbenzene-1,3-diamine, 2-chloro-5-methyl-$N^1$-(o-tolyl)benzene-1,3-diamine, $N^1$-(4-(tert-butyl)phenyl)-2-chloro-5-methylbenzene-1,3-diamine, 2-chloro-5-methyl-$N^1$-(4-((trifluoromethyl)thio)phenyl)benzene-1,3-diamine, 2-chloro-3-(3-chlorobenzyl)-5-methylaniline, 2-chloro-3-(3-methoxybenzyl)-5-methylaniline, 5-fluoro-$N^1$-(3-fluorophenyl)-2-methylbenzene-1,3-diamine, 5-fluoro-$N^1$-(3-methoxyphenyl)-2-methylbenzene-1,3-diamine, 5-fluoro-2-methyl-$N^1$-(m-tolyl)benzene-1,3-diamine, 5-fluoro-$N^1$-(3-fluorophenyl)-$N^1$,2-dimethylbenzene-1,3-diamine, $N^1$-(3-chlorophenyl)-5-fluoro-$N^1$,2-dimethylbenzene-1,3-diamine, 2-chloro-$N^1$-(3-chlorophenyl)-5-methylbenzene-1,3-diamine, 2-chloro-$N^1$-(3-fluorophenyl)-5-methylbenzene-1,3-diamine, 2-chloro-5-methyl-$N^1$-(m-tolyl)benzene-1,3-diamine, $N^1$-(3-chlorophenyl)-5-fluoro-2-methylbenzene-1,3-diamine, 5-fluoro-$N^1$,2-dimethyl-$N^1$-(m-tolyl)benzene-1,3-diamine, 5-fluoro-$N^1$-(3-methoxyphenyl)-$N^1$,2-dimethylbenzene-1,3-diamine, 2-chloro-$N^1$-(3-fluorophenyl)-$N^1$,5-dimethylbenzene-1,3-diamine, 2-chloro-$N^1$-(3-chlorophenyl)-$N^1$,5-dimethylbenzene-1,3-diamine, 2-chloro-$N^1$-(3-methoxyphenyl)-5-methylbenzene-1,3-diamine, 2-chloro-$N^1$,5-dimethyl-$N^1$-(m-tolyl)benzene-1,3-diamine, 2-chloro-3-(4-fluorobenzyl)-5-methylaniline, 3-(2-bromobenzyl)-2-chloro-5-methylaniline, 4-(3-amino-2-chloro-5-methylbenzyl)benzonitrile, 2-(3-amino-2-chloro-5-methylbenzyl)benzonitrile, 3-(3-amino-2-chloro-5-methylbenzyl)benzonitrile, 2-chloro-$N^1$-(3-methoxyphenyl)-$N^1$,5-dimethylbenzene-1,3-diamine, 2-chloro-5-methyl-3-(2-(trifluoromethoxy)benzyl)aniline, 2-chloro-5-methyl-3-(4-(trifluoromethyl)benzyl)aniline, 2-chloro-5-methyl-3-(4-(trifluoromethoxy)benzyl)aniline, 2-chloro-5-methyl-3-(3-(trifluoromethyl)benzyl)aniline, 2-chloro-3-(3-chloro-4-fluorobenzyl)-5-methylaniline, 2-chloro-3-(3,5-dimethylbenzyl)-5-methylaniline, 2-chloro-3-(3-chloro-2-fluorobenzyl)-5-methylaniline, 2-chloro-3-(5-fluoro-2-methylbenzyl)-5-methylaniline, 2-chloro-$N^1$-(3-isopropylphenyl)-5-methylbenzene-1,3-diamine, 2-chloro-$N^1$-(4-chlorophenyl)-5-methylbenzene-1,3-diamine, 2-chloro-$N^1$-(4-fluorophenyl)-5-methylbenzene-1,3-diamine, 2-chloro-$N^1$-(4-methoxyphenyl)-5-methylbenzene-1,3-diamine, 2-chloro-$N^1$-(4-chlorophenyl)-$N^1$,5-dimethylbenzene-1,3-diamine, 2-chloro-$N^1$-(3-isopropylphenyl)-$N^1$,5-dimethylbenzene-1,3-diamine, 2-chloro-$N^1$-(4-methoxyphenyl)-$N^1$,5-dimethylbenzene-1,3-diamine, 2-chloro-3-(4-fluoro-2-methylbenzyl)-5-methylaniline, 2-chloro-5-methyl-3-(pyridin-3-ylmethyl)aniline, 2-chloro-3-(3,4-difluorobenzyl)-5-methylaniline, 2-chloro-3-(4-fluoro-3-methylbenzyl)-5-methylaniline, 2-chloro-$N^1$-(4-fluorophenyl)-$N^1$,5-dimethylbenzene-1,3-diamine, 3-benzyl-2-chloro-5-methylaniline, 2-chloro-3-(3,5-difluoro-4-methoxybenzyl)-5-methylaniline, 2-chloro-$N^1$-(3,4-difluorophenyl)-5-methylbenzene-1,3-diamine, $N^1$-(3,4-difluorophenyl)-5-fluoro-2-methylbenzene-1,3-diamine, 2-chloro-$N^1$-(3,5-difluorophenyl)-$N^1$,5-dimethylbenzene-1,3-diamine, 2-chloro-$N^1$-(2,4-difluorophenyl)-5-methylbenzene-1,3-diamine, $N^1$-(2,4-difluorophenyl)-5-fluoro-2-methylbenzene-1,3-diamine, $N^1$-(3,5-difluorophenyl)-5-fluoro-2-methylbenzene-1,3-diamine, 2-chloro-$N^1$-(3,5-difluorophenyl)-5-methylbenzene-1,3-diamine, 3-benzyl-5-chloro-2-methylaniline, $N^1$-(2,4-difluorophenyl)-5-fluoro-$N^1$,2-dimethylbenzene-1,3-diamine, 2-chloro-$N^1$-(3,4-difluorophenyl)-$N^1$,5-dimethylbenzene-1,3-diamine, 2-chloro-$N^1$-(2,4-difluorophenyl)-$N^1$,5-dimethylbenzene-1,3-diamine, $N^1$-(3,4-difluorophenyl)-5-fluoro-$N^1$,2-dimethylbenzene-1,3-diamine, $N^1$-(3,5-difluorophenyl)-5-fluoro-$N^1$,2-dimethylbenzene-1,3-diamine, 2-chloro-5-methyl-$N^1$-(pyridin-2-yl)benzene-1,3-diamine, 2-chloro-5-methyl-$N^1$-(3-methylpyridin-2-yl)benzene-1,3-diamine, 5-chloro-3-(4-fluoro-3,5-dimethylbenzyl)-2-methylaniline, 5-chloro-2-methyl-3-(2-methylbenzyl)aniline, 5-chloro-3-(2-chlorobenzyl)-2-methylaniline, 3-(2-bromobenzyl)-5-chloro-2-methylaniline, 2-chloro-3-(2,6-difluorobenzyl)-5-methylaniline, 2-chloro-3-(2-chloro-6-fluorobenzyl)-5-methylaniline, 3-(4-bromobenzyl)-2-chloro-5-methylaniline, 5-chloro-2-methyl-3-(3-methylbenzyl)aniline, 5-fluoro-2-methyl-$N^1$-(pyridin-2-yl)benzene-1,3-diamine, $N^1$-(3-chloro-5-fluorophenyl)-5-fluoro-2-methylbenzene-1,3-diamine, 2-chloro-$N^1$-(3-chloro-5-fluorophenyl)-5-methylbenzene-1,3-diamine, $N^1$-(5-chloro-2-methylphenyl)-5-fluoro-$N^1$,2-dimethylbenzene-1,3-diamine, 2-chloro-$N^1$-(3-chloro-5-fluorophenyl)-$N^1$,5-dimethylbenzene-1,3-diamine, 2-chloro-$N^1$-(5-chloro-2-methylphenyl)-5-methylbenzene-1,3-diamine, 5-chloro-3-(3-chlorobenzyl)-2-methylaniline, 5-chloro-3-(3-fluorobenzyl)-2-methylaniline, 5-chloro-3-(2-fluorobenzyl)-2-methylaniline, 2-(3-amino-5-chloro-2-methylbenzyl)benzonitrile, 5-chloro-2-methyl-3-(4-methylbenzyl)aniline, $N^1$-(3-chloro-5-fluorophenyl)-5-fluoro-$N^1$,2-dimethylbenzene-1,3-diamine, 2-chloro-$N^1$,5-dimethyl-$N^1$-(pyridin-2-yl)benzene-1,3-diamine, 2-chloro-$N^1$,5-dimethyl-$N^1$-(3-methylpyridin-2-yl)benzene-1,3-diamine, 5-fluoro-$N^1$,2-dimethyl-$N^1$-(pyridin-2-yl)benzene-1,3-diamine, 2-chloro-$N^1$-(5-chloro-2-methylphenyl)-$N^1$,5-dimethylbenzene-1,3-diamine, 2-chloro-$N^1$-(3-fluoro-5-methylphenyl)-5-methylbenzene-1,3-diamine, 2-chloro-$N^1$-(5-chloro-3-methylpyridin-2-yl)-5-methylbenzene-1,3-diamine, $N^1$-(2-chloro-5-methylphenyl)-5-fluoro-2-methylbenzene-1,3-diamine, 5-fluoro-$N^1$-(3-fluoro-5-methylphenyl)-2-methylbenzene-1,3-diamine, 2-chloro-$N^1$-(2-chloro-5-methylphenyl)-5-methylbenzene-1,3-diamine, $N^1$-(5-chloro-2-methylphenyl)-5-fluoro-2-methylbenzene-1,3-diamine, $N^1$-(2-chloro-5-methylphenyl)-5-fluoro-$N^1$,2-dimethylbenzene-1,3-diamine, 2-chloro-$N^1$-(5-chloro-3-methylpyridin-2-yl)-$N^1$,5-dimethylbenzene-1,3-diamine, 5-fluoro-$N^1$-(3-fluoro-5-methylphenyl)-$N^1$,2-dimethylbenzene-1,3-diamine, 2-chloro-$N^1$-(2-chloro-5-methylphenyl)-$N^1$,5-dimethylbenzene-1,3-diamine, 5-fluoro-$N^1$-(2-fluoro-6-methylphenyl)-2-methylbenzene-1,3-diamine, 5-fluoro-$N^1$-(2-fluoro-3-methylphenyl)-2-methylbenzene-1,3-diamine, 2-chloro-$N^1$-(2-fluoro-3-methylphenyl)-5-methylbenzene-1,3-diamine, 5-chloro-3-(4-fluorobenzyl)-2-methylaniline, 3-(4-bromobenzyl)-5-chloro-2-methylaniline, 5-chloro-3-(4-chlorobenzyl)-2-methylaniline, 5-chloro-2-methyl-3-(3-(trifluoromethyl)benzyl)aniline, 5-chloro-3-(4-fluoro-3-methylbenzyl)-2-methylaniline, 5-chloro-3-(3,4-difluorobenzyl)-2-methylaniline, 5-chloro-3-(3-chloro-4-fluorobenzyl)-2-methylaniline, 5-chloro-3-(4-chloro-3-fluorobenzyl)-2-methylaniline, 5-fluoro-2-methyl-$N^1$-(3-(trifluoromethyl)pyridin-2-yl)benzene-1,3-diamine, 2-chloro-$N^1$-(2-fluoro-6-methylphenyl)-5-methylbenzene-1,3-diamine, 2-chloro-$N^1$-(4-chloro-2-fluorophenyl)-5-methylbenzene-1,3-diamine, 2-chloro-5-methyl-$N^1$-(3-(trifluoromethyl)pyridin-2-yl)benzene-1,3-diamine, $N^1$-(4-chloro-2-fluorophenyl)-5-fluoro-2-methylbenzene-1,3-diamine, 2-chloro-$N^1$-(3-chloro-5-(trifluoromethyl)phenyl)-5-methylbenzene-1,3-diamine, 2-chloro-$N^1$-(2-fluoro-6-methylphenyl)-$N^1$,5-dimethylbenzene-1,3-diamine, 2-chloro-$N^1$-(2-fluoro-3-methylphenyl)-$N^1$,5-dimethylbenzene-1,3-diamine, $N^1$-(4-chloro-2-fluorophenyl)-5-fluoro-$N^1$,2-dimethylbenzene-1,3-diamine, 5-fluoro-3-(2-fluorobenzyl)-2-methylaniline, 3-(2-chlorobenzyl)-5-fluoro-2-methylaniline, 5-fluoro-2-methyl-3-(2-(trifluoromethyl)benzyl)aniline, 3-(3-chlorobenzyl)-5-fluoro-2-methylaniline, 5-fluoro-$N^1$-(2-fluoro-6-methylphenyl)-$N^1$,2-dimethylbenzene-1,3-diamine, 5-fluoro-2-methyl-3-(3-methylbenzyl)aniline, 5-fluoro-3-(3-fluorobenzyl)-2-methylaniline, 5-fluoro-2-methyl-3-(2-methylbenzyl)aniline, 3-benzyl-5-fluoro-2-methylaniline, 2-chloro-3-(4-methoxybenzyl)-5-methylaniline, 3-(2-bromobenzyl)-5-fluoro-2-methylaniline, 5-fluoro-$N^1$-(2-fluoro-3-methylphenyl)-$N^1$,2-dimethylbenzene-1,3-diamine, 5-fluoro-$N^1$,2-dimethyl-$N^1$-(3-(trifluoromethyl)pyridin-2-yl)benzene-1,3-diamine, 5-chloro-2-methyl-$N^1$-(m-tolyl)benzene-1,3-diamine, 5-chloro-2-methyl-$N^1$-phenylbenzene-1,3-diamine, 2-chloro-$N^1$-(4-chloro-2-fluorophenyl)-$N^1$,5-dimethylbenzene-1,3-diamine, 2-chloro-$N^1$,5-dimethyl-$N^1$-(3-(trifluoromethyl)pyridin-2-yl)benzene-1,3-diamine, 2-chloro-$N^1$-(3-chloro-5-(trifluoromethyl)phenyl)-$N^1$,5-dimethylbenzene-1,3-diamine, 5-chloro-$N^1$,2-dimethyl-$N^1$-phenylbenzene-1,3-diamine, 5-chloro-$N^1$,2-dimethyl-$N^1$-(m-tolyl)benzene-1,3-diamine, $N^1$-(3-chloro-5-(trifluoromethyl)phenyl)-5-fluoro-2-methylbenzene-1,3-diamine, 5-chloro-$N^1$-(4-methoxyphenyl)-2-methylbenzene-1,3-diamine, 5-chloro-$N^1$-(3-chlorophenyl)-2-methylbenzene-1,3-diamine, $N^1$-(3-bromophenyl)-5-chloro-2-methylbenzene-1,3-diamine, 5-chloro-$N^1$-(2-fluorophenyl)-2-methylbenzene-1,3-diamine, 5-chloro-$N^1$-(3-fluorophenyl)-2-methylbenzene-1,3-diamine, 5-chloro-$N^1$-(4-methoxyphenyl)-$N^1$,2-dimethylbenzene-1,3-diamine, 2-(3-amino-5-fluoro-2-methylbenzyl)benzonitrile, 2-chloro-$N^1$-(2,3-dihydrobenzo[b][1,4]dioxin-6-yl)-5-methylbenzene-1,3-diamine, 5-fluoro-2-methyl-3-(2-(trifluoromethoxy)benzyl)aniline, 5-fluoro-2-methyl-3-(4-methylbenzyl)aniline, 3-(4-chlorobenzyl)-5-fluoro-2-methylaniline, 5-fluoro-2-methyl-3-(3-(trifluoromethoxy)benzyl)aniline, 3-(3-amino-5-fluoro-2-methylbenzyl)benzonitrile, 3-(4-bromobenzyl)-5-fluoro-2-methylaniline, 5-fluoro-2-methyl-3-(4-(trifluoromethoxy)benzyl)aniline, 2-chloro-$N^1$-(2-(difluoromethoxy)phenyl)-5-methylbenzene-1,3-diamine, 5-chloro-$N^1$-(2-fluorophenyl)-$N^1$,2-dimethylbenzene-1,3-diamine, 5-chloro-$N^1$-(3-fluorophenyl)-$N^1$,2-dimethylbenzene-1,3-diamine, 5-chloro-$N^1$-(3-chlorophenyl)-$N^1$,2-dimethylbenzene-1,3-diamine, 2-chloro-5-methyl-$N^1$-(2-(trifluoromethyl)benzyl)benzene-1,3-diamine, 5-fluoro-$N^1$-(4-fluoro-3-methylbenzyl)-2-methylbenzene-1,3-diamine, 5-chloro-$N^1$-(3-chlorobenzyl)-2-methylbenzene-1,3-diamine, 2-chloro-$N^1$-(2,3-dihydrobenzo[b][1,4]dioxin-6-yl)-$N^1$,5-dimethylbenzene-1,3-diamine, 5-chloro-2-methyl-$N^1$-(o-tolyl)benzene-1,3-diamine, 2-chloro-5-methyl-$N^1$-(pyrimidin-2-yl)benzene-1,3-diamine, 5-fluoro-2-methyl-$N^1$-(pyrimidin-2-yl)benzene-1,3-diamine, 5-fluoro-2-methyl-3-(4-(trifluoromethyl)benzyl)aniline, 2-bromo-3-(3-fluorobenzyl)-5-methylaniline, 3-(3-fluorobenzyl)-5-methyl-2-(methylthio)aniline, 5-chloro-$N^1$,2-dimethyl-$N^1$-(o-tolyl)benzene-1,3-diamine, 2-chloro-$N^1$,5-dimethyl-$N^1$-(pyrimidin-2-yl)benzene-1,3-diamine, 5-fluoro-2-methyl-$N^1$-(pyrazin-2-yl)benzene-1,3-diamine, 2-chloro-5-methyl-$N^1$-(pyrazin-2-yl)benzene-1,3-diamine, 2-chloro-5-methyl-$N^1$-(1-(pyrazin-2-yl)propan-2-yl)benzene-1,3-diamine, 2-chloro-5-methyl-$N^1$-((5-methylpyrazin-2-yl)methyl)benzene-1,3-diamine, 5-fluoro-2-methyl-$N^1$-(1-(pyrazin-2-yl)propan-2-yl)benzene-1,3-diamine, 5-fluoro-2-methyl-$N^1$-((5-methylpyrazin-2-yl)methyl)benzene-1,3-diamine, 5-fluoro-$N^1$,2-dimethyl-$N^1$-(pyrazin-2-yl)benzene-1,3-diamine, 5-fluoro-$N^1$,2-dimethyl-$N^1$-(pyrimidin-2-yl)benzene-1,3-diamine, 5-fluoro-2-methyl-3-(3-(trifluoromethyl)benzyl)aniline, 4-(3-amino-5-fluoro-2-methylbenzyl)benzonitrile, 5-fluoro-3-(4-fluoro-3-methylbenzyl)-2-methylaniline, 5-fluoro-3-(4-fluorobenzyl)-2-methylaniline, 3-(3-bromobenzyl)-5-fluoro-2-methylaniline, 3-(4-chloro-3-fluorobenzyl)-5-fluoro-2-methylaniline, 3-benzyl-2,5-dimethylaniline, 2,5-dimethyl-3-(3-methylbenzyl)aniline, 2-bromo-5-methyl-3-(2-methylbenzyl)aniline, 2-chloro-$N^1$,5-dimethyl-$N^1$-(pyrazin-2-yl)benzene-1,3-diamine, 5-chloro-2-methyl-$N^1$-(pyrazin-2-yl)benzene-1,3-diamine, 5-chloro-2-methyl-$N^1$-(pyrimidin-2-yl)benzene-1,3-diamine, 5-chloro-$N^1$,2-dimethyl-$N^1$-(pyrazin-2-yl)benzene-1,3-diamine, 5-chloro-$N^1$,2-dimethyl-$N^1$-(pyrimidin-2-yl)benzene-1,3-diamine, 3-(2-bromo-4-fluorobenzyl)-2-chloro-5-methylaniline, 3-(4-bromo-3-methylbenzyl)-2-chloro-5-methylaniline, 3-(4-bromo-2-fluorobenzyl)-2-chloro-5-methylaniline, 2-chloro-3-(4-fluoro-3-(trifluoromethyl)benzyl)-5-methylaniline, 3-(2-fluorobenzyl)-2,5-dimethylaniline, 3-(2-chlorobenzyl)-2,5-dimethylaniline, 3-(2-bromobenzyl)-2,5-dimethylaniline, 3-(4-fluorobenzyl)-2,5-dimethylaniline, 3-(4-bromobenzyl)-2,5-dimethylaniline, 3-(4-chlorobenzyl)-2,5-dimethylaniline, $N^1$-(benzo[d]thiazol-6-yl)-5-fluoro-2-methylbenzene-1,3-diamine, 2-chloro-$N^1$-(6-ethylpyridin-2-yl)-5-methylbenzene-1,3-diamine, $N^1$-(6-ethylpyridin-2-yl)-5-fluoro-2-methylbenzene-1,3-diamine, $N^1$-(benzo[d]thiazol-6-yl)-2-chloro-5-methylbenzene-1,3-diamine, 3-(2-chloro-5-fluorobenzyl)-5-fluoro-2-methylaniline, 3-(2-bromo-4-fluorobenzyl)-5-fluoro-2-methylaniline, 5-fluoro-3-(5-fluoro-2-methylbenzyl)-2-methylaniline, 3-(4-bromo-3-methylbenzyl)-5-fluoro-2-methylaniline, 3-(2-bromo-5-fluorobenzyl)-5-fluoro-2-methylaniline, 5-fluoro-3-(4-fluoro-3-(trifluoromethyl)benzyl)-2-methylaniline, 5-fluoro-3-(3-fluoro-5-methylbenzyl)-2-methylaniline, 3-(4-bromo-2-fluorobenzyl)-5-fluoro-2-methylaniline, 5-fluoro-3-(3-fluoro-5-methoxybenzyl)-2-methylaniline, $N^1$-(benzo[d]thiazol-6-yl)-5-fluoro-$N^1$,2-dimethylbenzene-1,3-diamine, $N^1$-(6-ethylpyridin-2-yl)-5-fluoro-$N^1$,2-dimethylbenzene-1,3-diamine, $N^1$-(benzo[d]thiazol-6-yl)-2-chloro-$N^1$,5-dimethylbenzene-1,3-diamine, 5-fluoro-2-methyl-3-(4-(methylthio)benzyl)aniline, $N^1$-(benzo[d]thiazol-6-yl)-5-chloro-2-methylbenzene-1,3-diamine, 5-chloro-$N^1$-(6-ethylpyridin-2-yl)-2-methylbenzene-1,3-diamine, 5-chloro-2-methyl-3-(2-(trifluoromethyl)benzyl)aniline, 3-(3-bromobenzyl)-5-chloro-2-methylaniline, 4-(3-amino-5-chloro-2-methylbenzyl)benzonitrile, 5-chloro-2-methyl-3-(2-(trifluoromethoxy)benzyl)aniline, 5-chloro-2-methyl-3-(pyridin-3-ylmethyl)aniline, 5-chloro-2-methyl-3-(4-(trifluoromethyl)benzyl)aniline, 3-(3-amino-5-chloro-2-methylbenzyl)benzonitrile, 5-chloro-2-methyl-3-(3-(trifluoromethoxy)benzyl)aniline, 5-chloro-2-methyl-3-(4-(methylthio)benzyl)aniline, 5-chloro-$N^1$-(6-ethylpyridin-2-yl)-$N^1$,2-dimethylbenzene-1,3-diamine, 5-fluoro-$N^1$-(3-fluoro-4-methoxyphenyl)-2-methylbenzene-1,3-diamine, 2-chloro-$N^1$-(3-fluoro-4-methoxyphenyl)-5-methylbenzene-1,3-diamine, 5-chloro-$N^1$-(3-fluoro-4-methoxyphenyl)-2-methylbenzene-1,3-diamine, 5-fluoro-$N^1$-(3-fluoro-4-methoxyphenyl)-$N^1$,2-dimethylbenzene-1,3-diamine, 2-chloro-$N^1$-(3-fluoro-4-methoxyphenyl)-$N^1$,5-dimethylbenzene-1,3-diamine, 5-fluoro-2-methyl-3-(3-nitrobenzyl)aniline, 5-fluoro-2-methyl-3-(pyridin-3-ylmethyl)aniline, 3-(4-fluorobenzyl)-5-methoxy-2-methylaniline, 5-methoxy-2-methyl-3-(2-methylbenzyl)aniline, 5-methoxy-2-methyl-3-(4-methylbenzyl)aniline, 3-(3-chlorobenzyl)-5-methoxy-2-methylaniline, 3-(2-chlorobenzyl)-5-methoxy-2-methylaniline, 3-(2-fluorobenzyl)-5-methoxy-2-methylaniline, 5-chloro-$N^1$-(3-fluoro-4-methoxyphenyl)-$N^1$,2-dimethylbenzene-1,3-diamine, 5-methoxy-$N^1$-(2-methoxyphenyl)-2-methylbenzene-1,3-diamine, $N^1$-(3-fluoro-4-methoxyphenyl)-5-methoxy-2-methylbenzene-1,3-diamine, 5-methoxy-$N^1$-(2-methoxyphenyl)-$N^1$,2-dimethylbenzene-1,3-diamine, $N^1$-(3-fluoro-4-methoxyphenyl)-5-methoxy-$N^1$,2-dimethylbenzene-1,3-diamine, 5-methoxy-2-methyl-$N^1$-(6-(trifluoromethyl)pyridin-2-yl)benzene-1,3-diamine, 5-fluoro-2-methyl-$N^1$-(6-(trifluoromethyl)pyridin-2-yl)benzene-1,3-diamine, 5-chloro-2-methyl-$N^1$-(6-(trifluoromethyl)pyridin-2-yl)benzene-1,3-diamine, 2-chloro-$N^1$-(4-fluoro-3-methoxyphenyl)-5-methylbenzene-1,3-diamine, $N^1$-(4-fluoro-3-methoxyphenyl)-5-methoxy-2-methylbenzene-1,3-diamine, 3-(3-fluorobenzyl)-5-methoxy-2-methylaniline, 5-methoxy-2-methyl-3-(3-methylbenzyl)aniline, 3-(4-chlorobenzyl)-5-methoxy-2-methylaniline, 5-methoxy-2-methyl-3-(3-nitrobenzyl)aniline, 3-(5-fluoro-2-methylbenzyl)-5-methoxy-2-methylaniline, 3-(3-chloro-4-fluorobenzyl)-5-methoxy-2-methylaniline, 2-chloro-5-methyl-$N^1$-(6-(trifluoromethyl)pyridin-2-yl)benzene-1,3-diamine, $N^1$-(4-fluoro-3-methoxyphenyl)-5-methoxy-$N^1$,2-dimethylbenzene-1,3-diamine, 5-methoxy-$N^1$,2-dimethyl-$N^1$-(6-(trifluoromethyl)pyridin-2-yl)benzene-1,3-diamine, 3-(3,4-difluorobenzyl)-5-methoxy-2-methylaniline, 3-(4-bromobenzyl)-5-methoxy-2-methylaniline, 2-chloro-$N^1$-(4-fluoro-3-methoxyphenyl)-$N^1$,5-dimethylbenzene-1,3-diamine, 5-chloro-$N^1$,2-dimethyl-$N^1$-(6-(trifluoromethyl)pyridin-2-yl)benzene-1,3-diamine, 2-chloro-$N^1$,5-dimethyl-$N^1$-(6-(trifluoromethyl)pyridin-2-yl)benzene-1,3-diamine, 5-fluoro-$N^1$,2-dimethyl-$N^1$-(6-(trifluoromethyl)pyridin-2-yl)benzene-1,3-diamine, 3-(3-fluoro-5-methylbenzyl)-5-methoxy-2-methylaniline, 3-(2-chloro-5-fluorobenzyl)-5-methoxy-2-methylaniline, 3-(2-bromobenzyl)-5-methoxy-2-methylaniline, 5-methoxy-2-methyl-3-(4-(trifluoromethyl)benzyl)aniline, 5-methoxy-2-methyl-3-(3-(trifluoromethyl)benzyl)aniline, 3-amino-5-(3-fluorobenzyl)-4-methylbenzonitrile, 3-benzyl-5-methoxy-2-methylaniline, 5-methoxy-2-methyl-3-(2-(trifluoromethoxy)benzyl)aniline, 5-methoxy-2-methyl-$N^1$-(2-(trifluoromethoxy)phenyl)benzene-1,3-diamine, 5-chloro-2-methyl-$N^1$-(2-(trifluoromethoxy)phenyl)benzene-1,3-diamine, 2-chloro-5-methyl-$N^1$-(2-(trifluoromethoxy)phenyl)benzene-1,3-diamine, 5-fluoro-2-methyl-$N^1$-(2-(trifluoromethoxy)phenyl)benzene-1,3-diamine, 1-(3-amino-5-fluoro-2-methylphenyl)-2-(2-chloro-4-methoxyphenoxy)ethan-1-one, 5-methoxy-2-methyl-3-(3-(trifluoromethoxy)benzyl)aniline, 3-(3-amino-5-methoxy-2-methylbenzyl)benzonitrile, 5-methoxy-2-methyl-3-(2-(trifluoromethyl)benzyl)aniline, 3-amino-5-benzyl-4-methylbenzonitrile, 3-amino-5-(3-cyanobenzyl)-4-methylbenzonitrile, 3-amino-5-(4-fluorobenzyl)-4-methylbenzonitrile, 3-amino-5-(4-chlorobenzyl)-4-methylbenzonitrile, 3-amino-4-methyl-5-(3-nitrobenzyl)benzonitrile, 3-amino-5-(3-bromobenzyl)-4-methylbenzonitrile and 3-amino-4-methyl-5-(2-(trifluoromethoxy)benzyl)benzonitrile.

* * * * *